(12) United States Patent
Patrick et al.

(10) Patent No.: US 8,142,414 B2
(45) Date of Patent: *Mar. 27, 2012

(54) METHODS OF INJECTING FLUIDS INTO JOINTS USING A HANDPIECE ASSEMBLY

(75) Inventors: Timothy Patrick, Alpharetta, GA (US); Richard Knostman, Alpharetta, GA (US); Carribeth Ramey, Suwanee, GA (US); Michael Axelrod, Roswell, GA (US)

(73) Assignee: Carticept Medical, Inc., Alpharetta, GA (US)

( * ) Notice: Subject to any disclaimer, the term of this patent is extended or adjusted under 35 U.S.C. 154(b) by 551 days.

This patent is subject to a terminal disclaimer.

(21) Appl. No.: 12/343,299

(22) Filed: Dec. 23, 2008

(65) Prior Publication Data

US 2009/0171194 A1 Jul. 2, 2009

Related U.S. Application Data

(63) Continuation of application No. 12/340,595, filed on Dec. 19, 2008.

(60) Provisional application No. 61/016,395, filed on Dec. 21, 2007.

(51) Int. Cl.
*A61M 31/00* (2006.01)
(52) U.S. Cl. .............. 604/518; 604/87; 604/88; 604/89; 604/257; 604/258; 604/259
(58) Field of Classification Search .............. 604/80–83, 604/85, 87, 89, 131, 151, 152, 154, 155, 604/257–259, 500, 506, 507, 511, 518–520
See application file for complete search history.

(56) References Cited

U.S. PATENT DOCUMENTS

| 3,556,079 A * | 1/1971 | Omizo .......................... 600/461 |
| 3,807,048 A * | 4/1974 | Malmin .......................... 433/81 |
| 4,676,256 A | 6/1987 | Golden |

(Continued)

FOREIGN PATENT DOCUMENTS

EP 0 538 241 2/1998

(Continued)

OTHER PUBLICATIONS

Valls, R. et al., "Sonographic Guidance of Needle Position for MR Arthrography of the Shoulder". American Journal of Roentgenology, Sep. 1997; 169(3): pp. 845-847.

(Continued)

*Primary Examiner* — Bhisma Mehta
*Assistant Examiner* — Larry R Wilson
(74) *Attorney, Agent, or Firm* — Knobbe, Martens, Olson & Bear LLP

(57) ABSTRACT

Systems for injecting fluids and/or other materials into a targeted anatomical location, in particular, an intra-articular space, include a handpiece assembly having a proximal end and a distal end, a needle extending from the distal end of the handpiece assembly, a fluid delivery module comprising a cassette and a fluid transfer device. A conduit is generally configured to place the fluid delivery module in fluid communication with the handpiece assembly. Medications, formulations and/or other fluids or materials contained within vials that are secured to the fluid delivery module can be selectively delivered into an anatomy through a needle located at the distal end of the handpiece assembly. In some embodiments, ultrasound or other imaging technologies can be used to locate a joint or other targeted anatomical location.

18 Claims, 104 Drawing Sheets

U.S. PATENT DOCUMENTS

| | | |
|---|---|---|
| 4,747,824 A | 5/1988 | Spinello |
| 4,790,823 A | 12/1988 | Charton et al. |
| 4,877,934 A | 10/1989 | Spinello |
| 4,950,245 A | 8/1990 | Brown et al. |
| 4,978,336 A | 12/1990 | Capozzi et al. |
| 5,125,837 A * | 6/1992 | Warrin et al. .................. 433/98 |
| 5,147,323 A | 9/1992 | Haber et al. |
| 5,180,371 A | 1/1993 | Spinello |
| 5,188,603 A | 2/1993 | Vaillancourt |
| 5,199,949 A | 4/1993 | Haber et al. |
| 5,243,982 A | 9/1993 | Mostl et al. |
| 5,253,578 A | 10/1993 | Hsu |
| 5,271,527 A | 12/1993 | Haber et al. |
| 5,281,198 A | 1/1994 | Haber et al. |
| 5,298,023 A | 3/1994 | Haber et al. |
| 5,314,412 A | 5/1994 | Rex |
| 5,318,522 A | 6/1994 | D'Antonio |
| 5,324,258 A | 6/1994 | Rohrbough |
| 5,336,188 A | 8/1994 | Kriesel |
| 5,354,284 A | 10/1994 | Haber et al. |
| 5,360,410 A | 11/1994 | Wacks |
| 5,378,233 A | 1/1995 | Haber et al. |
| 5,395,326 A | 3/1995 | Haber et al. |
| 5,425,366 A | 6/1995 | Reinhardt et al. |
| 5,445,614 A | 8/1995 | Haber et al. |
| 5,478,323 A | 12/1995 | Westwood et al. |
| 5,505,704 A | 4/1996 | Pawelka et al. |
| 5,520,658 A | 5/1996 | Holm |
| 5,542,934 A | 8/1996 | Silver |
| 5,584,815 A | 12/1996 | Pawelka et al. |
| 5,599,315 A | 2/1997 | Higashikawa |
| 5,620,479 A | 4/1997 | Diederich |
| 5,656,016 A | 8/1997 | Ogden |
| 5,658,247 A | 8/1997 | Henley |
| 5,666,946 A | 9/1997 | Langenback |
| 5,667,487 A | 9/1997 | Henley |
| 5,698,787 A | 12/1997 | Parzuchowski et al. |
| 5,704,918 A | 1/1998 | Higashikawa |
| 5,707,365 A | 1/1998 | Haber et al. |
| 5,725,494 A | 3/1998 | Brisken |
| 5,735,811 A | 4/1998 | Brisken |
| 5,752,515 A | 5/1998 | Jolesz et al. |
| 5,794,612 A | 8/1998 | Wachter et al. |
| 5,800,421 A | 9/1998 | Lemelson |
| 5,814,022 A | 9/1998 | Antanavich et al. |
| 5,830,187 A | 11/1998 | Kriesel et al. |
| 5,833,627 A | 11/1998 | Shmulewitz et al. |
| RE35,986 E | 12/1998 | Ritson et al. |
| 5,876,380 A | 3/1999 | Manganini et al. |
| 5,908,158 A | 6/1999 | Cheiman |
| 5,917,828 A | 6/1999 | Thompson |
| 5,924,997 A | 7/1999 | Campbell |
| 5,935,111 A | 8/1999 | Bunyan |
| 5,951,517 A | 9/1999 | Lampropoulos et al. |
| 5,961,494 A | 10/1999 | Hogan |
| 5,980,509 A | 11/1999 | Magruder et al. |
| 5,984,889 A | 11/1999 | Christ et al. |
| 5,997,497 A | 12/1999 | Nita et al. |
| 6,022,337 A | 2/2000 | Herbst et al. |
| 6,024,718 A | 2/2000 | Chen et al. |
| D422,361 S | 4/2000 | Herbst et al. |
| D423,665 S | 4/2000 | Herbst et al. |
| 6,045,533 A | 4/2000 | Kriesel et al. |
| D427,314 S | 6/2000 | Herbst et al. |
| 6,126,600 A | 10/2000 | Oxaal et al. |
| 6,132,400 A | 10/2000 | Waldenburg |
| 6,132,414 A | 10/2000 | Herbst et al. |
| 6,152,734 A | 11/2000 | Herbst et al. |
| 6,199,554 B1 | 3/2001 | Mann et al. |
| 6,200,289 B1 | 3/2001 | Hochman et al. |
| 6,223,936 B1 | 5/2001 | Jeanbourquin |
| 6,234,990 B1 | 5/2001 | Rowe et al. |
| 6,264,064 B1 | 7/2001 | Birtcher et al. |
| 6,273,864 B1 | 8/2001 | Duarte et al. |
| 6,308,714 B1 | 10/2001 | Peterson et al. |
| 6,322,532 B1 | 11/2001 | D'Sa et al. |
| 6,350,245 B1 | 2/2002 | Cimino |
| 6,352,683 B1 | 3/2002 | ten Cate |
| 6,390,815 B1 * | 5/2002 | Pond .............................. 433/80 |
| 6,394,956 B1 | 5/2002 | Chandrasekaran et al. |
| 6,416,740 B1 | 7/2002 | Unger |
| 6,428,517 B1 | 8/2002 | Hochman et al. |
| 6,461,296 B1 | 10/2002 | Desai |
| 6,475,148 B1 | 11/2002 | Jackson et al. |
| 6,487,447 B1 | 11/2002 | Weimann et al. |
| 6,488,628 B1 | 12/2002 | Reiss |
| 6,491,657 B2 | 12/2002 | Rowe et al. |
| 6,508,783 B2 | 1/2003 | DeVore |
| 6,527,718 B1 | 3/2003 | Connor et al. |
| 6,537,249 B2 | 3/2003 | Kriesell et al. |
| 6,565,538 B2 | 5/2003 | Quinn et al. |
| 6,565,539 B1 | 5/2003 | Zinger et al. |
| 6,585,696 B2 | 7/2003 | Petersen et al. |
| 6,589,158 B2 | 7/2003 | Winkler |
| 6,601,581 B1 | 8/2003 | Babaev |
| 6,607,502 B1 | 8/2003 | Maguire et al. |
| 6,610,033 B1 | 8/2003 | Melanson et al. |
| 6,610,042 B2 | 8/2003 | Leon et al. |
| 6,635,017 B1 | 10/2003 | Moehring et al. |
| 6,645,181 B1 | 11/2003 | Lavi et al. |
| 6,652,482 B2 | 11/2003 | Hochman |
| 6,659,950 B2 | 12/2003 | Taheri |
| 6,689,067 B2 | 2/2004 | Sauer et al. |
| 6,689,108 B2 | 2/2004 | Lavi et al. |
| 6,695,786 B2 | 2/2004 | Wang et al. |
| 6,702,749 B2 | 3/2004 | Paladini et al. |
| 6,716,168 B2 | 4/2004 | Nock et al. |
| 6,719,729 B2 | 4/2004 | Sogaro |
| 6,723,064 B2 | 4/2004 | Babaev |
| 6,723,068 B2 | 4/2004 | Lavi et al. |
| 6,726,650 B2 | 4/2004 | Schneider et al. |
| 6,726,658 B2 | 4/2004 | Hochman |
| 6,731,971 B2 | 5/2004 | Evans et al. |
| 6,733,451 B2 | 5/2004 | Rabiner et al. |
| 6,786,885 B2 | 9/2004 | Hochman et al. |
| 6,796,964 B2 | 9/2004 | Eidson et al. |
| 6,808,514 B2 | 10/2004 | Schneider et al. |
| 6,842,641 B2 | 1/2005 | Weimann et al. |
| 6,858,020 B2 | 2/2005 | Rusnak |
| 6,875,179 B2 | 4/2005 | Ferguson et al. |
| 6,887,216 B2 | 5/2005 | Hochman et al. |
| 6,905,482 B2 | 6/2005 | Hochman |
| 6,908,433 B1 | 6/2005 | Pruter |
| 6,917,828 B2 | 7/2005 | Fukuda |
| 6,929,609 B2 | 8/2005 | Asafusa |
| 6,936,033 B2 | 8/2005 | McIntosh et al. |
| 6,939,329 B1 | 9/2005 | Verkaart |
| 6,945,954 B2 | 9/2005 | Hochman et al. |
| 6,966,899 B2 | 11/2005 | Hochman et al. |
| 6,972,005 B2 | 12/2005 | Boehm et al. |
| 6,994,686 B2 | 2/2006 | Cruise et al. |
| 7,037,269 B2 | 5/2006 | Nix et al. |
| 7,041,081 B2 | 5/2006 | Minezaki et al. |
| 7,077,827 B2 | 7/2006 | Greenfield |
| 7,078,015 B2 | 7/2006 | Unger |
| 7,169,128 B2 | 1/2007 | Kriesel et al. |
| 7,214,210 B2 | 5/2007 | Kamen et al. |
| 7,235,063 B2 | 6/2007 | D'Antonio et al. |
| D558,340 S | 12/2007 | Hochman et al. |
| D566,265 S | 4/2008 | Hochman et al. |
| 7,361,163 B2 | 4/2008 | Cohen |
| D579,540 S | 10/2008 | Hochman et al. |
| D579,546 S | 10/2008 | Birath et al. |
| 7,445,125 B2 | 11/2008 | Ellsworth |
| 7,449,008 B2 | 11/2008 | Hochman |
| 7,473,432 B2 | 1/2009 | Cevc et al. |
| 7,510,397 B2 | 3/2009 | Hochman |
| 7,618,409 B2 | 11/2009 | Hochman |
| 7,625,354 B2 | 12/2009 | Hochman |
| 7,789,552 B2 | 9/2010 | Girvin et al. |
| 2001/0049608 A1 | 12/2001 | Hochman |
| 2001/0051798 A1 | 12/2001 | Hochman |
| 2001/0055610 A1 | 12/2001 | Nagata et al. |
| 2002/0045850 A1 | 4/2002 | Rowe et al. |
| 2002/0055702 A1 | 5/2002 | Atala et al. |
| 2002/0077588 A1 | 6/2002 | Schneider et al. |
| 2002/0123678 A1 | 9/2002 | Lerner et al. |

| | | | |
|---|---|---|---|
| 2002/0133101 A1 | 9/2002 | DeVore | |
| 2002/0150539 A1 | 10/2002 | Unger | |
| 2002/0151868 A1 | 10/2002 | Taheri | |
| 2002/0156376 A1 | 10/2002 | Wang | |
| 2002/0183701 A1 | 12/2002 | Hochman et al. | |
| 2003/0028112 A1 | 2/2003 | Paladini et al. | |
| 2003/0073908 A1 | 4/2003 | Desai | |
| 2003/0078533 A1 | 4/2003 | Weimann et al. | |
| 2003/0120154 A1 | 6/2003 | Sauer | |
| 2003/0120201 A1 | 6/2003 | Abergel | |
| 2003/0120217 A1 | 6/2003 | Abergel | |
| 2003/0204141 A1 | 10/2003 | Nock et al. | |
| 2003/0229304 A1 | 12/2003 | Babaev | |
| 2003/0233046 A1 | 12/2003 | Ferguson | |
| 2004/0002647 A1 | 1/2004 | Desai | |
| 2004/0019318 A1 | 1/2004 | Wilson et al. | |
| 2004/0039368 A1 | 2/2004 | Reilly et al. | |
| 2004/0064102 A1 | 4/2004 | Yamada | |
| 2004/0092821 A1 | 5/2004 | Hering | |
| 2004/0097805 A1 | 5/2004 | Verard et al. | |
| 2004/0097806 A1 | 5/2004 | Hunter | |
| 2005/0038387 A1 | 2/2005 | Kriesel et al. | |
| 2005/0043681 A1 | 2/2005 | Rusnak | |
| 2005/0075620 A1 | 4/2005 | Iger | |
| 2005/0123482 A1 | 6/2005 | Unger | |
| 2005/0171486 A1 | 8/2005 | Hochman | |
| 2005/0177054 A1 | 8/2005 | Yi et al. | |
| 2005/0203413 A1 | 9/2005 | Fichtinger et al. | |
| 2005/0228256 A1 | 10/2005 | Labadie et al. | |
| 2005/0260084 A1 | 11/2005 | Rusnak | |
| 2005/0283110 A1 | 12/2005 | Atala et al. | |
| 2006/0106283 A1 | 5/2006 | Wallace et al. | |
| 2006/0122555 A1 | 6/2006 | Hochman | |
| 2006/0247578 A1 | 11/2006 | Arguedas et al. | |
| 2006/0258977 A1 | 11/2006 | Lee | |
| 2007/0032723 A1 | 2/2007 | Glossop | |
| 2007/0073235 A1 | 3/2007 | Estes et al. | |
| 2007/0073267 A1 | 3/2007 | Muller | |
| 2007/0083155 A1 | 4/2007 | Muller | |
| 2007/0088268 A1 | 4/2007 | Edwards | |
| 2007/0088271 A1 | 4/2007 | Richards | |
| 2007/0129630 A1 | 6/2007 | Shimko | |
| 2007/0156092 A1 | 7/2007 | Estes et al. | |
| 2007/0167905 A1 | 7/2007 | Estes et al. | |
| 2007/0191781 A1 | 8/2007 | Richards et al. | |
| 2007/0197954 A1 | 8/2007 | Keenan | |
| 2007/0213660 A1* | 9/2007 | Richards et al. | 604/82 |
| 2007/0244442 A1 | 10/2007 | Chowhan | |
| 2007/0282221 A1 | 12/2007 | Wang et al. | |
| 2007/0299398 A1 | 12/2007 | Alferness et al. | |
| 2007/0299399 A1 | 12/2007 | Alferness et al. | |
| 2007/0299400 A1 | 12/2007 | Alferness et al. | |
| 2008/0015512 A1 | 1/2008 | D'Antonio et al. | |
| 2008/0045902 A1 | 2/2008 | Estes et al. | |
| 2008/0045925 A1 | 2/2008 | Stepovich et al. | |
| 2008/0058732 A1 | 3/2008 | Harris | |
| 2008/0060970 A1 | 3/2008 | Wheeler et al. | |
| 2008/0086108 A1 | 4/2008 | Falkel et al. | |
| 2008/0091104 A1 | 4/2008 | Abraham | |
| 2008/0091109 A1 | 4/2008 | Abraham | |
| 2008/0103564 A1 | 5/2008 | Burkinshaw | |
| 2008/0154188 A1 | 6/2008 | Hochman | |
| 2008/0213729 A1 | 9/2008 | Hochman | |
| 2008/0281265 A1 | 11/2008 | Hochman | |
| 2008/0306436 A1 | 12/2008 | Edwards | |
| 2009/0018485 A1 | 1/2009 | Krespi et al. | |
| 2009/0030366 A1 | 1/2009 | Hochman | |
| 2009/0103490 A1 | 4/2009 | Lakshmikanthan | |
| 2009/0171191 A1 | 7/2009 | Patrick et al. | |
| 2009/0171192 A1 | 7/2009 | Patrick et al. | |
| 2009/0171193 A1 | 7/2009 | Patrick et al. | |
| 2009/0171194 A1 | 7/2009 | Patrick et al. | |
| 2009/0171316 A1 | 7/2009 | Patrick et al. | |
| 2009/0326482 A1 | 12/2009 | Hochman | |
| 2011/0021905 A1 | 1/2011 | Patrick et al. | |

FOREIGN PATENT DOCUMENTS

| | | |
|---|---|---|
| EP | 0 814 860 | 11/1999 |
| EP | 1 013 269 | 6/2000 |
| EP | 1 072 283 | 1/2001 |
| EP | 0 781 150 | 11/2002 |
| EP | 0 660 714 | 7/2003 |
| EP | 0 814 719 | 10/2003 |
| EP | 1 370 321 | 12/2003 |
| EP | 0 950 373 | 3/2005 |
| EP | 1 568 324 | 8/2005 |
| EP | 1 119 389 | 12/2005 |
| EP | 1 707 231 | 10/2006 |
| EP | 1 504 713 | 7/2008 |
| GB | 2359756 | 9/2001 |
| JP | 10314166 A2 | 2/1998 |
| JP | 10314168 A2 | 2/1998 |
| JP | 10314171 A2 | 2/1998 |
| JP | 11267127 A2 | 5/1999 |
| JP | 2001/252272 A | 9/2001 |
| JP | 2004/154290 A2 | 3/2004 |
| WO | WO 97/10023 | 3/1997 |
| WO | WO 97/15232 | 5/1997 |
| WO | WO 97/18855 | 5/1997 |
| WO | WO 97/34656 | 9/1997 |
| WO | WO 97/40858 | 11/1997 |
| WO | WO 98/00194 | 1/1998 |
| WO | WO 98/02097 | 1/1998 |
| WO | WO 98/07367 | 2/1998 |
| WO | WO 98/25655 | 6/1998 |
| WO | WO 98/55104 | 12/1998 |
| WO | WO 98/57696 | 12/1998 |
| WO | WO 99/11182 | 3/1999 |
| WO | WO 99/27981 | 6/1999 |
| WO | WO 99/49909 | 10/1999 |
| WO | WO 99/51295 | 10/1999 |
| WO | WO 99/51296 | 10/1999 |
| WO | WO 99/66980 | 12/1999 |
| WO | WO 00/02588 | 1/2000 |
| WO | WO 00/62858 | 10/2000 |
| WO | WO 01/01845 | 1/2001 |
| WO | WO 01/07110 | 2/2001 |
| WO | WO 02/07601 | 1/2002 |
| WO | WO 02/055131 | 7/2002 |
| WO | WO 02/058530 | 8/2002 |
| WO | WO 02/074175 | 9/2002 |
| WO | WO 02/076547 | 10/2002 |
| WO | WO 03/002189 | 1/2003 |
| WO | WO 03/011105 | 2/2003 |
| WO | WO 03/096255 | 11/2003 |
| WO | WO 03/105693 | 12/2003 |
| WO | WO 2004/004709 | 1/2004 |
| WO | WO 2004/073769 | 9/2004 |
| WO | WO 2005/014079 | 2/2005 |
| WO | WO 2005/055849 | 6/2005 |
| WO | WO 2005/056104 | 6/2005 |
| WO | WO 2006/129099 | 12/2006 |
| WO | WO 2007/002079 | 1/2007 |
| WO | WO 2007/039905 | 4/2007 |
| WO | WO 2007/064937 | 6/2007 |
| WO | WO 2007/082189 | 7/2007 |
| WO | WO 2007/094001 | 8/2007 |
| WO | WO 2007/106558 | 9/2007 |
| WO | WO 2007/110076 | 10/2007 |
| WO | WO 2007/127176 | 11/2007 |

OTHER PUBLICATIONS

Press Release in 2 pages by Milestone Scientific, Inc., dated Jul. 13, 2006 and entitled, "Milestone Scientific Receives 510(k) Premarket Notification Acceptance from FDA for CompuFlo™ Computer Controlled Infusion Pump; Company to Pursue Strategic Relationships with Marketing Leaders in Medical Field," retrieved from the website of Milestone Scientific, Inc. at www.milesci.com/press-releases/pr_milestone-compuflo-510k-notification_13jul06.html.

Press Release in 2 pages by Milestone Scientific, Inc., dated Jan. 18, 2005 and entitled, "Milestone Scientific (MS) Announces Second Successful Epidural Clinical Study Using Its CompuFlo™ Technology," retrieved from the website of BioSpace, Inc. at www.biospace.com/news_story.aspx?NewsEntityId=18728720.

Press Release in 3 pages by Milestone Scientific, Inc., dated Dec. 6, 2004 and entitled, "Milestone Scientific Inc. Announces Patent Protection on Two Critical Elements of Its CompuFlo™ Technology," retrieved from the website of The Free Library by Farlex at www.thefreelibrary.com/Milestone+Scientific+Inc.+Announces+Patent+Protection+On+Two+Critical...-a0132631635.

Helfer, A., "Profound Anesthesia Made Easy with the STA System". Endo Tribune, Nov. 2008, pp. 10-11.

Online Article entitled, "Harvard Clinical Technology Names Ohmeda Exclusive Worldwide Distributor of New Dual Syringe Infusion Pump," dated Apr. 3, 1997, retrieved from the website of AllBusiness.com at www.allbusiness.com/health-care/medical-practice-pediatrics/7036362-1.html.

Kinnealey, E. et al., "Infusion Pumps with 'Drug Libraries' at The Point of Care—A Solution for Safer Drug Delivery," dated Jan. 30, 2003, retrieved from the National Patient Safety Foundation website at www.npsf.org/download/Kinnealey.pdf.

Caglar-Yagci et al. "Safety and Efficacy of Ultrasound-Guided Intra-Articular Hylan G-F 20 Injection in Osteoarthritis of the Hip: A Pilot Study". Physical Medicine and Rehabilitation Department, Rheumatol Int. Jun. 2005; 25(5):341-4. Epub Mar. 5, 2004. Ankara Physical Medicine and Rehabilitation Education and Research Hospital, Ankara, Turkey.

Hien et al. "Articular Punctures and Injections Controlled by Ultrasound". Arbeitsgruppe Orthopadische Sonographie, Friedrichshafener Str. 11, D-8000 Munchen 60, Germany. [Includes English Summary], Aug. 8, 1990.

Knorre et al. "Comparative Study of Therapy: Ultrasound, Cryotherapy and Intra-Articulare Cortisonoids to Treat Alterations of the Shoulder Joint Due to Inflammation. with 2 Figures". Z. Physiother. Jg. Oct. 26, 1990, 42/4 (221-225) Rheumatologische Klinik, Bezirkskrankenhaus Magdeburg, Klinikbereich Vogelsang, Vogelsang-Gommern, 3301, German Democratic Republic. [Includes English Summary].

Koski et al. "Verification of Palpation-Guided Intra-Articular Injections Using Glucocorticoid-Air-Saline Mixture and Ultrasound Imaging (GAS-Graphy)." Clin Exp Rheumatol. May-Jun. 2006;24(3):247-52. Mikkeli Central Hospital, Porrassalmenkatu 35-37, Mikkeli, Finland.

Koski. "Ultrasound Guided Injections in Rheumatology". J Rheumatol. Sep. 2000;27(9):2131-8. The Lea Hirvonen Library, Mikkeli Central Hospital, Finland.

Migliore et al. "Efficacy and Safety of Viscosupplementation by Ultrasound-Guided Intra-Articular Injection in Osteoarthritis of the Hip". Osteoarthritis Cartilage. Apr. 2003;11(4):305-6. Department of Internal Medicine, S.Pietro-Fatebenefratelli Hospital, Rome, Italy.

Migliore et al. "Intra-Articular Treatment with Hylan G-F 20 under Ultrasound Guidance in Hip Osteoarthritis. Clinical Results After 12 months Follow-up". Reumatismo, 2005; 57(1): 36-43. Department of Internal Medicine, S. Pietro-Fatebenefratelli Hospital, Rome, Italy.

Migliore et al. "18-Month Observational Study on Efficacy of Intraarticular Hyaluronic Acid (Hylan G-F 20) Injections under Ultrasound Guidance in Hip Osteoarthritis". Reumatismo 2006;58(1): 39-49. S.Pietro-Fatebenefratelli Hospital, Rome, Italy.

Qvistgaard et al. "Guidance by Ultrasound of Intra-Articular Injections in the Knee and Hip Joints". Osteoarthritis and Cartilage. Aug. 2001; 9(6):512-7. The Parker Institute, Department of Rheumatology, H:S Frederiksberg Hospital, Copenhagen, Denmark.

Raza et al. "Ultrasound Guidance Allows Accurate Needle Placement and Aspiration from Small Joints in Patients with Early Inflammatory Arthritis". Rheumatology, 2003, 42.

Rutten et al. "Injection of the Subacromial-Subdeltoid Bursa: Blind or Ultrasound-Guided?" Acta Orthop. Apr. 2007; 78(2):254-7. Department of Radiology, Jeroen Bosch Hospital's-Hertogenbosch, The Netherlands.

Smith et al. "Office-Based Ultrasound-Guided Intra-Articular Hip Injection: Technique for Physiatric Practice". Arch Phys Med Rehabil. Feb. 2006;87(2):296-8.Department of Physical Medicine and Rehabilitation, Mayo Clinic College of Medicine, Rochester, MN 55905, USA.

Sofka et al. "Ultrasound-Guided Interventions in the Foot and Ankle". RS. Semin Musculoskelet Radiol. Jun. 2002; 6(2):163-8. Review.

Product Summary in 1 page related to, in part, Harvard 2 Dual Syringe Pump with Occlusion Detection, retrieved at www.cgs.com.br/H/A017.pdf (retrieved on or about Mar. 2010).

Product Brochure in 2 pages for Cardinal Health Alaris® Products Alaris® SE Single/Dual Channel Pumps (retrieved on or about Mar. 2010).

* cited by examiner

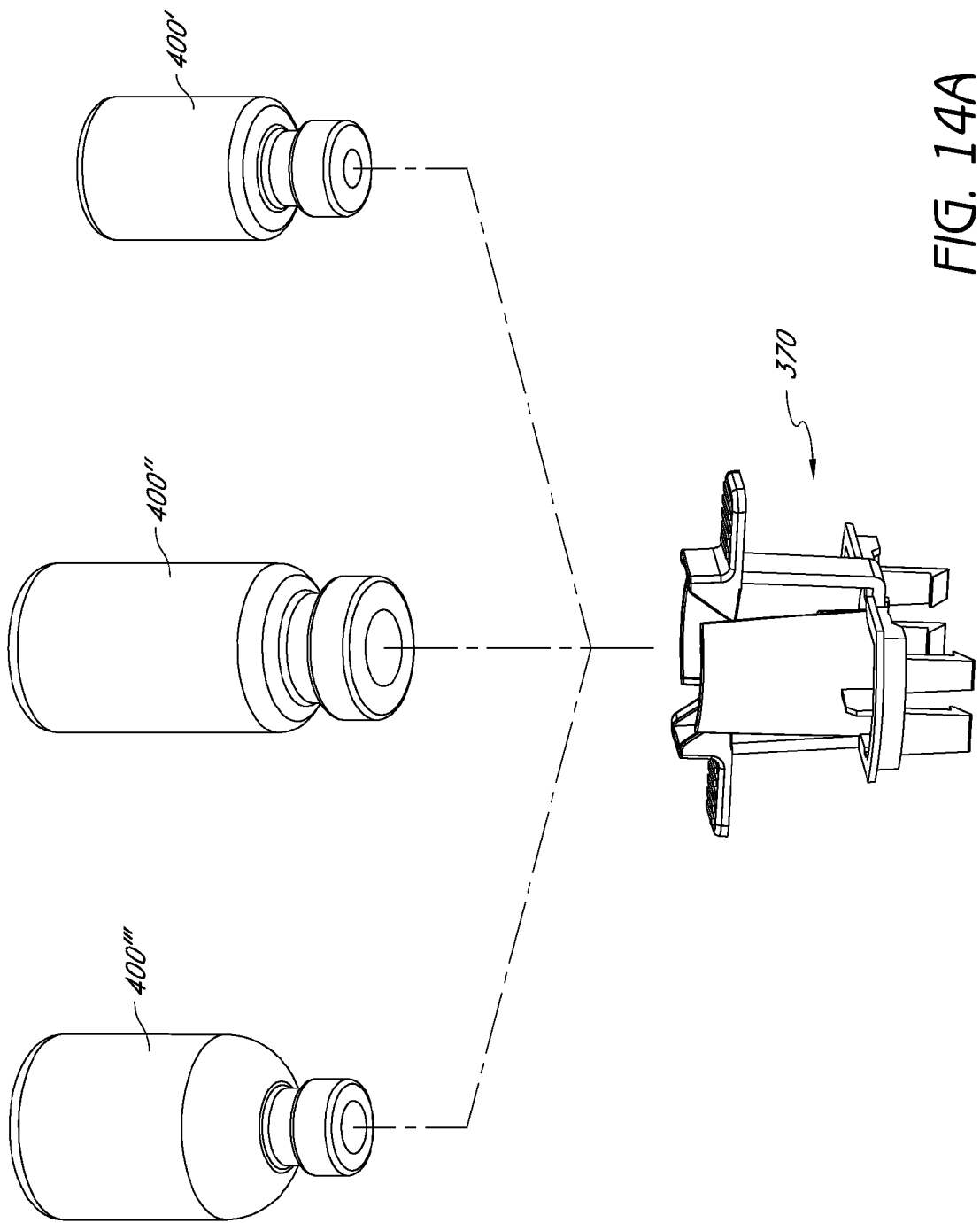

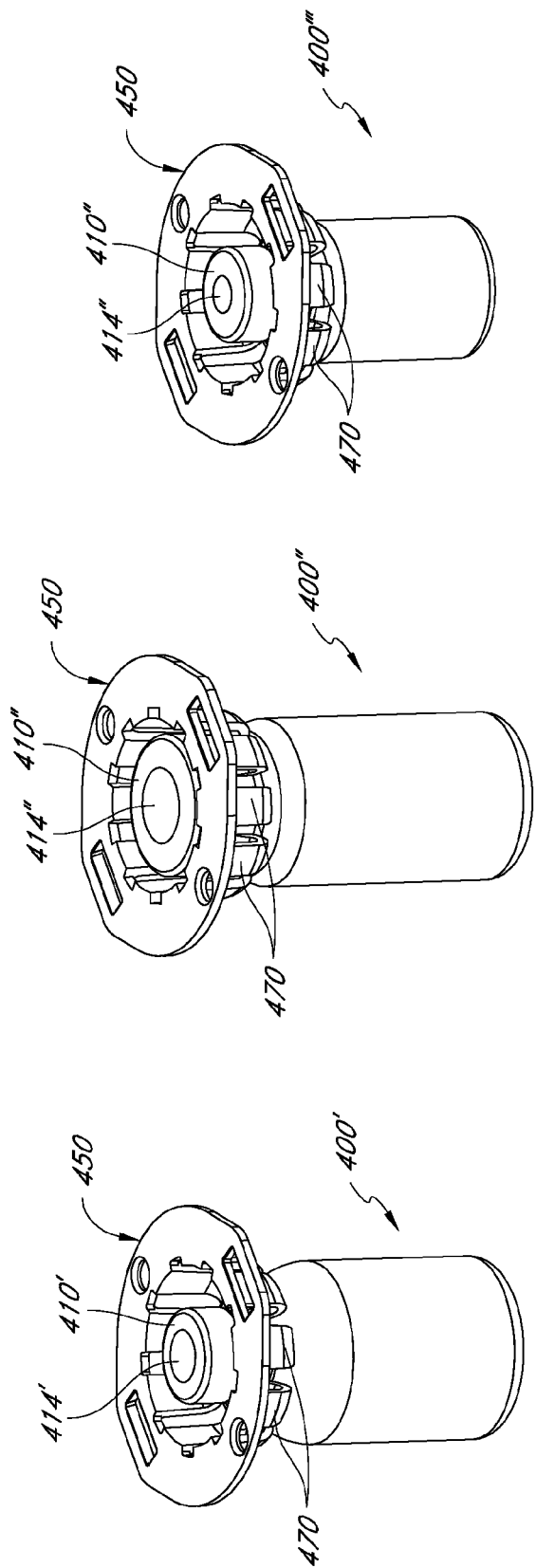

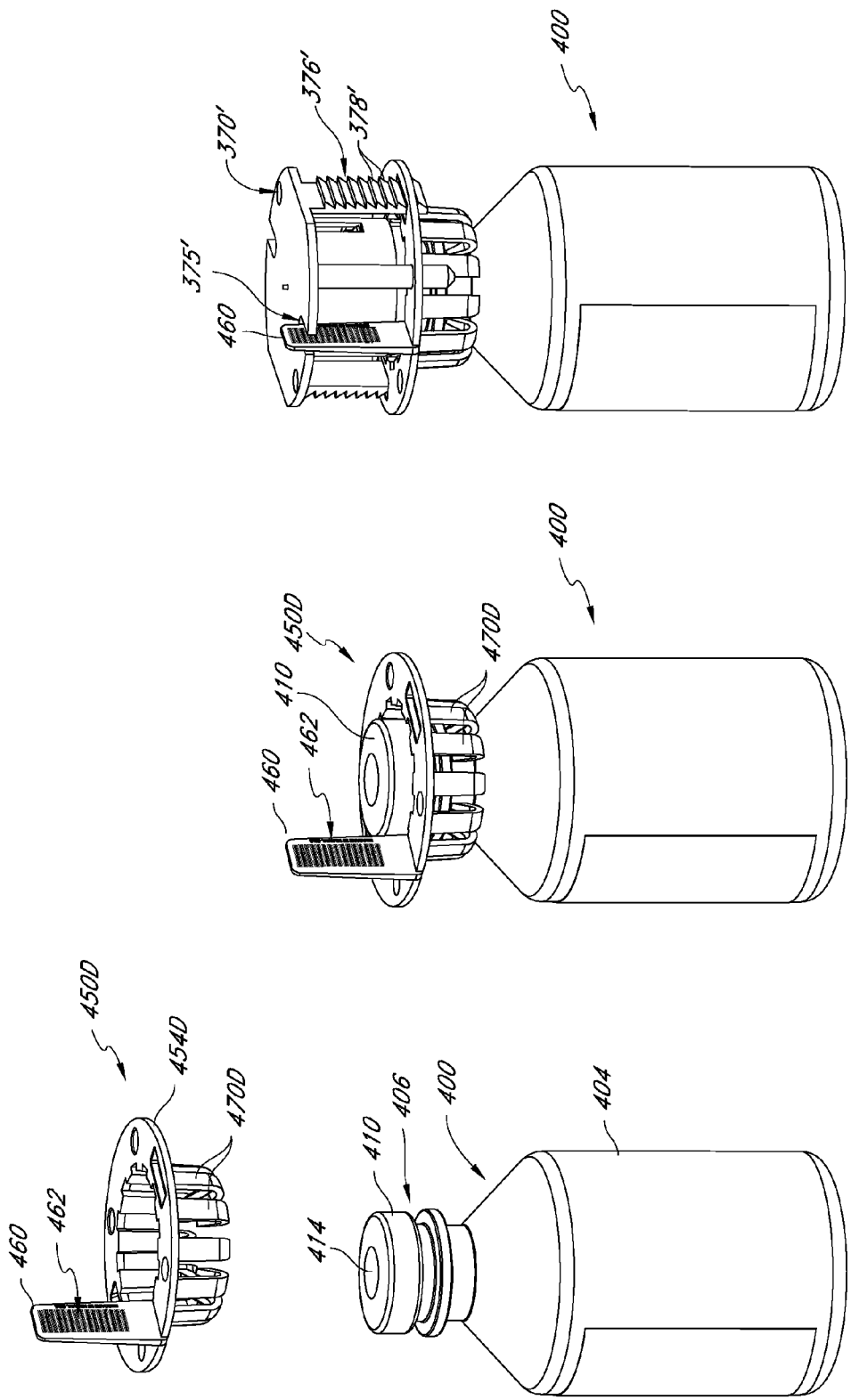

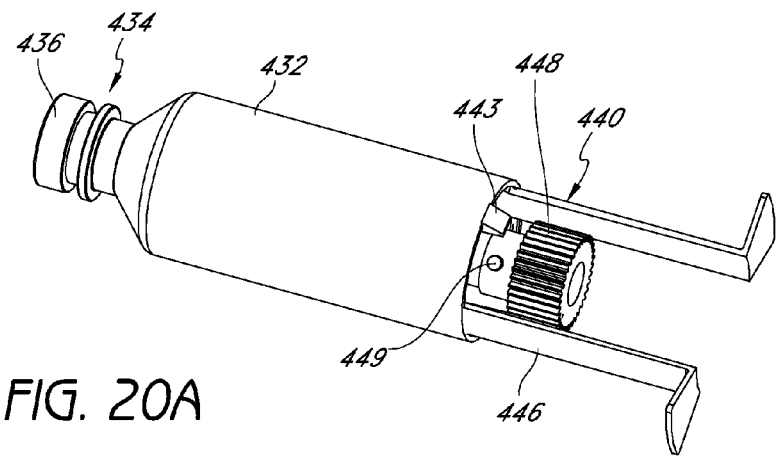
FIG. 20A
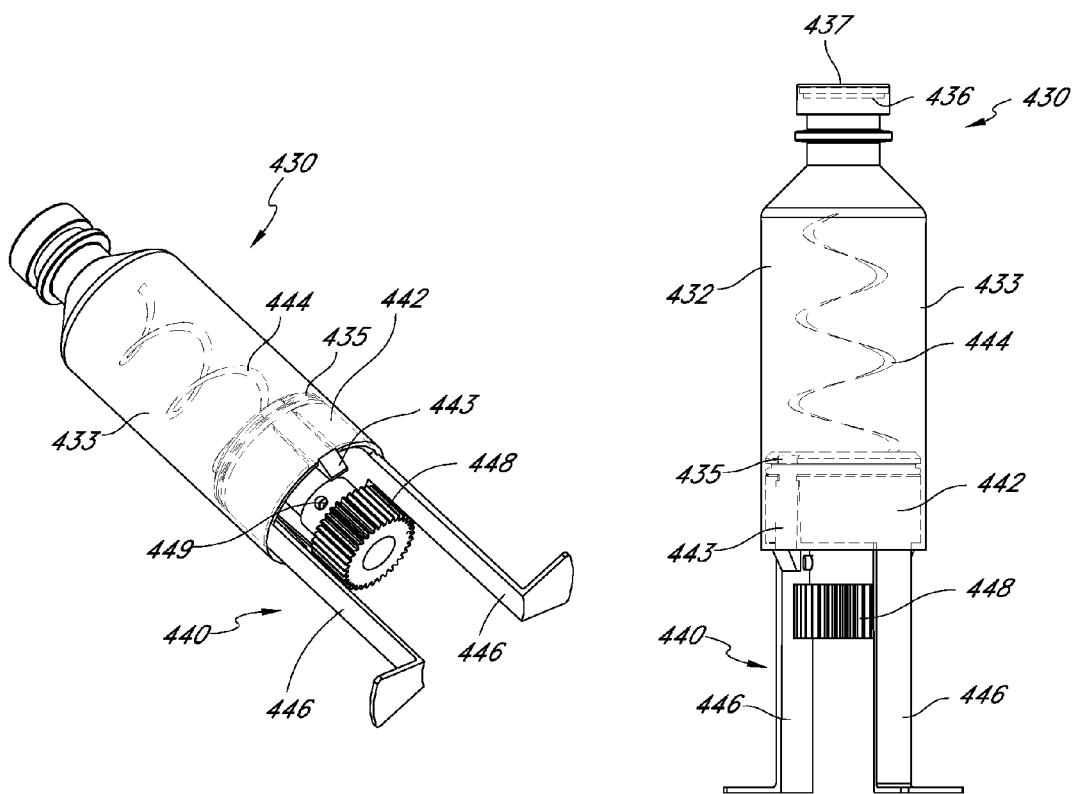
FIG. 20B
FIG. 20C

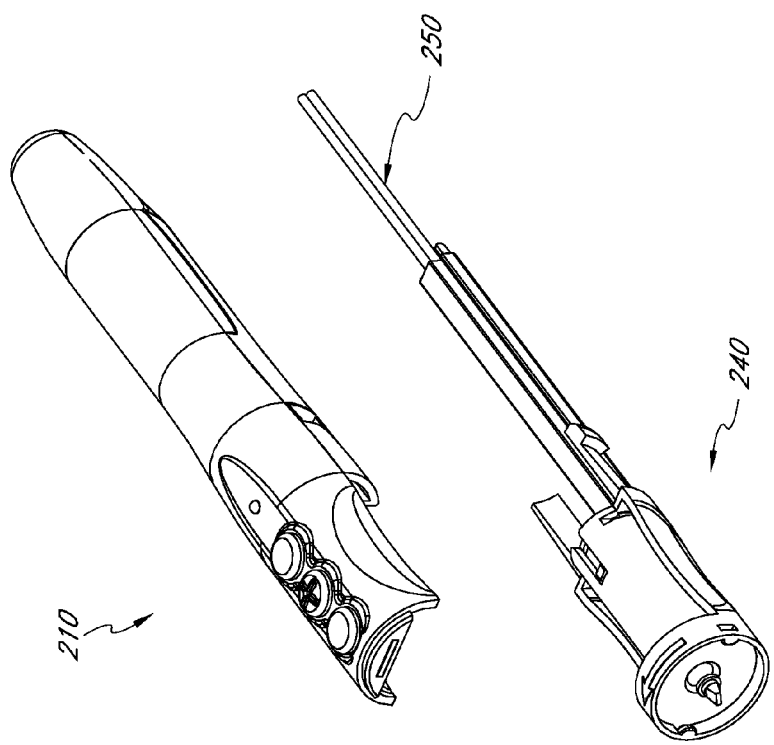
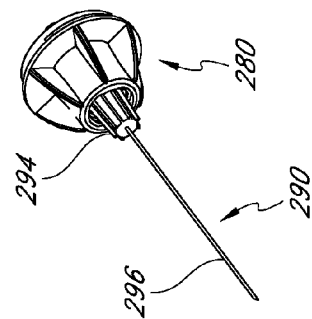
FIG. 21B

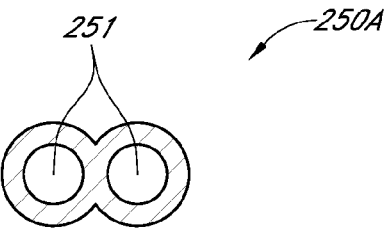
FIG. 27A
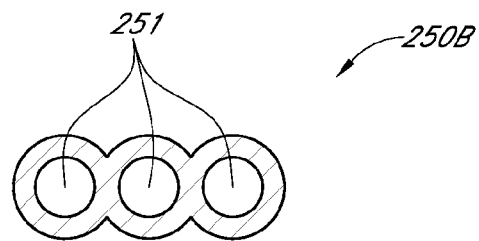
FIG. 27B
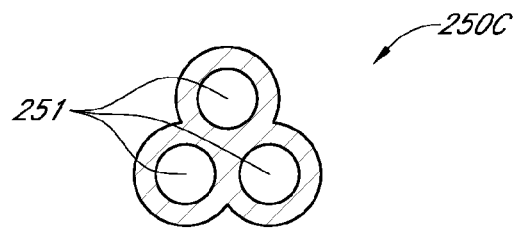
FIG. 27C
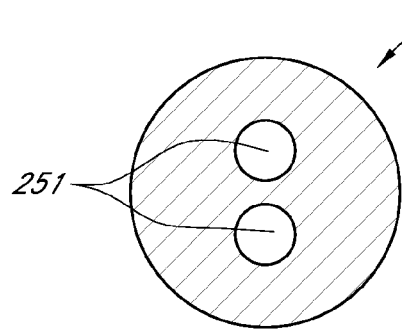 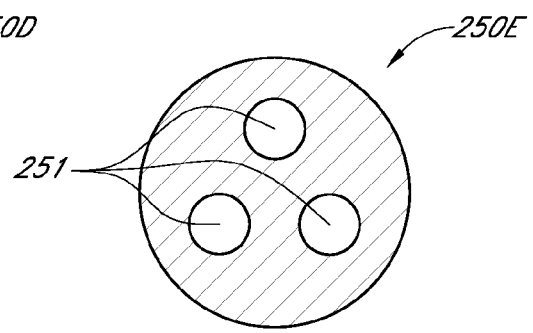
FIG. 27D         FIG. 27E

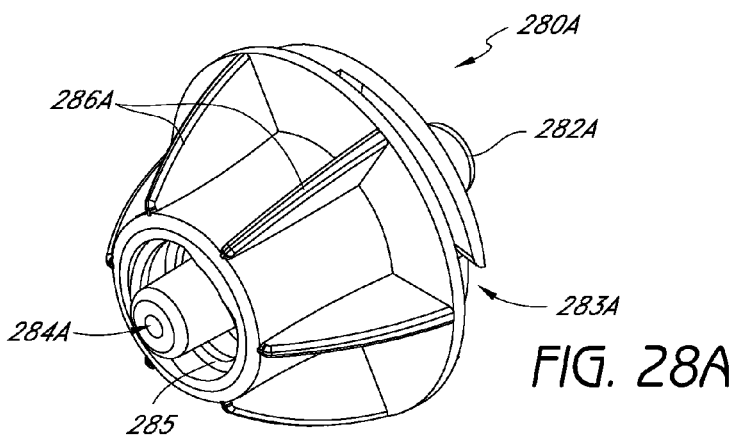
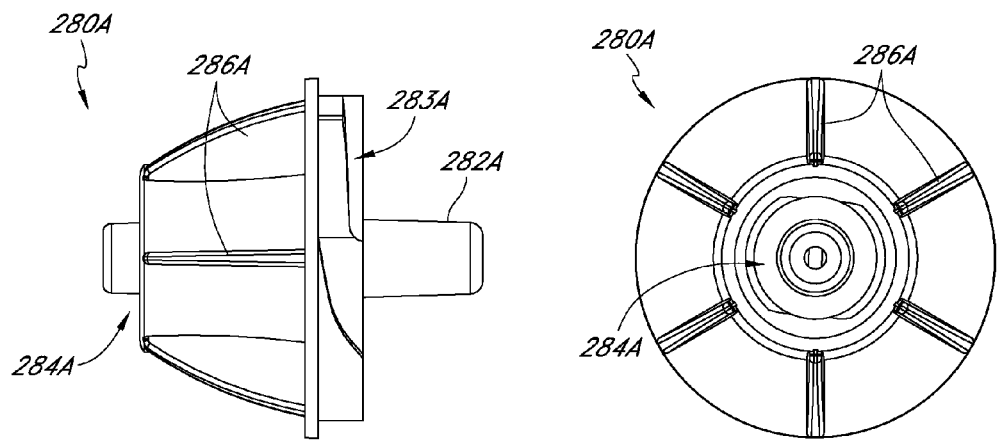
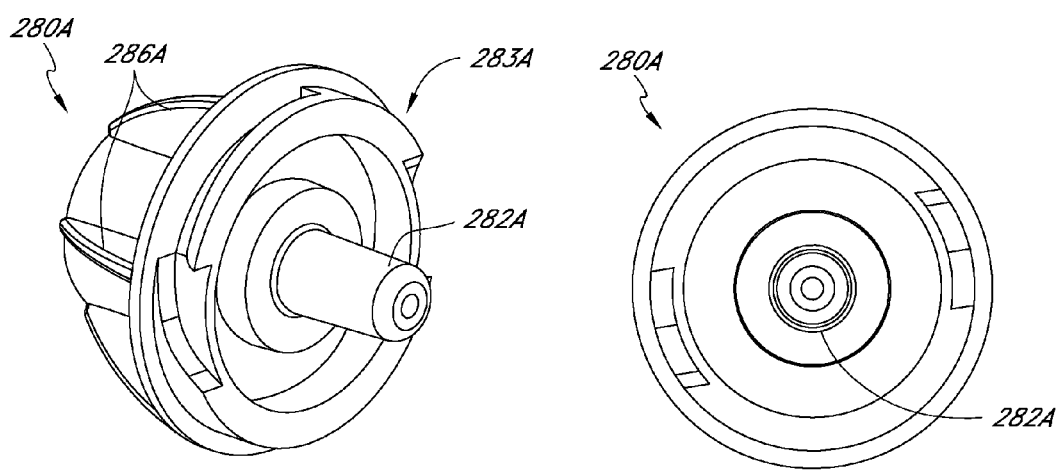

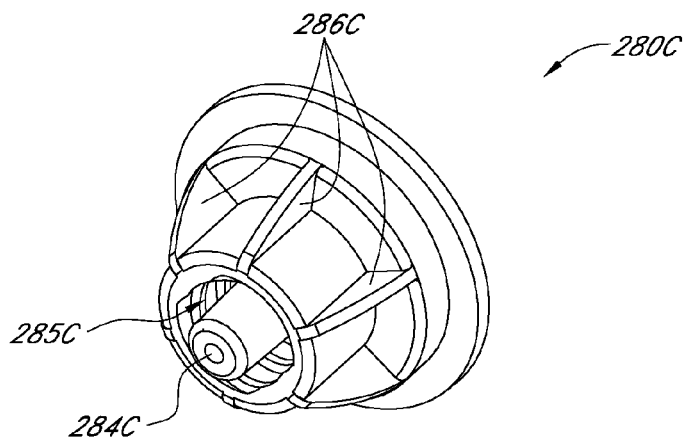
FIG. 30A
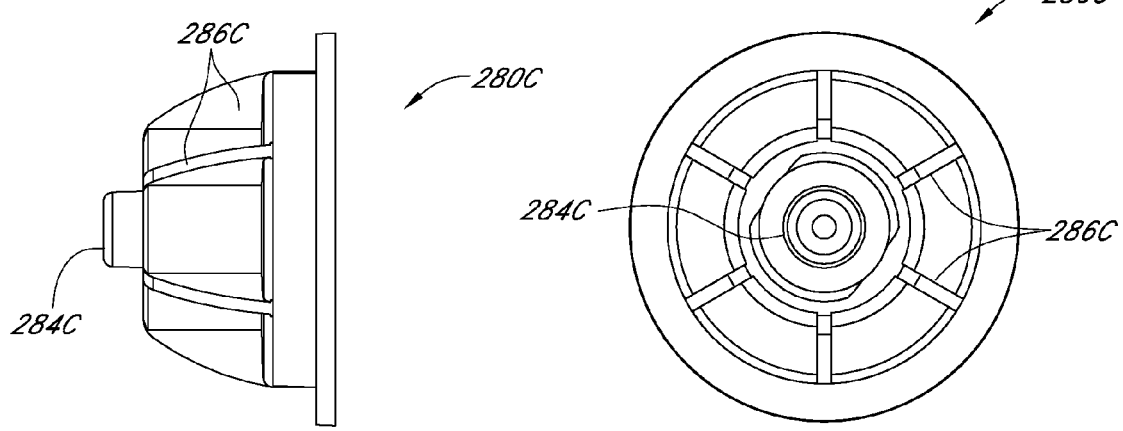
FIG. 30B
FIG. 30C
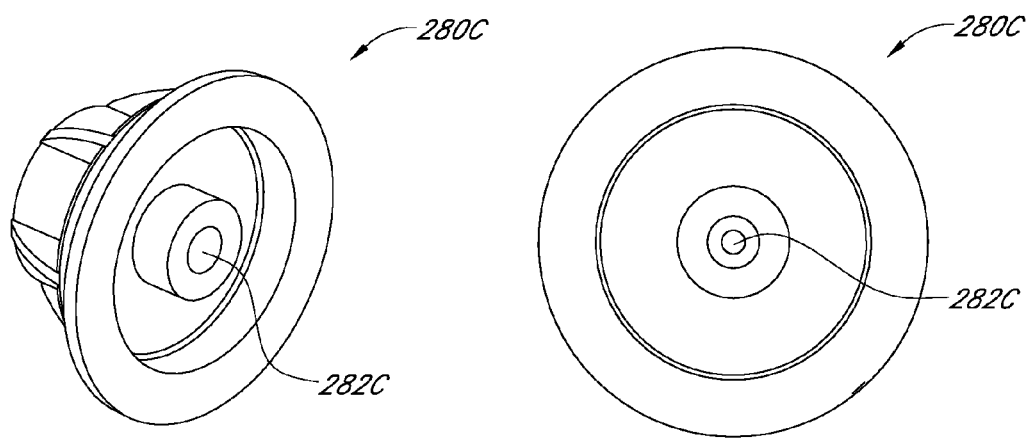
FIG. 30D
FIG. 30E

METHODS OF INJECTING FLUIDS INTO JOINTS USING A HANDPIECE ASSEMBLY

CROSS REFERENCE TO RELATED APPLICATIONS

This is a continuation of U.S. patent application Ser. No. 12/340,595, filed Dec. 19, 2008, which claims the benefit under 35 U.S.C. §119(e) of U.S. Provisional Application No. 61/016,395, filed Dec. 21, 2007, the entireties of which are hereby incorporated by reference herein.

BACKGROUND

1. Field of the Inventions

This application relates generally to injection and/or aspiration devices, systems and methods, and more specifically, to devices, systems and methods of delivering pharmaceuticals or other substances and/or other fluids into and/or out of an intra-articular space.

2. Description of the Related Art

Physicians, clinicians and/or other medical personnel often need to deliver a volume of medication, other fluid and/or other material to (or aspirate fluid from) an anatomical location, such as, for example a joint (e.g., toe, knee, wrist, shoulder, ankle, finger, spine, etc.). Accordingly, a needle can be inserted through a patient's skin and into the targeted location. A syringe or other fluid source that is in fluid communication with the needle can then be used to deliver the desired volume or other dosage of fluid and/or other material to the targeted joint or other anatomical location.

Current injection practice generally involves palpation by the physician of a bony prominence on the patient's anatomy to serve as a "landmark" to guide the injection into the targeted location. The injection is completed by advancing the needle, which is typically connected to a disposable glass or plastic syringe, into the target area. The syringe plunger is then advanced to deliver the fluid. In many cases, current treatment methods do not offer precise or accurate delivery.

SUMMARY

Embodiments of the present invention are particularly advantageous because they offer precise and accurate delivery of medications. For example, studies have shown that conventional needles miss the target location quite frequently. Many medications utilized for the treatment of arthritis, such as steroids and other medicaments can provide benefit to the patient only if they are injected directly into the patient's synovial fluid. Further, certain medications, such as steroids, break down connective tissue and cause other tissue damage. Therefore, when such medications or other formulations are not precisely delivered to the target intra-articular location, adverse tissue damage can occur to one or more anatomical locations of patients.

Moreover, in order to deliver a second medication, other fluid and/or other material to the same anatomical location, physicians or other medical personnel require multiple needle penetrations or leave the needle within the targeted intra-articular space, while unhooking the tubing or other conduit which is in fluid communication with the needle. Forceps or other tools are often used to disconnect and/or connect the tubing or other conduits to the needle in order to deliver a different medication or fluid to the patient. This can complicate the process for the physician or other person performing the procedure and breaks the sterile fluid path, thereby increasing the chance for infection. In addition, the process can prove to be uncomfortable and painful to the patient. Thus, several embodiments of the present inventions are directed to the delivery of two or more fluids or other medications to a patient with single needle penetration and/or without the use of tools to disconnect and/or connect the tubing or other conduits to the needle.

According to certain embodiments, a handpiece assembly for simultaneous or sequential delivery of multiple fluids into a joint comprises a core, a clip, a disposable tip, a needle, a first lumen and a second lumen. In any of the arrangements disclosed herein, a handpiece assembly can be configured to deliver medications, pharmaceutical compositions, drugs, cells, liquid and non-liquid fluids and flowable materials, nanoparticles, cement, microbeads and/or the like. In one embodiment, the handpiece assembly is configured to simultaneously or sequentially deliver an anesthetic and a steroid for treating a joint. In one embodiment, the core comprises at least one button, dial, knob, switch, rollerball, rollerwheel and/or other controller configured to control a rate of flow of at least one of a first fluid and a second fluid. In some configurations, the first fluid is adapted to flow through the first lumen and the second fluid is configured to flow through the second lumen. In other arrangements, the handpiece assembly can include three or more lumens for delivering three or more different fluids and/or other materials to a joint or other anatomical location. The controller can be configured to control whether the first and second fluids are delivered simultaneously or sequentially through the handpiece assembly and/or other components or portions (e.g., a tip, needle, etc.). In any of the embodiments described herein, two, three, four or more controllers are used.

In some arrangements, simultaneous delivery of said fluids is performed by combining the first and second fluids in the handpiece assembly. In one embodiment, the core of the handpiece assembly is in data communication with a fluid delivery module. In other configurations, the first and second lumens are adapted to direct said fluids from a fluid delivery module, through the clip, through the disposable tip and to the needle. In another embodiment, each of the lumens comprises a valve to prevent backflow of said fluids toward the fluid delivery module. The needle can be configured to be removably attached to the disposable tip and the disposable tip can be configured to be removably attached to the clip. In some embodiments, the needle is configured to be positioned within a joint to selectively deliver at least one said first fluid or said second fluid to said joint.

According to other arrangements, the first and second fluids are configured to be combined within the clip under a simultaneous delivery scheme. In one embodiment, the first and second fluids are configured to be combined at or near an interface between the clip and the disposable tip under a simultaneous delivery scheme. In another embodiment, the first and second fluids are configured to be combined at a distal end of the clip, near an interface between the clip and the disposable tip under a simultaneous delivery scheme. According to other arrangements, the first and second fluids are maintained separate until immediately upstream of the disposable tip. In some configurations, the handpiece assembly comprises one or more buttons and/or other controllers. In any of the embodiments disclosed herein, a handpiece assembly can include any type of controller, such as, multi-mode buttons, multi-depth buttons, rheostats, dials, knobs, switches, rollerballs, rollerwheels and/or combinations thereof.

According to certain arrangements, the one or more buttons and/or other controllers of the handpiece assembly are configured to control the rate of flow of at least one of the first fluid and the second fluid between a no flow condition, a first flowrate condition and at least a second flowrate condition. In any of the embodiments disclosed herein, the buttons and/or other controllers are configured to have additional modes and or functions. In addition, in some arrangements, the buttons and/or other controllers are configured to control or otherwise regulate the flow of one, two, three or more different fluid and/or other material streams through a handpiece assembly.

In certain embodiments, the handpiece assembly further comprises a third lumen, such that a third fluid is configured to be selectively conveyed therethrough. In one arrangement, the one or more buttons and/or other controllers are configured to control a rate of flow of the first fluid, the second fluid and/or the third fluid. The fluids being conveyed through the handpiece assembly can be configured to flow from the fluid delivery module to the needle either sequentially or simultaneously. For example, in one embodiment, two or more of the various fluid and/or other material streams can be delivered simultaneously through the handpiece assembly and the downstream needle.

According to certain arrangements, the core of the handpiece assembly includes a first controller configured to control the rate of flow of the first fluid, a second controller configured to control the rate of flow of the second fluid and a third controller configured to control the rate of flow of the third fluid. In any of the embodiments described herein, the buttons or other controllers on the core or other portions of the handpiece assembly can be used to control one or more other properties or aspects of the injection procedure. For example, in one embodiment, the buttons and/or other controllers control an ultrasound or other imaging device, regulate the sequence of delivery and/or the like. In another embodiment, at least one function of the imaging device or system is configured to be selectively controlled by an imaging controller and/or another portion or component of the handpiece. In some arrangements, the imaging controller of the handpiece comprises a button, dial, switch, knob, rollerball, rollerwheel and/or the like.

In some embodiments, a handpiece device for use in an anatomical injection system comprises an outer housing enclosing a handpiece interior. The outer housing of the handpiece device or assembly can be configured to be grasped and manipulated by a user. In some arrangements, the handpiece device additionally includes a first and second conduit routed through the handpiece interior. In other arrangements, more or fewer conduits may be routed through the handpiece. According to one embodiment, the handpiece device further comprises a disposable tip having a first end and a second end, with the first end being adapted to removably receive a needle and the second end configured to secure to the outer housing.

In one embodiment, the first conduit is configured to place the needle in fluid communication with a first reservoir of a fluid delivery module and the second conduit is configured to place the needle in fluid communication with a second reservoir of the fluid delivery module. In alternative embodiments, additional conduits can place the needle in fluid communication with additional reservoirs of the fluid delivery module. In certain embodiments, the handpiece device includes at least one button or other controller positioned along the outer housing. Such a button or other controller can be adapted to selectively regulate a flow of fluids through at least one of the first conduit, the second conduit and/or any additional conduits that may be present. In some configurations, the handpiece device is adapted to deliver fluids and/or other materials through the first and second conduits to the needle simultaneously or sequentially. In one embodiment, each of the conduits comprises a check valve, a duckbill valve and/or any other type of valve to prevent fluid backflow toward the fluid delivery module. The needle positioned at the distal end of the handpiece device can be positioned within a joint to selectively deliver fluids thereto.

According to other arrangements, the one or more buttons and/or other controllers are in data communication with a fluid delivery module and/or any other portion of the injection system. The handpiece can additionally include a common chamber located upstream of the needle, wherein such a common chamber is configured to receive fluids and/or other materials from the first and second conduits. In any of the embodiments disclosed herein, the handpiece can include additional conduits configured to deliver fluids and/or other materials to a common chamber or other portion or area of the handpiece. In some configurations, the common chamber is located at or near a distal end of the outer housing of the handpiece device. However, in other embodiments, the common chamber is located at or near an interface between the outer housing and the disposable tip. In certain arrangements, the controller includes one or more buttons, dials, knobs, switches, rollerballs, rollerwheels, other controller and/or any other device configured to allow a user to regulate one or more aspects of an injection procedure.

According to some embodiments, an injection system configured for simultaneous or sequential delivery of different fluids into a patient includes a fluid delivery module adapted to receive a first container and at least a second container. In some arrangements, the fluid delivery module is configured to receive three or more vials or other containers. In one embodiment, the fluid delivery module comprises a first reservoir, a second reservoir and/or additional reservoirs that are configured to be placed in fluid communication with fluids and/or other materials contained within the containers secured to the fluid delivery module. In certain embodiments, the injection additionally includes a handpiece comprising a core, a clip, a disposable tip, a needle positioned at a distal end of said disposable tip, a first conduit and at least a second conduit. In some arrangements, the core comprises one or more buttons and/or other controllers configured to control a rate of flow of fluids through the first conduit and/or the second conduit. Such buttons and/or other controllers can be configured to control the flow of fluids through additional conduits that may be included in a handpiece assembly. In other embodiments, the buttons and/or other controllers can regulate one or more other aspects of the injection system and/or devices or systems operatively connected to the injection system, such as, an ultrasound or other imaging device. In certain arrangements, at least one function of the imaging device or system is configured to be selectively controlled by an imaging controller and/or another portion or component of the handpiece. In some arrangements, the imaging controller of the handpiece comprises a button, dial, switch, knob, rollerball, rollerwheel and/or the like.

In some arrangements, the first fluid is configured to flow through the first conduit and the second fluid is configured to flow through the second conduit. In embodiments that include more than two conduits, additional fluids and/or other materials can be configured to be conveyed through such conduits. According to some arrangements, the first and second conduits are configured to direct fluids and/or other materials from the fluid delivery module, through the clip and the disposable tip and to the needle. The one or more buttons and/or other controllers of the handpiece assembly can be configured to control whether the first, second and/or additional fluids are delivered from the fluid delivery module to the needle simultaneously or sequentially. In one embodiment, the simultaneous delivery of fluids and/or other materials is performed by combining the fluids in the handpiece. According to certain arrangements, the core is in data communication with the fluid delivery module. Further, each of the conduits can include a valve or other feature or device to help prevent backflow of the fluids from the handpiece toward the fluid delivery module. In some embodiments, the disposable tip is configured to be removably attached to the clip. In any of the embodiments described herein, the needle is configured to be positioned within a target anatomical location to selectively deliver one or more medicants, other fluids and/or other materials to a joint or other anatomical location of a patient.

In some embodiments, the controller comprises at least one button, dial, knob, switch, lever, rollerball, rollerwheel, other modulating device and/or the like. According to other arrangements, the handpiece assembly comprises a multi-function button configured to permit a user to select between a no flow condition and at least two flow conditions of varying speed. In one embodiment, such a button permits a user to selectively adjust the flowrate or any other flow property of one or more fluids and/or other materials being conveyed through the handpiece assembly. For example, the button and/or other controller can permit a user to choose between two, three or more distinct flowrates. Alternatively, the rheostat, button and/or other controller can permit a user to select between various non-distinct flowrates or other settings. In certain arrangements, the handpiece assembly includes one or more multi-depth buttons that are configured to be moved to one of two, three or more different depths. In one embodiment, each distinct or non-distinct depth corresponds to a different rate of flow for the first fluid, the second fluid and/or additional fluids and/or other materials being conveyed from the fluid delivery module to the needle. According to other embodiments, the core comprises a battery that is configured to be recharged using induction, simple charging (e.g., using a DC or AC connection), pulse charging and/or other charging methods or devices. In some arrangements, the battery of the core is configured to be inductively or otherwise recharged when the handpiece is positioned within a docking station of the fluid delivery module.

According to certain embodiments disclosed in the present application, a method of injecting two, three or more fluids into a joint or other anatomical location (e.g., organ, bone, etc.) of a patient using a handpiece assembly includes providing a handpiece assembly. In some arrangements, the handpiece assembly includes a core, a clip, a disposable tip, a needle, a first conduit and a second conduit. In other configurations, the handpiece assembly comprises three or more conduits. A first fluid or other material is configured to flow through the first conduit and a second fluid or other material is configured to flow through the second conduit. Other fluids or materials can be configured to flow through additional conduits of the handpiece assembly. In one embodiment, the core comprises at least one button or other controller adapted to control a rate of flow and/or other flow characteristics of the first fluid, second fluid and/or other fluids or materials being conveyed through the conduits of the handpiece assembly.

In certain embodiments, the core is configured to be in data and fluid communication with a fluid delivery module. The first, second and/or additional conduits are configured to convey fluids and/or other materials through the clip and the disposable tip, and to the needle. The conduits are routed through an interior of the handpiece assembly. In addition, the each conduit comprises a valve or other device to prevent backflow of fluids and/or materials flowing therethrough. In some embodiments, the needle is configured to be removably attached to the disposable tip, and the disposable tip is configured to be removably attached to the clip of the handpiece assembly. The needle is configured to be positioned within a joint or other anatomical location to selectively deliver a first fluid, a second fluid and/or additional fluids or materials to a target joint or other anatomical location.

The method additionally comprises positioning the needle into a joint or other target anatomical location of a patient, and delivering a volume of the first fluid, the second fluid and/or additional fluids or materials to the needle. In some arrangements, the one or more buttons and/or other controllers of the handpiece assembly are configured to control a rate of flow of the first fluid, second fluid and/or additional fluids or materials through the conduits. In one embodiment, the one or more controllers control whether the first and second fluids are delivered simultaneously or sequentially. In other arrangements, simultaneous delivery of fluids and/or other materials is performed by combining the first, second and/or additional fluids and/or other materials in the handpiece assembly. In some embodiments, the fluids are configured to be combined within the clip, at or near an interface between the clip and the disposable tip at a distal end of the clip, near an interface between the clip and the disposable tip and/or at any other location of the handpiece assembly. In one embodiment, the various fluids and/or other materials conveyed through the handpiece assembly are maintained separate until immediately upstream of the disposable tip.

According to certain arrangements, the controller comprises one or more buttons, dials, knobs, switches, rollerballs, rollerwheels and/or any other devices adapted to be modulated or adjusted. The buttons or other controllers are configured to regulate the rate of flow of the first fluid, the second fluid and/or any other fluids adapted to pass through the handpiece assembly. In some embodiments, such buttons or other controllers can permit a user to select between a no flow condition, a first flowrate condition and at least a second flowrate condition. In some arrangements, the handpiece assembly additionally includes a third conduit configured to convey a third fluid and/or other material therethrough. The buttons and/or other controllers can be configured to control a rate of flow of the first fluid, second fluid, third fluid and/or additional fluids or other materials. In one embodiment, the fluids are configured to sequentially or simultaneously flow through the clip and the disposable tip of the handpiece assembly to the needle. In other embodiments, the core comprises a first button or controller configured to control a rate of flow of the first fluid, a second button or controller configured to control a rate of flow of the second fluid and a third button or controller configured to control a rate of flow of the third fluid. Additional buttons or other controllers can be provided to regulate the flow of additional fluid or other material streams through the handpiece assembly. According to some configurations, the method additionally comprises monitoring a position of a distal end of the needle using an ultrasound, radio frequency, spectroscopy and/or other imaging device or system to accurately locate a target joint or other anatomical location of the patient. In some arrangements, at least one function of the imaging device or system is configured to be selectively controlled by an imaging controller and/or another portion or component of the handpiece. In some arrangements, the imaging controller of the handpiece comprises a button, dial, switch, knob, rollerball, rollerwheel and/or the like.

In certain embodiments, a method of injecting two, three or more medicaments, fluids and/or other materials into an anatomy using a handpiece assembly includes providing a handpiece assembly that comprises a main body and needle removably positioned at a distal end of the main body. The handpiece assembly includes a first conduit and at least a second conduit that are positioned within an interior of the main body. In any of the embodiments described herein, the method can include the injection of three or more medicaments, fluids and/or other materials. A first fluid or other material is configured to flow through a first conduit, and a second fluid or other material is configured to flow through the second conduit. In one embodiment, the main body comprises at least one button and/or other controller configured to regulate a rate of flow of the first fluid, the second fluid and/or additional fluids or materials through the various conduits of the handpiece assembly. The handpiece assembly is configured to be in data and fluid communication with a fluid delivery module. In certain arrangements, the first and second conduits are configured to convey fluids and/or other materials to the needle. Each of the conduits can include a valve and/or other retrograde flow devices to prevent backflow of the fluids and/or other materials toward a proximal end of the main body. According to some embodiments, the needle is configured to be positioned within a target anatomical location to selectively deliver a volume of the first fluid, the second fluid and/or additional fluids or materials to a target anatomical location. The method further comprises positioning the needle into an anatomy and delivering a volume of the first fluid, the second fluid and/or additional fluids or materials through the conduits to the needle. In some embodiments, positioning the needle into an anatomy comprises using an ultrasound, radio frequency, spectroscopy and/or other imaging device or system to accurately locate the target anatomical location. The one or more buttons and/or other controllers are configured to control a rate of flow of the first fluid, the second fluid and/or additional fluid or other material streams conveyed through the conduits of the handpiece assembly. Simultaneous delivery of the various fluids and/or other materials can be performed by combining such fluids in the handpiece assembly.

According to certain embodiments, under a simultaneous delivery scheme, the first, second and/or other fluids are configured to be combined within the main body, at a distal end of the main body, immediately upstream of a proximal end of the needle and/or at any other location. In other arrangements, different fluid and/or other material streams are maintained separate until immediately upstream of the needle. In other arrangements, the controller includes one or more push buttons, dials, knobs, switches, rollerballs, rollerwheels, rheostats and/or the like. In one embodiment, a button or other controller is configured to control the rate of flow of one or more various fluid streams passing through the conduits of the handpiece between a no flow condition, a first flowrate condition and at least a second flowrate condition. The buttons or other controllers can be configured to provide additional flowrate settings.

In certain embodiments, a method of injecting two or more different medicants or other materials contained in nonspecific fluid containers into a patient using a single needle penetration comprises providing an injection system. The injection system includes a fluid delivery module and a handpiece assembly. According to one embodiment, the fluid delivery module comprises a first loading area configured to receive a first container and a second loading area configured to receive a second container. A fluid delivery module can include additional loading areas to receive additional containers. In some configurations, the first container comprises a first medicament and the second container comprises a second medicament. In certain embodiments, the loading areas are configured to securely receive vials or other containers of various types, sizes and shapes. In one embodiment, such containers comprise standard or non-standard vials. In another embodiment, the vials are supplied to a clinician or other user of an injection system by a manufacturer or supplier of such medicaments, fluids and/or other materials.

According to certain arrangements, the injection system is configured to receive instructions for delivering the first, second and/or additional medicaments. The medicaments can include medications, pharmaceutical compositions, drugs, cells, liquid and non-liquid fluids and flowable materials, nanoparticles, cement, microbeads and/or the like. In one embodiment, the injection system is configured to simultaneously or sequentially deliver an anesthetic and a steroid for treating a joint. In one embodiment, the fluid delivery module is configured to transfer at least a portion of the first medicament from the first container to a first reservoir of the fluid delivery module and at least a portion of the second medicament from the second container to a second reservoir of the fluid delivery module.

In certain arrangements, the handpiece assembly is configured to receive a needle. The handpiece assembly is adapted to selectively be in fluid communication with the first, second and/or additional reservoirs of the fluid delivery module. In one embodiment, the handpiece assembly is maneuverable to position the needle within the patient. In another arrangement, based at least in part on instructions entered by a user, the injection system is configured to combine the first, second and/or additional medicaments or other materials prior to their delivery to the patient. In an alternative embodiment, the injection system is configured to administer the first, second and/or additional medicaments and/or other materials sequentially. The method further comprises delivering a volume of the first medicament from the fluid delivery module to the patient through the needle of the handpiece assembly based at least in part on instructions provided to the injection system, and delivering a volume of the second medicament from the fluid delivery module to the patient through the needle of the handpiece assembly based at least in part on instructions provided to the injection system. In other embodiments, additional medicaments and/or other materials are selectively delivered from the fluid delivery module to the patient through the needle of the handpiece assembly.

In certain arrangements, the handpiece assembly comprises at least one button and/or other controller configured to receive instructions for delivery of the first, second and/or additional medicaments and/or other materials. In one embodiment, the fluid delivery module is configured to transfer a predetermined volume of the first medicament and the second medicament to the patient. In another arrangement, the fluid delivery module comprises a motor to facilitate the delivery of the various medicaments and/or other materials to the patient. According to some embodiments, the first medicament comprises an anesthetic and the second medicament comprises a steroid.

In another configuration, the fluid delivery module further comprises a third loading area adapted to receive a third container comprising a third medicament or other material. The injection system is configured to receive instructions for simultaneously or sequentially delivering the first, second and third medicaments through the handpiece assembly to a patient. In certain embodiments, the first, second, third and/or additional medicaments are delivered either simultaneously or sequentially to a joint or other target anatomical location of a patient. In one embodiment, the fluid delivery module comprises a display configured to provide status information about an injection procedure, such as, the volume of the first or second medicaments delivered through the handpiece assembly or remaining in the first and second reservoirs of the fluid delivery module. In some arrangements, one or more of the containers secured to the loading areas of the fluid delivery module are original manufacturer's vials. In another embodiment, the needle is secured to a removable tip of the handpiece assembly. The method can additionally include monitoring a position of a distal end of the needle using an ultrasound, radio frequency, spectroscopy and/or other imaging device or system to accurately locate a target anatomical location (e.g., joint, organ, etc.). In any of the embodiments disclosed herein, the imaging device or system can be configured to cooperate with the injection system. In some embodiments, the imaging device or system is in data communication with the handpiece assembly, the fluid delivery module and/or another portion of the injection system. In some embodiments, one or more buttons or other controllers of the handpiece assembly are configured to control one or more aspects of the imaging device or system (e.g., capturing an image, zoom, etc.).

According to certain embodiments, a method of treating a joint of a patient by selectively delivering at least two different fluids through a single needle penetration includes providing an injection system. The injection system comprises a fluid delivery module and a handpiece assembly. In one embodiment, the handpiece assembly comprises a disposable tip with a needle positioned at a distal end of the tip. In certain arrangements, the handpiece assembly comprises one or more buttons or other controllers configured to be operated while a user grasps the handpiece assembly. In some embodiments, a user can handle, manipulate and/or otherwise operate one or more of these buttons or other controllers without having to let go of the handpiece assembly. In certain configurations, the fluid delivery module comprises a first loading area adapted to receive a first container and a second loading area adapted to receive a second container. The first container comprises a first fluid, and the second container comprises a second fluid. A fluid delivery module can include additional loading areas for securing additional containers thereto. In some arrangements, the first fluid or other material is configured to be selectively placed in fluid communication with a first reservoir of the fluid delivery module and a first conduit of the handpiece assembly after the first container is secured to the first loading area. In addition, the second fluid or other material is configured to be selectively placed in fluid communication with a second reservoir of the fluid delivery module and a second conduit of the handpiece assembly after the second container is secured to the second loading area. In one embodiment, the first and second conduits are routed through an interior of the handpiece assembly.

In any of the arrangements disclosed herein, the first loading area and second loading area are configured to securely receive vials or other containers of various types, designs, sizes and shapes. In some embodiments, such containers comprise medications, pharmaceutical compositions, drugs, cells, liquid and non-liquid fluids and flowable materials, nanoparticles, cement, microbeads and/or the like. In one embodiment, the first fluid comprises an anesthetic and the second fluid comprises a steroid. In some embodiments, such containers comprise standard or non-standard vials. In one embodiment, the vials are supplied, either directly or indirectly, to a clinician or other user of an injection system by a manufacturer or supplier of such medicaments, fluids and/or other materials. The injection system is configured to receive instructions for delivering the first, second and/or additional fluids or other materials to the needle of the handpiece assembly. In one arrangement, the fluid delivery module is configured to simultaneously or sequentially transfer a volume of the first fluid, the second fluid and/or additional fluids or materials to the needle through the first, second and/or additional conduits. In one embodiment, the handpiece assembly is configured to be in data communication with the fluid delivery module of the injection system. The handpiece assembly is maneuverable to position the needle within the patient.

According to some arrangements, under a simultaneous injection mode, the first, second and/or additional fluids or materials are combined within the handpiece assembly at a location upstream of the needle. The method additionally comprises delivering a volume of the first fluid from the fluid delivery module to the patient through the needle and through the first conduit based at least in part on instructions provided to one or more of the buttons and/or other controllers of the handpiece assembly. In some embodiments, the method comprises delivering a volume of the second fluid from the fluid delivery module to the patient through the needle and through the second conduit based at least in part on instructions provided to one or more of the buttons and/or other controllers of the handpiece assembly. In one embodiment, the controller comprises at least one button, knob, dial, switch, lever, rheostat, rollerball, rollerwheel and/or the like. In some embodiments, each of the conduits comprises a valve or other device to prevent backflow of fluids and/or other materials toward the fluid delivery module. In some arrangements, the method additionally includes monitoring a position of the distal end of the needle using an ultrasound, radio frequency, spectroscopy and/or other imaging device or system to accurately locate a joint or other target anatomical area of the patient.

In accordance with other embodiments disclosed in the present application, a system for injecting two, three or more different medicaments into a patient through a single needle penetration using nonspecific fluid containers includes a fluid delivery module and a handpiece. The fluid delivery module comprises a first loading area configured to secure a first fluid container and a second loading area configured to secure a second fluid container. In some embodiments, the first fluid container comprises a first medicament and/or other fluid or material, and the second fluid container comprises a second medicament and/or other fluid or material. The first loading area and the second loading area are configured to securely receive containers of various types, sizes and shapes. In some embodiments, such containers comprise standard or non-standard vials, ampoules and/or the like. In one embodiment, the vials are supplied to a clinician or other user of an injection system by a manufacturer or supplier of such medicaments, fluids and/or other materials.

In one embodiment, a disposable needle is configured to removably attach to a distal end of said handpiece. The needle is configured to be positioned within or near a joint or another portion of a patient's anatomy. In certain configurations, the fluid delivery module is adapted to receive instructions for delivering the first and second medicaments and/or other materials to the needle through an interior portion of the handpiece. In any of the embodiments disclosed herein, the fluid delivery module may be adapted to receive and subsequently deliver through the handpiece additional medicaments and/or other fluids. In some arrangements, first and second reservoirs are positioned within an interior of the fluid delivery module. The fluid delivery module can be configured to transfer at least a portion of the first medicament from the first fluid container to the first reservoir, and at least a portion of the second medicament from the second fluid container to the second reservoir. According to some arrangements, a first conduit is configured to selectively place the handpiece in fluid communication with the first reservoir of the fluid delivery module and a second conduit is configured to selectively place the handpiece in fluid communication with the second reservoir of the fluid delivery module. The injection system can include additional conduits for placing the handpiece in fluid communication with additional reservoirs of the fluid delivery module. In one embodiment, the first and second conduits are positioned within an interior portion of said handpiece. In certain embodiments, the fluid delivery module is configured to combine the first and second fluids prior to delivery to the patient. Alternatively, the fluid delivery module can be configured to administer the first and second fluids sequentially, depending on the instructions received by the fluid delivery module, the handpiece and/or any other component or portion of the injection system. In one arrangement, each of the conduits comprises a valve to prevent backflow of fluids toward the fluid delivery module.

According to other embodiments, the handpiece comprises at least one button or other controller configured to receive at least one instruction related to an injection procedure. In some configurations, the controller comprises at least one button, dial, knob, rheostat, rollerball, rollerwheel, switch and/or the like. In another arrangement, the fluid delivery module comprises a motor to facilitate delivery of the first, second and/or additional fluids and/or other materials from the reservoirs to the conduits and needle. In one embodiment, the fluid delivery module additionally comprises a display configured to receive at least one instruction related to an injection procedure and/or configured to provide status information regarding a particular injection procedure. In some embodiments, the first, second and/or additional fluids are delivered either simultaneously or sequentially to a joint or other anatomical location of a patient. In certain configurations, the status information provided by the display of the fluid delivery module comprises the volume of the first or second fluids already delivered through the handpiece assembly or remaining in the first and second reservoirs of the fluid delivery module. In other arrangements, at least one of the first fluid container and the second fluid container is a nonspecific fluid container. In one embodiment, the first and/or second fluid container comprises an original manufacturer's vial (e.g., having a capacity of 5 ml, 10 ml, 50 ml, 100 ml, less than 5 ml, greater than 100 ml, ranges between these values and/or the like). In one embodiment, the fluid delivery module is in data communication with an ultrasound, radio frequency, spectroscopy and/or other imaging device or system configured to locate a targeted joint or other anatomical location within the patient.

According to certain embodiments, a system for injecting two or more different fluids into a patient using a single needle penetration includes a fluid delivery module having a base and a disposable portion. The disposable portion comprises a first loading area and at least a second loading area, such that each of the loading areas is configured to securely receive a container thereon. The system further comprises a first reservoir configured to be placed in fluid communication with an interior of a first container securely positioned within the first loading area, and a second reservoir configured to be placed in fluid communication with an interior of a second container securely positioned with the second loading area. In other embodiments, the system comprises additional loading areas and corresponding reservoirs to accommodate additional fluids and/or other materials. In some embodiments, the first reservoir comprises a first outlet, and the second reservoir comprises a second outlet. The base of the fluid delivery module comprises a fluid transfer device adapted to selectively transfer fluids from the first reservoir to the first outlet and from the second reservoir to the second outlet. In one embodiment, the disposable portion is configured to be removably positioned within a recess of the base.

The injection system additionally includes a handpiece assembly comprising a handle portion configured to be grasped and manipulated by a user and a tip having at least one internal passage. The handle portion includes an interior and a chamber. The tip additionally includes a proximal end and a distal end. In one embodiment, the proximal end of the tip is secured to the handle portion. In another arrangement, the internal passage is in fluid communication with the chamber when the tip is secured to the handle portion. The injection system further comprises a needle extending from the distal end of the tip. According to certain configurations, the needle is adapted to be positioned within an anatomy of a patient. In one embodiment, the system further includes a first conduit placing the first outlet in fluid communication with the chamber of the handpiece assembly, and a second conduit placing the second outlet in fluid communication with the chamber. In certain arrangements, the handpiece assembly comprises at least one controller configured to at least partially control the delivery of fluids from at least one of the first and second reservoirs through the chamber and to the needle. In some arrangements, fluids and/or other materials conveyed within the first and second conduits are maintained separate upstream of the chamber. In some embodiments, each of the conduits comprises a valve to prevent backflow of said fluids toward the fluid delivery module.

In certain arrangements, the chamber is located at or near an interface between the handle portion and the tip of the handpiece assembly, upstream of an interface between the handle portion and the tip of the handpiece assembly or at any other location. In another embodiment, one or more of the loading areas are configured to receive a nonspecific container. The nonspecific container can include a vial as originally supplied by a drug manufacturer. In one embodiment, the controller comprises at least one button, dial, knob, switch, rheostat, lever, rollerball, rollerwheel and/or the like positioned along an exterior surface of the handle portion of the handpiece assembly. In one embodiment, the button comprises a multi-mode and/or multi-depth button that permits a user to vary a flowrate and/or other flow characteristic of the fluids through the handpiece assembly based on the depth or other position of the button. In another arrangement, the injection system is operatively connected to an ultrasound, radio frequency, spectroscopy and/or other imaging device or system configured to assist a user in advancing the needle to a desired anatomical position within the patient. In any of the embodiments described or otherwise disclosed herein, one or more of the loading areas is adapted to continuously or intermittently rotate a fluid container positioned thereon in order to mix the contents of a vial or other container positioned within the loading area.

According to certain embodiments disclosed in the present application, a method of injecting a plurality of fluids into multiple patients using nonspecific fluid containers includes providing an injection system. The injection system includes a fluid delivery module and a handpiece. The handpiece comprises a clip, a disposable tip, a reusable core and at least one button or other controller. In addition, the fluid delivery module comprises a first loading area configured to secure a first container, and a second loading area configured to secure a second container. In some embodiments, a fluid delivery module can comprise three or more loading areas to receive additional containers. In some embodiments, the loading areas are configured to securely receive vials or other containers of various types, designs, shapes and/or sizes. In some arrangements, the fluid delivery module is configured to receive instructions for delivering the first, second and/or additional fluids or materials for a first patient. Further, the fluid delivery module is configured to receive instructions for delivering the first, second and/or additional fluids or materials for a second patient. In some arrangements, the instructions are modifiable between patients. According to some embodiments, the fluid delivery module is configured to transfer at least a portion of the first fluid from the first container to a first reservoir and at least a portion of the second fluid from the second container to a second reservoir. In one embodiment, the first and second reservoirs are positioned within an interior of the fluid delivery module. In certain configurations, a distal end of the disposable tip of the handpiece is adapted to receive a first disposable needle for use with a first patient and a second disposable needle for use with a second patient. In one embodiment, the tip is configured to be disposed between patients. The disposable tip can comprise a valve to prevent reverse flow of the first, second and/or additional fluids from the needle into the clip of the handpiece. In certain embodiments, the handpiece is configured to be in fluid communication with the first and second reservoirs of the fluid delivery module. In certain arrangements, the handpiece is maneuverable to position the needle within the patient. In one embodiment, the fluid delivery module and handpiece are configured to combine the first and second fluids and/or other materials prior to delivery to the patient. In an alternative embodiment, the fluid delivery module and handpiece are configured to administer the first and second fluids and/or other materials sequentially, depending on the instructions received by the fluid delivery module and/or the handpiece.

In some arrangements, the controller of the handpiece comprises at least one button, knob, dial, switch, rheostat, rollerball, rollerwheel and/or other device configured to receive instructions for controlling at least one aspect of an injection procedure. According to another embodiment, the fluid delivery module is configured to simultaneously or sequentially transfer a predetermined volume of the first fluid and the second fluid to a patient. In one arrangement, the fluid delivery module comprises a motor to facilitate the delivery of the fluids to a patient. In other arrangements, the first fluid comprises an anesthetic and the second fluid comprises a steroid. In certain configurations, the first and second fluids are delivered either simultaneously or sequentially to a joint in a patient. In another embodiment, the injection system further comprises a display adapted to provide information regarding the delivery of the first and second fluids into a patient. In some arrangements, the first and/or the second containers comprise vials as supplied by a drug manufacturer or another nonspecific container. According to other embodiments, the method further includes monitoring a position of the distal tip of the needle using an ultrasound, radio frequency, spectroscopy and/or other imaging device or system operatively connected to the injection system to accurately locate a target anatomical location of a patient.

In some embodiments, a method of locating a target anatomical location of a patient and injecting at least two different medicaments into the target anatomical location using a single needle penetration includes providing an injection system. The injection system comprises a fluid delivery module and a handpiece having at least one controller. The fluid delivery module comprises a first loading area configured to secure a first container and a second loading area configured to secure a second container. In other embodiments, a fluid delivery module includes additional loading areas configured to secure additional containers. The first container comprises a first medicament or other material and the second container comprises a second medicament or other material. In one embodiment, the handpiece is configured to be in fluid and data communication with the fluid delivery module. In other arrangements, the fluid delivery module is configured to selectively transfer a portion of the first medicament, the second medicament and/or additional medicaments or other materials to the handpiece. In one embodiment, a distal end of said handpiece is configured to receive a needle. The handpiece is maneuverable to position the needle within the patient. The method further comprises locating the needle at or near the target anatomical location using an imaging device that is in data communication with the injection system. In certain embodiments, the injection system is configured to combine the first and second medicaments prior to delivery to the patient. Alternatively, the injection system is configured to administer the first and second medicaments sequentially, depending on the instructions received by the injection system. In addition, the method comprises delivering a volume of the first medicament, the second medicament and/or additional medicaments or other materials to the patient through the needle based on instructions received by the injection system.

According to some embodiments, the fluid delivery module is configured to receive instructions for delivering the first and second medicaments using one or more buttons or other controllers positioned on the handpiece. In one embodiment, the imaging device is operatively connected to the injection system using a hardwired or a wireless connection. In another configuration, at least one function of the imaging device or system is configured to be selectively controlled by an imaging controller and/or another portion or component of the handpiece. In some arrangements, the imaging controller of the handpiece comprises a button, dial, switch, knob, rollerball, rollerwheel and/or the like. In another embodiment, the fluid delivery module comprises a motor to facilitate the delivery of the medicaments and/or other materials to the handpiece. In one embodiment, the first and second medicaments are delivered either simultaneously or sequentially through the handpiece to the patient. In another arrangement, the fluid delivery module comprises a display configured to display or otherwise provide the volume of the first and/or second medicaments already delivered to the patient or remaining within the fluid delivery module or other status information regarding the injection procedure. In one embodiment, the display comprises a touchscreen that is configured to receive instructions that help control an injection procedure. In certain embodiments, the first and/or second containers are standard or non-standard vials supplied by a manufacturer or some other nonspecific container.

According to other embodiments, a system for injecting at least two fluids into an anatomy of a patient includes a handpiece assembly having a proximal end and a distal end. The handpiece assembly comprises at least one controller and a needle extending from the distal end of the handpiece assembly. The system further includes a fluid delivery module configured to securely receive at least a first container comprising a first fluid and a second container comprising a second fluid. The fluid delivery module is configured to selectively transfer a volume of the first fluid and/or the second fluid into the patient. According to some embodiments, the system further includes a first conduit configured to convey the first fluid from the fluid delivery module to the needle and a second conduit configured to convey the second fluid from the fluid delivery module to the needle. In one embodiment, the first and second conduits are routed through an interior of the handpiece assembly. In another embodiment, the system further includes an imaging device operatively connected to the fluid delivery module, the handpiece assembly and/or any other portion of the injection system. The imaging device is configured to help a user advance the needle to a joint or another target location of the patient's anatomy. In one embodiment, the transfer of the first, second and/or additional fluids or other materials from the fluid delivery module to the needle is at least partially controlled using the at least one button or other controller of the handpiece assembly. In one embodiment, the imaging device comprises an ultrasound device.

In several embodiments, the injection systems, devices and methods described herein are configured to use nonspecific containers. As used herein, nonspecific containers shall be given its ordinary meaning and shall include, without limitation, containers that vary in size or shape, such as original vial from a drug manufacturer, formulator and/or supplier. Thus, a nonspecific container may include, without limitation, a standard or non-standard vial or other container that includes one or more medications, formulations and/or other active or non-active ingredients. The size (e.g., diameter, height, etc.), capacity, shape, material of construction, closure type and/or other details can vary between different nonspecific containers. For example, the nonspecific container used by a first drug manufacturer or supplier may comprise a relatively small or wide vial, while the nonspecific container used by a second drug manufacturer or supplier may comprise a relatively large or narrow vial.

According to one preferred embodiment, an injection system is configured to selectively deliver two or more medications, formulations and/or other fluids or substances into or near a joint of a patient (or another target anatomical location) using a single needle penetration. The injection system includes a fluid delivery module that is adapted to receive vials or other containers comprising the medicaments and/or other materials to be transferred to the patient through a needle positioned along the distal end of a downstream handpiece assembly. In some embodiments, vials or other containers comprising the desired medicaments and/or other substances to be used in a particular injection procedure are nonspecific containers that are secured to corresponding loading areas of the fluid delivery module or other portion of the system with the assistance of adapter.

According to a second preferred embodiment, the injection system comprises a handpiece assembly that includes a removable tip, needle and one or more other components or portions. Nonspecific containers (e.g., vials) containing one, two or more different medicaments and/or other substances can be secured onto a fluid delivery module and be subsequently placed in fluid communication with the handpiece assembly. The various types of medicaments and/or other substances can be administered, in sequential injection procedures, to a plurality of patients in a manner that permits the clinician or other user to selectively modify and customize the manner in which the various substances loaded onto the fluid delivery module are administered to each patient (e.g., modifying the sequence of delivery, the volume or other amount of each medication and/or other substance delivered, etc.).

Such systems, devices and methods can be adapted to allow a clinician to quickly and efficiently treat one or more joints of multiple patients. Moreover, the system permits a clinician to customize the injection protocol according to the patient being treated or as otherwise desired or required. In addition, pain and discomfort to the patient being treated is generally reduced by the various embodiments of the injection system disclosed herein. The various medicaments and/or other materials can be delivered simultaneously or according to a desired sequence. A clinician or other user can advantageously regulate the delivery of the medicaments and/or other materials into the patient using buttons or other controllers conveniently positioned on the handpiece assembly or another component of the injection system.

In some arrangements, an injection system is configured to be in data communication with and operate concurrently with an ultrasound wand and/or other imaging or intra-anatomical location systems or technologies.

According to some embodiments of the present inventions, a system for injecting two or more fluids into a targeted anatomical location includes a handpiece assembly having a proximal end and a distal end, a needle extending from the distal end of the handpiece assembly, a fluid delivery module comprising a fluid transfer device and at least two openings for inserting fluid containers and a conduit being at least partially routed through an interior of the handpiece assembly, the conduit being configured to place the fluid delivery module in fluid communication with the needle. According to some embodiments, the fluid transfer device is configured to transfer fluid from fluid containers placed within the openings of the fluid delivery module to the targeted anatomical location. In some embodiments, the targeted anatomical location comprises a bone, organ, muscle tissue, other tissue, a bodily cavity or any other portion of the anatomy. In other embodiments, the anatomical location comprises an intra-articular space (e.g., ankle, wrist, hand joint, knee, foot joint, spine joint, shoulder joint, any other joint or space, etc.), bone, muscle tissue, other tissue, an organ and/or the like.

According to other embodiments, a method for injecting at least two fluids into a targeted anatomical location comprises inserting a needle into the targeted anatomical location, the needle being in fluid communication with a handpiece assembly and a fluid delivery module, loading at least a first and second fluid into the fluid delivery module, instructing the fluid delivery module to deliver the first fluid through the handpiece assembly and the needle, instructing the fluid delivery module to deliver the second fluid through the handpiece assembly and the needle and removing the needle from the anatomical location.

In one embodiment, a method for aspirating and injecting fluids into a targeted anatomical location is provided. In one embodiment, the method comprises inserting a needle into the targeted anatomical location, the needle being in fluid communication with a handpiece assembly and a fluid delivery module, aspirating a first fluid through the handpiece assembly and the needle, loading at least a second fluid into the fluid delivery module, delivering the second fluid through the handpiece assembly and the needle, and removing the needle from the anatomical location. The first fluid can comprise one or more endogenous and/or exogenous fluids (e.g., naturally occurring fluids, such as synovial fluid, lavage fluids, serum, etc.). The second fluid can comprise one or more endogenous and/or exogenous fluids. In some embodiments, endogenous fluids include fluids that were pre-existing in the target area prior to delivery of the needle and/or a second fluid. For example, an endogenous fluid may include a diagnostic fluid, a visualization fluid, an anesthetic, or a lavage fluid such as saline, for which aspiration prior to delivery of the exogenous fluid may be desirable or any other fluid. Exogenous fluids include, but are not limited to, medications, pharmaceutical compositions, drugs, cells, liquid and non-liquid fluids and flowable materials, nanoparticles, cement, microbeads, therapeutics or diagnostic fluids, imaging fluids, lavage fluids and/or the like, and any combinations thereof. In one embodiment, the system for dual aspiration and fluid delivery comprises a single conduit for both aspiration and delivery. In another embodiment, the system comprises separate aspiration and delivery conduits.

In several embodiments, an imaging device is used to guide the insertion of the needle, the aspiration of fluid, and/or the delivery of fluid to the target. In one embodiment, the imaging device comprises an ultrasound device.

In some embodiments, a method of transferring a volume of fluid to an anatomical location comprises providing a module having an imaging component and an injection component, the injection component being configured to receive and selectively deliver a volume of fluid to a needle. The method further includes inserting the needle into an anatomy, positioning the needle in a targeted anatomical location using the imaging component and injecting a volume of fluid into the targeted anatomical location using the injection component.

BRIEF DESCRIPTION OF THE DRAWINGS

These and other features, aspects and advantages of the present application are described with reference to drawings of certain embodiments, which are intended to illustrate, but not to limit, the inventions. The drawings include one hundred sixty-three (163) figures. It is to be understood that the attached drawings are for the purpose of illustrating concepts and embodiments of the present invention and may not be to scale.

FIG. 3I illustrates an exploded perspective view of the nest or loading area of FIG. 3C configured to receive a vial or other container;

FIG. 3O illustrates a detailed bottom perspective view of the nest or loading area of FIG. 3K with the clamp hidden for clarity;

FIG. 3S illustrates a perspective view of the nest or loading area of FIG. 3K mechanically connected to a drive assembly according to one embodiment;

FIG. 14A illustrates a perspective view of three different vials and a nest or loading area of a cassette onto which the vials may be secured according to one embodiment;

FIG. 15E illustrates the vial adapter of FIG. 15A secured to the top of three different vials;

FIGS. 19A-19C illustrate various perspective views of a vial and a vial adapter comprising an identification flag according to one embodiment;

FIGS. 20A and 20B illustrate perspective views of a vial configured to maintain its internal contents mixed according to one embodiment;

FIG. 20C illustrates a side view of the vial of FIGS. 20A and 20B;

FIG. 21B illustrates an exploded perspective view of the handpiece assembly of FIG. 21A;

FIGS. 27A-27E illustrate cross-sectional views of different embodiments of multi-lumen delivery lines configured for use with an injection system;

FIG. 28A illustrates a front perspective view of a tip configured for use in a handpiece assembly according to one embodiment;

FIG. 28B illustrates a side view of the tip of FIG. 28A;

FIG. 28C illustrates a front view of the tip of FIG. 28A;

FIG. 28D illustrates a rear perspective view of the tip of FIG. 28A;

FIG. 28E illustrates a rear view of the tip of FIG. 28A;

FIG. 40 illustrates a perspective view of a handpiece assembly according to another embodiment;

FIG. 41 illustrates a perspective view of a handpiece assembly according to another embodiment;

FIG. 42 illustrates an exploded side view of a handpiece assembly according to another embodiment;

FIGS. 43A and 43B illustrate different perspective views of a handpiece assembly according to another embodiment;

FIG. 44 illustrates a schematic cross-sectional view of a tip configured to permit aspiration of fluids and/or other materials from an anatomical location according to one embodiment;

FIG. 45 illustrates a perspective view of an imaging wand connected to the fluid delivery module of an injection system according to one embodiment;

FIG. 46 illustrates a detailed perspective view of the imaging wand of FIG. 45;

FIG. 47 illustrates a perspective view of a user simultaneously manipulating both an imaging wand and a handpiece assembly of an injection system to treat a patient's foot according to one embodiment;

FIGS. 48A-48D illustrate various screenshots from the visual display of a fluid delivery module during an injection procedure according to one embodiment;

FIGS. 49A-49D illustrate various screenshots from the visual display of a fluid delivery module during an injection procedure according to another embodiment;

FIG. 50A illustrates a screenshot from the visual display of a fluid delivery module during an injection procedure according to another embodiment;

FIG. 50B illustrates a screenshot from the visual display of a fluid delivery module during an injection procedure according to another embodiment;

Figure 51:
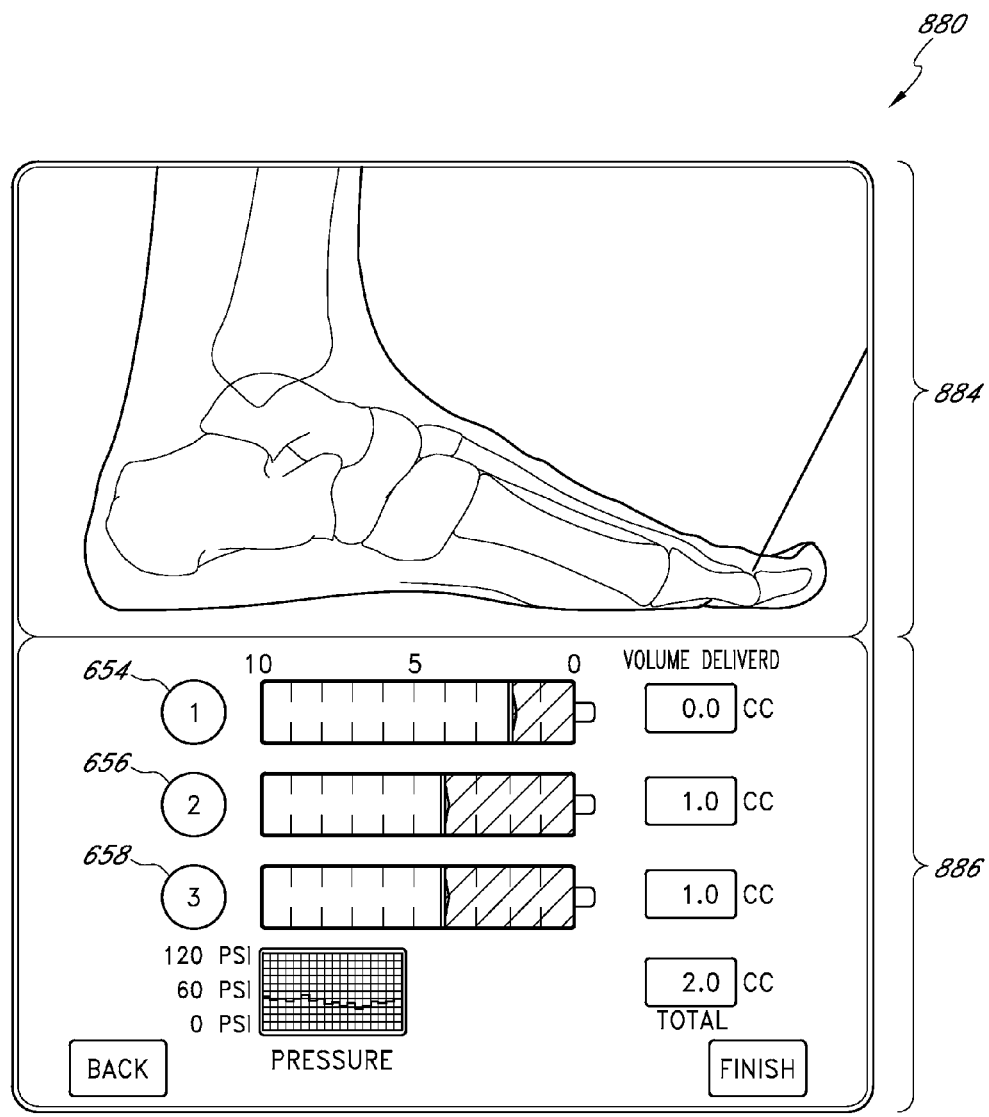
Figure 52:
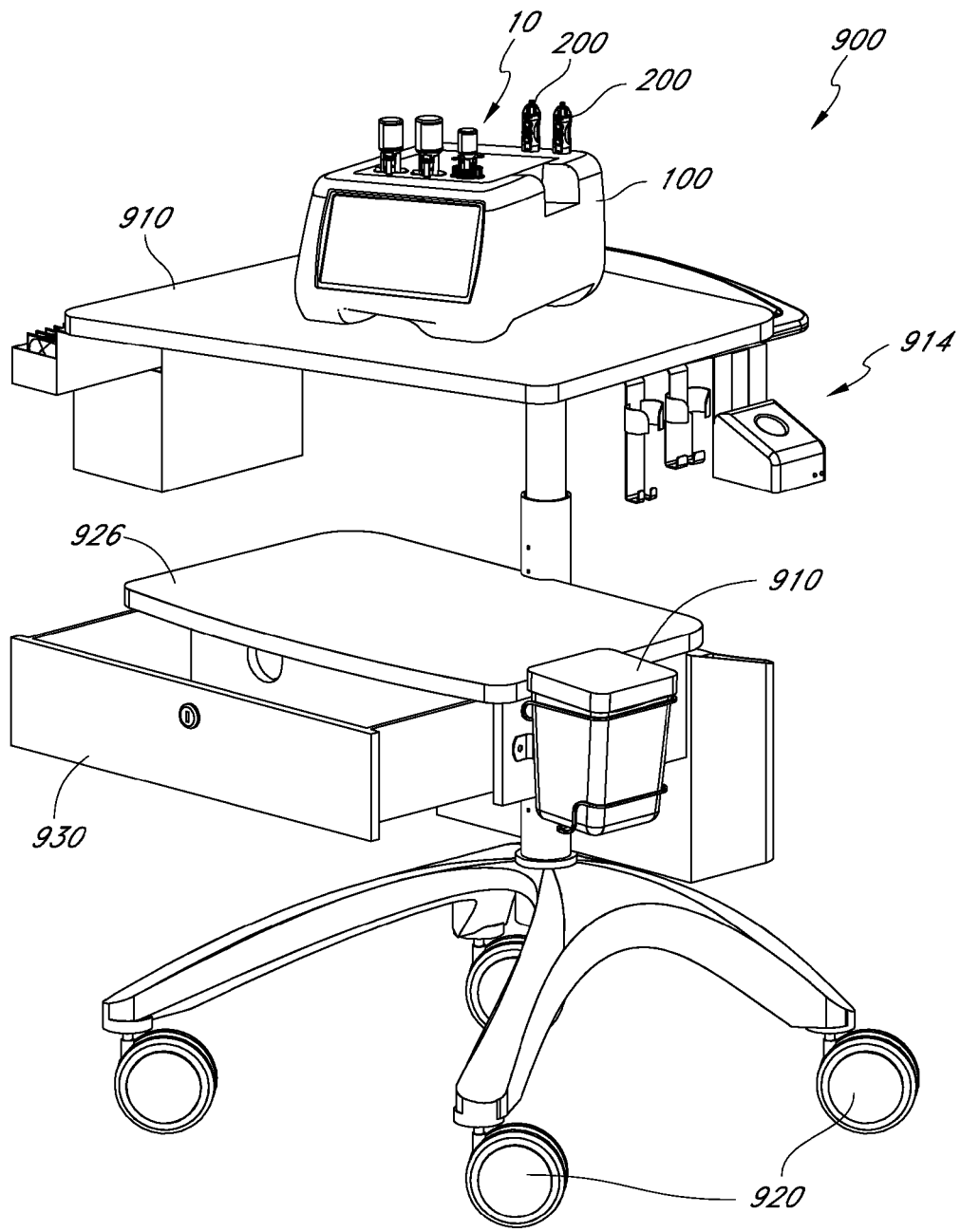
Figure 53:
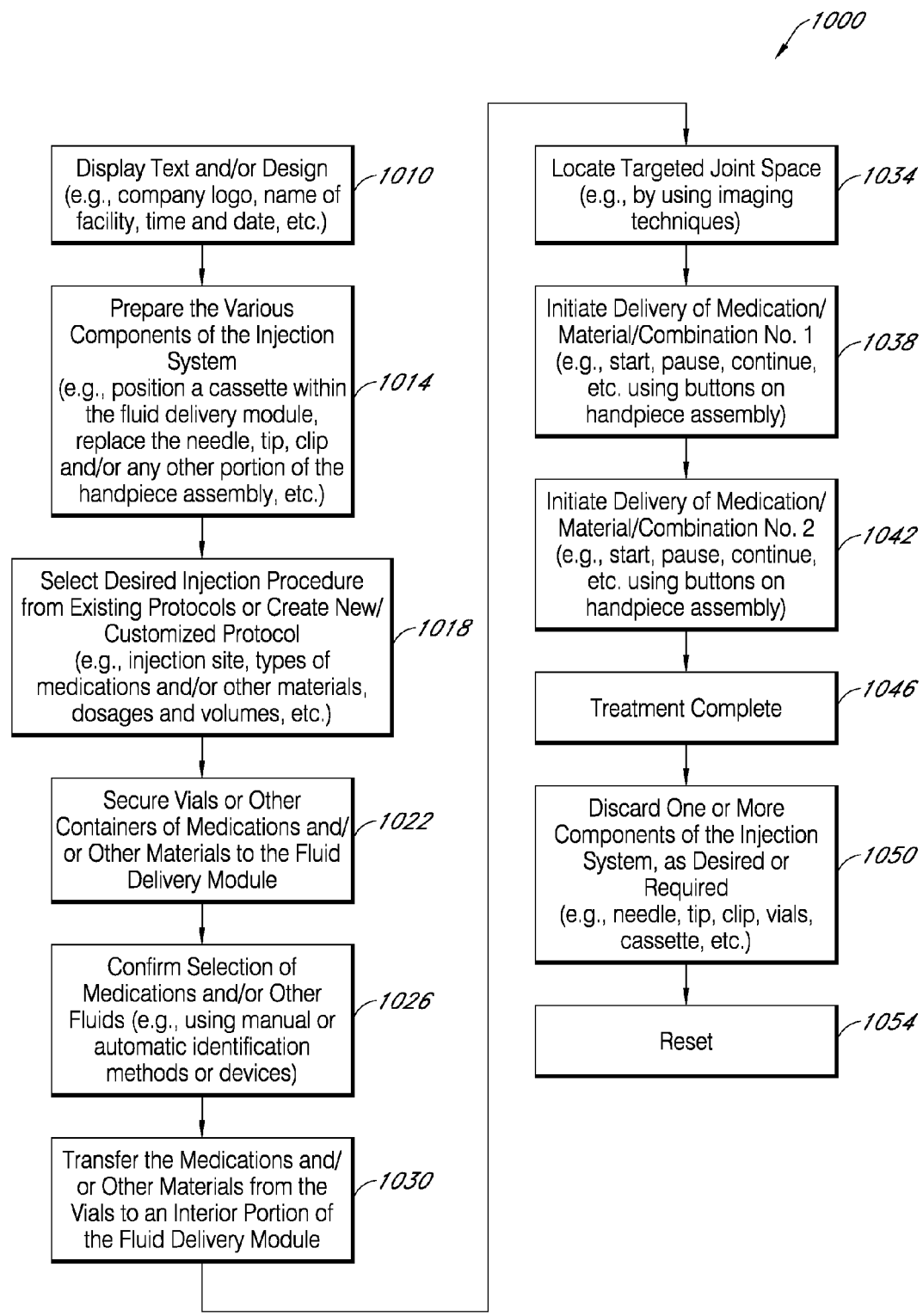
Figure 54:
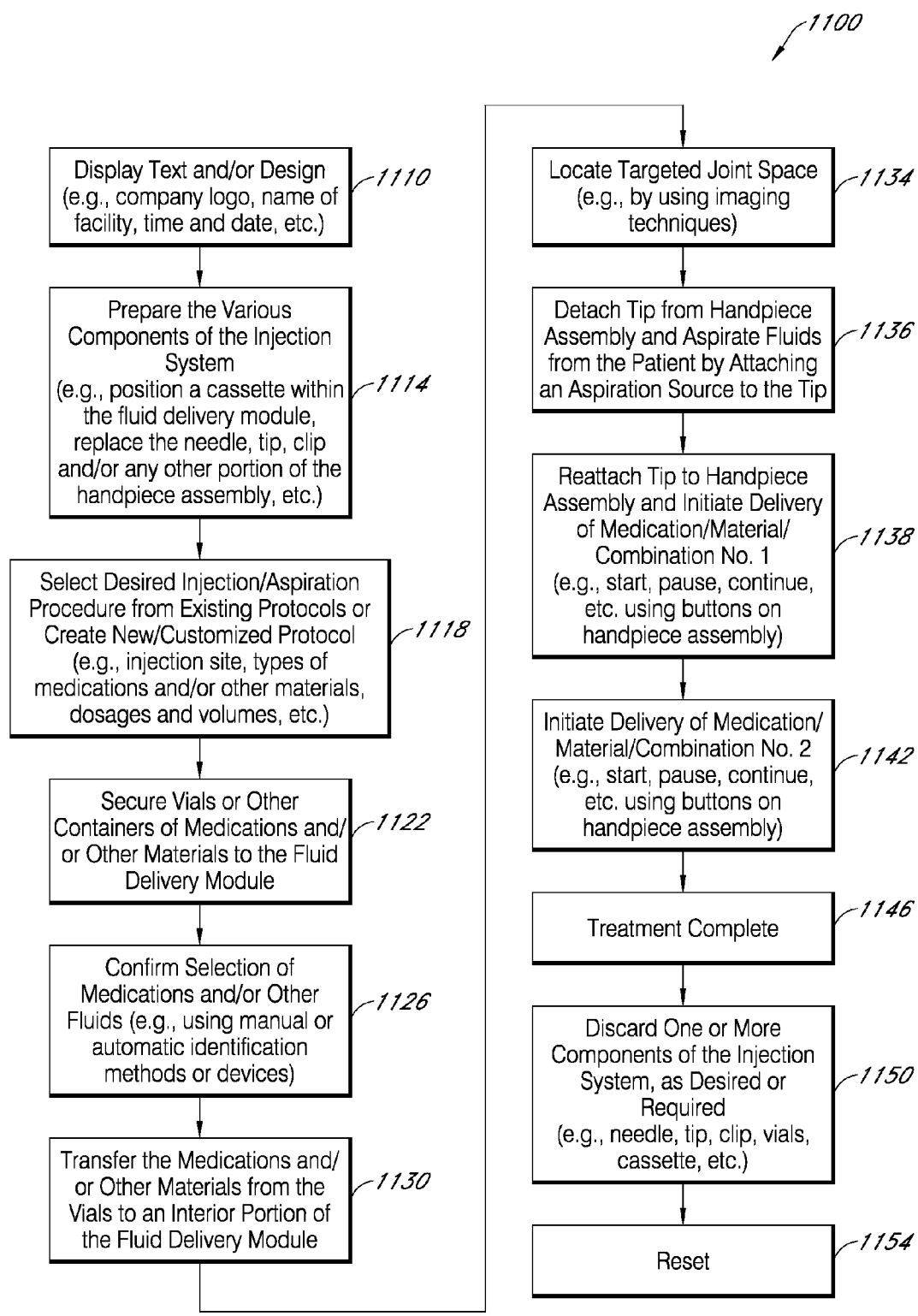

FIG. 51 a screenshot from the visual display of a fluid delivery module comprising details of both the delivery of materials and imaging during an injection procedure according to one embodiment;

FIG. 52 illustrates a perspective view of a movable cart configured to support an injection system according to one embodiment;

FIG. 53 schematically illustrates a flowchart of one embodiment of a sequence for delivering medication to an intra-articular space; and FIG. 54 schematically illustrates a flowchart of another embodiment of a sequence for delivering medication to an intra-articular space.

DETAILED DESCRIPTION OF THE PREFERRED EMBODIMENTS

The discussion and the figures illustrated and referenced herein describe various embodiments of an injection system and device, as well as methods related thereto. A number of these embodiments of the injection systems, devices and methods are particularly well suited to transfer a volume of one or more fluids to (or from) an intra-articular space, a bone, an organ or other cavity of the human anatomy (e.g., foot, ankle, toe, knee, hand, finger, etc.). Such devices, systems and methods are well-suited for treating osteoarthritis, rheumatoid arthritis, other inflammatory diseases and/or other joint diseases. However, the various devices, systems, methods and other features of the embodiments disclosed herein may be utilized or applied to other types of apparatuses, systems, procedures and/or methods, whether medically-related or not.

As discussed in greater detail herein, this application discloses devices, systems and methods of locating an intra-articular or other anatomical space and delivering and/or withdrawing fluids (e.g., medications, pharmaceutical compositions, drugs, cells, liquid and non-liquid fluids and flowable materials, nanoparticles, cement, microbeads, etc.) to/from such an intra-articular space (e.g., knee, ankle, elbow, shoulder, wrist, finger, toe, hip, facet joint, vertebra, other spinal joints or spaces, etc.). The devices, systems and methods disclosed herein, according to several embodiments, facilitate the delivery and/or aspiration of two or more different fluids and/or other materials to and/or from an intra-articular space or other anatomical location by advantageously using a single needle penetration. This can help decrease pain and discomfort to patients during the treatment of various joint or other medical disorders. Such systems, devices and methods can be especially useful for treatment of smaller joints, such as, for example, thumbs, other fingers, toes and/or the like, which are highly innervated. In addition, such devices and methods can simplify the execution of related procedures by physicians and other medical personnel. Accurately locating an intra-articular space is sometimes very difficult, especially when the targeted joints are relatively small (e.g., fingers, toes, etc.). The devices, systems and methods disclosed herein, according to several embodiments, facilitate the location of such intra-articular or other anatomical spaces.

A. General

Figure 1:
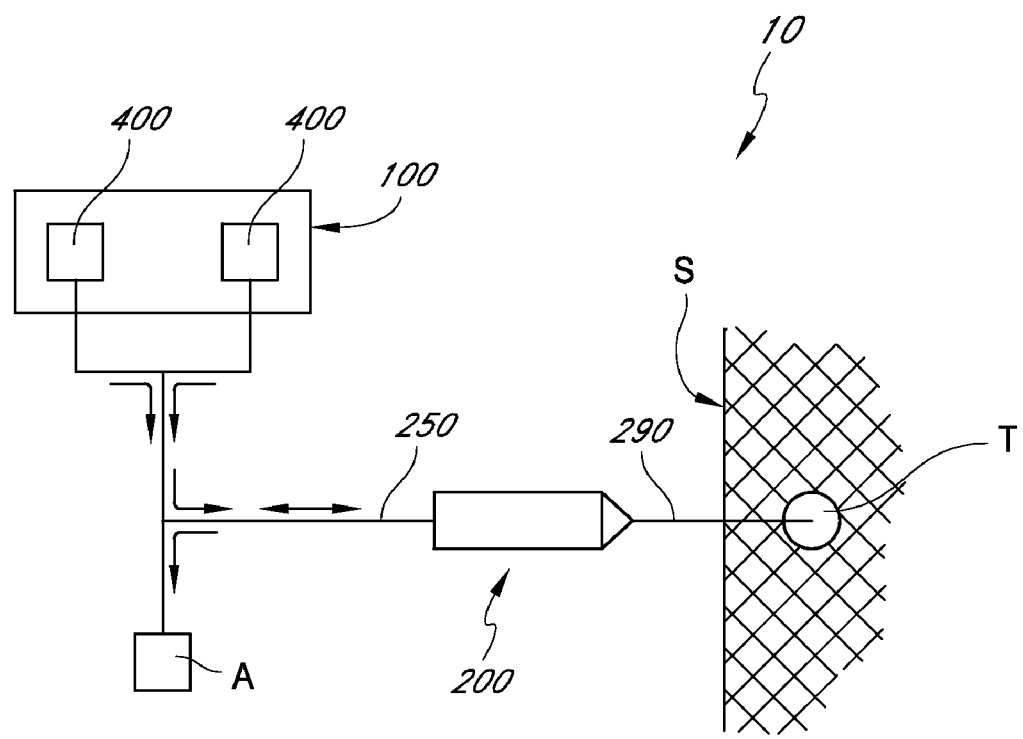
FIG. 1 illustrates a schematic of an articular injection system according to one embodiment.

FIG. 1 schematically illustrates one embodiment of an injection/aspiration system 10. As shown, the system 10 can include a handpiece 200 that comprises a needle 290 positioned along its distal end. In FIG. 1, the distal end of the needle 290 is depicted as having been positioned within a targeted area T of an articular space (e.g., within or near a joint, synovial space, etc.). In order to reach the targeted area T, the needle 32 may be routed through skin S and/or one or more other tissue layers of an anatomy. The targeted space T for treatment need not be within an articular cavity. For example, such a location may be on the outside or in the vicinity of a joint, another internal organ or location and/or the like.

In the illustrated embodiment, a delivery line 250 (e.g., multi-lumen tubing) or other some other conduit can be used to deliver one or more fluids and/or other materials to and/or from the targeted anatomical area T via the handpiece assembly 200. In some embodiments, the materials delivered to the target anatomical location include one or more medications, other formulations, other fluids or substances, such as, for example, pharmaceutical compositions, drugs, cells, liquid and non-liquid fluids and flowable materials, nanoparticles, cement, microbeads, therapeutics or diagnostic fluids, imaging fluids, lavage fluids, other endogenous or exogenous fluids or materials and/or the like. As shown, the delivery line 250, and thus, the handpiece assembly 200, can be placed in fluid communication with a fluid delivery module 100. As discussed in greater detail herein, the fluid delivery module 100 can be advantageously configured to accurately deliver one, two or more different fluids, compositions, other substances or materials and/or the like to the handpiece assembly 200. In some embodiments, as described in greater detail herein, the fluid delivery module 100 is an electromechanical software-controlled device that uses motors, pumps and/or other devices to pull fluids and/or other materials from multi-dose vials or other containers and push them through the cassette for delivery through a downstream handpiece assembly. Further, in some embodiments, the needle 290 can be placed in fluid communication with an aspiration source A in order to selectively remove fluids and/or other materials or substances from a targeted anatomical location. The terms "handpiece," "handpiece assembly" and "handpiece device" are used interchangeably herein.

According to some embodiments, the aspiration source A comprises a syringe, a pump or any other device or system that is configured to create a negative or vacuum pressure in the needle 290. As illustrated and discussed herein with reference to other arrangements, the aspiration source A can be connected to the handpiece assembly 200. Alternatively, the aspiration source A can be a separate item from the handpiece assembly 200 and/or any other component of the system 10. For example, the aspiration source A can be as simple as a disposable syringe that is configured to be placed in fluid communication with the needle 290 by removing all or a portion of the handpiece assembly 200.

With continued reference to the schematic embodiment of FIG. 1, the fluid delivery module 100 can advantageously include a pump or other fluid transfer device (e.g., syringes operated by a motor, actuator and/or other mechanical device) to transfer one or more medications, fluids and/or other substances or materials to the targeted anatomical location T (e.g., toe, knee, other intra-articular space, etc.). In some embodiments, such fluids, substances and/or materials can be included in vials 400 or other containers that may be conveniently secured to the fluid delivery module 100.

According to other embodiments, the fluid transfer device comprises a peristaltic pump, a syringe pump, a gear pump, a bladder pump, a diaphragm pump, a metering pump and/or any other type of pump. Such a fluid transfer device can be adapted to deliver solids, non-Newtonian fluids, other non-flowable materials and/or the like (e.g., cement, microbeads, etc.) to a desired anatomical location.

The general arrangement of the systems, systems and methods illustrated and discussed herein permits one or more fluids, substances or other materials to be delivered to and/or removed from an intra-articular space with a single needle penetration. Therefore, pain and/or discomfort to a patient can be advantageously reduced. This may be especially important when transferring fluids to and/or from the intra-articular space of a small joint, such as, for example, a toe, thumb, other finger and/or the like. Such small joints are typically highly innervated, making them more sensitive to pain. Further, the complexity and other difficulties associated with executing such procedures can be reduced for physicians or other clinicians. In addition, as discussed in greater detail herein, such systems (or equivalents or variations thereof) can be configured to easily and accurately deliver a desired quantity of medications and/or other fluids, substances or materials, or a combination thereof, to a desired anatomical location.

According to some embodiments, an anesthetic is initially delivered into the patient using the injection system. For example, a desired volume of Lidocaine and/or any other anesthetic can be selectively delivered within the anatomy to reduce the pain and discomfort to the patient. In some arrangements, such an anesthetic is delivered while the needle at the distal end of a handpiece assembly is advanced through the skin and other anatomical tissues and portions. Alternatively, the anesthetic can be delivered once the needle has been accurately positioned at or near the target anatomical location (e.g., joint, organ, etc.). Further, in several embodiments, the delivery of an anesthetic is followed by the delivery of a second anesthetic (e.g., a slow-acting anesthetic), a steroid (e.g., Depo-Medrol®) and/or any other material (e.g., hyaluronic acid, saline, pain-relieving medications, pharmaceutical compositions, other medications or drugs, cells, liquid and non-liquid fluids and flowable materials, nanoparticles, cement, microbeads, etc.) as desired or required. For example, a physician or other clinician may have particular injection protocols or schemes for treating certain diseases, conditions and/or patients. As discussed in greater detail herein, the various medications, formulations and/or other fluids and/or other materials can be delivered into a patient simultaneously or sequentially.

Figure 2A:
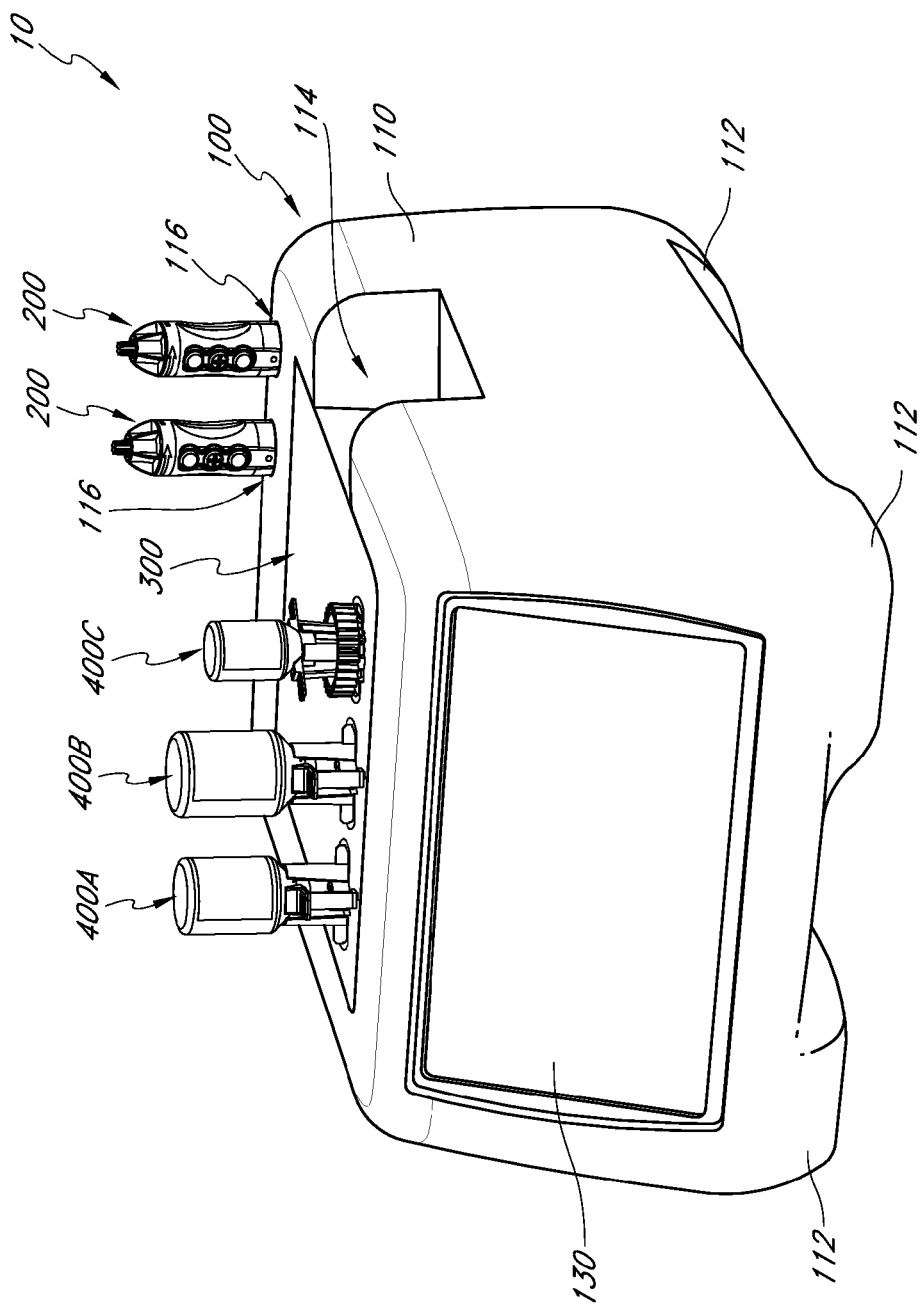
FIG. 2A illustrates a perspective view of an articular injection system according to one embodiment.

FIG. 2A illustrates one embodiment of an injection system 10 configured to deliver one or more medications, formulations and/or other fluids or materials to a joint or other target location within the anatomy. As shown, the system 10 can include a fluid delivery module 100, one or more handpiece assemblies 200 and a cassette 300 or cartridge, which in some arrangements, is configured to be removably secured to the fluid delivery module 100. As discussed in greater detail herein, the intra-articular delivery system 10 can be configured so that one or more vials 400A, 400B, 400C or other containers comprising medications and/or other fluids, substances or materials can be easily loaded onto the cassette 300 or other portion of the fluid delivery module 100. In some embodiments, a cassette or other portion of the fluid delivery module is configured to receive off-the-shelf medication and/or fluid packages in multi-dose vials. Further, in certain arrangements, a cassette or other portion of the fluid delivery module is configured to receive one or more non-specific fluid containers.

Such medications, fluids, materials and/or substances can be accurately and conveniently administered to a targeted anatomical location (e.g., a joint), through a needle (not shown) located at the distal end of the handpiece assembly 200. As discussed in greater detail herein (see FIGS. 21A-44), the handpiece assembly 200 can be adapted to be in fluid communication with the fluids and/or other materials contained within the vials 400A, 400B, 400C or other containers. In addition, in some arrangements, the system 10 may be used to selectively aspirate fluids and/or other substances from an intra-articular space or other portion of the anatomy, either in lieu of or in addition to delivering one or more fluids and/or other substances within the anatomy.

The needle positioned at the distal end of the handpiece assembly can be advantageously configured to be delivered through the skin and other tissues of a patient so as to adequately reach the targeted joint (e.g., toe, ankle, knee, spine, hand, finger, neck, etc.) or other anatomical location (e.g., organ). In several embodiments, the needle has a gauge of 18 G-30 G and a length of about 0.5 to 5.0 inches (e.g., 1.0 to 1.5 inches). In other arrangements, the gauge, length and/or other details of the needle can be greater or smaller than the range indicated herein, as desired or required by a particular application. Further, the needle can comprise surgical-grade stainless steel and/or any other suitable materials (e.g., other metals, alloys, etc.).

B. Fluid Delivery Module

With continued reference to FIG. 2A, the intra-articular delivery system 10 can include a display 130 along one or more of its outer surfaces. As discussed in greater detail herein, the display 130 can provide various data and other information to the user. In some embodiments, the fluid delivery module 100 comprises a data input device (e.g., keyboard, keypad, dials, buttons, etc.) to permit a user to enter data and/or other information regarding a particular procedure. For example, in one arrangement, the display 130 comprises a touchscreen configured to both provide information to and receive information from a user.

As shown in FIG. 2A, the fluid delivery module 100 can include one or more charging receptacles 116 or other docking stations, each of which may be sized, shaped and otherwise configured to receive a handpiece assembly 200. In some embodiments, a docking station 116 is adapted to recharge one or more batteries of the handpiece assembly 200. For example, as discussed in greater detail herein, such a station can be configured to inductively or otherwise recharge a core portion of a handpiece assembly 200 when the handpiece assembly 200 is not in use.

In addition, the fluid delivery module 100 can include one or more other components or features to enhance the function, aesthetic appearance and/or other aspect of the system 10. For example, in FIG. 2A, the fluid delivery module 100 comprises a recess or groove 114 along its upper end that facilitates positioning the cassette 300 into and/or out of the top of the module 100. The quantity, location, shape, size and/or details of such recesses or grooves 114 can be different than depicted in FIG. 2A. Moreover, an intra-articular injection system 10 can include one or more other components or features, as desired or required by a particular application.

As shown in the embodiment of FIG. 2A, the housing 110 or outer chassis of the fluid delivery module 100 can include generally rounded corners. Alternatively, however, the housing 110 can comprise any other shape, size, configuration and/or feature. Further, the fluid delivery module 100 can include generally smooth or glossy surfaces that are configured to withstand frequent cleaning. In some arrangements, the fluid delivery module 100 is waterproof or water-resistant or substantially waterproof or water-resistant. Smooth exterior surfaces of the module 100 can facilitate cleaning and prevent residual contamination from remaining on the housing. Further, the fluid delivery module 100 can be configured to maintain vials and/or other containers secured thereon at a particular thermal setting or temperature range. For example, the module 100 can include a temperature control system (e.g., cooling/heating device, temperature sensor, regulator, etc.) that permits the module 100 to maintain a pharmaceutical or other material to be delivered into a patient within a desired temperature range. This can be especially important for the delivery of formulations or other substances that degrade or are otherwise transformed when not temperature-controlled (e.g., refrigerated, heated, etc.).

With continued reference to FIG. 2A, a bottom portion of the housing 110 or chassis can include a plurality of feet 112 or other support members. In some embodiments, the feet 112 are configured to maintain a desired clearance between the housing 110 and the surface on which the fluid delivery module 100 rests. In addition, the feet 112 can facilitate in the handling (e.g., lifting, repositioning, etc.) of the module 100. Further, the feet or other support members 112 can comprise a non-slip or non-skid surface or texture to prevent the undesirable movement of the module 100 during transport or use.

In some embodiments, as illustrated in FIG. 2A, a touchscreen display 130 of a fluid delivery module 100 is generally rectangular. In certain arrangements, the display 130 comprises a flat panel touchscreen having a 7-inch color TFT LCD. The resolution of the display 130 can be 800×600 with a total of 480,000 pixels and a brightness rating of 300 cd/m$^3$. In addition, the touchscreen display 130 can use restive technology for sending touch input. In some embodiments, the touchscreen is compatible with and/or without the use of gloves. However, the type, size, resolution, brightness, compatibility and/or other details about the display 130 can vary, as desired or required. For example, the touchscreen display 130 can comprise a 16 to 9 aspect ratio. However, the type, shape, size, aspect ratio, resolution and/or other characteristics of the display 130 can vary, as desired or required. As discussed in greater detail herein, the touchscreen display 130 can be adapted to identify one or more characteristics regarding the pharmaceutical or other container (e.g., syringe, vial, etc.) secured to the module 100. In addition, the touchscreen display 130 can be configured to display status information, patient information (e.g., name, vital signs, known allergies, etc.), imaging information, injection procedure programming and/or status information and/or any other information. Further, the touchscreen display 130 and/or another data entry device can permit a physician, other clinician or other user to control the operation of the procedure (e.g., verify patient, verify fluids or other materials to be delivered, locate target joint, start, stop, reduce/increase flowrate or other rate of delivery, etc.) and/or to enter other data within the system 10.

According to some arrangements, the touchscreen display 130 is configured to illustrate text and/or images (e.g., icons). The use of icons can facilitate the physician or other user in performing the required injection and/or aspiration procedure. For example, the touchscreen display 130 can be configured to display a list of various body parts (e.g., foot, hand, spine, knee, other body parts or organs, etc.) into which a desired injection is to occur. Once a user selects the general anatomical area targeted by the procedure, the touchscreen display 130 can provide a more detailed selection list of available target sites within that general area. For example, if a foot is selected, the touchscreen display 130 can provide a more detailed list of joints associated with the foot (e.g., ankle, toe, etc.). Alternatively, the display 130 can provide a list of various injection protocols from which to choose. In other embodiments, the touchscreen display 130 can include "UP" and "DOWN" softkeys (FIGS. 48A-48D and 49A-49D) arrows or any other icons, text and/or other images that facilitate the user during the execution of the corresponding procedure.

In some embodiments, the selected icon or other portion of the display 130 can be configured to change color, shade, shape and/or the like when a user selects it. Further, the fluid delivery module 100 can be configured to provide audible verification that a selection was made (e.g., tone, beep, etc.). It will be appreciated that a touchscreen display 130 and/or any other component of the fluid delivery module 100 can include one or more other features, as required or desired by a particular application. As discussed, an injection system can also include a voice command/notification system that permits a user to receive audile updates from the system (e.g., volume dispensed, volume remaining, etc.) and/or to control the operation of the system using audible instructions (e.g., "START," "STOP," "DECREASE DELIVERY RATE," "INCREASE DELIVERY RATE," "PAUSE," "TERMINATE" and/or the like). The above disclosure regarding the display 130 (e.g., touchscreen device) and other features can be applied to any other embodiment of a fluid delivery module disclosed herein or equivalents thereof.

Figure 2B:
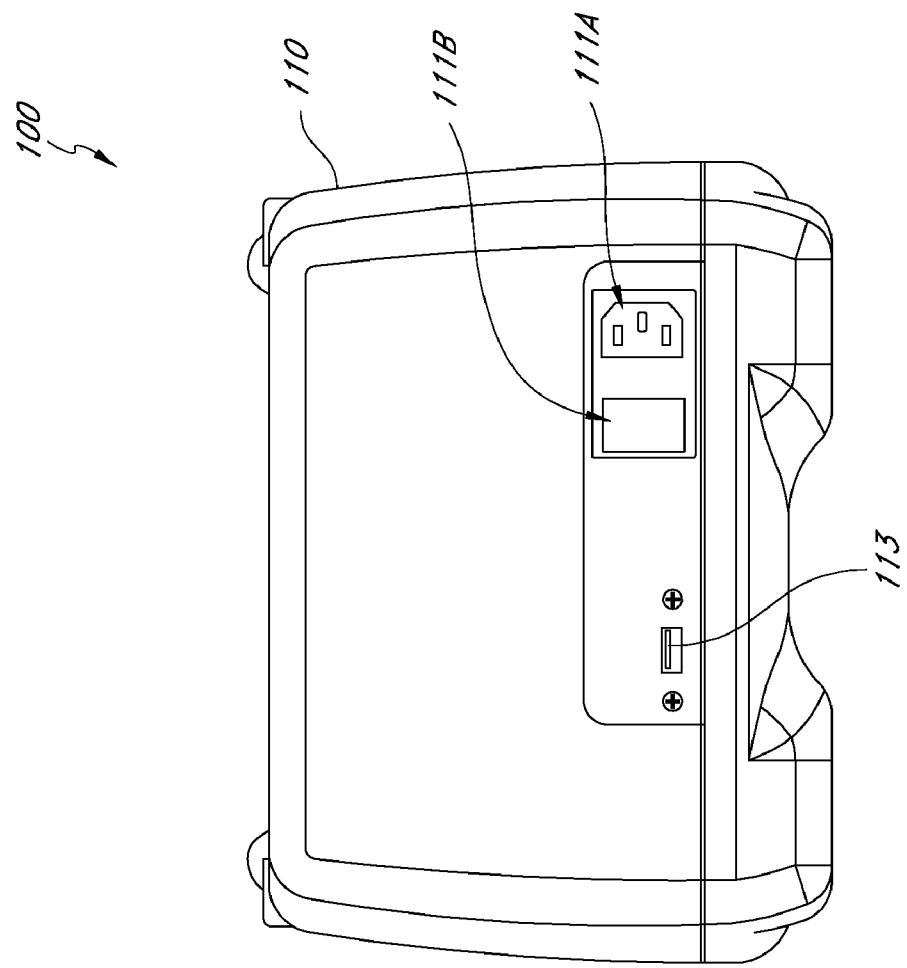
FIG. 2B illustrates a rear view of the fluid delivery module of the articular injection system of FIG. 2A.
Figure 2C:
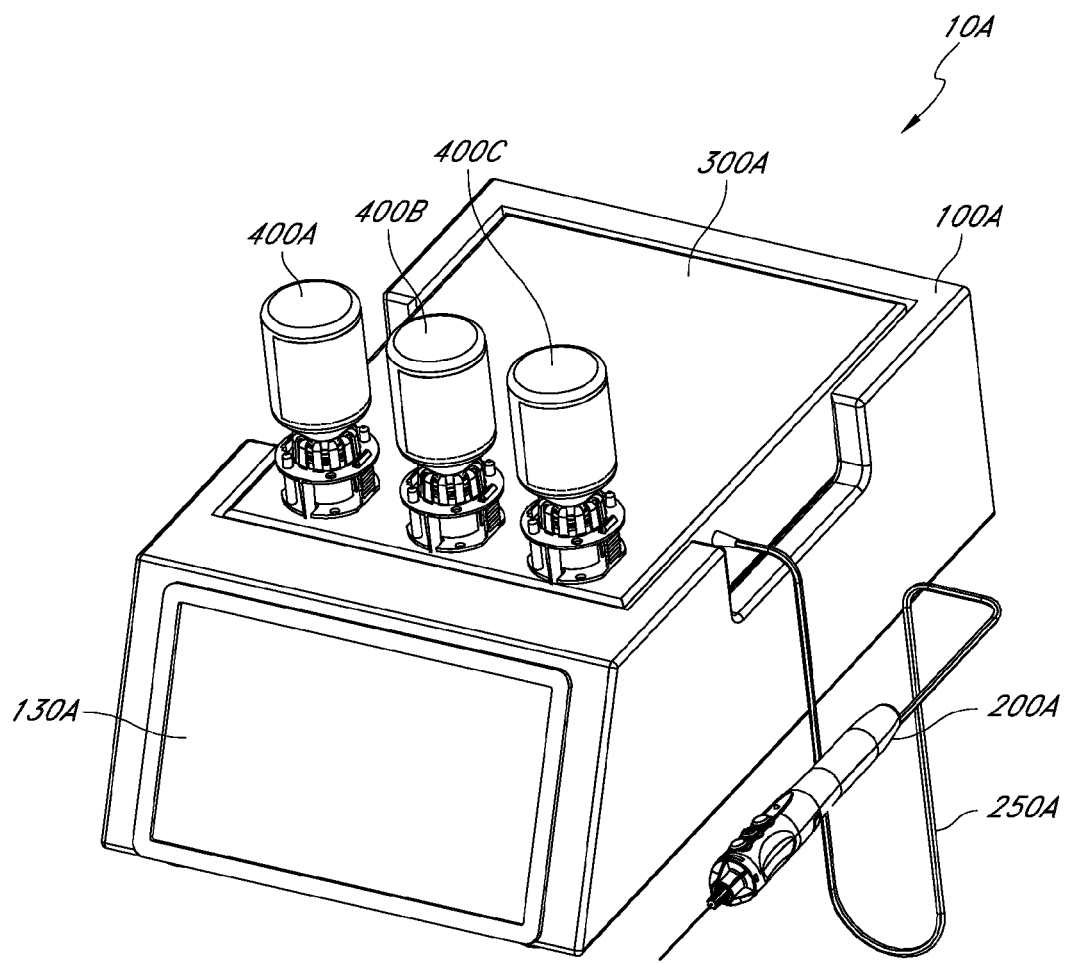
FIG. 2C illustrates a perspective view of an articular injection system according to another embodiment.
Figure 2D:
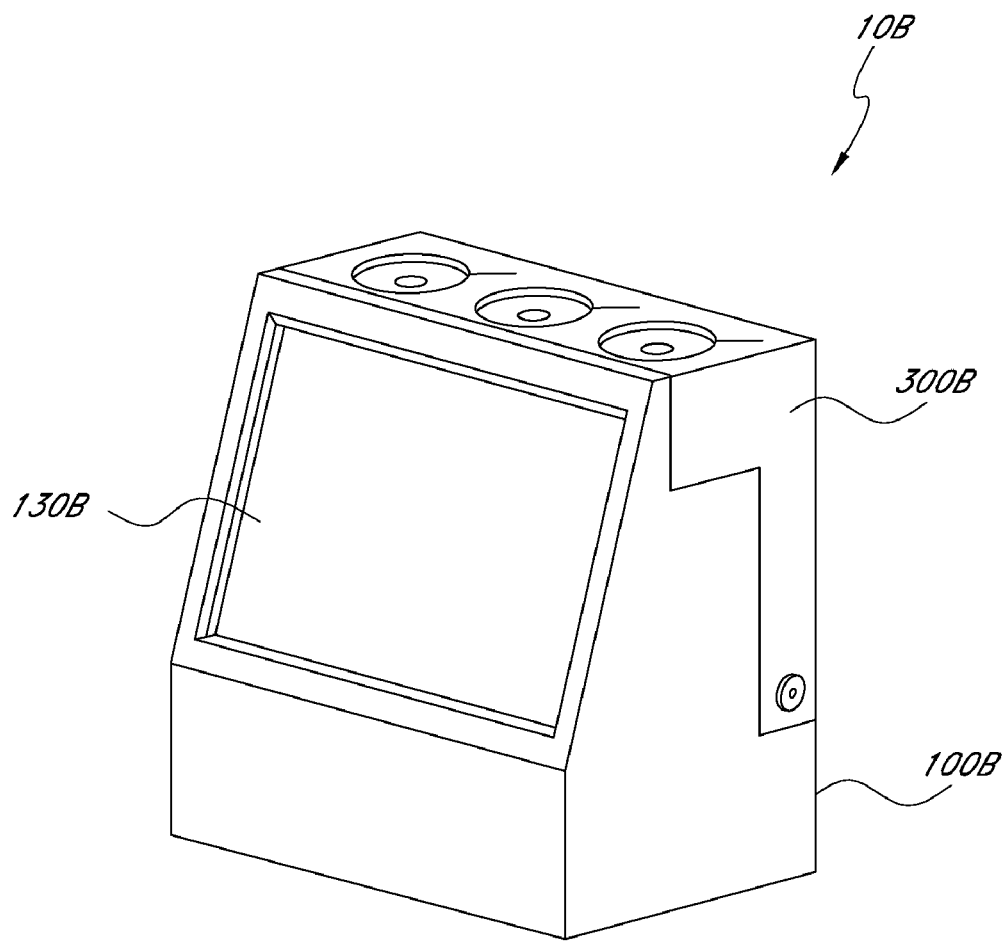
FIG. 2D illustrates a perspective view of an articular injection system according to another embodiment.
Figure 2E:
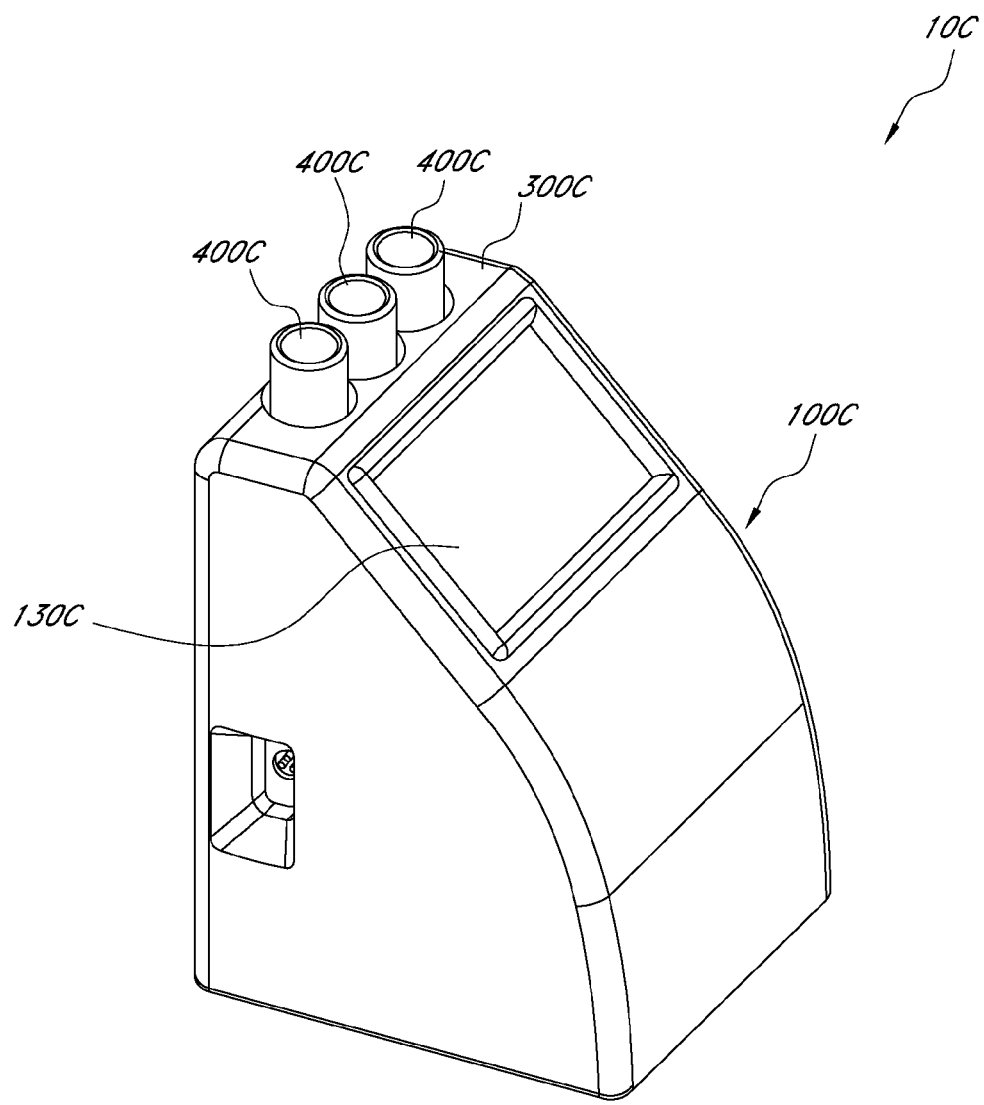
FIG. 2E illustrates a perspective view of an articular injection system according to another embodiment.
Figure 2F:
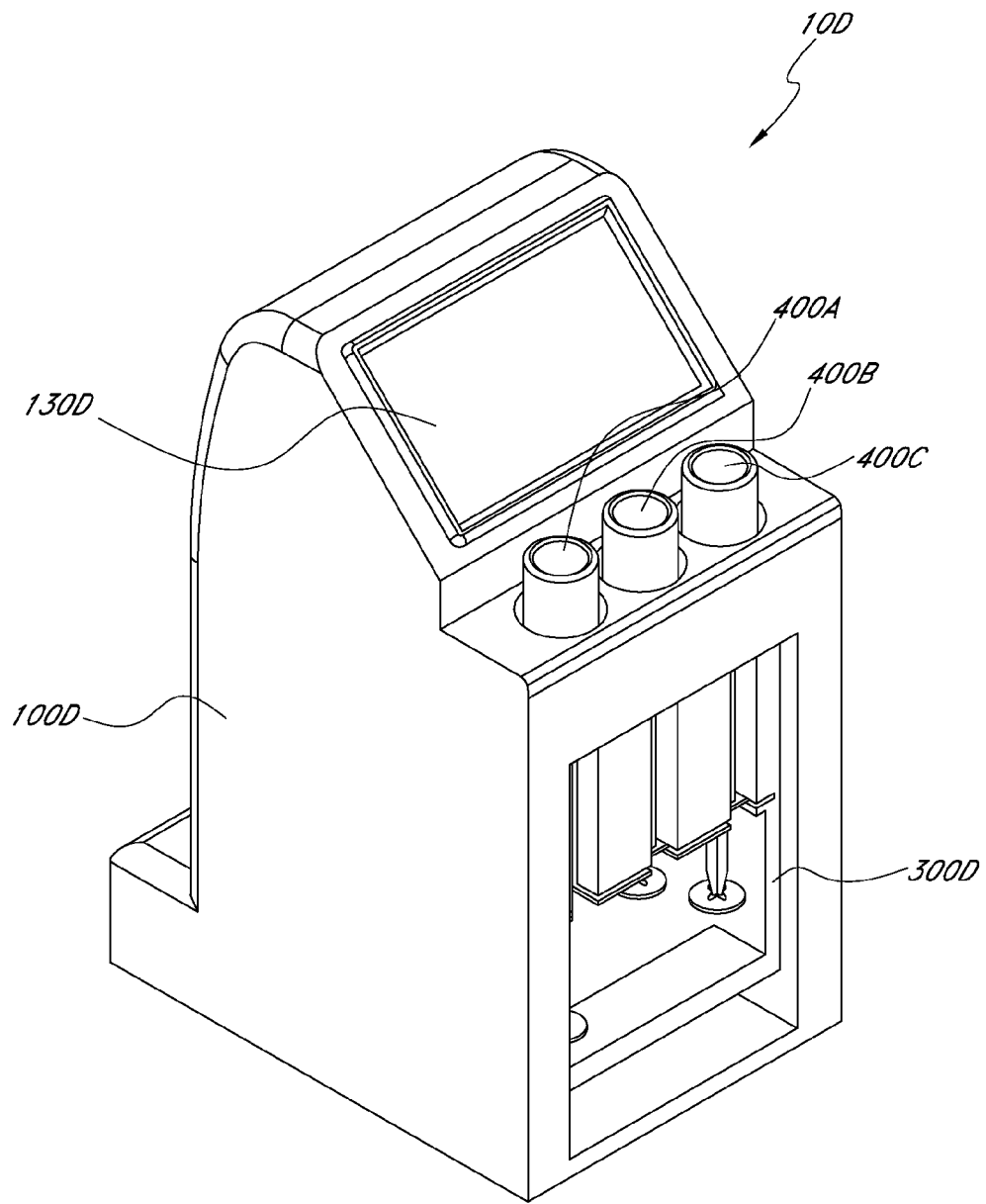
FIG. 2F illustrates a perspective view of an articular injection system according to another embodiment.
Figure 2G:
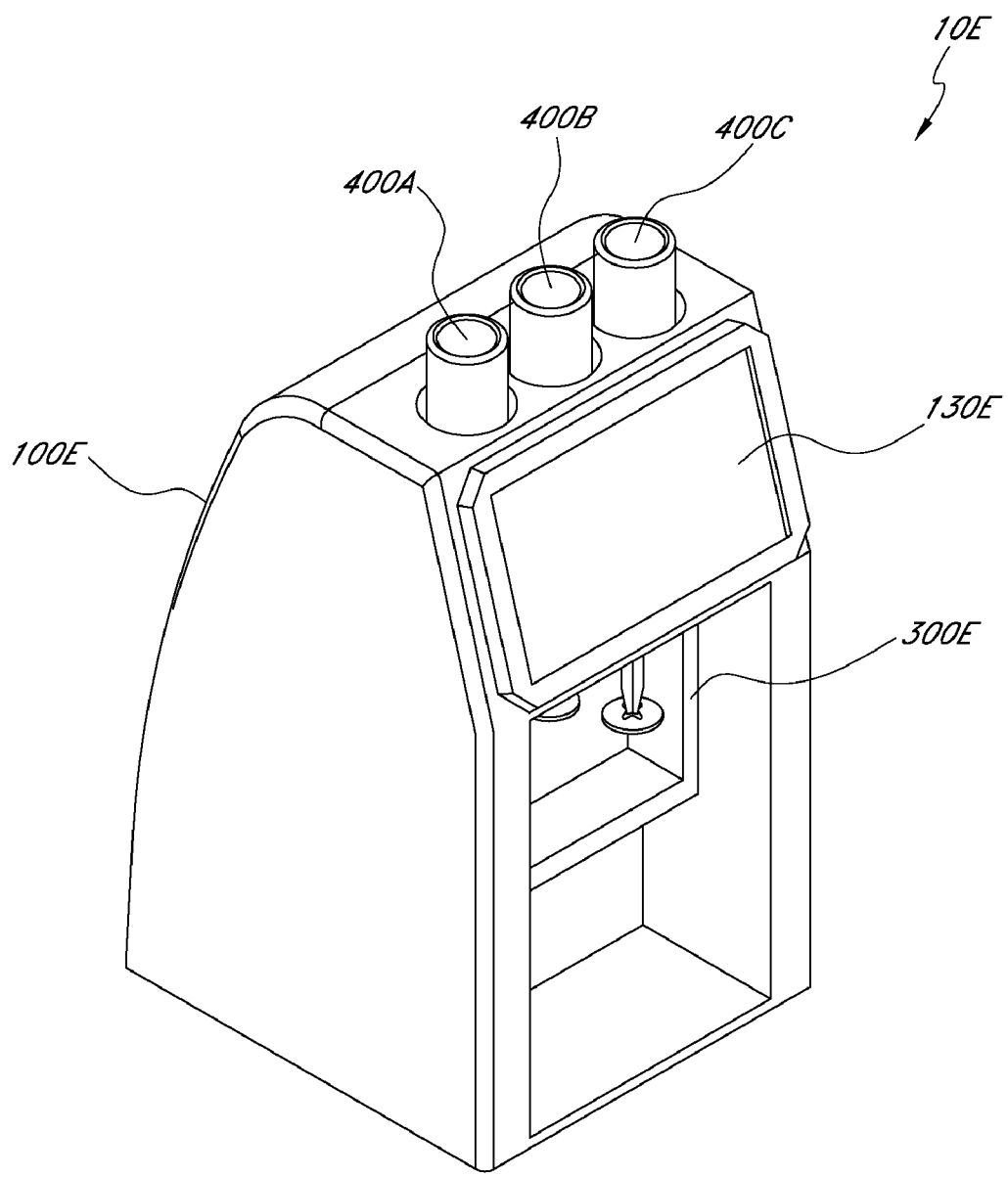
FIG. 2G illustrates a perspective view of an articular injection system according to another embodiment.

Another embodiment of an intra-articular injection system 10A is illustrated in FIG. 2C. The depicted injection system 10A is similar to the one discussed herein with reference to FIG. 2A. However, the 100A of the injection system 10A illustrated in FIG. 2C comprises a less contoured shape that the one illustrated in FIG. 2A. As shown, the handpiece assembly 200A can be placed in fluid communication with the vials 400A, 400B, 400C loaded onto the cassette 300A via tubing 250A or other conduit.

Additional embodiments of fluid delivery modules 100B-100E and cassettes 300B-300E configured to be positioned therein for use with intra-articular injection systems 10B-10E are illustrated in FIGS. 2D-2G. As shown in these alternative arrangements, the fluid delivery modules and/or the cassette positioned therein can have a more vertical orientation than in the embodiments illustrated in FIGS. 2 and 2C. As a result, the vials (not shown) containing the medications, formulations, other fluids, substances or materials and/or the like can be secured to different portions of the fluid delivery module and/or cassette.

With continued reference to FIGS. 2D-2G, the position of the display 130B-130E and/or any other component or feature of the respective injection system 10B-10E can be varied, as desired or required.

The fluid delivery module 100 and/or any other components of the injection system 10 can be powered by one or more power sources. For example, in some embodiments, the fluid delivery module 100 comprises an AC power cord or other connection. In such arrangements, the AC transformer can be situated either within or outside of the module housing 110. As illustrated in FIG. 2B, a power port 111A positioned along the rear or side of the housing 110 can be configured to receive a power cord or other power supply connection. In other embodiments, the fluid delivery module 510 is powered by one or more batteries (e.g., rechargeable lithium batteries, etc.), either in addition to or in lieu of the AC power supply. This can provide an extra measure of protection to ensure that an injection procedure is not interrupted because of a power outage. In addition, the use of batteries and an external AC power transformer can generally increase the portability of the system and help reduce its overall size. However, other types of devices and/or methods can be used to provide electrical power to the fluid delivery module 110 and/or other components of the injection system 10. As illustrated in FIG. 2B, the fluid delivery module 100 can include one or more other ports or slots 111B, 113 configured to operatively connect the module 100 to one or more other devices, processors and/or the like (e.g., ultrasound or other imaging device, network, personal computer, etc.). Such ports or slots can be standard (e.g., USB, mini-B, parallel, etc.) or non-standard, as desired or required. For example, the depicted fluid delivery module 100 comprises a single USB port 113.

Further, a fluid delivery module 100 can comprise one or more memory, communication and/or other types of slots. Thus, the module 100 can be upgraded with additional programs, functions and/or other capabilities. In some embodiments, as discussed, a fluid delivery module 100 comprises a USB 113 or other port that is configured to communicate with a personal computer or other device (e.g., the hospital's computing network, a monitoring device, another medical device, etc.). In yet other arrangements, the fluid delivery module 100 includes a wireless communication system (e.g., modem, Wi-Fi, RFID, Bluetooth, etc.) that permits it to communicate with other components of the injection system (e.g., handpiece assembly) and/or one or more other computing systems or devices. These types of communication devices can permit a user to transfer data (e.g., continuously or intermittently) to and/or from the module 100, as desired or required. For example, new software or software patches can be periodically installed onto the module 100, either automatically or manually.

The fluid control module 100 can comprise and/or be in communication with a processor, control device and/or the like. This can permit the module 100 to adequately process data and control the operation of the various components of the fluid injection/aspiration system (e.g., the core or other portions of the handpiece assembly, fluid transfer device, display, etc.). In some embodiments, the required processor and/or control unit are included within the housing 112 of the module 110. Alternatively, such components can be external to the module 100. In such arrangements, the fluid delivery module 100 can be placed in data communication with an exterior processor and/or control unit using one or more hardwired and/or wireless communications.

Cassette

Figure 3A:
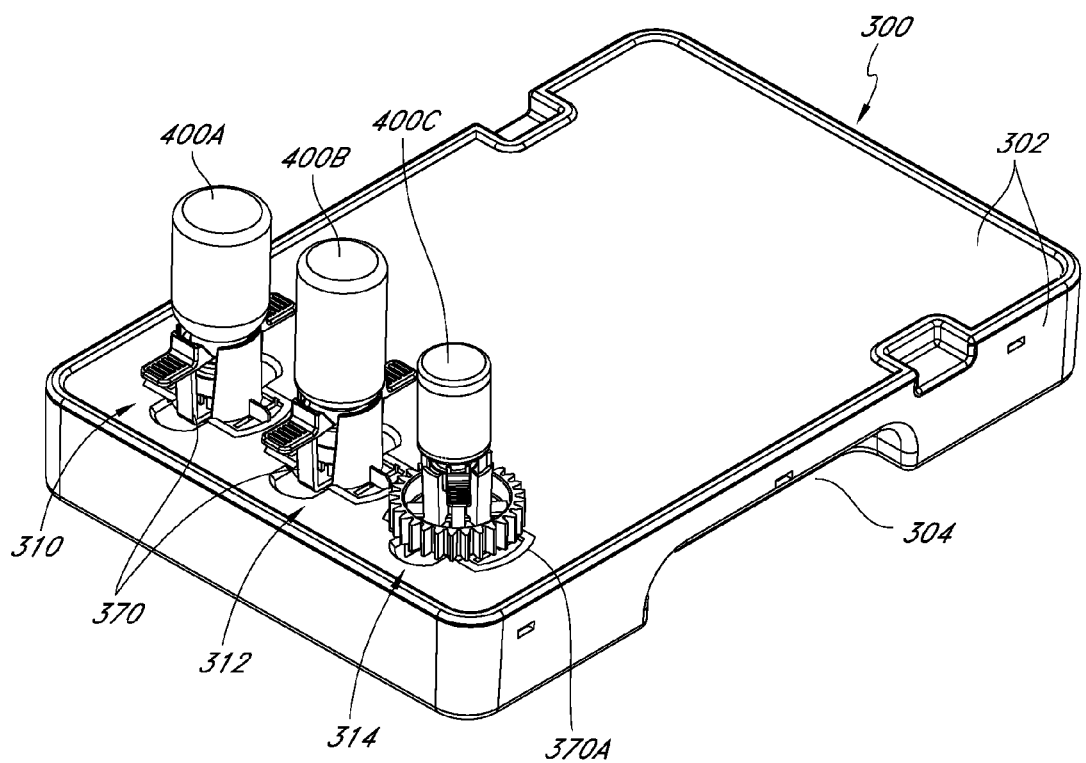
FIG. 3A illustrates a perspective view of a cassette for a fluid delivery module and configured to receive vials or other containers according to one embodiment.

FIG. 3A illustrates one embodiment of a cassette 300 configured to be positioned within a fluid delivery module 100 (FIG. 2A). As discussed and illustrated in greater detail herein, the cassette 300 can comprise an outer housing 302 that is configured to enclose one or more internal components (e.g., manifolds, syringes or other reservoirs, etc.). The depicted cassette 300 has a generally rectangular shape. In several arrangements, the approximate dimensions of the cassette 300 are 9.7 inches long, 6.5 inches wide and 1.6 inches tall. In other embodiments, the cassette is permanently secured to the fluid delivery module 100 or forms a generally unitary structure with the fluid delivery module. Further, in some embodiments, the cassette 300 and/or any of its components or portions comprise one or more plastic, other polymeric, metal and/or other synthetic or natural materials, or combinations of same. However, the shape, size, materials of construction and/or other characteristics of the cassette 300 can vary, as desired or required for a particular application or use. In addition, the cassette 300 can comprise one or more finger wells 304, grooves or recessed areas that facilitate placement of the cassette 300 into and/or out of the corresponding area of a fluid delivery module 100.

As discussed in greater detail herein, the cassette 300 can be a disposable item that is replaced periodically (e.g., once, twice or more often per day). In other embodiments, the cassette 300 may be configured to be replaced more or less often than indicated above, as desired or required. Alternatively, the cassette 300 can be removed and replaced when one or more medications or other fluids or substances being delivered using the intra-articular injection system are changed. This can help prevent cross-contamination between different types of substances, different dosages of substances and/or the like. According to some arrangements, the cassette 300 is replaced along with one or more other components of the injection system, such as, for example, the clip of the handpiece assembly and the delivery line (e.g., multi-lumen tubing) that places the handpiece assembly in fluid communication with the cassette 300.

In the embodiment depicted in FIG. 3A, up to three vials 400A-400C or other containers may be secured to receiving sites 310, 312, 314 located along the top surface of the cassette 300. In some embodiments, each receiving site comprises a nest or loading area that is adapted to accept a standard or non-standard vial or other container. The cassette 300 can include more or fewer receiving sites 310, 312, 314, as desired or required. In addition, the location, spacing and other details of the receiving sites 310, 312, 314 can be different than illustrated in FIG. 3A. As discussed in greater detail herein, once the vials 400A-400C or other containers are secured to the cassette 300, the injection system can be configured to transfer the contents of such vials or other containers within the fluid delivery module 100 and accurately deliver the interior contents of one or more of such vials 400A-400C to a targeted anatomical location in a precise and accurate manner. In the illustrated embodiment, larger vials 400A, 400B (e.g., 50 ml capacity) are secured to two receiving sites of the cassette, while a smaller vial 400C (e.g., 5 ml capacity) is secured to one receiving site. For example, the smaller vial 400C can be secured to a nest or loading area of the cassette 300 that is configured to keep the internal contents of such vial mixed. As discussed in greater detail herein, such mixing may be desired or required for certain medicants or other materials, such as, for example, steroids or other solutions or mixtures that have a tendency to settle or that require mixing. In certain arrangements, the receiving sites of the cassette are configured to receive a variety of different vials or other containers.

Figure 3B:
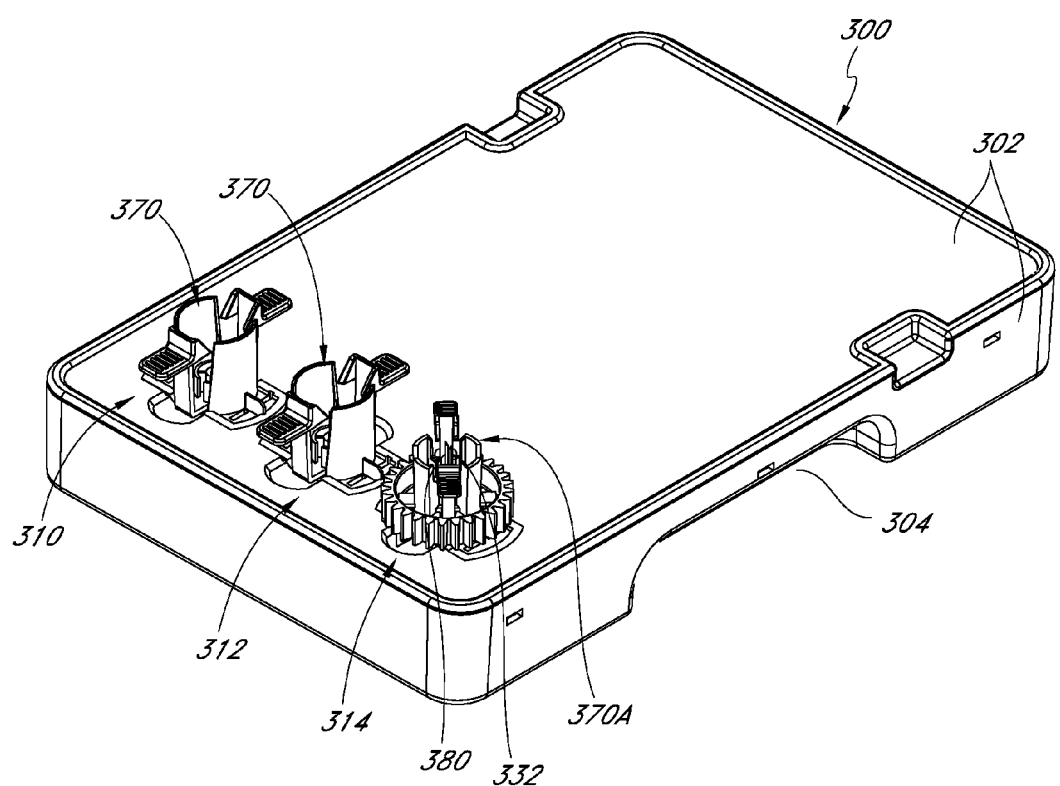
FIG. 3B illustrates the cassette of FIG. 3A with the vials removed from the loading areas or nests.

FIG. 3B illustrates the embodiment of the cassette of FIG. 3A with no vials or other containers secured to the receiving sites 310, 312, 314. In the depicted arrangement, each receiving site 310, 312, 314 comprises a nest 370, loading area or other component or portion to which a vial may be secured. The loading area 370 or nest can be a separate member that is joined to the housing 302 or other portion of the cassette 300 using one or more attachment devices or methods. Alternatively, the loading area 370 or nest (or an equivalent thereof) can form a unitary structure with the cassette 300 (e.g., the loading area or nest can be molded or manufactured as a single piece with the housing 302 or other portion of the cassette 300 or fluid delivery module). As used herein, the term loading area is a broad term and includes, without limitation, a nest, docketing port or station, an opening, a slot and/or any other component, area or portion configured to receive a vial or other container. Accordingly, the terms loading area, nest and the like are used interchangeably herein.

With continued reference to FIG. 3B, the nests or loading areas 370 can be sized, shaped and otherwise adapted to securely receive the top portions (e.g., neck areas) of various vials or other containers. Accordingly, the clinician or other user of the injection system can easily, quickly and conveniently position multi-dose vials (e.g., standard or non-standard vials as supplied to the clinician) onto the fluid delivery module. Thus, the need to transfer liquids from such vials to other reservoirs or containers of an injection system can be advantageously eliminated. As discussed in greater detail herein, this can provide several benefits and other advantages. For example, potentially time-consuming efforts to transfer the medicaments, fluids and/or other substances to the injection system can be reduced or eliminated. Relatedly, the use of such nests or other loading areas can make the injection procedure safer, as the likelihood of contamination of the various fluids or other substances (e.g., with the outside environment, between the various medicament streams, etc.) can be reduced. Further, the amount of wasted fluids or other materials that would otherwise remain as unused residual within the vials or other containers that are supplied to the user can be advantageously reduced or eliminated.

Figure 3C:
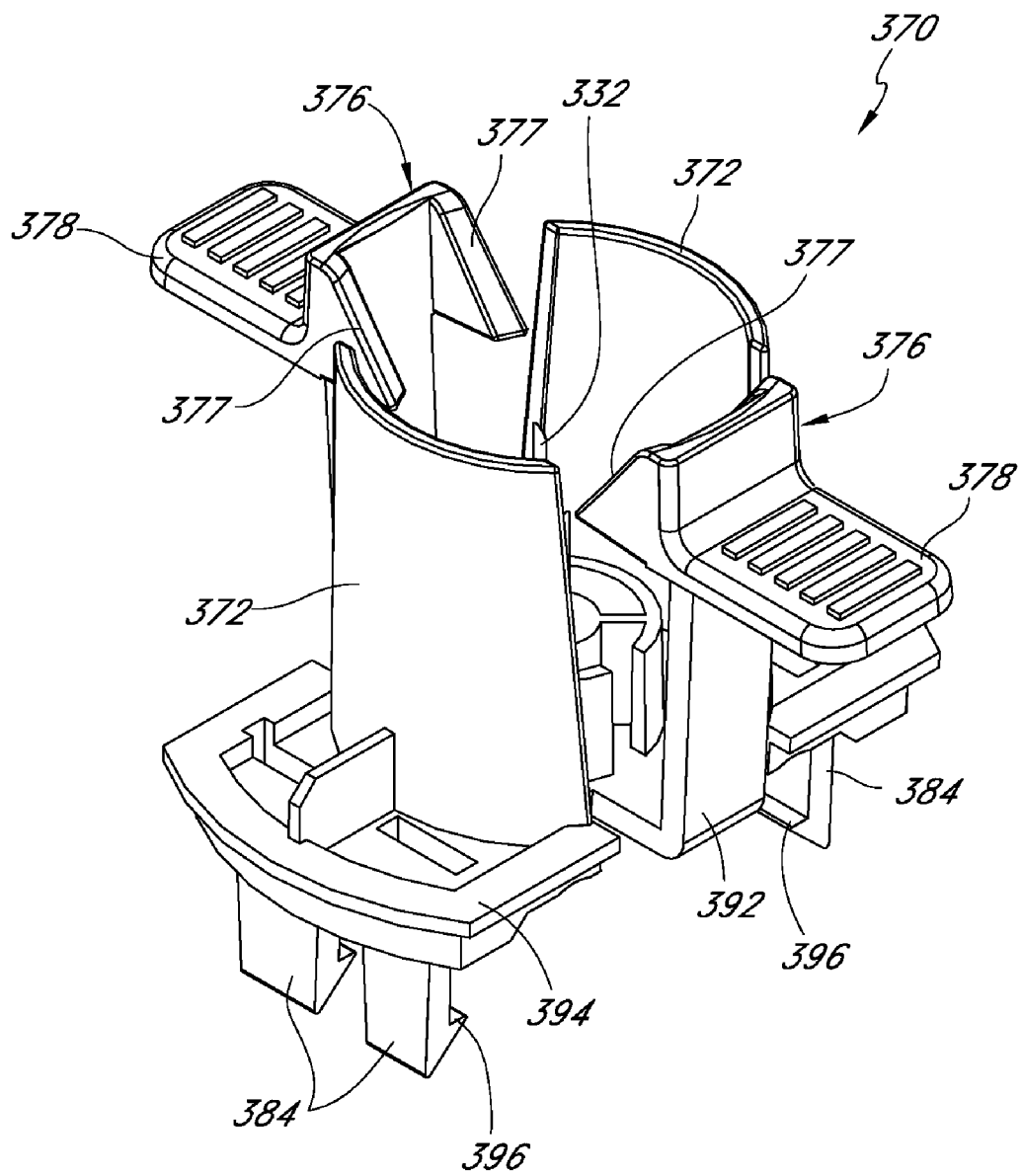
FIG. 3C illustrates a top perspective view of a nest or loading area configured for use with a cassette according to one embodiment.

FIG. 3C illustrates one embodiment of a nest 370 or loading area which is configured to be secured to a cassette and which is adapted to receive a vial or other container therein. As discussed herein with reference to FIGS. 3A and 3B, the nest 370 or loading area and the cassette 300 can be separate items that are attached to one another using one or more connection devices or methods. Alternatively, the cassette 300 and the nest 370 can be integrally formed with one another. For example, in the embodiment of FIG. 3C, the lower portion of the loading area or nest 370 comprises four tabs 384 that are adapted to snap or otherwise connect to the cassette 300 and/or a component located on or within the cassette. In other arrangements, a nest can include more or fewer that four tabs 384 as desired or required. Further, one or more other connection devices (e.g., threads, screws, other mechanical fasteners, rivets, etc.) or methods (e.g., gluing, welding, etc.) can be used to attach the nest 370 to the cassette 300, either in lieu of or in addition to the tabs 384. As shown, each tab 384 can include a protruding portion 396 adapted to engage a corresponding portion or component of the cassette (e.g., manifold, housing, etc.) to which it attaches. Other views of the loading area 370 of FIG. 3C are illustrated in FIGS. 3D-3H.

With continued reference to FIGS. 3C-3H, the nest 370 or loading area can include a cylindrical portion 372 that generally defines an interior region into which a vial or other container may be positioned. In the illustrated arrangement, the cylindrical portion 372 comprises two walls that are positioned opposite of one another. Alternatively, the portion of the nest 370 that defines an interior region for accepting a vial or other container can include more or fewer walls or other members or features. In addition, such a portion 372 can have a different size, shape (e.g., non-cylindrical, rectangular, etc.) and/or other characteristics, as desired or required. For example, according to several arrangements, the diameter or other cross-sectional dimension of the cylindrical portion 372 is approximately between 0.4 and 0.7 inches (e.g., 0.4 inches, 0.5 inches, 0.6 inches, 0.7 inches, etc.) or values below, above or between such values. However, in other embodiments, the size, shape and/or other details regarding the loading area or nest can vary, as desired or required.

According to certain embodiments, the nest 370 or loading area comprises two wings 376 or other flexible members that are configured to releasably secure a vial or other container within the nest. As shown in FIGS. 3C-3H, each wing 376 can include a vertical portion 392 which is generally parallel to the adjacent walls of the cylindrical portion 372 and which helps to define the interior region of the nest 370 or loading area. These vertical portions 392 of the wings 376 and the cylindrical portions can be secured to a base 394 of the nest 370. The tabs 384 or other members used to connect the nest 370 to the cassette 300 can also extend from the base 394. In other embodiments, the nest 370 includes more or fewer than two wings 376 or other flexible members. Further, the shape, size, design and/or other characteristics of the wings 376 can be different than discussed and illustrated herein.

Figure 3D:
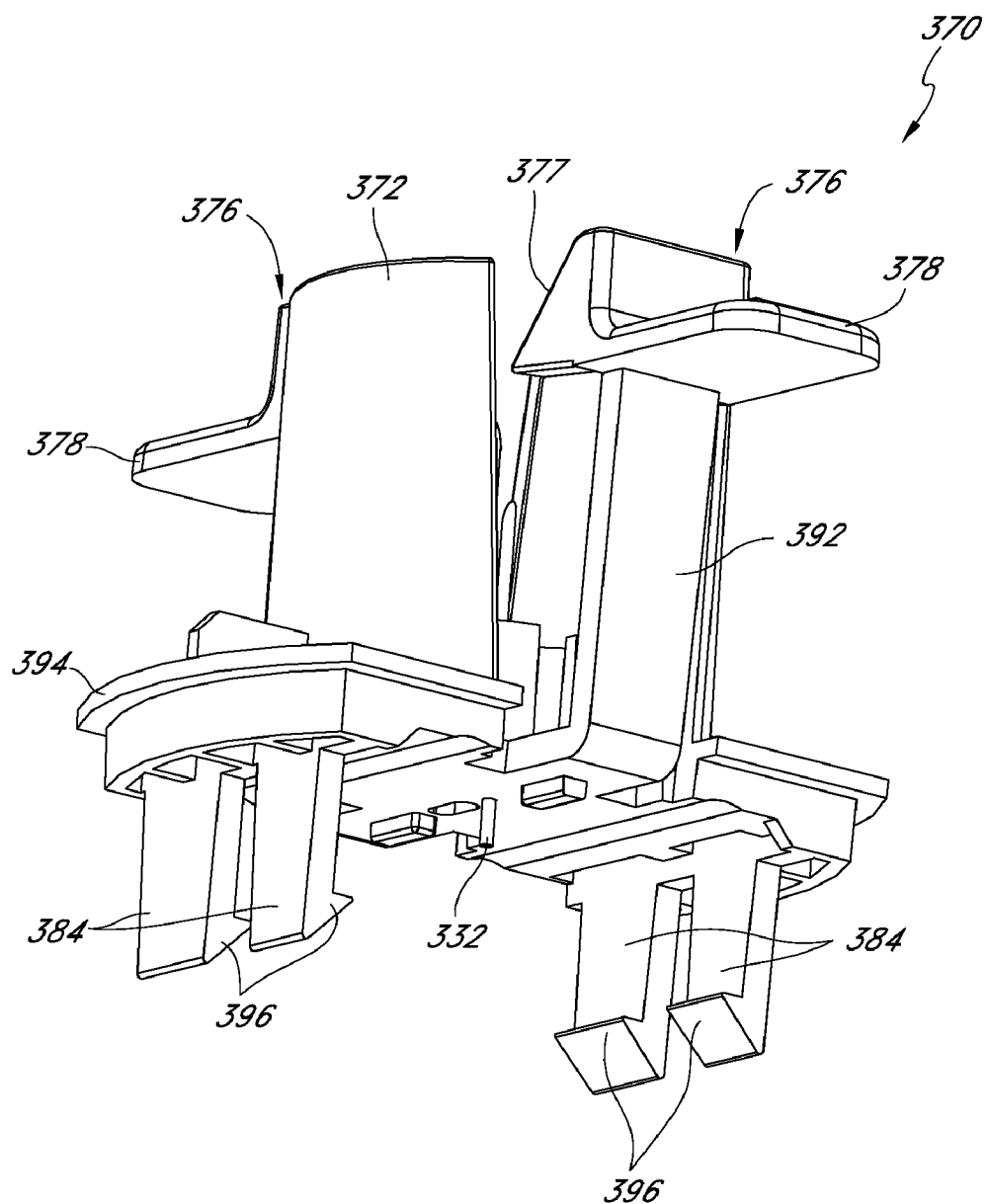
FIG. 3D illustrates a bottom perspective view of the nest or loading area of FIG. 3C.
Figure 3E:
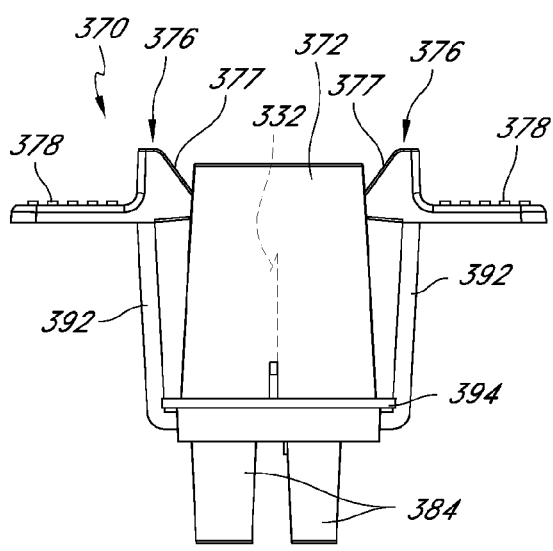
FIGS. 3E and 3F illustrate different side views of the nest or loading area of FIG. 3C.
Figure 3F:
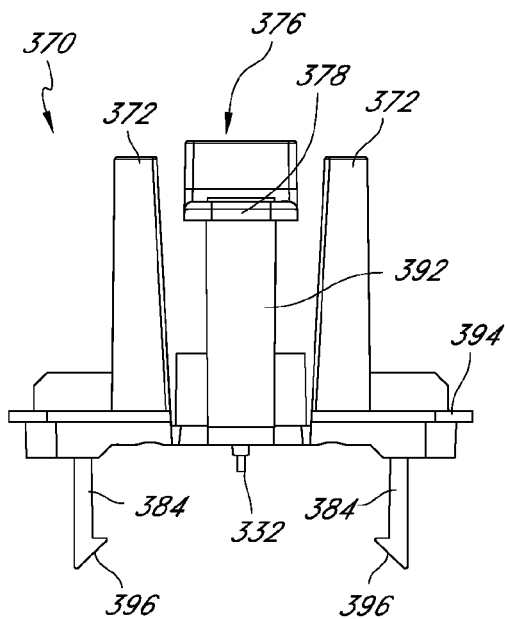
Figure 3G:
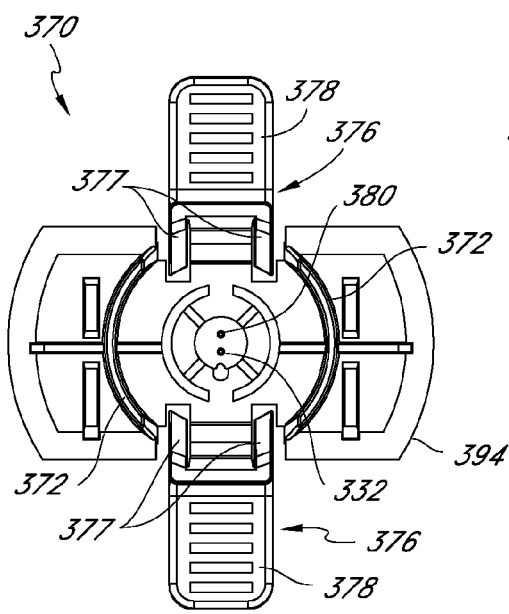
FIG. 3G illustrates a top view of the nest or loading area of FIG. 3C.
Figure 3H:
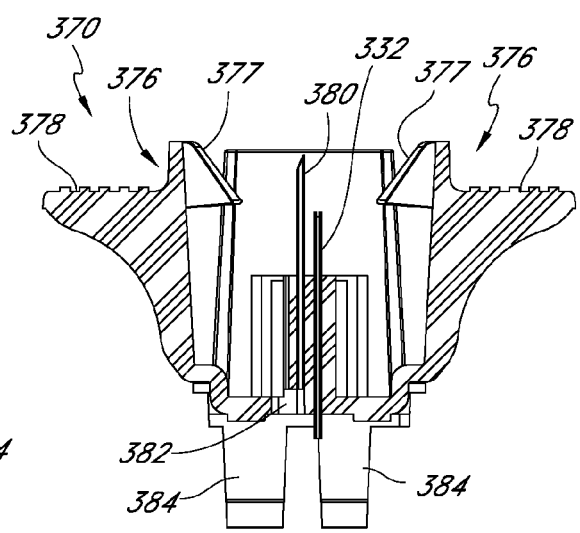
FIG. 3H illustrates a cross-sectional view of the nest or loading area of FIG. 3C.
Figure 31:
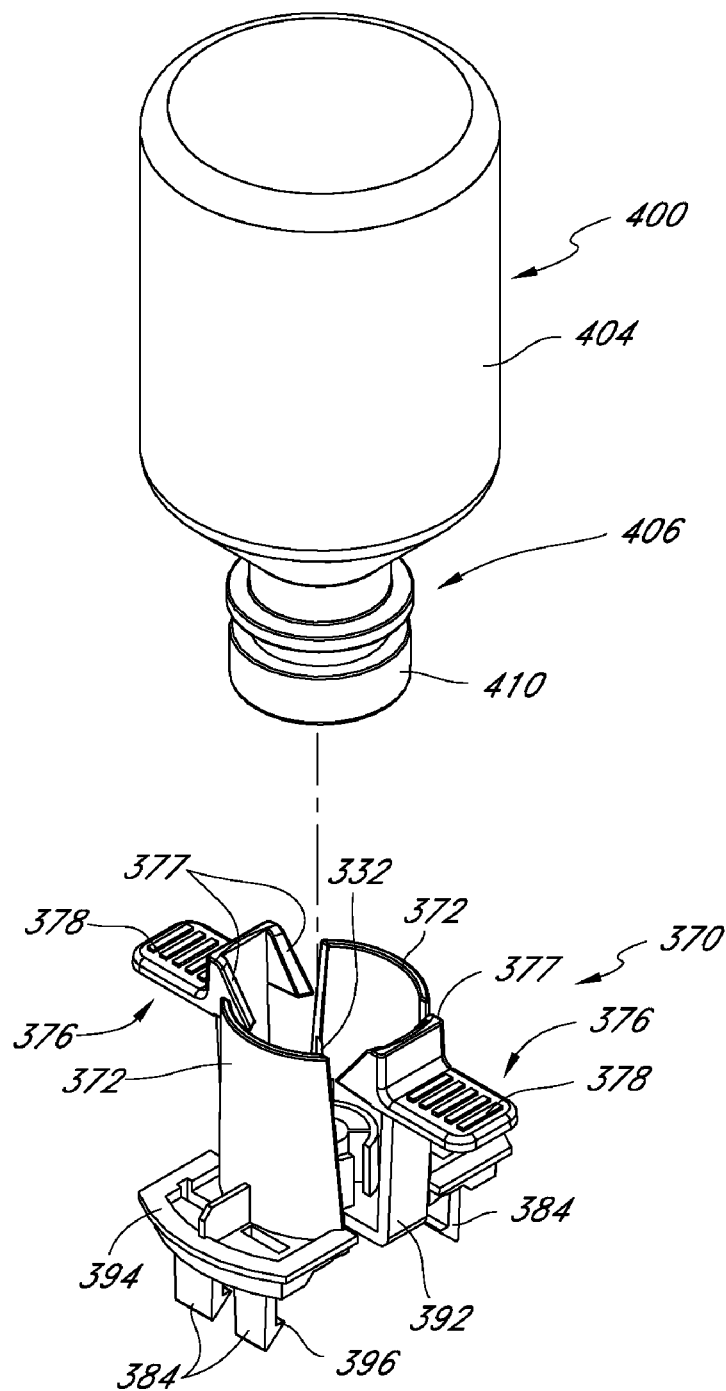
FIG. 31A illustrates a front perspective view of a tip configured for use in a handpiece assembly according to another embodiment.
FIG. 31B illustrates a side view of the tip of FIG. 31A.
FIG. 31C illustrates a front view of the tip of FIG. 31A.
FIG. 31D illustrates a rear perspective view of the tip of FIG. 31A.
FIG. 31E illustrates a rear view of the tip of FIG. 31A.

An upper portion of each wing 376 can include an inwardly-facing locking member 377 which is configured to maintain the neck 406 or other closure 410 of a vial 400 or other container within the interior region of the nest 370 or loading area (FIG. 3I). In some arrangements, as depicted in FIGS. 3C-3E, the locking member 377 comprises one or more sloped portions. In addition, an upper portion of each wing 376 can include a handle member 378 which is used to selectively move the wing 376 away from the interior region of the nest 370 or loading area. According to some arrangements, the handle member 378 comprises a generally horizontal rectangular portion which is adjacent to or near the locking member 377. Alternatively, the shape, size, location and/or other details of the handle member 378 can vary, as desired or required.

As illustrated in FIGS. 3C, 3D, 3E, 3G and 3H, a main needle 332 and a vent needle 380 can be positioned within an interior region of the loading area or nest 370. Thus, when a vial or other container is secured therein, the main needle 332 and the vent needle 380 can help place the internal contents of the vial (e.g., medicament, other fluid, other material or substance, etc.) in fluid communication with one or more subcomponents of the cassette 300 (e.g., manifold, syringe or other reservoir, etc.) and other components of the injection system. According to some arrangements, the main needle 332 and the vent needle 380 are approximately 0.5-1.5 inches long and have a gauge of approximately 15-30. The vent needle 380 and the main needle 332 can have different lengths, gauges and/or other properties from one another. However, the gauge, length, location and/or other characteristics of the main needle 332 and/or the vent needle 380 can be different than disclosed herein, as desired or required for a particular application or use. In certain arrangements, the needles 332, 380 comprise surgical-grade stainless steel and/or any other materials suitable for insertion into a patient (e.g., other metals, alloys, etc.).

The main needle 332 and/or the vent needle 380 can be attached to the nest 370. Alternatively, one or both of the needles 332, 380 can be attached to the cassette housing 302 or another portion of the cassette 300. In the embodiment illustrated in FIGS. 3C-3H, the main needle 332 extends below the bottom of the cylindrical portion 372 of the loading area or nest 370, thereby enabling the needle 332 to place another component (e.g., manifold) of the cassette 300 in fluid communication with the interior of the respective vial or other container secured to the nest 370. As best depicted in the cross-sectional view of FIG. 3H, the vent needle 380 can terminate at a vent area 382 that allows the vent needle 380 to be in fluid communication with the surrounding atmosphere. This permits ambient air to enter into the vial or other container to displace the volume of fluids and/or other substances which are removed from the vial or other container. Accordingly, the emptying of the vials or other containers secured to the cassettes 300 is advantageously facilitated.

According to some embodiments, the nests 370 or loading areas are supplied with protective covers or other members (not shown) that are configured to be removably positioned within the interior region defined by the walls of the cylindrical portion 372. Such covers or other members can help shield the needles 332, 380 and other sterile portions of the nest 370 from the environment (e.g., against contamination). In addition, the covers can help protect the clinician or other user against injury (e.g., accidental punctures) that may be caused by the protruding needles.

Figure 3J:
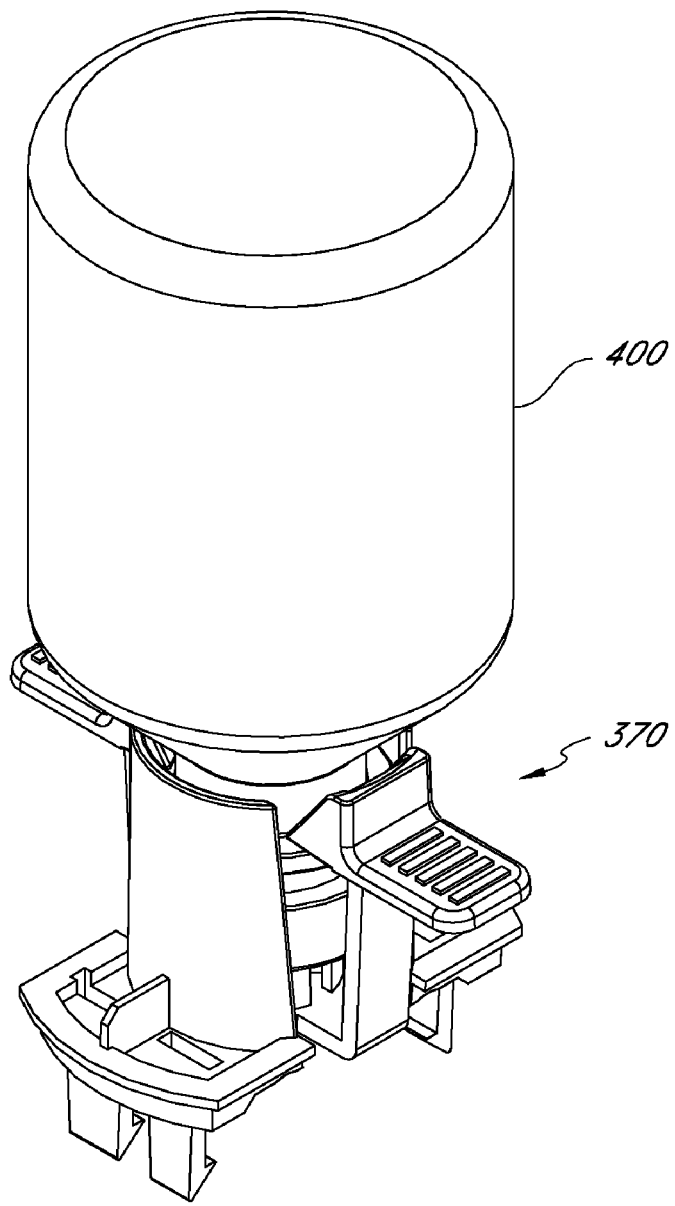
FIG. 3J illustrates a perspective view of a vial secured within the nest or loading area of FIG. 3I.
Figure 3K:
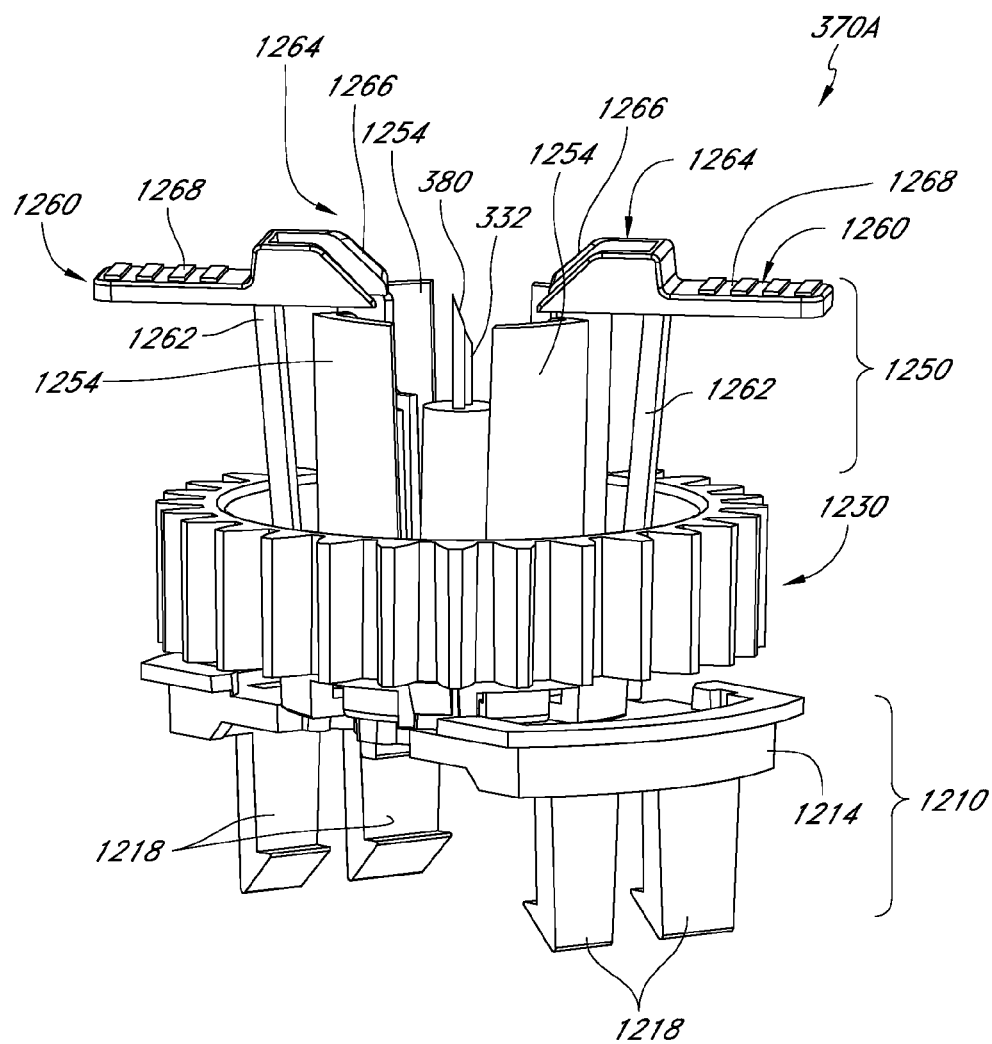
FIG. 3K illustrates a top perspective view of a nest or loading area of a cassette configured to mix the internal contents of a vial or other container secured therein according to one embodiment.

FIG. 3I illustrates a perspective view of a vial 400 being oriented in a manner for insertion into a nest 370 or loading area. In order to secure a vial 400 or other container to the nest 370, a clinician or other user can align the closure 410 or other portion of the vial's neck 406 with the interior region defined by the walls of the cylindrical portion 372 and the wings 376. In some embodiments, during this process, the closure 410 or other leading surface of the vial 400 will first contact the sloped or slanted surfaces of the locking member 377. As the vial 400 is urged downwardly (e.g., into the interior region of the nest 370), the closure 410 or other leading surface of the vial 400 can slide against the locking members 377 of wings 376, thereby causing the wings 376 to separate outwardly from each other. If the vial 400 is urged far enough into the interior area, the ends of the locking members 377 (e.g., the slanted surfaces) can move above the closure 410 of the vial so that the wings 376 resiliently move inwardly (e.g., toward each other) within the neck 406 of the vial 400. Thus, in some embodiments, the vial 400 or other container cannot be removed from the interior region of the nest 370 because the locking members 377 of the wings 376 engage the adjacent surfaces of the closure 410 or other portion of the vial 400. Consequently, as illustrated in FIG. 3J, the vial 400 or other container can "snap" into the nest 370 or loading area and can be removably locked or otherwise secured thereto.

As discussed, the nest 370 or loading area can be adapted to receive vials or other containers of different shapes, sizes, designs, configurations and/or the like. According to some embodiments, the loading area 370 can accommodate vials (e.g., standard or non-standard vials having a capacity of 5 ml, 10 ml, 50 ml, 100 ml or the like) as provided, either directly or indirectly, to the clinician or other user by a pharmaceutical manufacturer or supplier. In other arrangements, the nest 370 or loading area is configured to receive other types of vials or containers. As discussed, once a vial 400 or other container is positioned within the loading area 370, a main needle 332 and a vent needle 380 can penetrate a septum or other portion of the vial's closure 410 to access the interior of such vial 400. Thus, the internal contents of the vial 400 (e.g., medicaments, other fluids or materials, etc.) can be placed in fluid communication with other portions of the cassette and fluid delivery module.

In order to remove a vial 400 or other container from the nest 370, the clinician or other user can pull the handles 378 of the wings 376 away from each other so the locking members 377 can move far enough apart to permit the closure 410 of the vial to be lifted out of the interior region. In some embodiments, the handles 378 are configured so that they may be grasped and separated using a single hand. This can permit a user to conveniently separate the wings 376 of the loading area 370 with one hand while removing the vial 400 or other container with the other. In other arrangements, one or more different ways of securing a vial to a nest 370 or loading area or removing it therefrom can be used.

As discussed, one or more of the cassette's nests or loading areas can be configured to continuously or intermittently mix the contents (e.g., steroids) of a vial or other container secured thereto. In some arrangements, it is desirable or necessary to maintain the internal contents of a vial or other container mixed while such vial or other container is positioned on the cassette. For example, certain types of formulations that include a relatively high solids concentration may need to be mixed to ensure that a consistent and homogeneous dose is provided to the patient during an injection procedure. Other types of fluids, materials and/or other mixtures may require to be continuously or intermittently mixed to problems other than settling and/or to otherwise remain effective before being injected into a patient. Thus, one or more devices or methods of agitating the internal contents of a vial or other container can be advantageously provided.

One embodiment of such a nest 370A or loading area is illustrated in FIGS. 3K-3P. As shown, the nest 370A can comprise an attachment member 1210, a gear member 1230 and a clamp 1250. In other embodiments, the nest or loading area can include more, fewer and/or different subcomponents or portions. The various subcomponents and/or portions of the loading area 370A can be adapted to secure to one another, and in some arrangements, rotate or otherwise move relative to one another. As discussed in greater detail herein, a separate motor or other mechanical device can be used to move the gear and/or any other portion of the nest 370 or loading area in order to selectively rotate a vial or other container secured thereto. Accordingly, a desired amount of mixing can be accomplished for medicaments, other fluids and/or other substances contained within such a vial. This may be particularly important with vials that contain a relatively high concentration of solids, fluids or other materials that are prone to settling, stratification or some other non-homogenous phenomenon and/or materials that otherwise require mixing (e.g., steroids).

Figure 3L:
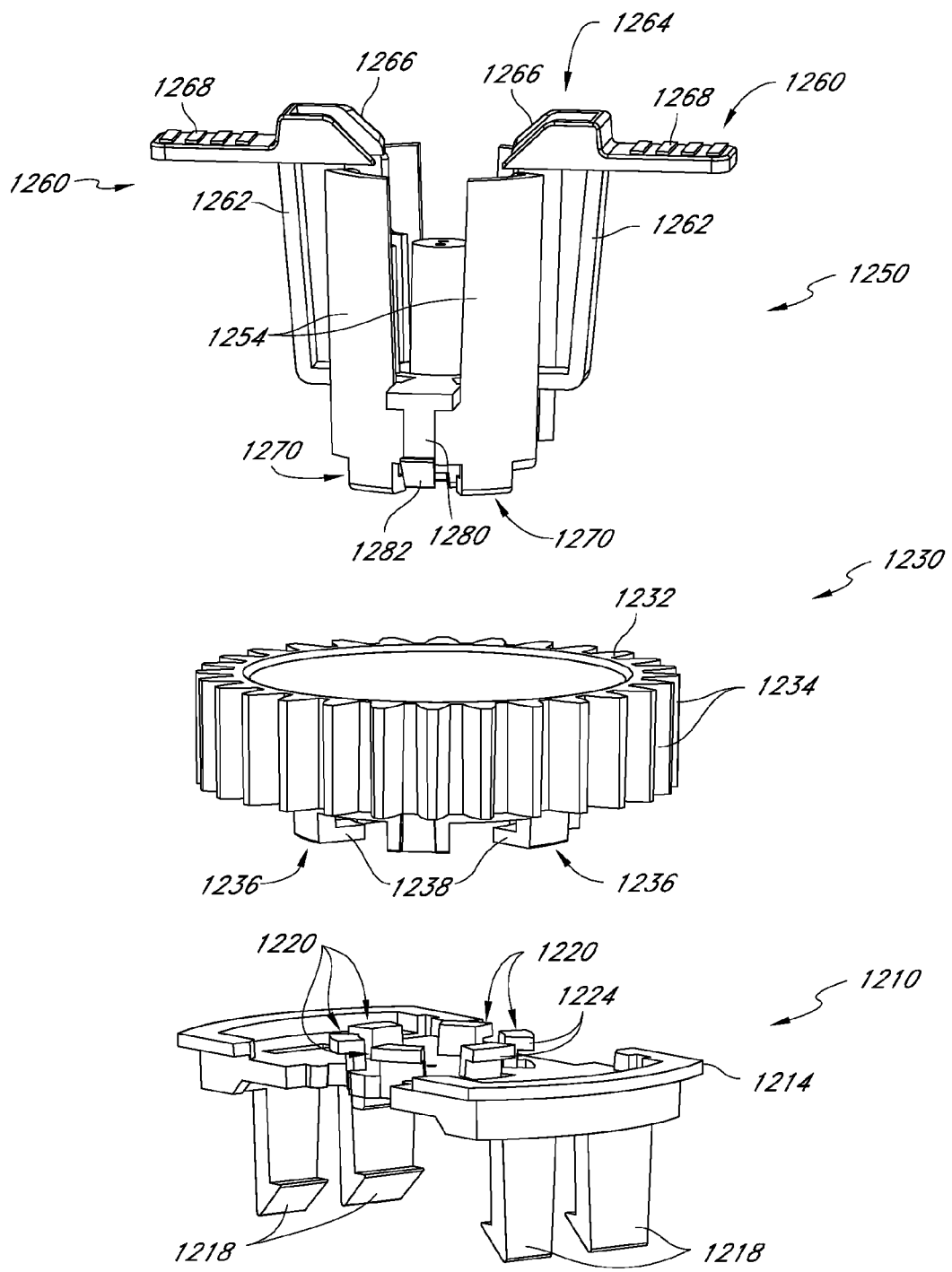
FIG. 3L illustrates an exploded perspective view of the nest or loading area of FIG. 3K.

With reference to the exploded perspective view of FIG. 3L, the attachment member 1210 can be similar to the lower portion of the nest 370 of FIG. 3C in that it is configured to secure to a cassette or another portion of a fluid delivery module. For example, as shown, the attachment member 1210 can include a base 1214 and a plurality of tabs 1218 extending therefrom. As discussed, the tabs 1218 can be used to engage a corresponding feature or area of a cassette (e.g., manifold, housing, etc.) and/or another portion of a fluid delivery module. Further, the attachment member 1210 can include a plurality of engagement members 1220 along an upper portion of the base 1214. In some arrangements, these engagement members 1220 comprise flanges 1224 that generally extend outwardly, toward the outer perimeter of the nest 370A. As described in greater detail herein, these engagement members 1220 can be sized, shaped and otherwise configured to mate with and permit rotation relative to corresponding members or features of the gear member 1230 and the clamp 1250.

Figure 3M:
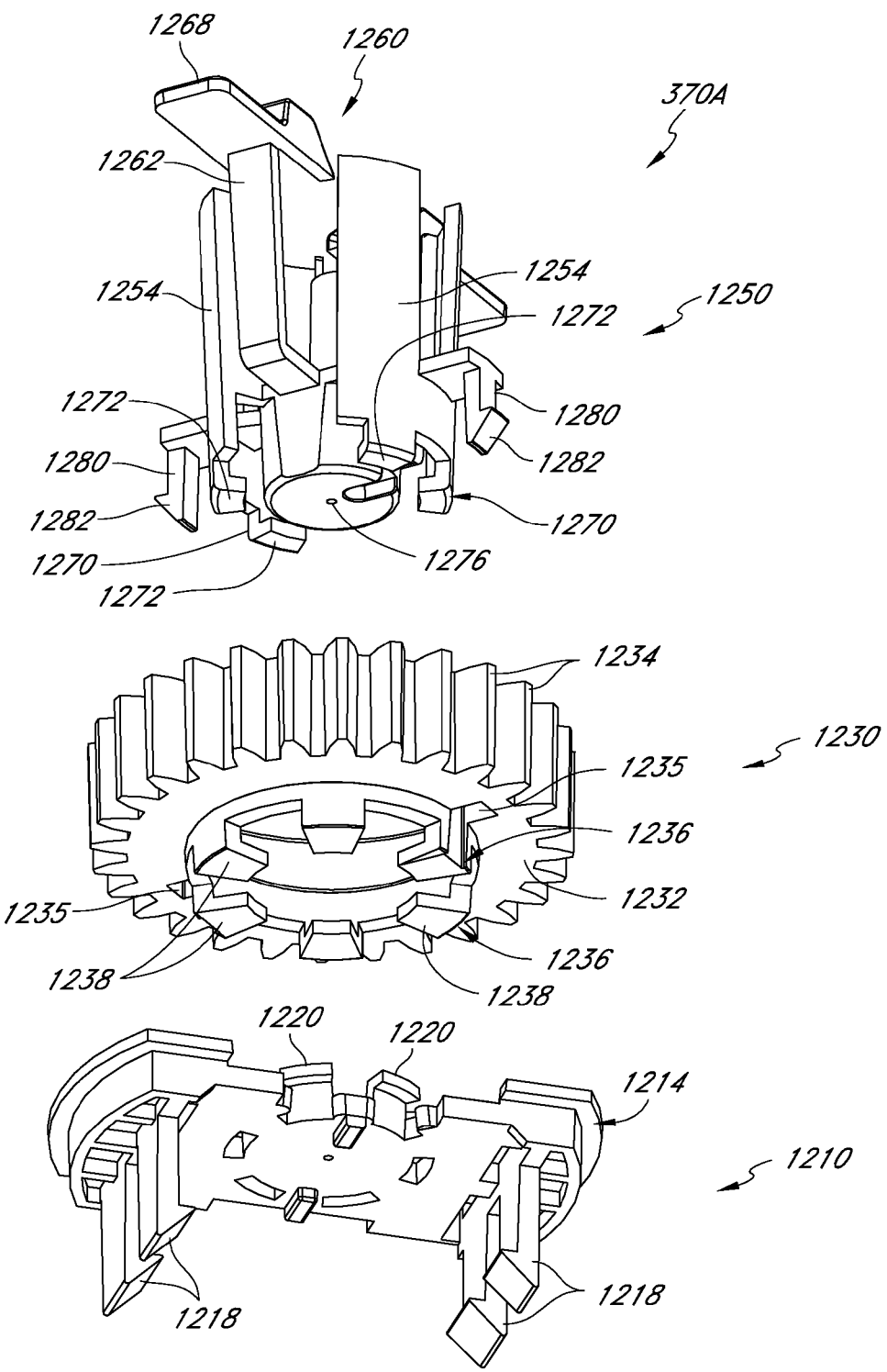
FIG. 3M illustrates an exploded bottom perspective view of the nest or loading area of FIG. 3K.
Figure 3N:
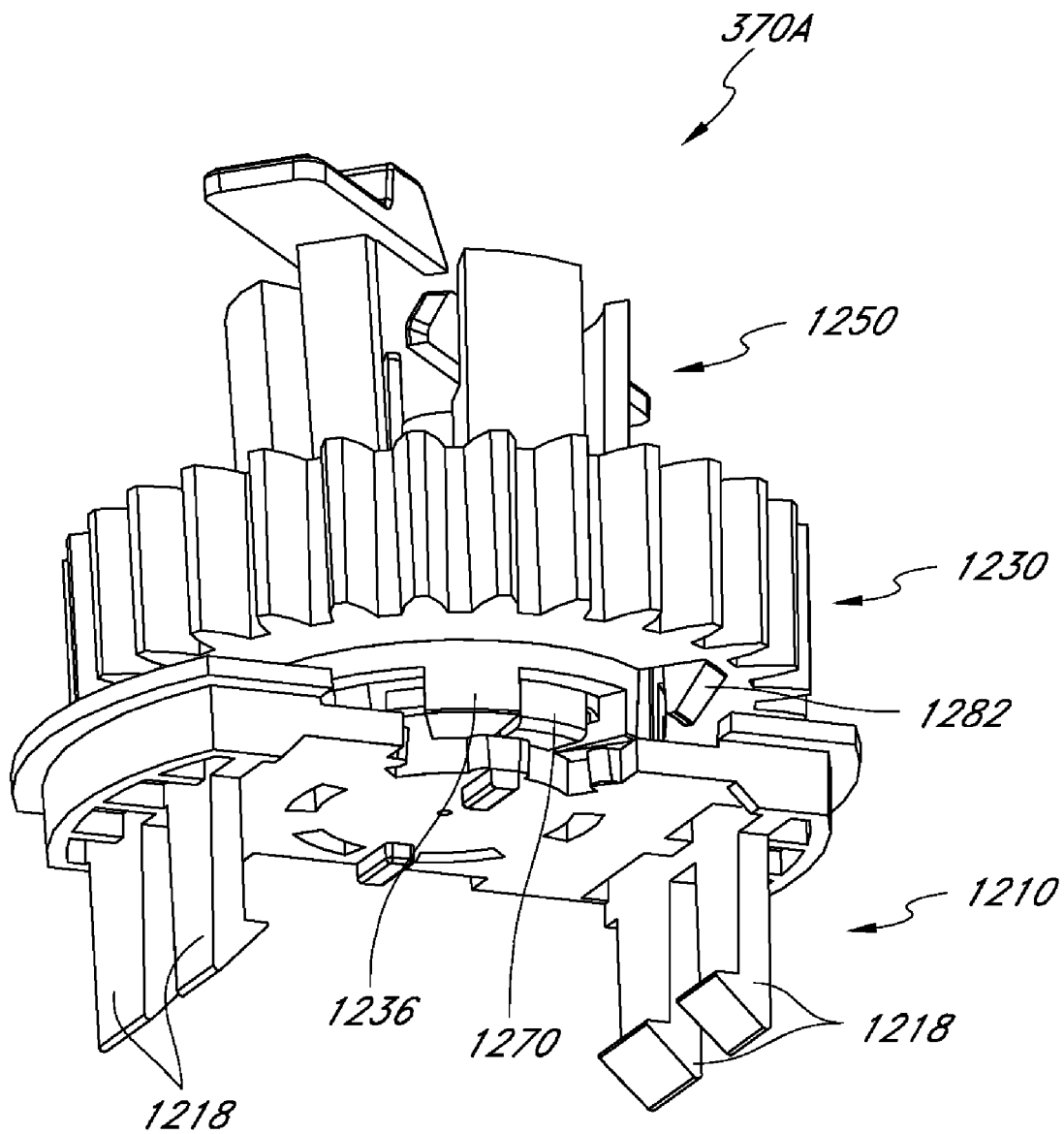
FIG. 3N illustrates a bottom perspective view of the nest or loading area of FIG. 3K.
Figure 30:
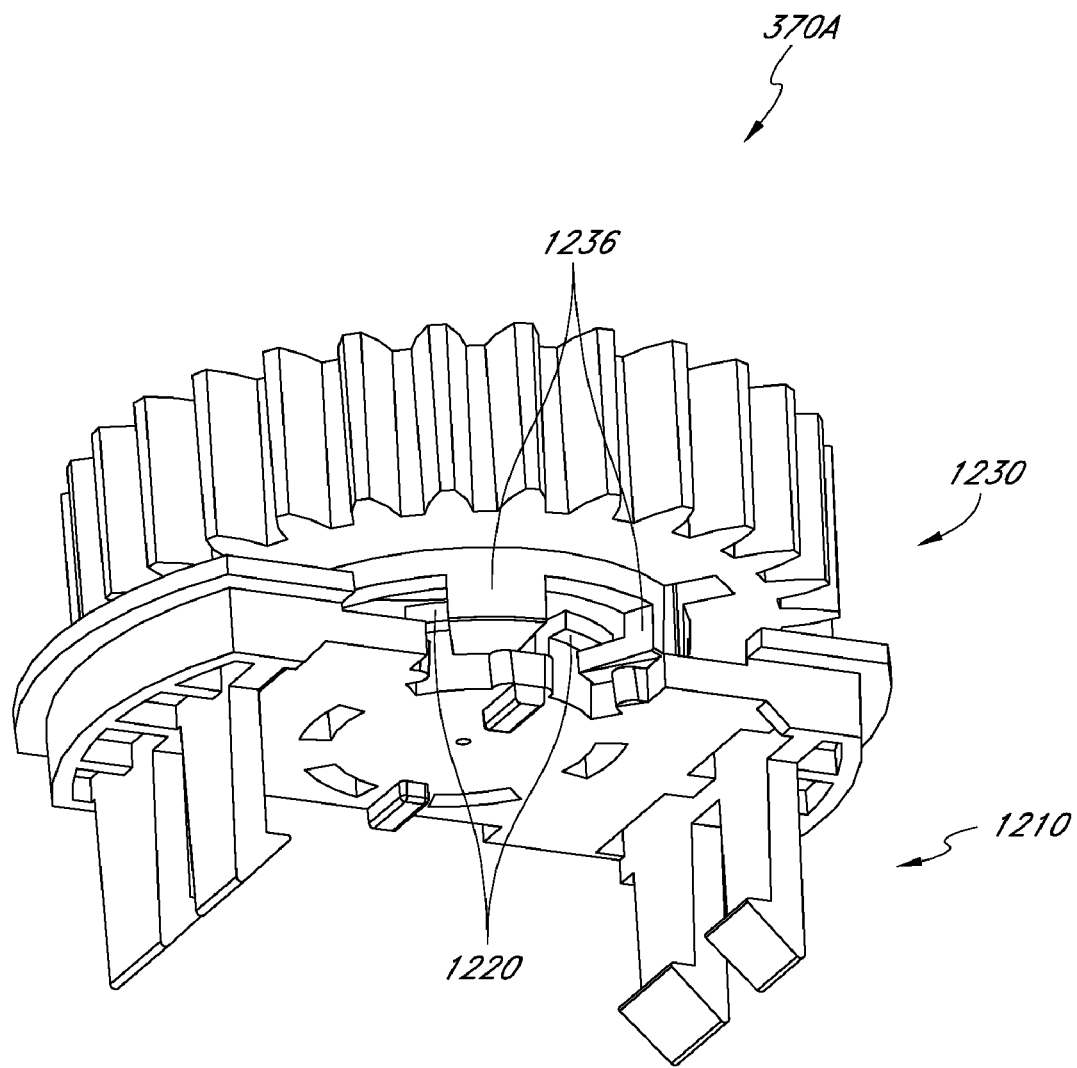
FIG. 30A illustrates a front perspective view of a tip configured for use in a handpiece assembly according to another embodiment.
FIG. 30B illustrates a side view of the tip of FIG. 30A.
FIG. 30C illustrates a front view of the tip of FIG. 30A.
FIG. 30D illustrates a rear perspective view of the tip of FIG. 30A.
FIG. 30E illustrates a rear view of the tip of FIG. 30A.
Figure 3P:
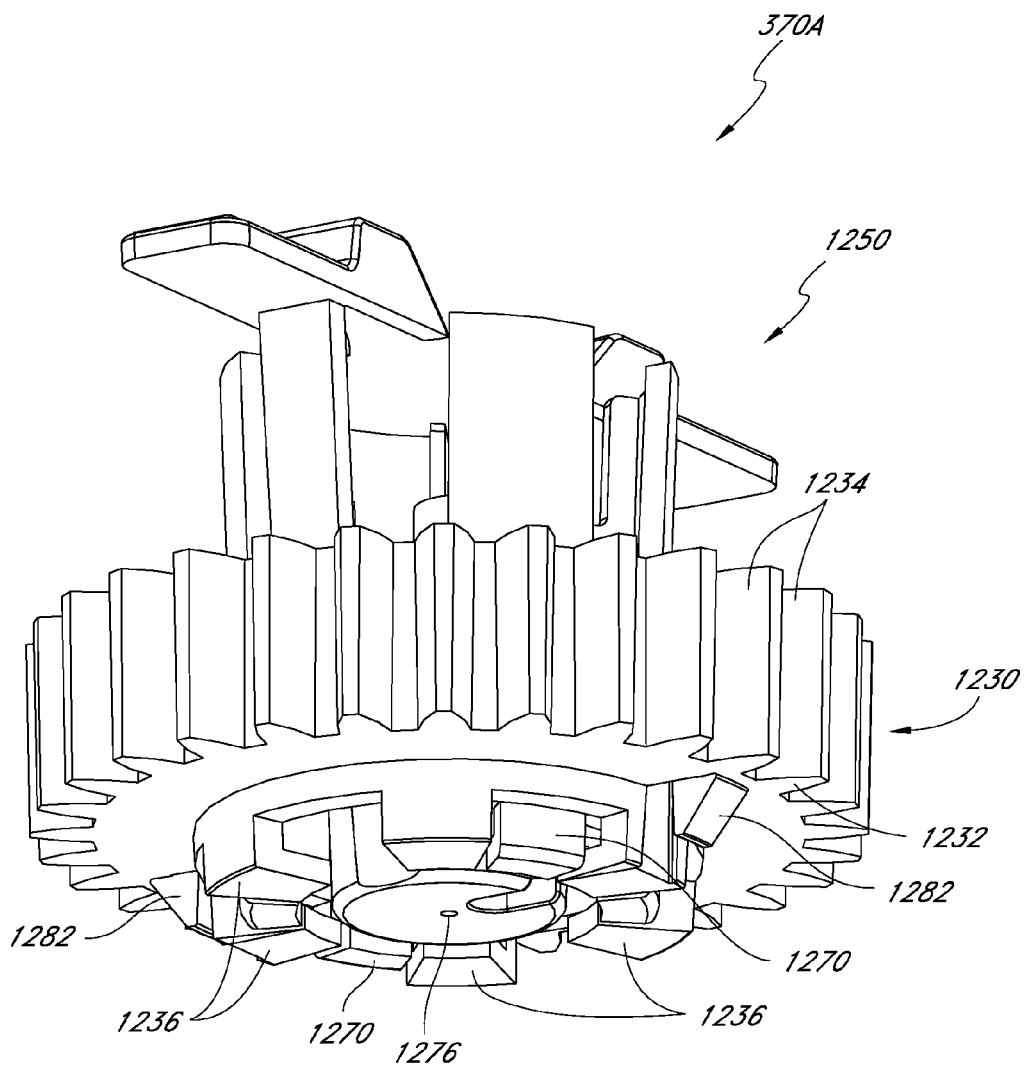
FIG. 3P illustrates a detailed bottom perspective view of the nest or loading area of FIG. 3K with the attachment member hidden for clarity.

With continued reference to FIG. 3L, the gear member 1230 can include a helical gear 1232 having a plurality of gear teeth 1234 along its periphery. In addition, the gear member 1230 can be configured to attach to a clamp 1250. For example, in the depicted embodiment, the clamp 1250 comprises two attachment members 1280 that generally extend downwardly. As shown, each attachment member 1280 can include a securement portion 1282 that is configured to securely fit within a corresponding opening 1235 of the gear member 1230 (FIG. 3M). FIG. 3P illustrates a bottom perspective view of the nest 370A with the attachment member hidden in order to reveal the interaction between the clamp 1250 and the gear member 1230 when these components are secured to each other. Thus, the securement portion 1282 of each attachment member 1280 can be moved sufficiently far within the corresponding opening 1235 so that the securement portion 1282 moves underneath the bottom surface of the gear 1234. According to some arrangements, the clamp 1250 is connected to the gear member 1230 in a manner that prevents or substantially prevents any relative movement (e.g., separation, rotation, etc.) between the two components.

With continued reference to FIG. 3M, the bottom of both the clamp 1250 and the gear member 1230 can comprise one or more engagement members 1270, 1236 that are sized, shaped and otherwise configured to complement and rotate relative to the engagement members 1220 of the attachment member 1210. For example, in the depicted arrangement, each engagement member 1270, 1236 of the clamp 1250 and the gear member 1230 includes an inwardly-facing flange 1272, 1238 that fits underneath the flanges 1220 of the attachment member 1210 when the nest 370A or loading area is properly assembled. Thus, the inwardly-facing engagement members 1270, 1236 of the clamp 1250 and gear member 1230 can be allowed to rotate relative to the outwardly-facing engagement members 1220 of the attachment member 1210. However, the respective tabs 1272, 1238, 1224 can be configured to prevent separation of the gear member 1230 from the adjacent attachment member 1210.

According to some embodiments, when the clamp 1250 is adequately connected to the gear member 1230, the engagement members 1270 of the clamp 1250 are configured to fit within corresponding slots or other openings of the gear member 1230. Thus, as illustrated in the perspective views of FIGS. 3N-3P, the engagement members 1270, 1236 of the two components can form an inwardly-facing flange that is adapted to mate with and rotate relative to the outwardly-facing flanges 1224 of the attachment member 1210. As a result, the clamp 1250 (and a vial or other container positioned therein) can be continuously or intermittently rotated relative to the attachment member 1210 and the cassette to which it is secured in order to provide the necessary or desired mixing or agitation to the medicaments, other fluid or substance and/or other contents of the vial.

Figure 3Q:
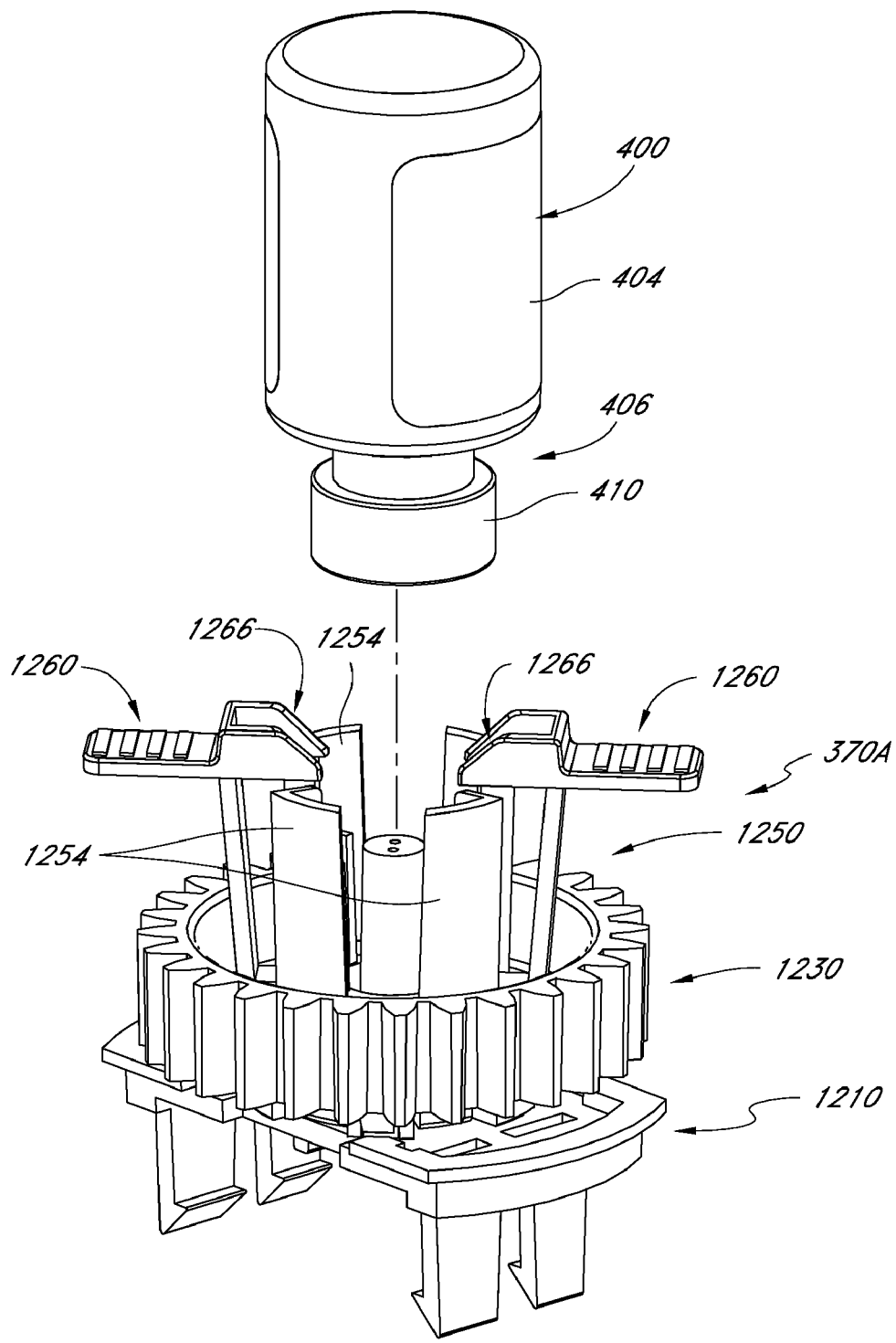
FIG. 3Q illustrates an exploded perspective view of the nest or loading area of FIG. 3K configured to receive a vial or other container.
Figure 3R:
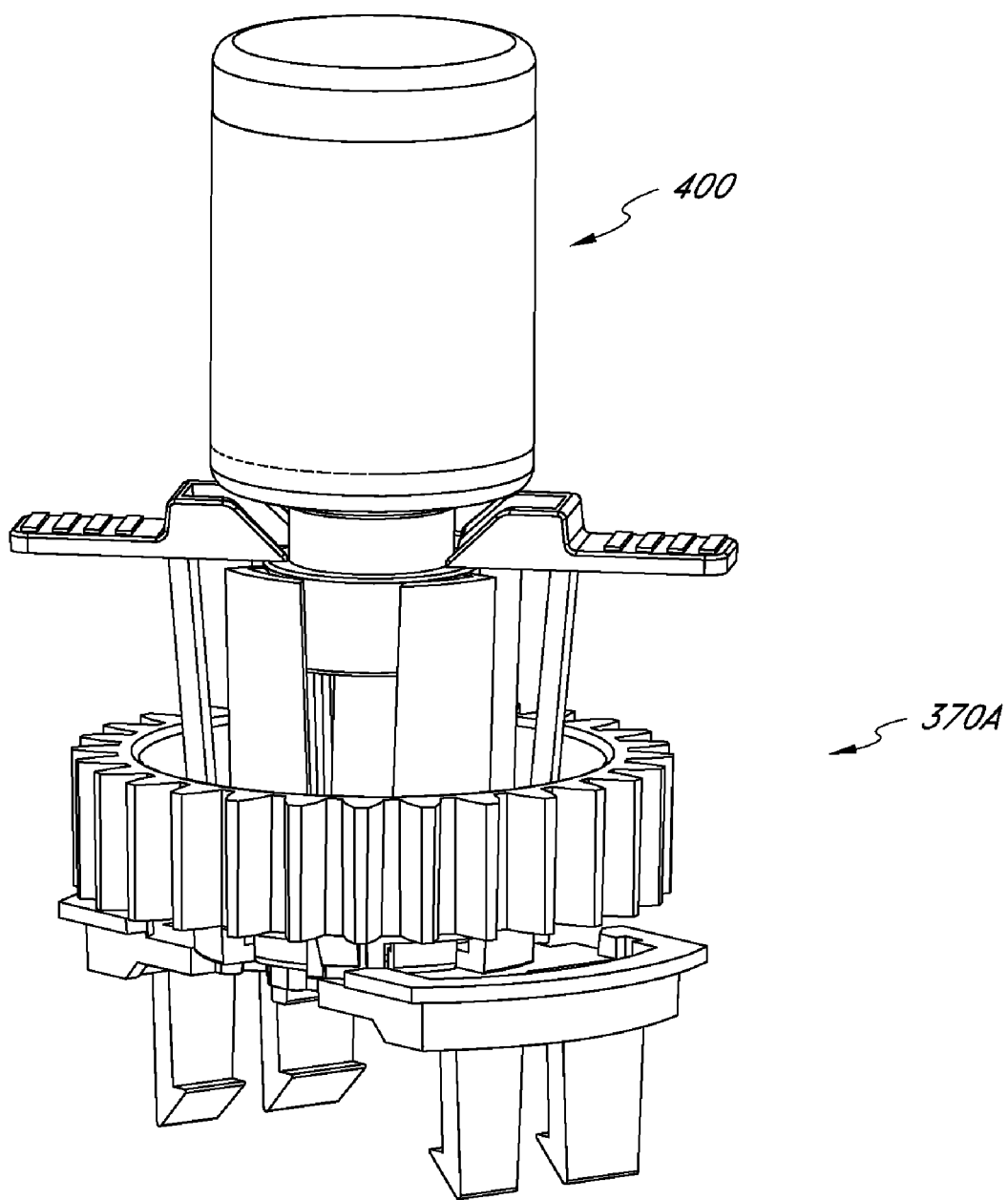
FIG. 3R illustrates a perspective view of a vial secured within the nest or loading area of FIG. 3K.

As illustrated in FIGS. 3Q and 3R, a vial 400 or other container can be secured within an interior region of the nest's clamp 1250 in a similar manner as described herein with reference to the nest 370 of FIG. 3C-3J. For example, clamp 1250 can include one or more walls 1254 or other portions that generally define a cylindrical region. In some arrangements, such a cylindrical region is sized, shaped and otherwise configured to accommodate vials or other containers having a variety of sizes, shapes, capacities, designs and/or other characteristics. In addition, as discussed with reference to FIGS. 3C-3J, the clamp 1250 can include oppositely-oriented wings 1260 that are configured to resiliently move outwardly when a vial or other container is inserted within the nest 370A or loading area. Accordingly, inwardly-facing locking members 1264 of the wings 1260 can releasably engage the closure or other portion of a vial when such a vial is inserted sufficiently deep into the interior region of the nest 370A or loading area. In some embodiments, the locking members 1264 comprise slanted surfaces that force the wings 1260 to move outwardly when a vial is being positioned within the nest 370A. In order to remove the vial 400 or other container from the nest 370A, the handles 1268 can be moved outwardly (e.g., away from each other) so that the closure 410 of the vial 400 can disengage from the adjacent surfaces of the wings' locking members 1264.

With reference to FIG. 3S, the gear member 1230 of the nest 370A or loading area can be selectively rotated by mating the gear 1232 with a complementary gear 1292 or other portion of a drive assembly 1290. The gear 1292 can be mechanically connected to a motor (not shown) or other mechanical device configured to rotate the drive gear and other mechanically-coupled members or components (e.g., shaft 1292). According to some embodiments, such a motor or other mechanical device is positioned within or on the fluid delivery module of an injection system. The gear 1292, shaft 1294 and other portions of the drive assembly 1290 can be removed in order to facilitate replacement of a cassette. For example, in one embodiment, the shaft 1294 of the drive assembly 1290 is routed through an opening of the cassette 300. Therefore, the gear 1292, the shaft 1294, the bolt or other coupling 1296 that ensures that the gear 1292 remains adequately secured to the shaft and/or any other components or portions of the drive assembly 1290 can be removed in order to allow the user to remove or replace a cassette 300. In other embodiments, the drive assembly 1290 is positioned or is otherwise configured to permit replacement of a cassette 300 without having to remove or otherwise manipulate the drive assembly 1290.

According to certain arrangements, the speed, frequency and other rotation details of the gear member 1230 (and thus the vial or other container secured within the nest 370A) can be varied. For example, the rotational speed can be automatically selected based on the type of medicaments, other fluids and/or other materials contained within a vial. Alternatively, the clinician or other used can manually set and/or adjust such rotational details, either before or during a procedure (e.g., by instructions provided to the touchscreen display of the fluid delivery module, by manipulating one or more controllers of the handpiece assembly and/or the like).

In any of the arrangements disclosed herein, or variations thereof, the nests or loading areas and/or other components of the cassette comprise one or more plastic, metal and/or other rigid, semi-rigid and/or flexible materials. The materials can be selected to withstand the various elements and potentially damaging conditions to which they may become exposed, including, but not limited to, forces, moments, temperature and pH variations, other physical or chemical factors and/or the like.

Figure 4A:
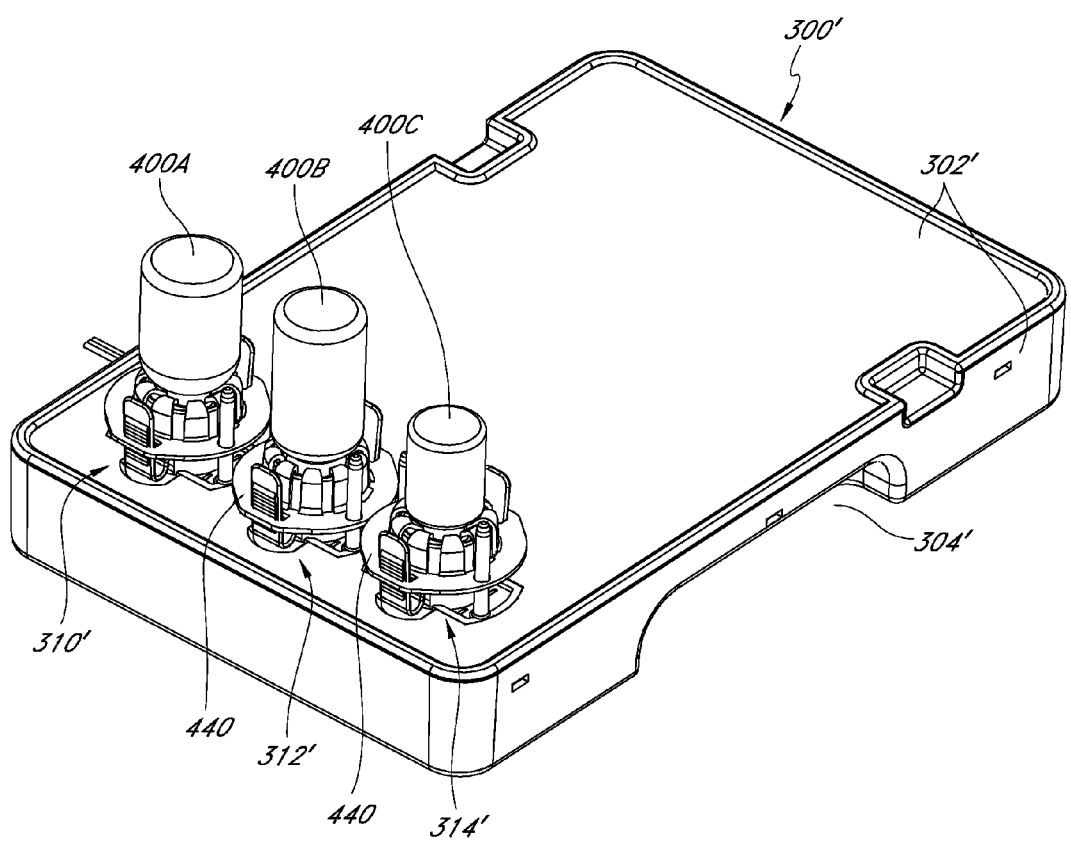
FIG. 4A illustrates a perspective view of a cassette configured to be inserted within a fluid delivery module according to another embodiment.
Figure 4B:
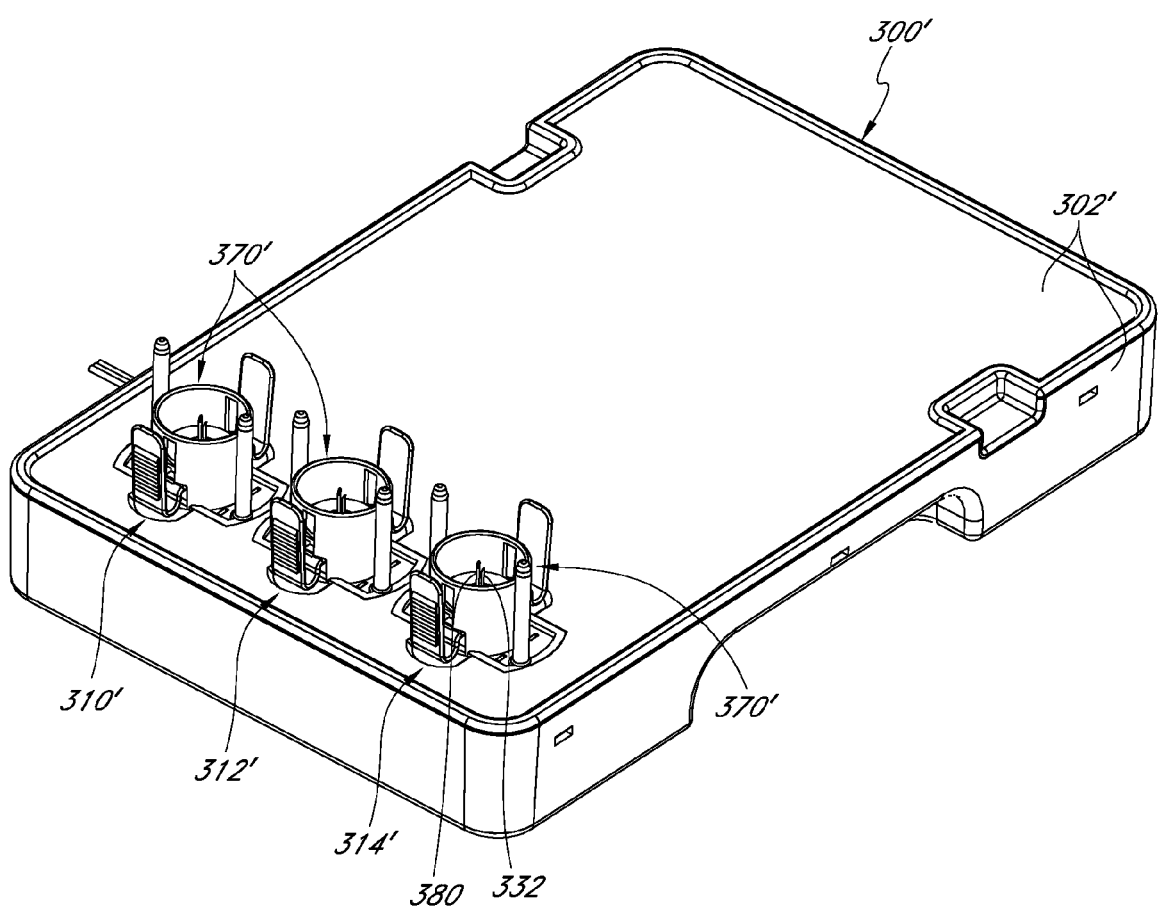
FIG. 4B illustrates a perspective view of the cassette of FIG. 4A with the vials removed from the loading areas or nests.

FIGS. 4A and 4B illustrate another embodiment of a cassette 300' configured to be positioned within a fluid delivery module, such as the one discussed herein with reference to FIG. 2A. In general, the depicted arrangement is similar to the cassette 300 of FIG. 3A in that it includes three receiving areas 310', 312', 314', each of which is adapted to accept a vial or other container. However, the receiving areas of the cassette shown in FIG. 4A include different types of nests 370' or loading areas than those of FIG. 3A. As shown, the nests 370' or loading areas of FIGS. 4A and 4B are adapted to engage and secure to vial adapters 440 that are positioned over the closure portions (e.g., neck, top, etc.) of the vials.

Detailed views of one embodiment of a loading area or nest 370' configured to be used in the cassette of FIGS. 4A and 4B are illustrated in FIGS. 5A-5F. As shown, the nest 370' can include a generally cylindrical portion 372' that is shaped, sized and otherwise configured to receive at least a portion of a vial or other container (e.g., the closure, neck, top, etc.). For example, according to several arrangements, the diameter of the cylindrical portion 372' is approximately 0.5 to 0.7 inches. However, in other embodiments, the size, shape and/or other details regarding the loading area or nest can vary, as desired or required. As discussed in greater detail herein, a main needle 332 and a vent needle 380 can be positioned within the interior of the cylindrical portion 372' of the loading area or nest 370'. Thus, when a vial or other container is secured to the nest, the main needle 332 and the vent needle 380 can help place the internal contents of the vial (e.g., medication, other fluid, other material or substance, etc.) in fluid communication with one or more subcomponents of the cassette 300 (e.g., syringe or other reservoir) and other components of the articular injection system. According to some arrangements, the main needle 332 is approximately 0.540 to 0.625 inches long and has a gauge of 22, and the vent needle 380 is approximately 0.950 long and has a gauge of 22. However, the gauge, length and/or other characteristics of the main needle 332 and/or the vent needle 380 can be different than disclosed herein, as desired or required for a particular application or use. For example, in some embodiments, the main needle 332 is about 0.1 to 2 inches long and has a gauge from about 15 to about 30, and the vent needle 380 is about 0.1 to 2 inches long and has a gauge from about 15 to about 30. The needles 332, 380 can comprise surgical-grade stainless steel and/or any other suitable materials (e.g., other metals, alloys, etc.).

With continued reference to the embodiment illustrated in FIGS. 5A-5F, the lower portion of the loading area or nest 370' comprises four tabs 384' that are adapted to snap or otherwise connect to the cassette 300 and/or a component located on or within the cassette. In other arrangements, a nest can include more or fewer that four tabs 384' as desired or required. Further, one or more other connection devices (e.g., threads, screws, other mechanical fasteners, rivets, etc.) or methods (e.g., gluing, welding, etc.) can be used to attach the nest 370' to the cassette 300, either in lieu of or in addition to the tabs 384'.

As shown, the loading area or nest 370 can include one or more wings 376' or similar members positioned adjacent to the cylindrical portion 372'. In the depicted arrangement, the wings 376' comprise a plurality of teeth 378' or other engagement members along a portion of their outer surface. As discussed and illustrated in greater detail herein, such wings 376' and teeth 378' positioned thereon can be used to releasably maintain the position of a vial or other container relative to the nest 370'. In addition, the loading area or nest can comprise one or more posts 374' or other positioning members that are used to properly align the vial and any item or component (e.g., adapter) attached thereto in relation to the cassette 300. One or more other features or devices can be used to secure a vial to and/or align a vial with the cassette 300.

The main needle 332 and/or the vent needle 380 can be attached to the nest 370'. Alternatively, one or both of the needles 332, 380 can be attached to the housing 302 or another portion of the cassette 300. In the embodiment illustrated in FIGS. 5C, 5D and 5F, the main needle 332 extends below the bottom of the cylindrical portion 372' of the loading area or nest 370', thereby enabling the needle 332 to place another component (e.g., manifold) of the cassette 300 in fluid communication with the interior of the respective vial or other container secured onto the nest 370'. As best depicted in the cross-sectional view of FIG. 5F, the vent needle 380 can terminate at a vent area 382' that allows the vent needle 380 to be in fluid communication with ambient air. This permits air to enter into the vial or other container to displace the volume of fluids and/or other substances which are removed from the vial or other container. Accordingly, the emptying of the vials and other containers secured to the cassettes 300 is advantageously facilitated.

Figure 5A:
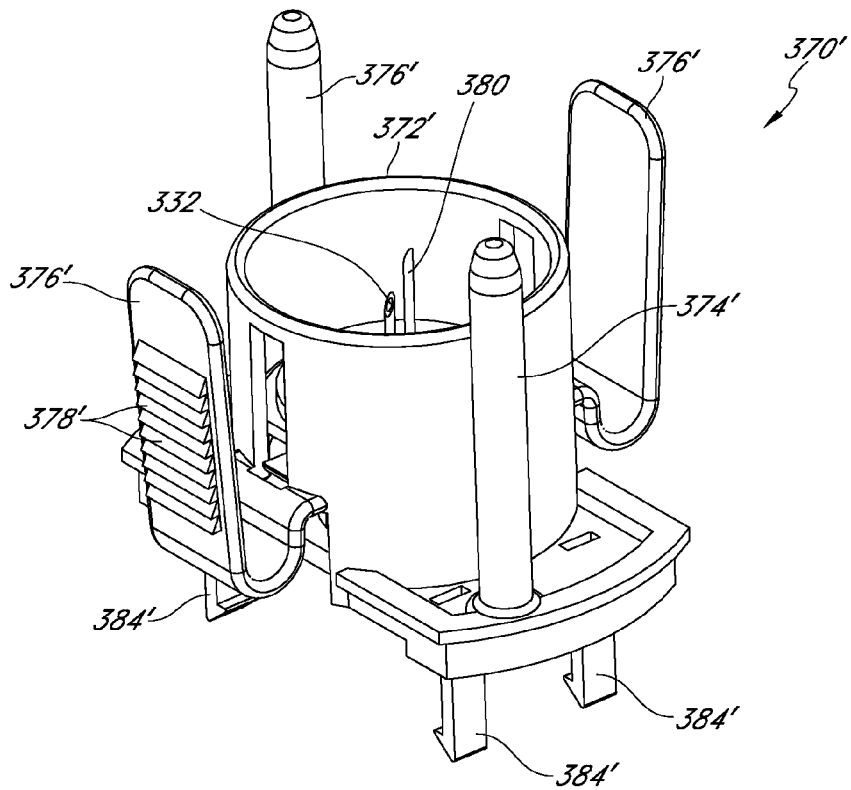
FIG. 5A illustrates a top perspective view of a nest or loading area configured for use with a cassette according to one embodiment.
Figure 5B:
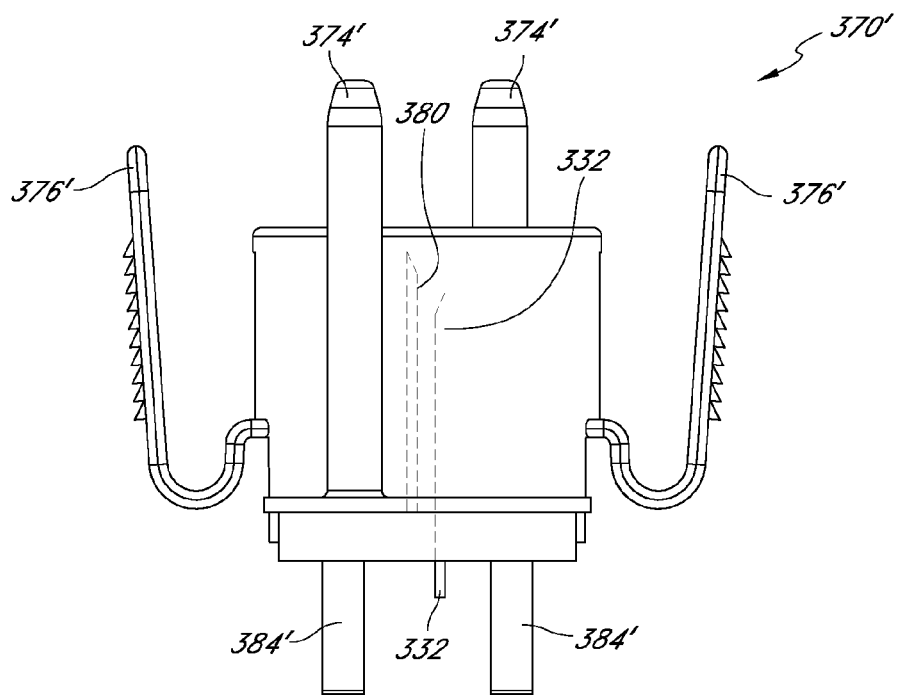
FIGS. 5B and 5C illustrate side views of the nest of FIG. 5A.
Figure 5C:
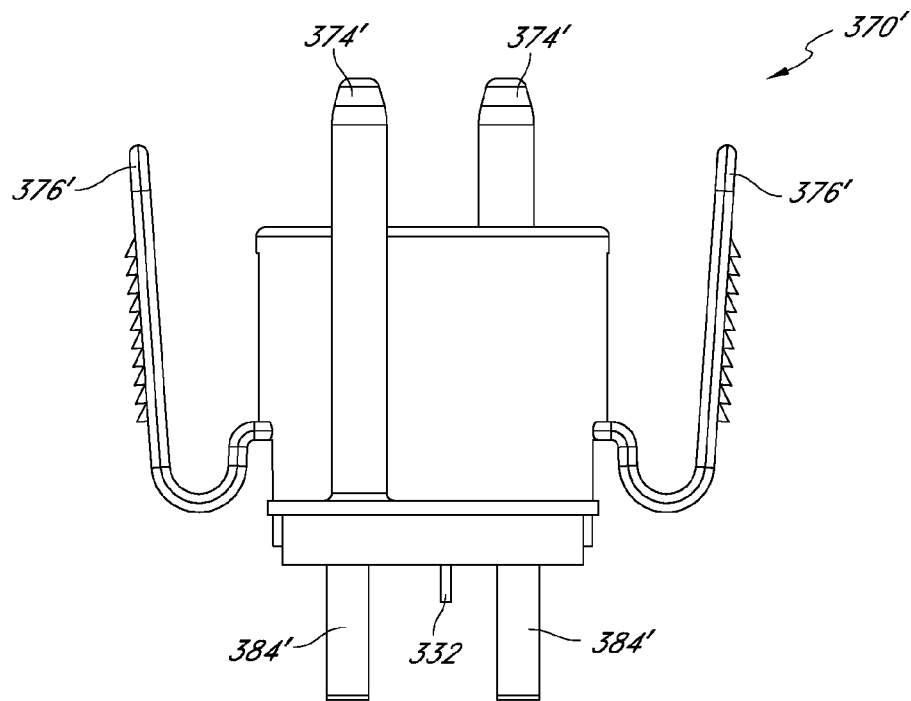
Figure 5D:
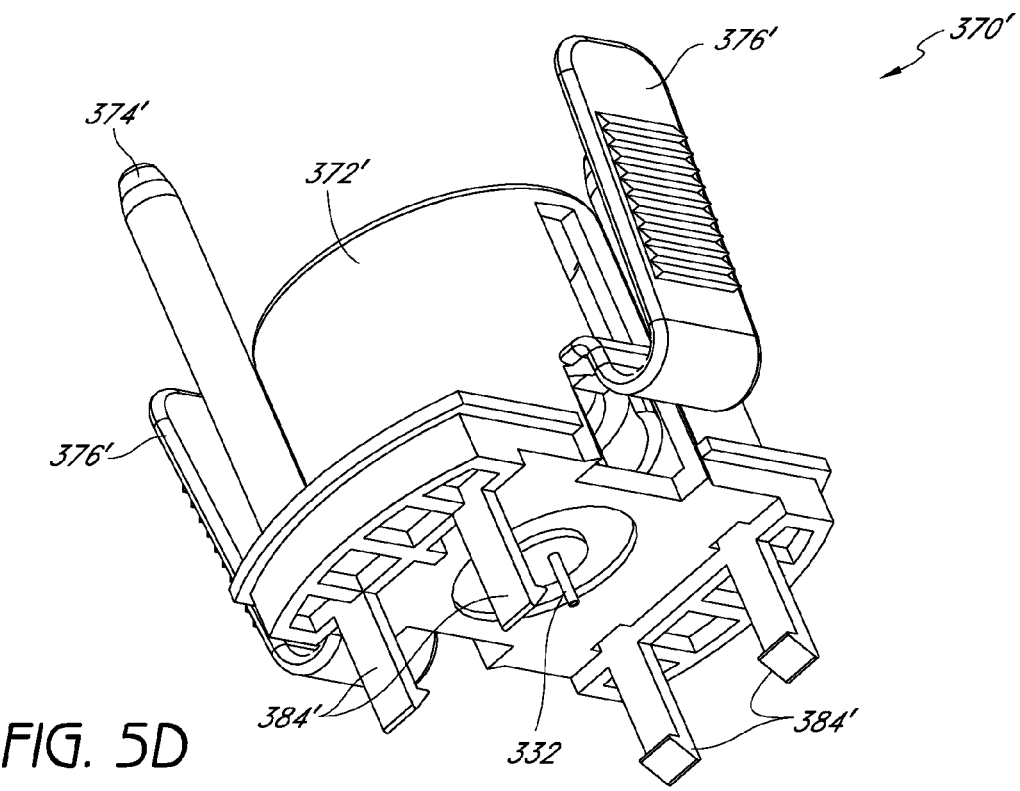
FIG. 5D illustrates a bottom perspective view of the nest of FIG. 5A.
Figure 5E:
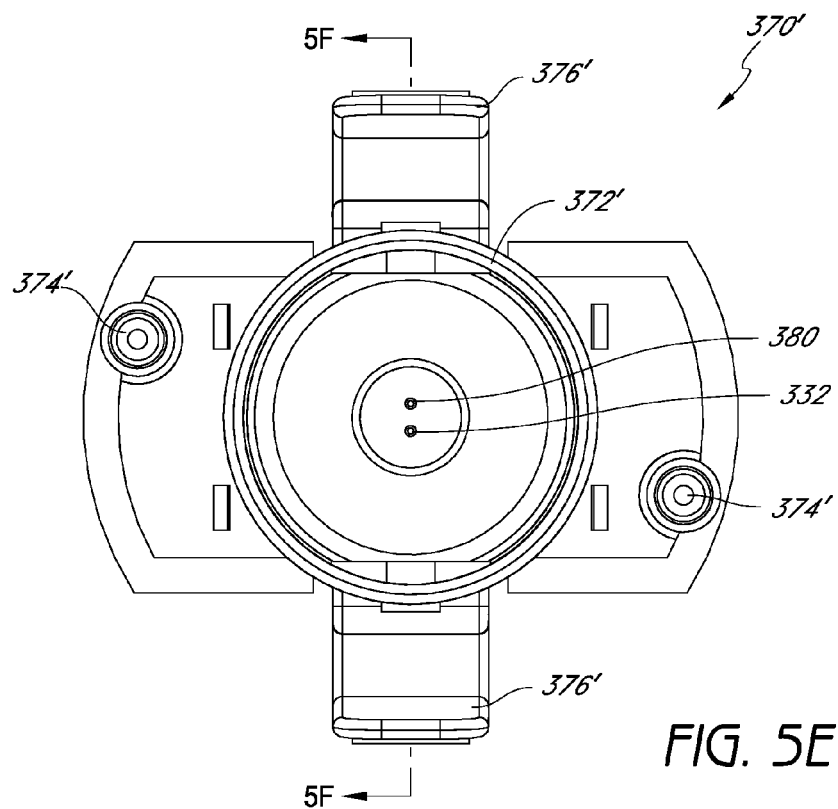
FIG. 5E illustrates a top view of the nest of FIG. 5A.
Figure 5F:
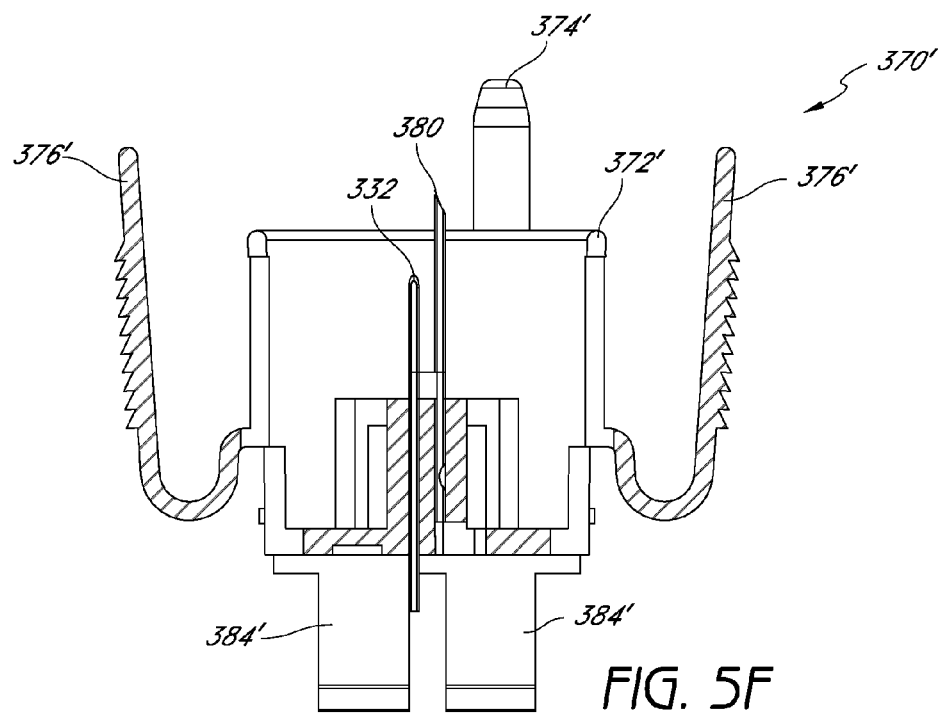
FIG. 5F illustrates a cross-sectional view of the nest of FIG. 5A.
Figure 6:
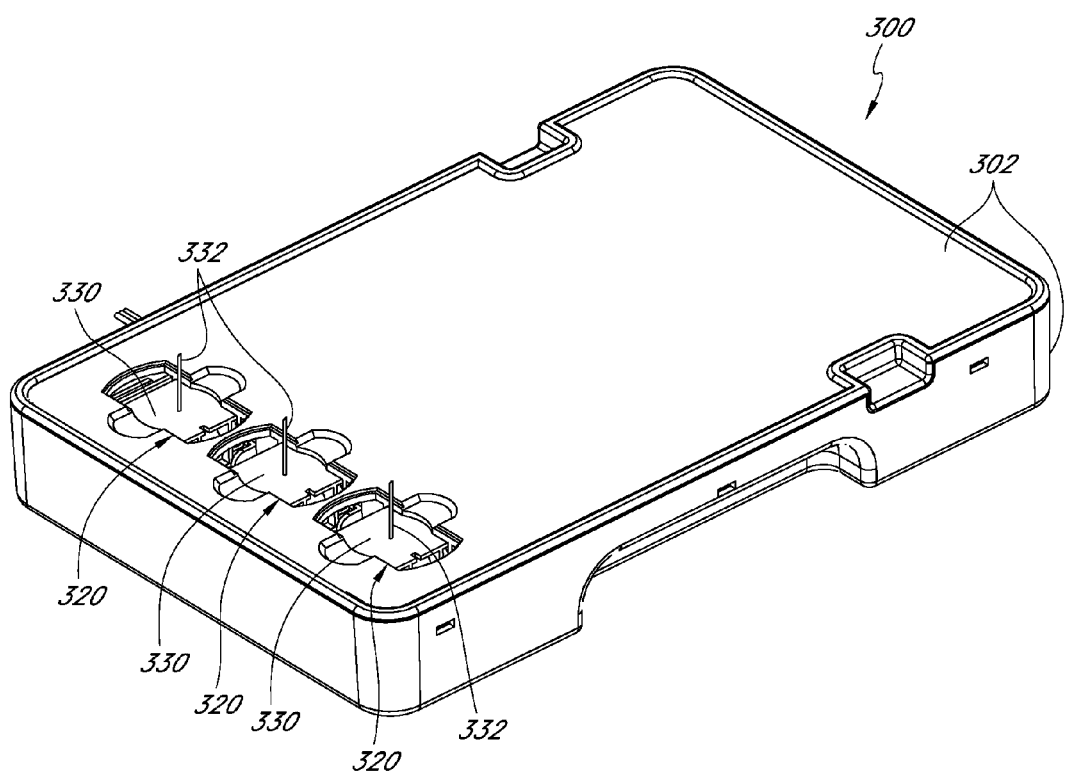
FIG. 6 illustrates a perspective view of one embodiment of a cassette with the loading areas or nests removed.

FIG. 6 illustrates the cassette 300 of FIG. 3A or 4A with the respective loading areas or nests 370, 370A, 370' removed. In the depicted embodiment, each of the main needles 332 that extends through the interior of the cylindrical portion of the respective nest 370, 370A, 370' (see FIGS. 3C-3R and 5A-5F) is attached to a manifold 330 positioned within the interior of the cassette 300. In some arrangements, the cassette is adapted to receive one or more of the various nest configurations disclosed herein or variations thereof. For example, as illustrated in FIGS. 3A and 3B, a cassette 300 can include two nests 370 of the same type and one nest 370A configured to provide mixing to the internal contents of a vial or other container secured therein. Additional details regarding the manifold 330 and other components and features of the cassette 300 are provided herein with reference to FIGS. 7A-12B.

Figure 7A:
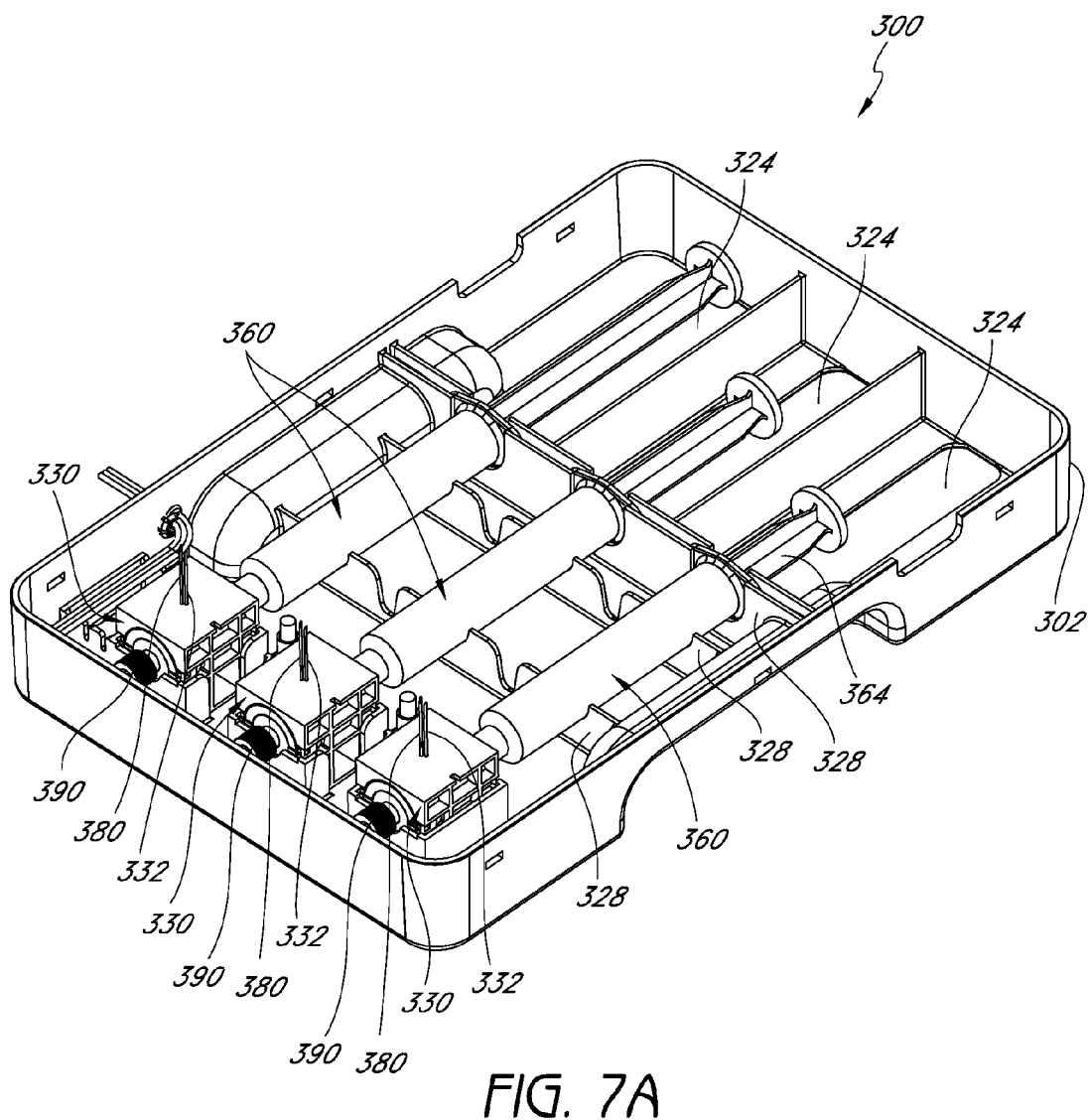
FIG. 7A illustrates a perspective view of the cassette of FIG. 6 with the top surface of the cassette housing removed for clarity.
Figure 7B:
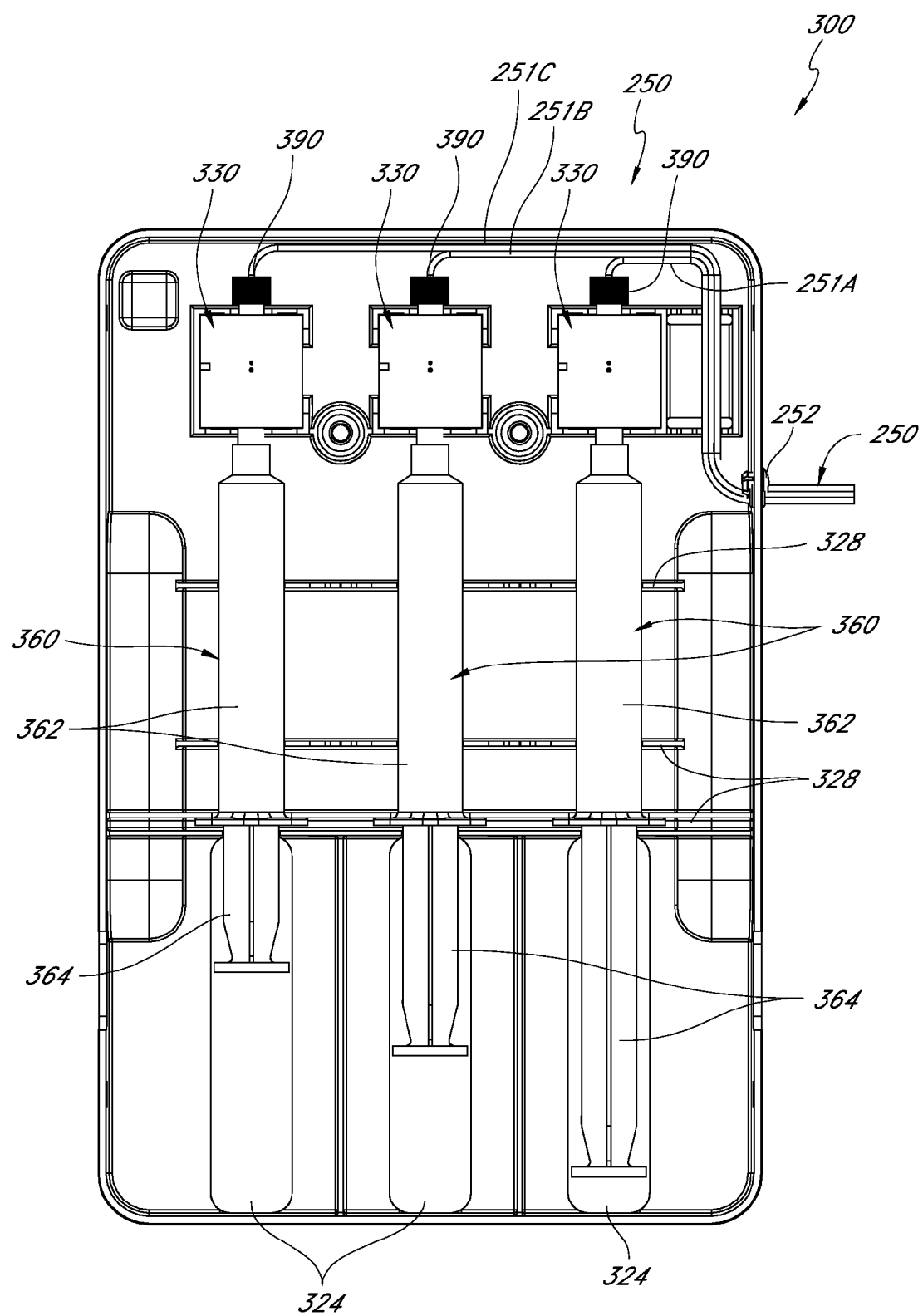
FIG. 7B illustrates a top view of the cassette of FIG. 6 with the top surface of the cassette housing removed for clarity.

In FIGS. 7A and 7B, the top portion of a cassette housing 302 has been removed to reveal the interior of the cassette 300. As shown, the cassette 300 can comprise one manifold 330 and one syringe 360 for each receiving station 310, 312, 314, 310', 312', 314' (FIGS. 3A and 4A). In the illustrated embodiment, the interior of the cassette 300 includes grooves and other recesses into which the various components of the cassette 300 can be positioned. For example, one or more interior surfaces (e.g., bottom, top, etc) of the cassette 300 can comprise rectangular recesses 326 and/or other features that are sized, shaped and otherwise configured to receive the manifolds 330. In addition, the cassette 300 can include one or more other positioning baffles 328 or other members that are configured to support and securely maintain the position of the syringes 360 and/or any other component of the cassette 300. In the depicted arrangement, the positioning baffles 328 include slots that are sized, sized and otherwise adapted to receive one or more portions of the syringes 360. It will be appreciated that in other embodiments the manifolds 330, syringes 360 and/or any other component or feature can be secured to the cassette 300 using one or more other attachment method or device (e.g., adhesives, fasteners, etc.), either in addition to or in lieu of the recesses 326, positioning baffles 328 and other features illustrated in FIG. 7A.

With continued reference to FIGS. 7A and 7B, each syringe 360 positioned within the cassette 300 can include an inner plunger 364 that is slidably movable within an outer barrel 362. In some embodiments, such syringes 360 are standard plastic, sterile syringes. Alternatively, the syringes 360 can be non-standard syringes that are specifically designed for use with a cassette 300. In addition, the syringes 360 can comprise one or more other materials (e.g., glass), as desired or required. As discussed and illustrated in greater detail herein, movement of the inner plunger 364 away from the outer barrel 362 (e.g., in a direction generally away from the manifold 330), can cause fluids and/or other materials from the respective vial 400A-400C (FIGS. 3A and 4A) to be drawn into the interior of the syringe 360. Once one or more fluids and/or other materials have been loaded into the syringe 360, a stepper motor, a pump, another mechanical or pneumatic device and/or the like can be used to selectively move the inner plunger 364 toward the manifold 330, thereby delivering a desired volume of such fluids and/or other materials to the handpiece assembly of the articular injection system. As discussed in greater detail herein, a stepper motor or other device can be used to initially move the inner plunger 364 away from the manifold 330 in order to transfer fluids and/or other materials from a vial into the corresponding syringe 360 or other reservoir.

According to some arrangements, in part for patient safety, the pump or other fluid transfer device is configured to accurately measure and regulate the flowrate and/or pressure of a medication, fluid and/or other material being delivered to a patient. Thus, the system can comprise pressure and/or flow measurement devices (e.g., pressure transducers, flowmeters, etc.). Pressure sensing devices can be used to ensure that the pressure or vacuum created by the discharge of the medication, fluid or other material within the anatomy does not exceed a particular threshold level. This can help prevent or reduce the likelihood of damage occurring to the patient being treated using the injection/aspiration system. Such an internal force measurement system can be configured to automatically shut off the pump or other transfer device when the discharge pressure exceeds a maximum level (e.g., 3 psi. levels lower or higher than 3 psi, etc.). In other arrangements, the fluid delivery module and/or any other portion of the injection system (e.g., handpiece assembly) can include a visual and/or audible alarm or other similar feature to alert the user than a threshold pressure has been attained, either in lieu of or in addition to any automatic shut-off mechanism. It will be appreciated that such safety features can be included in any of the embodiments of the modules or systems disclosed herein.

In the illustrated arrangement, the cassette 300 includes a plurality of slots 324 or other openings adjacent to the syringe plunger 364 (e.g., generally along the normal range of slidable motion of the plunger 364 relative to the barrel 362). Thus, an arm, lever or other actuation device mechanically or operatively connected to a motor or other movement device can be used to slidably move the inner plunger 364 relative to the outer barrel 362 of the syringe 360 to selectively transfer fluids and/or other materials into or out of the syringes 360.

With continued reference to the cassette 300 illustrated in FIG. 7B, as a fluid and/or other material is selectively expelled through a syringe 360, it travels through an interior portion of the downstream manifold 330 to an outlet coupling 390. In some embodiments, the outlet coupling 390 places the syringe 360 and manifold 330 in fluid communication with an outlet conduit 251A-251C. Collectively, the different conduits 251A-251C can comprise a delivery line 250 that is configured to deliver fluids and/or other materials from the cassette 300 to a handpiece assembly for injection into a targeted anatomical location (e.g., a joint). As shown in FIG. 7B, the delivery line 250 can be routed out of the interior of the cassette 300 through an opening 252 located along the outer housing.

Figure 7C:
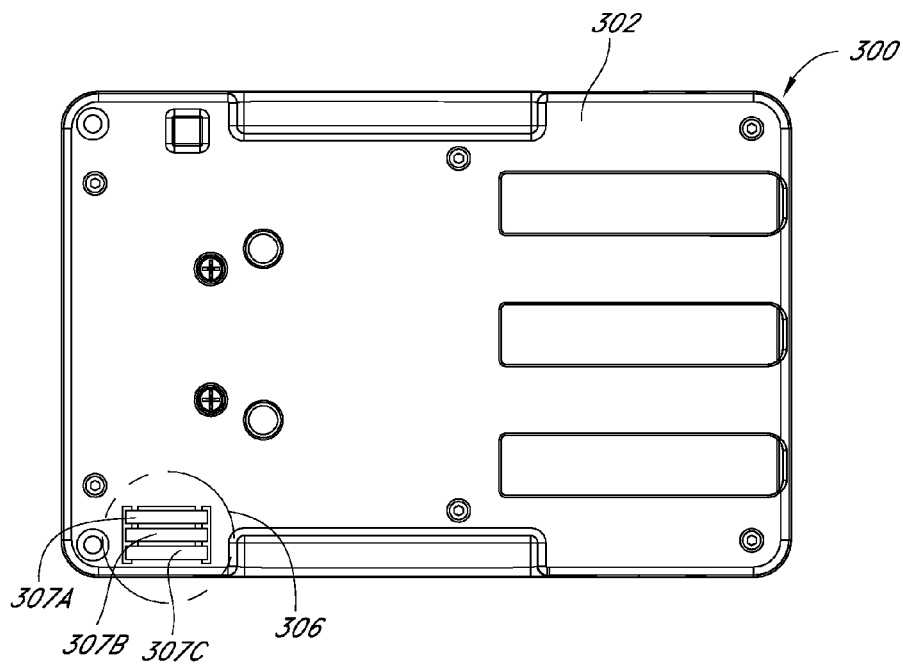
FIG. 7C illustrates a bottom view of a cassette comprising a viewing area for the delivery line according to one embodiment.

According to some embodiments, the injection system can be adapted to detect the presence of air or other gases within any of the conduits that place the cassette or another portion of the fluid delivery module in fluid communication with a downstream handpiece assembly. This can help reduce or eliminate the likelihood of a potentially dangerous, harmful, painful or otherwise unintended air infusion into a patient's anatomy. Thus, as illustrated in FIG. 7C, a cassette 300 can include a viewable area 306 along one or more portions of its housing 302 that allows for visual inspection of the various conduits configured to convey fluids and/or other materials from the manifolds of the cassette to the handpiece assembly. The viewable area 306 can include a separate inspection strip 307A-307C for each conduit of the delivery line.

Figure 7D:
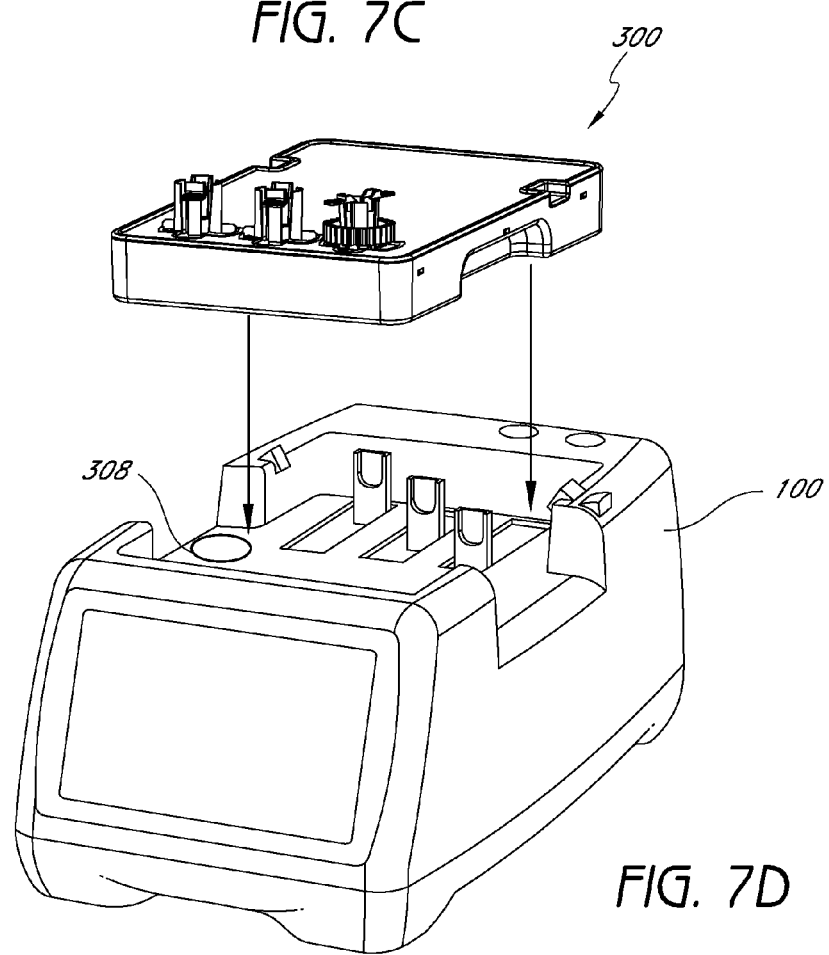
FIG. 7D illustrates a perspective view of a fluid delivery module comprising an optical sensor for detecting air or other gases within a delivery line according to one embodiment.

In some arrangements, the viewing area 306 is positioned along a bottom surface of the cassette housing 302 and is configured to align with an optical sensor 308 housed on or within the fluid delivery module 100 (FIG. 7D). Thus, portions of the conduits that are immediately adjacent to the viewable area 306 can be at least partially transparent or translucent to permit the optical sensor 308 to detect the characteristics of the fluids and/or other materials passing therethrough. Accordingly, air or other gas bubbles within the conduits can be detected by the optical sensor 308 as they travel past the inspection strips 307A-307C of the cassette 300. Once one or more bubbles are detected, the injection system can be configured to terminate the injection procedure, provide a warning to the clinician or other user and/or take any other action. According to some embodiments, the air or other gas bubbles are purged from the system before the injection procedure can be resumed. For example, a predetermined volume of fluid and/or other substance being conveyed in the conduits where air or gas was detected can be wasted or otherwise sacrificed to ensure that it has been eliminated from the system.

In certain arrangements, the optical sensor 308 is configured to detect the presence of air or other gas bubbles within a conduit by monitoring the refractive index of the conduits, as air and other gases refract light differently than the liquids and/or solids being transferred within the delivery line. The fluid delivery module 100 and/or any other portion of the injection system can include one or more other devices or methods for detecting the presence of undesirable air or other gases within the delivery line, either in addition to or in lieu of the optical sensor system described and illustrated herein. For example, one or more mechanical sensors, pressure sensors, ultrasonic sensors, capacitance sensors, or combinations thereof, can be used in addition to or instead of optical sensors.

Figure 8:
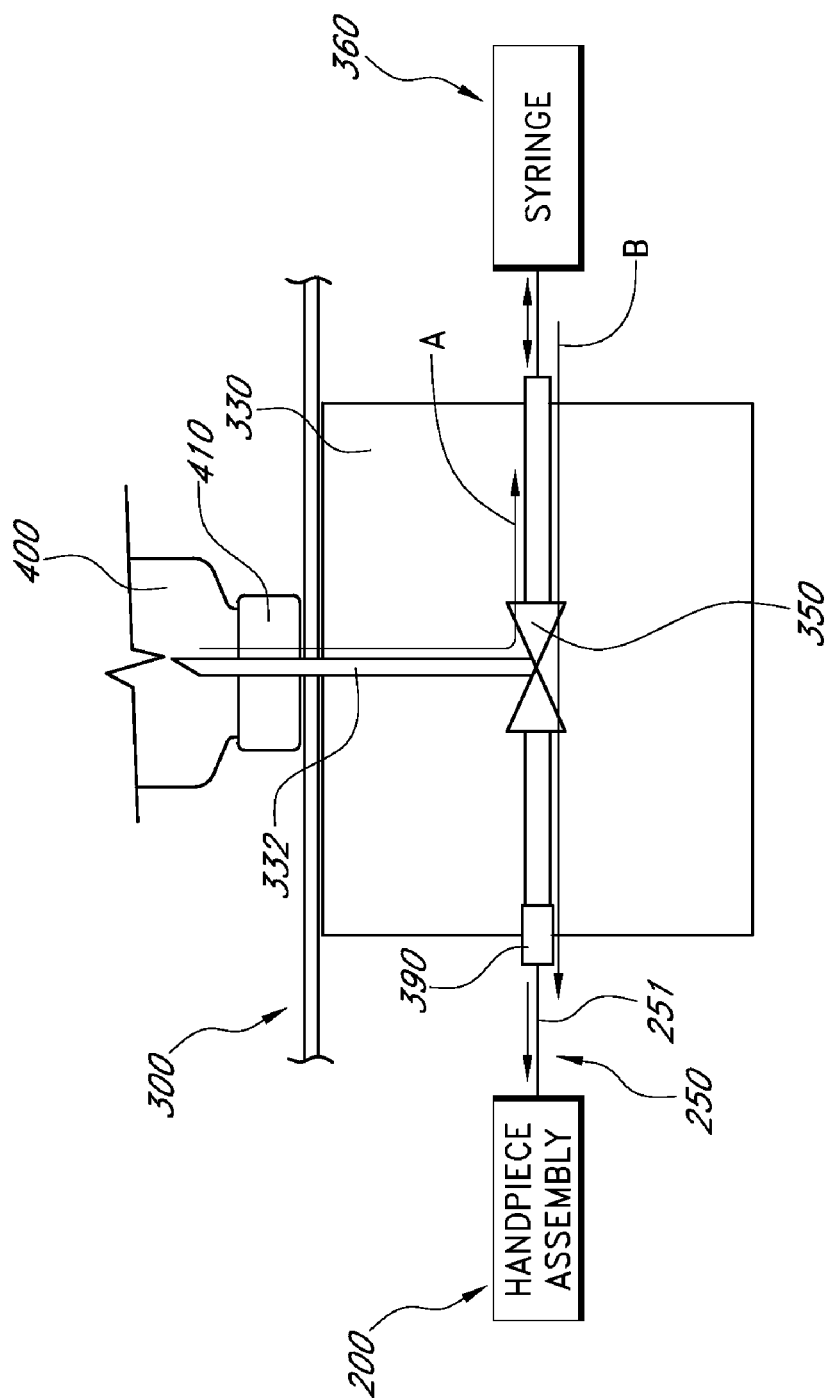
FIG. 8 illustrates a schematic of the transfer of fluids and/or other materials between a vial, a manifold and a syringe or other reservoir positioned within a cassette according to one embodiment.

FIG. 8 illustrates one embodiment of a schematic generally representing the movement of fluids and/or other materials within and between various components of an articular injection system, such as, for example, a vial 400, a manifold 330, a syringe 360, other components or portions of a cassette 300, a handpiece assembly 200 and/or the like. As shown, once a vial 400 is properly secured to a receiving site of a cassette 300, a main needle 332 can be configured to extend into the interior of the vial 400. In some embodiments, the closure 410 of vial 400 comprises a septum or other pierceable membrane or member (not shown) through which the needle 332 may pass. As a result, the medication, other fluid and/or other materials contained within the vial 400 can be advantageously placed in fluid communication with the main needle 332.

Next, in order to load the syringe 360 with the internal contents of the vial 400, the inner plunger of the syringe 360 can be retracted relative to the outer barrel. As discussed in greater detail herein, a motor, actuator or other device within the fluid delivery module can be used to selectively move the inner plunger relative to the outer barrel. Accordingly, the suction created within the syringe 360 can cause the fluid and/or other materials contained within the vial 400 to be drawn into the syringe 360 in the direction generally represented by arrow A in FIG. 8. Thus, fluids and/or other materials can be delivered from the vial 400 to the syringe 360 through a valve 350 or other flow-control device. In some embodiments, the valve 350 comprises a combination duckbill-umbrella valve that is configured to permit flow in the direction generally represented by arrow A when suction is created within the syringe 360. This can help ensure that no fluids or other materials are inadvertently transferred toward the delivery line 250 and handpiece assembly located downstream of the manifold 330. Alternatively, one or more other types of valves and/or flow schemes may be used.

With continued reference to the schematic of FIG. 8, once fluids and/or other materials have been transferred from the vial 400 to the syringe 360, the fluid delivery module can be used to selectively transfer a desired volume or amount of such fluids and/or other materials to a downstream handpiece assembly 200. In one embodiment, the syringe 360 is configured to draw out the entire contents of the vial 400 during the initial loading stage. Alternatively, only a portion of the internal contents of a vial 400 or other container can be transferred to the syringe 360 before such contents are selectively delivered to the handpiece assembly 200 and/or other downstream components of the injection system.

Once a syringe 360 has been properly loaded with fluids and/or other materials, a desired volume of such fluids and/or other materials can be selectively transferred through the manifold 330. The transfer of fluids and/or materials from the syringe 360 to downstream components of the injection system (e.g., delivery line 250, handpiece assembly 200, etc.) can be accomplished with the help of a mechanical, hydraulic and/or other type of device. For example, a stepper motor or other actuator can be configured to operate the syringe 360 (e.g., move the inner plunger relative to the outer barrel) in order to selectively transfer fluids and/or other materials from the syringe 360 toward the manifold 330. In the depicted embodiment, fluids and/or other materials are transferred from the syringe toward the delivery line 250 in a direction generally represented by arrow B. Thus, fluids and/or other materials can be routed through the same valve 350 that is used to control the transfer of fluids and/or other materials from the vial 400 (or other container) to the syringe 360. For example, the valve 350 or other flow control device can be configured to allow flow in a direction generally represented by arrow B when a sufficiently high positive pressure is created within the syringe 360. This can be accomplished by using a specially-designed valve 350 (e.g., a combination duckbill-umbrella valve) that regulates flow of fluids and/or other materials in certain desired directions depending on the type of forces and pressures exerted within the syringe 360 (e.g., negative or suction, positive, etc.). Additional details regarding flow through such a combination duckbill-umbrella valve 350 are provided herein in reference to the discussion of FIGS. 11A-11C.

In other embodiments, the quantity, type, orientation, general configuration and other details of the passages, valves and/or other components of the manifold 330 and/or other components of a cassette 300 can vary, as desired or required. Further, the general manner in which the syringes 360 are filled with the internal contents of the vials or other containers can be different than discussed and illustrated herein. For example, in some embodiments, the contents of the vials 400 can gravity flow into desired portion (e.g., syringe 360, other reservoir, etc.) of the cassette 300. In other arrangements, the vials 400 or other containers can be directly secured within an interior of the cassette 300 or other portion of the fluid delivery module. Moreover, a cassette 300 need not include a syringe 360, a manifold 330 and/or any other component or feature illustrated and discussed herein. Other methods or devices can be utilized to load a fluid and/or other material into cassette 300 for later delivery to a downstream handpiece assembly 200 or other component of an articular injection system.

With continued reference to the schematic of FIG. 8, a fluid or other material exiting through an outlet fitting 390 of the manifold 330 can be routed to a conduit 251. Conduits 251 from two or more different manifolds 330 can comprise a delivery line 250, which, as discussed in greater detail herein, can advantageously place the cassette 300 in fluid communication with a handpiece assembly 200.

Figure 9A:
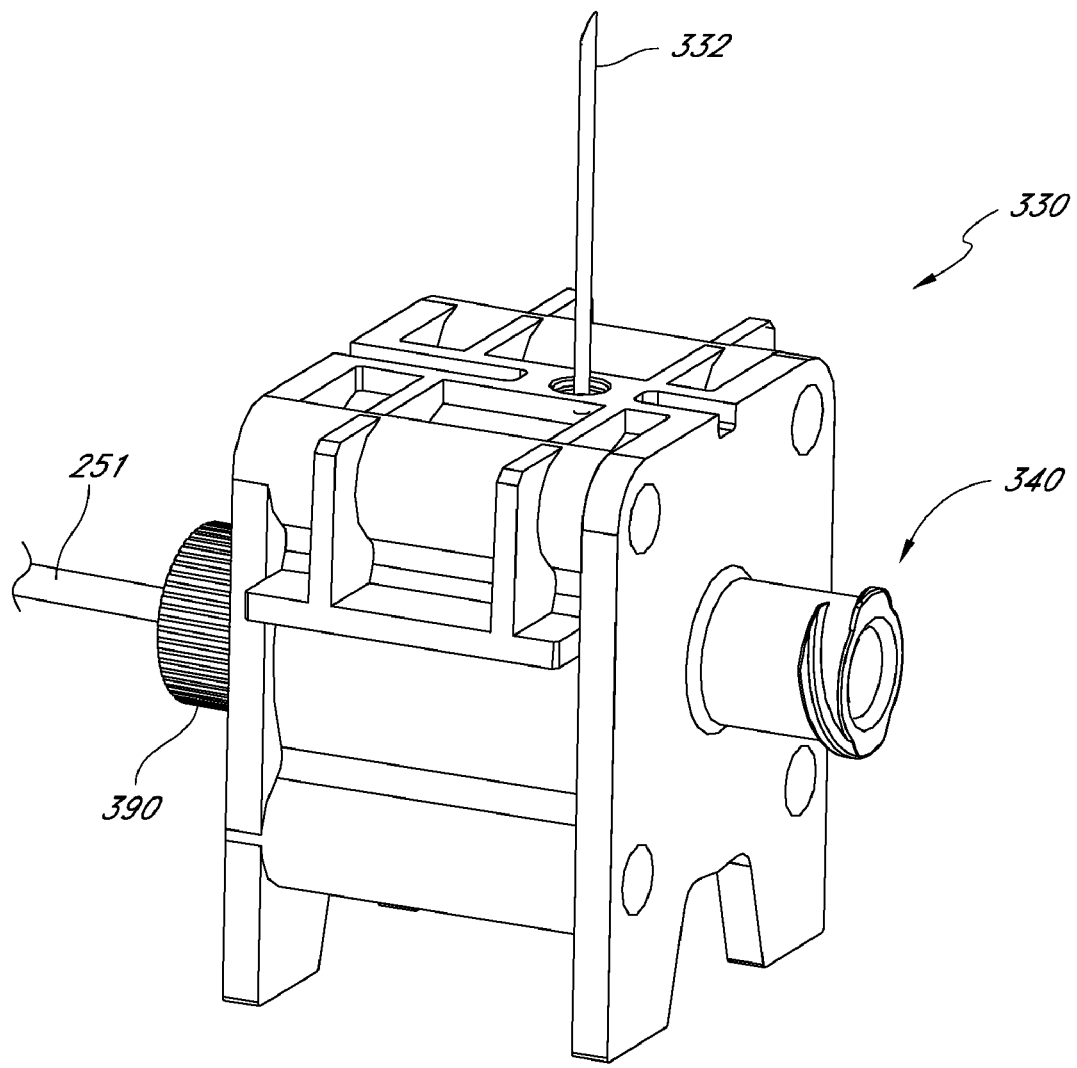
FIG. 9A illustrates a perspective view of a manifold configured for use in a cassette according to one embodiment.

FIG. 9A illustrates one embodiment of a manifold 330 for use in a cassette 300. As shown, the manifold 330 can include an inlet 340 into which the distal end of a syringe or other reservoir attaches. In some embodiments, the inlet 340 (and/or the outlet) of the manifold 330 is adapted to receive a standard or non-standard fitting or corresponding mating portion (e.g., a luer, a coupling 390, etc.). As discussed, an outlet coupling 390 can be used to place the manifold 330 in fluid communication with a downstream conduit 251. In some embodiments, a main needle 332 is used to place one or more internal fluid passages of the manifold 330 in fluid communication with a vial or other container that may be removably secured to a cassette. The main needle 332 can be attached to the manifold 330. Alternatively, the main needle 332 can be attached to a loading area or nest 370, 370', 370A or any other component or portion of the cassette 300 or fluid delivery module.

Figure 9C:
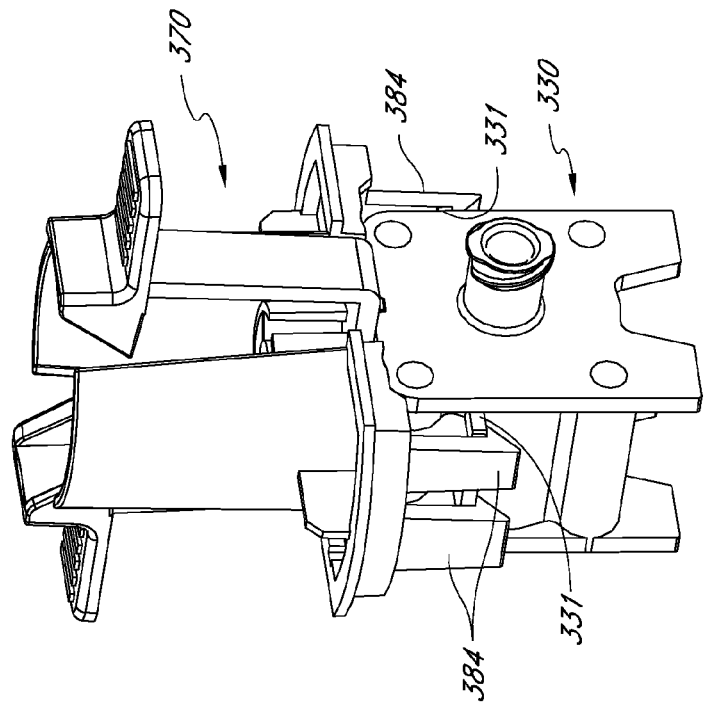
FIG. 9C illustrates a perspective view of the manifold of FIG. 9B with a nest or loading area secured thereto.
Figure 9B:
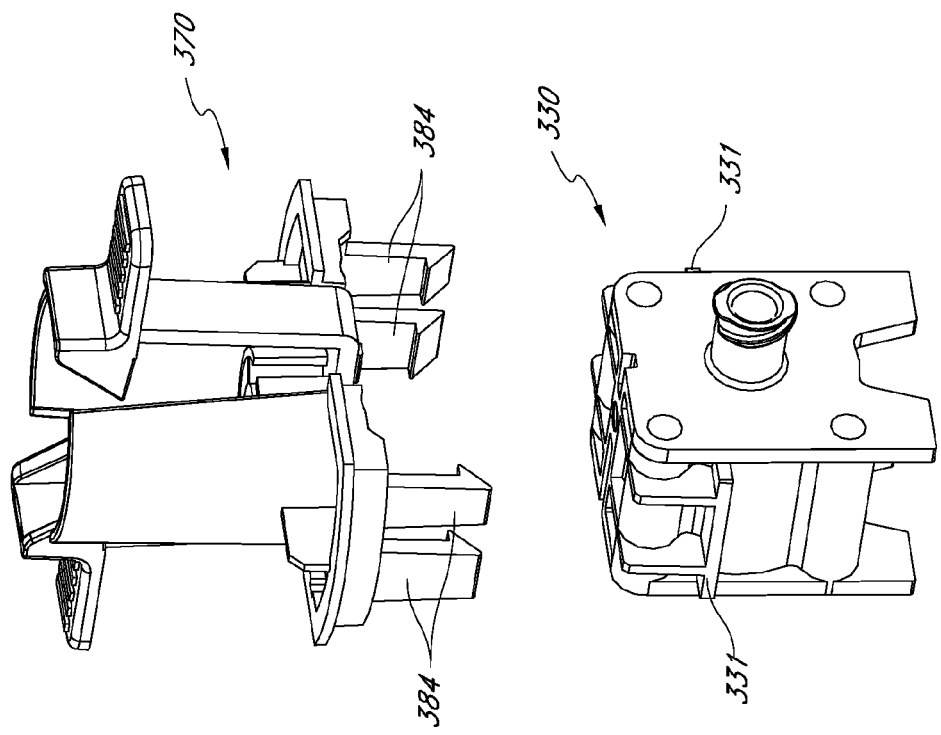
FIG. 9B illustrates an exploded perspective view of the manifold of FIG. 9A and a nest or loading area configured to be positioned thereon according to one embodiment.

One embodiment of a loading area or nest 370 secured to the manifold 330 of FIG. 9A is illustrated in FIGS. 9B and 9C. As discussed herein with reference to FIGS. 3C-3H, the nest 370 can include a plurality of tabs 384 or other members that are adapted to snap onto or otherwise engage one or more portions of the manifold 330 or cassette. In the illustrated arrangement, the ends of such tabs 384 are shown resiliently engaged to one or more features (e.g., ribs 331) located along an exterior surface of the manifold 330. For clarity, the top surface of the cassette housing has been omitted in FIGS. 9B and 9C. In other embodiments, however, the nest 370 can be secured to the manifold 330 and/or other portion of the cassette 300 using one or more other devices or methods, either in lieu of or in addition to the snaps 384.

Figure 9D:
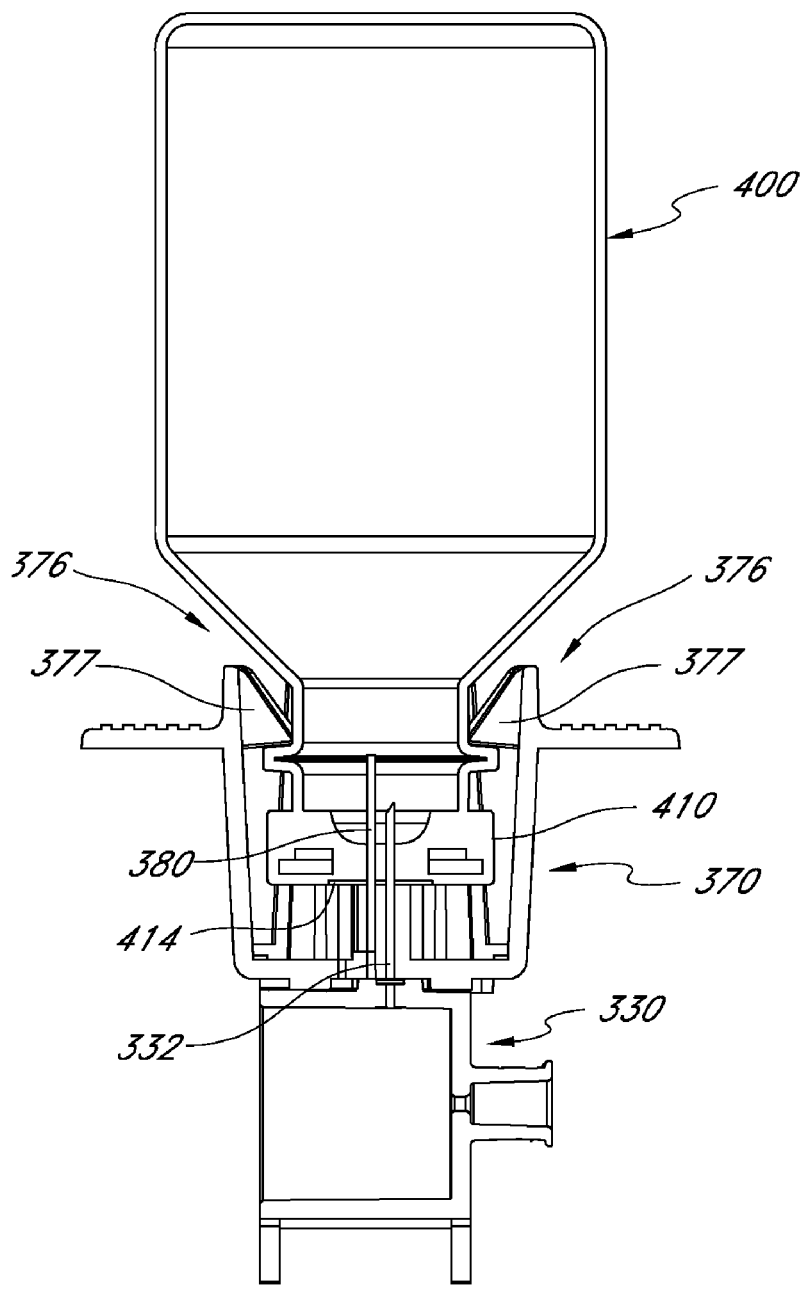
FIG. 9D illustrates a cross-sectional view of the manifold and nest or loading area of FIGS. 9B and 9C.
Figure 9F:
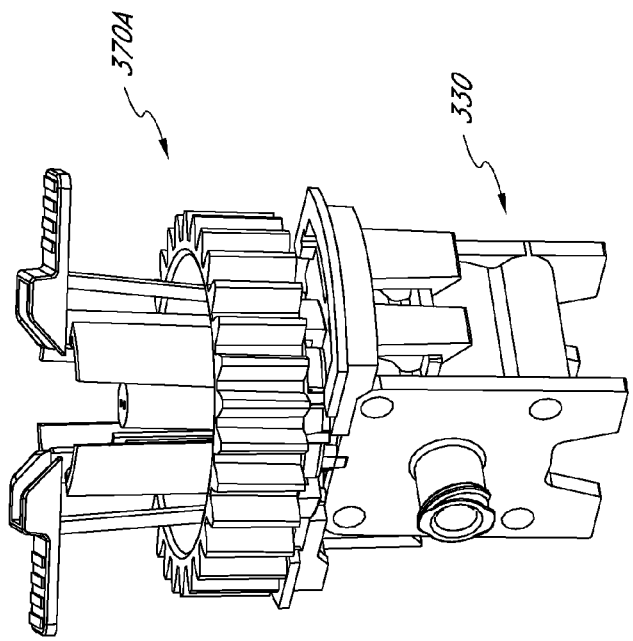
FIG. 9F illustrates a perspective view of the manifold of FIG. 9E with a nest or loading area secured thereto.
Figure 9E:
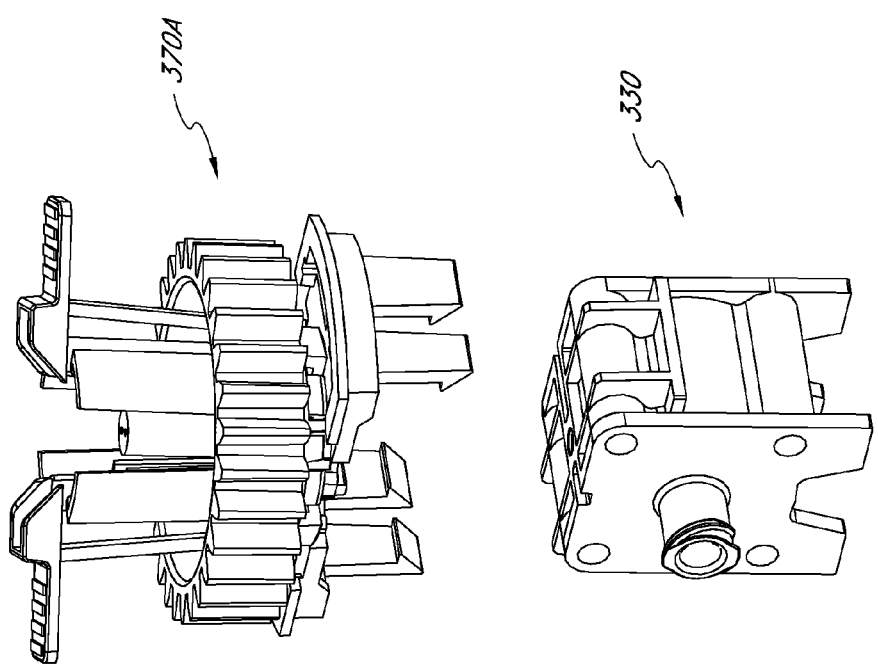
FIG. 9E illustrates an exploded perspective view of the manifold of FIG. 9A and a nest or loading area configured to be positioned thereon according to another embodiment.

FIG. 9D illustrates a cross-sectional view of a vial 400 positioned within a nest 370 or loading area of FIGS. 9B and 9C. As shown, the closure 410 of the vial 400 is secured underneath the locking member 377 of each wing 376 of the nest 370. Accordingly, a main needle 332 and a vent needle 380 have penetrated a septum 414 or other pierceable membrane of the closure 410, thereby accessing the interior of the vial 400. Thus, the main needle 332 can advantageously place the fluids and/or other materials contained within the vial 400 in fluid communication with the manifold 330 to which the nest 370 is attached. In addition, as illustrated in the perspective views of FIGS. 9E and 9F, a nest 370A or loading area configured to rotate a vial or other container positioned therein (see FIGS. 3K-3S) may be secured to a cassette manifold 330.

Figure 9G:
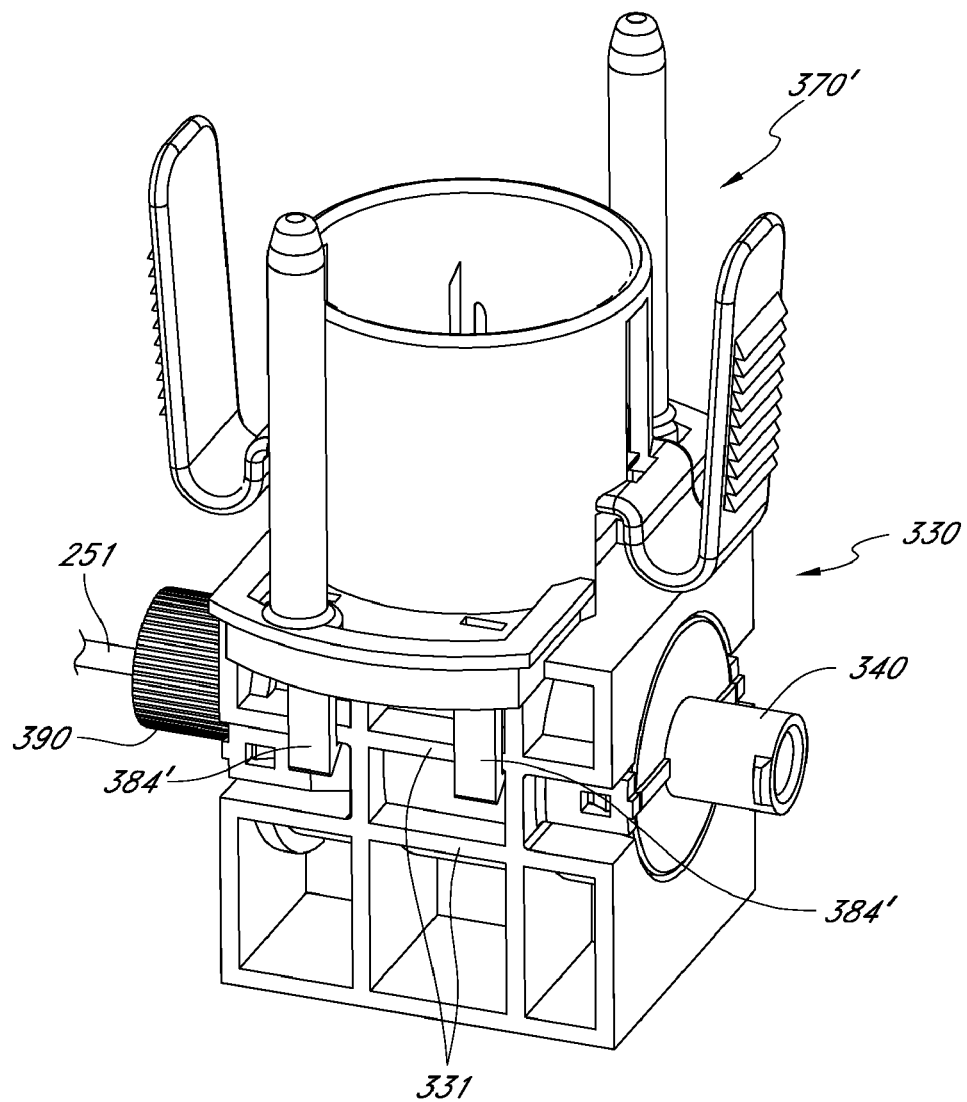
FIG. 9G illustrates a perspective view of a cassette manifold with a nest or loading area positioned thereon according to yet another embodiment.

A different embodiment of a nest 370' connected to a manifold 330 of a cassette is illustrated in FIG. 9G. The depicted nest 370' is similar to the one discussed herein with reference to FIGS. 5A-5F. Therefore, a vial adapter (not shown) may need to be positioned on a container (e.g., vial) before such a container is secured to the nest 370'. As with other arrangements disclosed herein, the nest 370' of FIG. 9G can include a plurality of tabs 384 or other members that are adapted to snap onto or otherwise engage one or more portions of the manifold 330 or cassette (e.g., ribs 331).

Figure 10A:
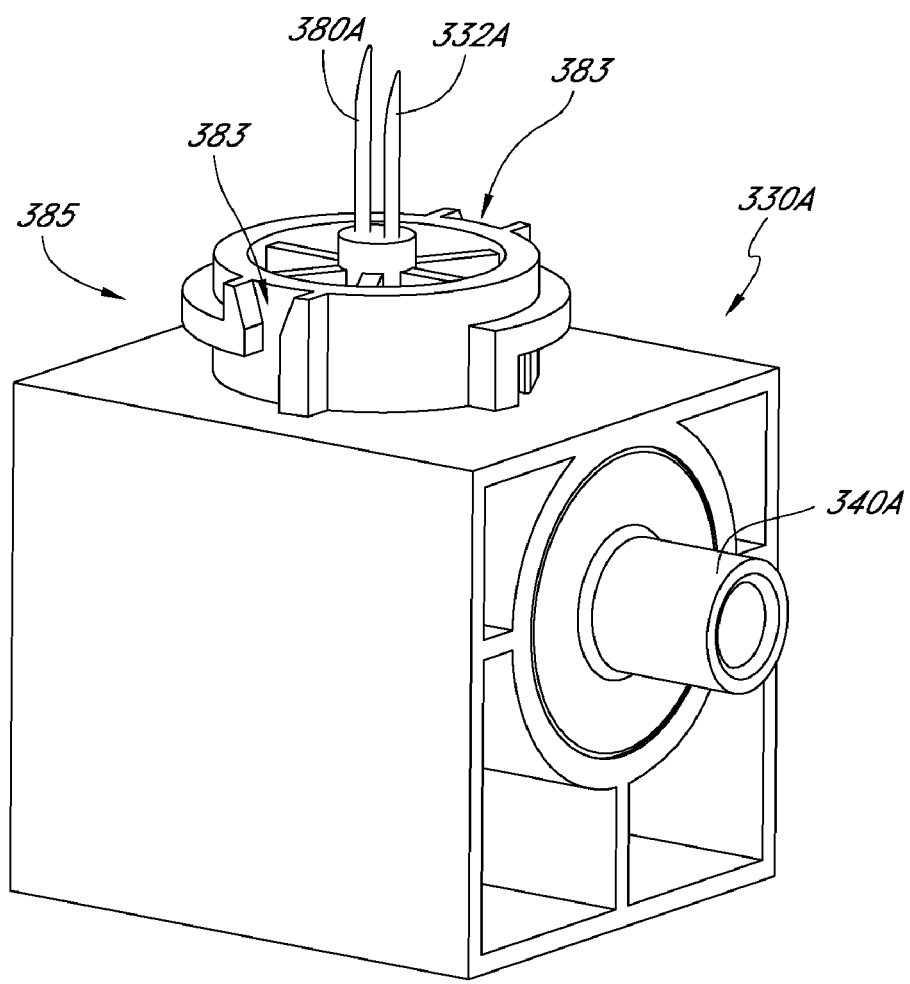
FIG. 10A illustrates a perspective view of a manifold configured for use in a cassette according to another embodiment.

Another embodiment of a manifold 330A adapted for use with a cassette or other portion of a fluid delivery module is illustrated in FIG. 10A. As shown, an upper portion of the manifold 330A can include a projecting portion 385 through which the main needle 332A and/or the vent needle 380A may extend. The projecting portion 385 can include a generally cylindrical shape or any other shape, as desired or required. In the illustrated embodiment, the projecting portion 385 comprises a ring 386 that extends at least partially around the outside of the projecting portion 385. The ring 386, other raised feature and/or the like can be sized, shaped and otherwise configured to mate with a corresponding portion of a loading area or nest onto which a vial may be secured. For example, in some embodiments, the top of a manifold 330A or a top portion of the cassette housing is configured to securely receive a nest thereon using a turn-lock connection or some other attachment device or method.

Figure 10B:
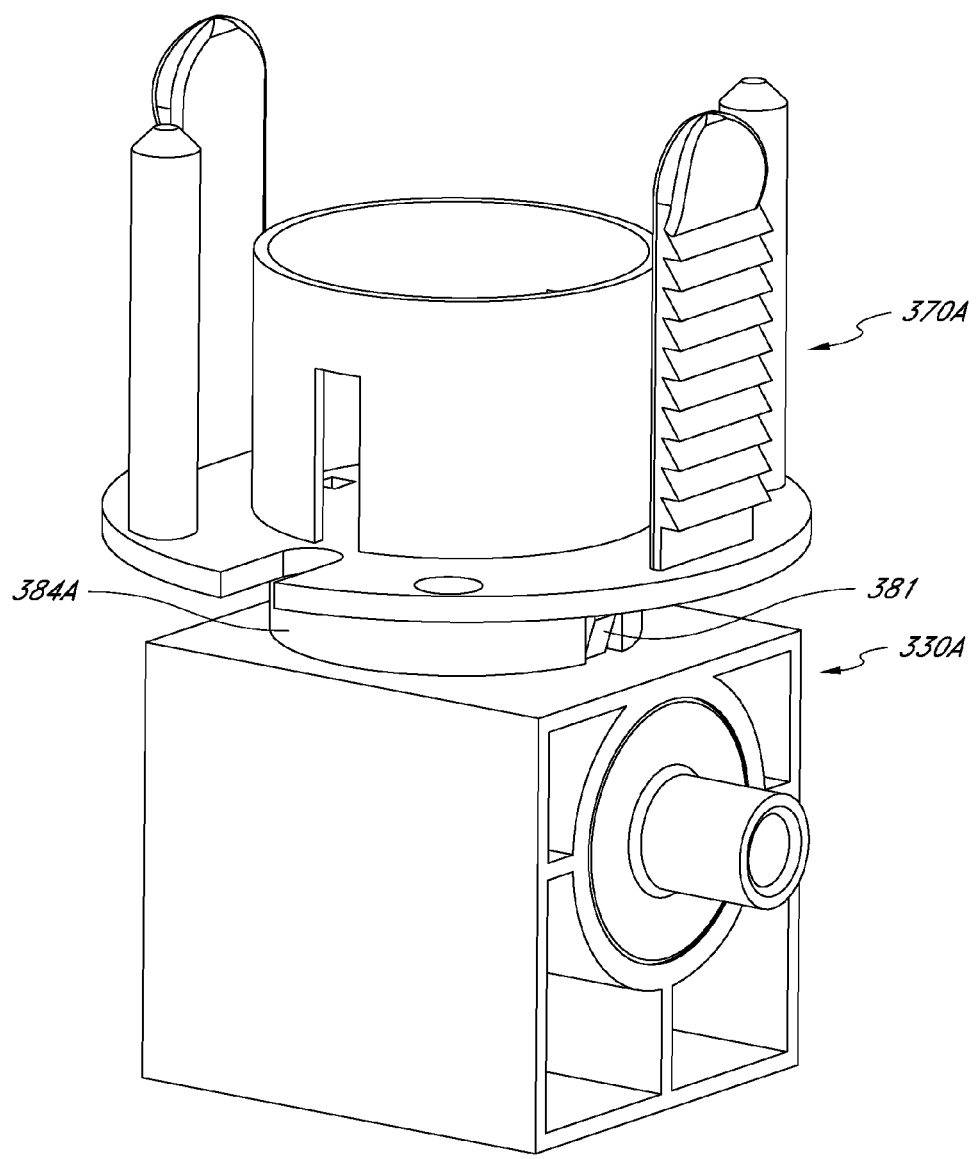
FIG. 10B illustrates a perspective view of the manifold of FIG. 10A with a loading area or nest positioned thereon according to one embodiment.
Figure 10C:
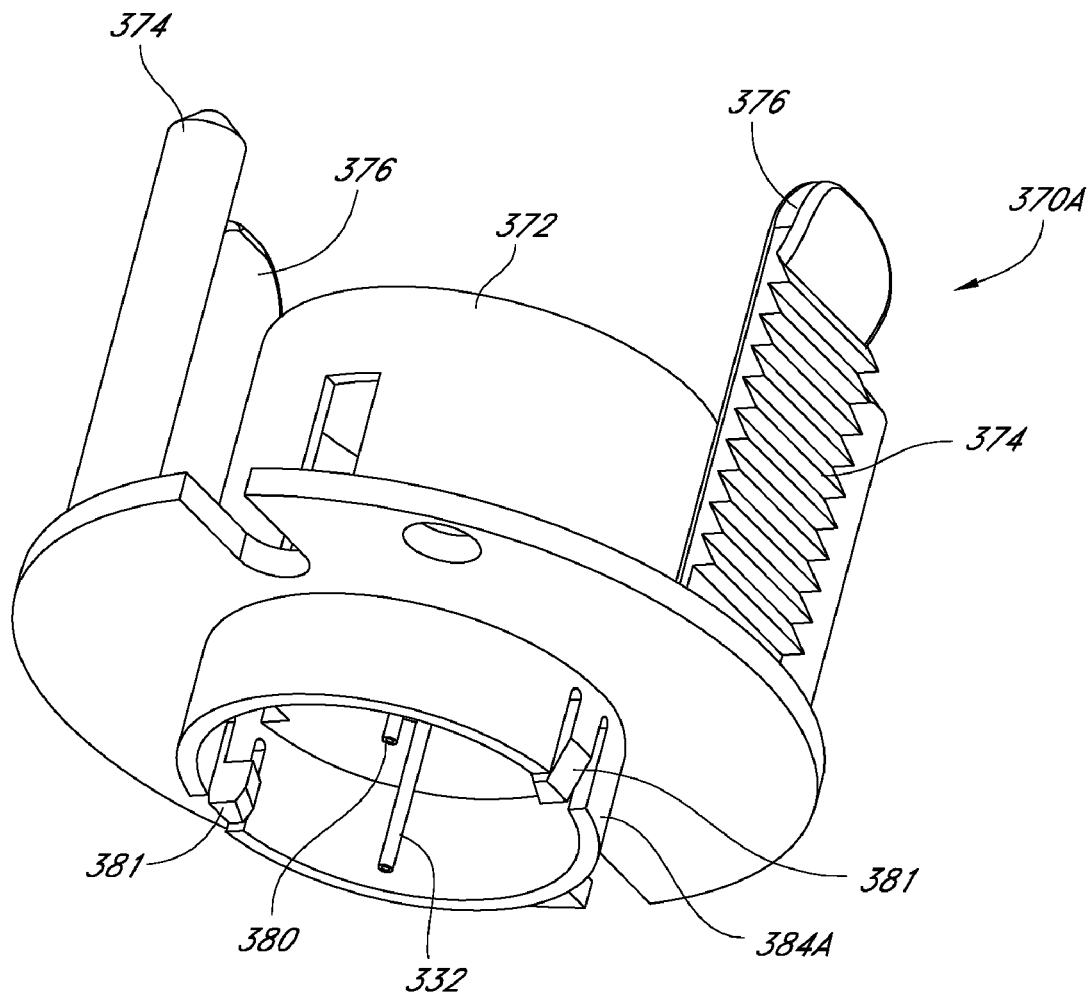
FIG. 10C illustrates a perspective view of a loading area or nest according to one embodiment.

FIG. 10B illustrates one embodiment of the manifold 330A of FIG. 10A secured to a loading area or nest 370A. In addition, FIG. 10C illustrates a bottom perspective view of the nest 370A of FIG. 10B. As shown, a bottom portion 384A of the nest 370A can be configured to engage the ring 386 or other feature of the projecting portion 385 of the manifold 330A. For example, the bottom portion 384A can comprise a generally cylindrical section having a pair of tabs 381 that extend inwardly. Such tabs 381 can be sized, shaped and otherwise adapted to be positioned below and rotatably slide relative to the ring 386 or other feature of the manifold 330A. In one embodiment, the tabs 381 are aligned with and inserted through corresponding notches 383 along the projecting portion 385 of the manifold 330A. Then, the nest 370A can be rotated (e.g., quarter revolution, half revolution, etc.) relative to the manifold 330A in order to move tabs 381 below the ring 386 or other exterior feature of the projecting portion 385. As a result, the nest 370A and the manifold 330A can be secured to each other. Alternatively, one or more other methods of releasably joining a nest to a manifold can be used. Moreover, a nest and an adjacent manifold can be permanently attached to each other, as desired or required by a particular application or use.

As illustrated in FIG. 10C, the main needle 332 can extend from the bottom of the loading area or nest 370A so that it may be advantageously placed in fluid communication with one or more passages, valves or other fluid components of the manifold 330A. The size, shape, general design and/or other details of the nest 370A, the manifold 330A and/or any other component or feature of the cassette or articular injection system can be varied as desired or required.

Figure 11A:
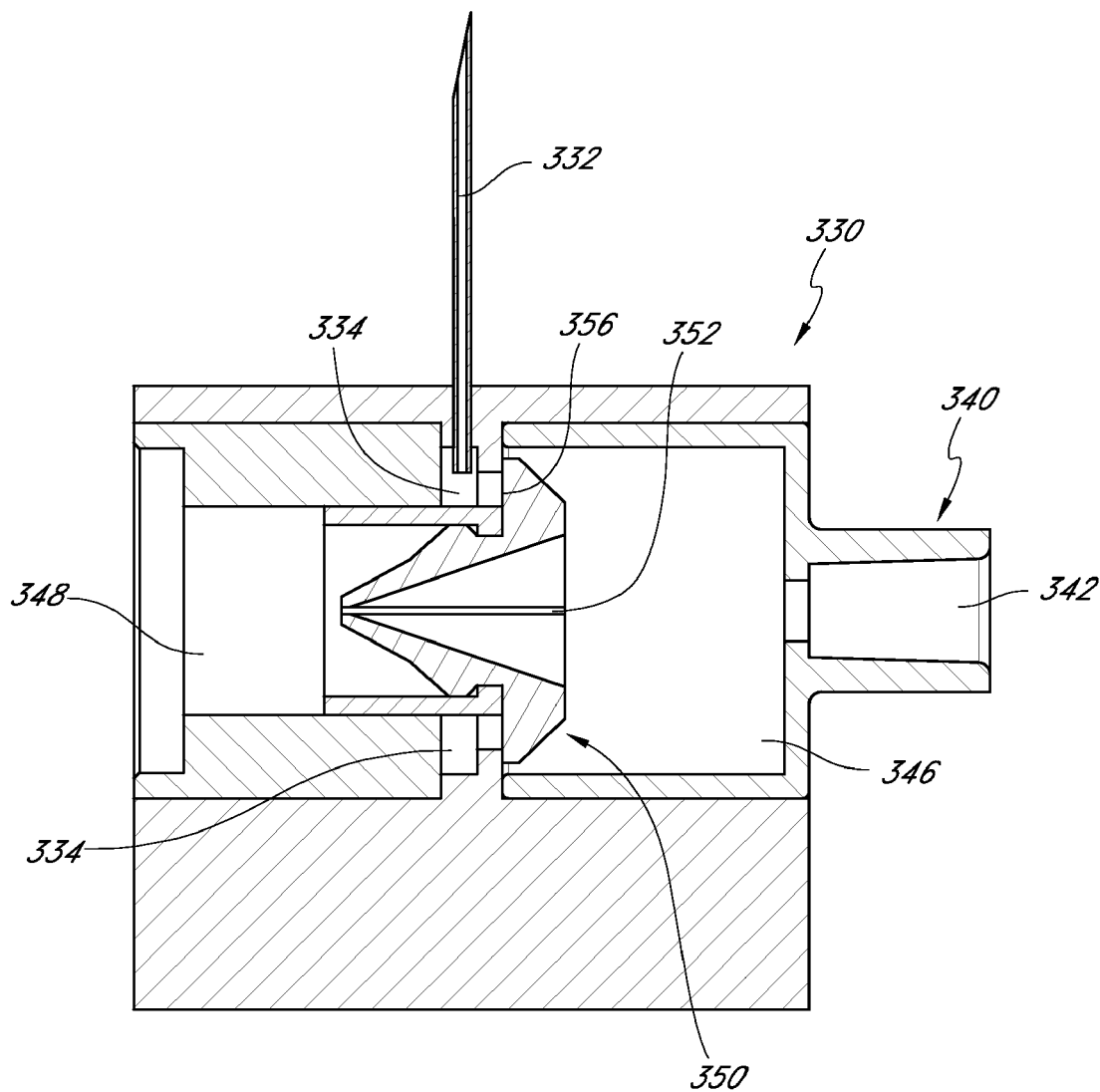
FIG. 11A illustrates a schematic cross-sectional view of the interior of a manifold according to one embodiment.

The schematic cross-sectional view of FIG. 11A illustrates the internal configuration of a manifold 330 according to one embodiment. As discussed, a main needle 332 can be used to place the manifold 330 in fluid communication with a vial or other container (not shown) positioned within a loading area, nest or other receiving area of a cassette or other portion of the fluid delivery module. In FIG. 11A, the main needle 332 attaches to an upper portion of the manifold 330 and terminates at a void 334 located within an interior of the manifold 330. In some arrangements, the void 334 comprises an annular area that completely or partially surrounds a valve 350 (e.g., combination duckbill-umbrella valve). However, the type, shape, size and/or other details of the void 334, valve 350, general fluid scheme and other components or features of the manifold can be different than illustrated and discussed herein, as desired or required.

With continued reference to FIG. 11A, the manifold 330 can be configured so that the void 334 is selectively placed in fluid communication with an upstream cavity 346 to permit fluids and/or other materials to be advantageously transferred from the main needle 332 to the inlet 340 of the manifold 330. As discussed, such a step can be performed when there is a desire to fill the syringe 360 (FIGS. 7A and 7B) or other reservoir of the cassette that is positioned upstream of the inlet 340. Consequently, some or all of the contents (e.g., medication, formulation, other fluids or substances, etc.) of a vial or other container with which the main needle 332 is in fluid communication can be delivered to the syringe or other reservoir positioned within the cassette or other portion of the fluid delivery module.

Figure 11B:
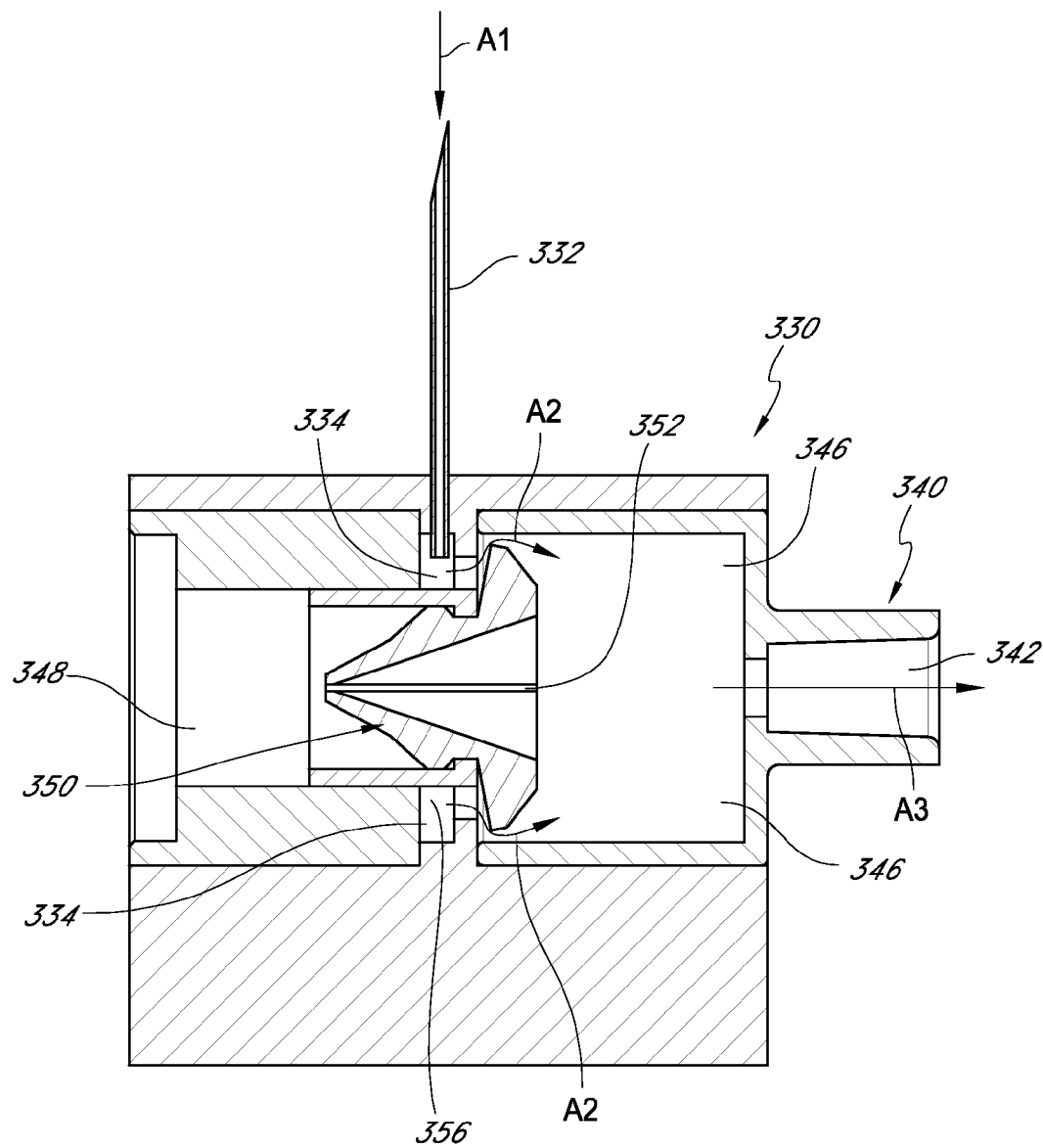
FIG. 11B illustrates a schematic cross-sectional view of the manifold of FIG. 11A when fluids and/or other materials are being transferred from a vial to the syringe or other reservoir according to one embodiment.

FIG. 11B schematically illustrates the manifold of FIG. 11A while fluids and/or other materials are being transferred from the main needle 332 to the inlet 340 of the manifold 330. As discussed herein with reference to FIGS. 7A and 7B, a suction force can be applied to the upstream cavity 346 of the manifold (e.g., by moving the inner plunger away from the outer barrel of a syringe). Thus, if the tip of the syringe is attached to, inserted into or otherwise placed in fluid communication with the inlet 340 of the manifold 330, a corresponding suction force can be created within the upstream cavity 346.

As shown in FIG. 11B, if such a vacuum force is sufficiently high, the umbrella portion 356 of the combination valve 350 can move away from the void 334, thereby allowing fluids and/or other materials to be delivered from the main needle 332 to the upstream cavity 346 in a direction generally represented by arrows $A_1$ and $A_2$ in FIG. 11B. From the upstream cavity 346, the fluids and/or other contents of a vial can be routed to a syringe (not shown) or other reservoir attached to or placed in fluid communication with the inlet 340 of the manifold 330. For example, in the depicted embodiment, fluids and/or other materials can be delivered into a syringe that is positioned within the inlet nozzle 342 in a direction generally represented by arrow $A_3$. Once the suction force is terminated or sufficiently reduced (e.g., by stopping the movement of the inner plunger relative to the outer barrel of the syringe), the umbrella portion 356 of the valve 350 will seat against the void 334, thereby preventing the flow of materials from the main needle 332 to the upstream cavity 346.

Figure 11C:
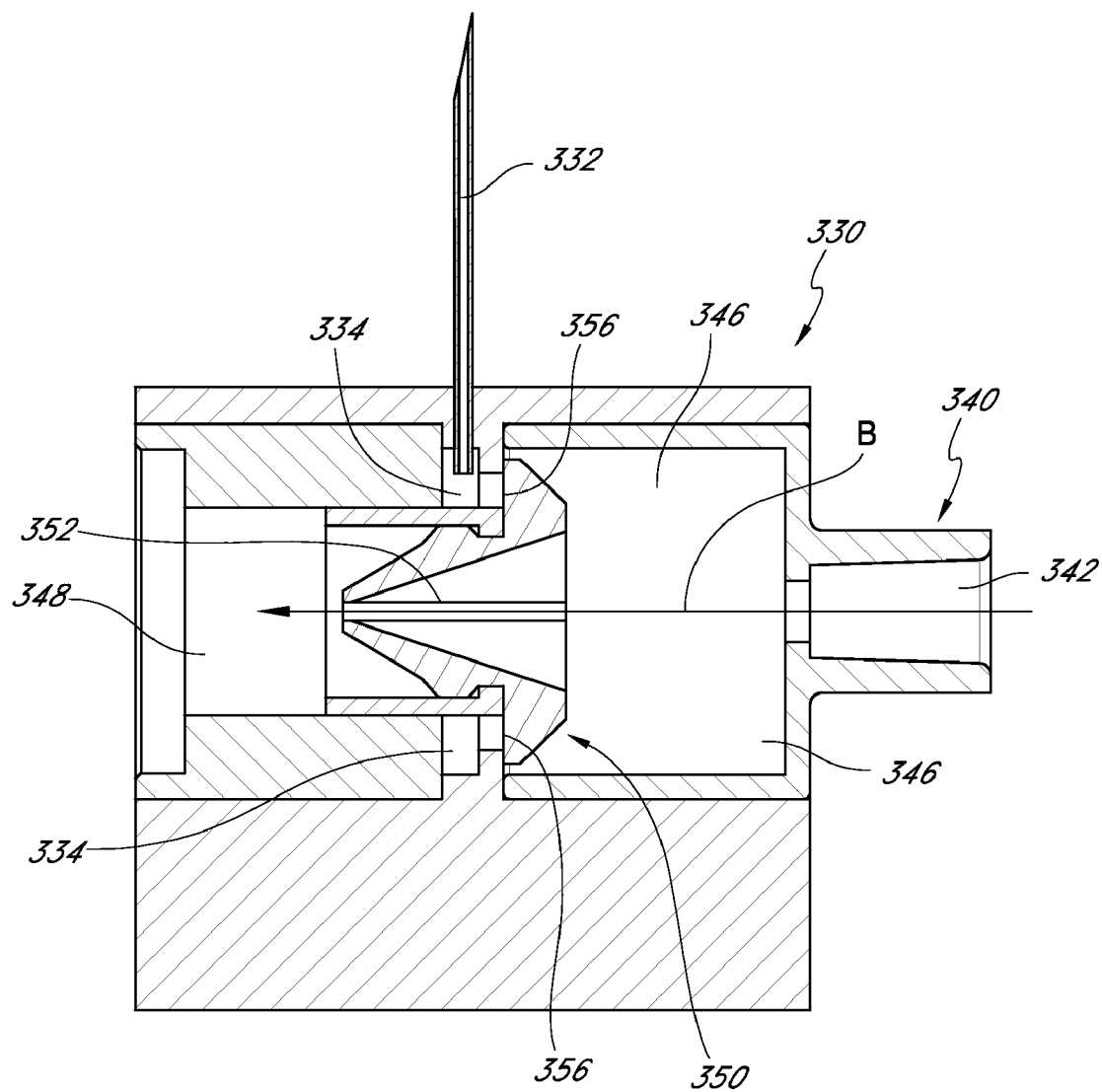
FIG. 11C illustrates a schematic cross-sectional view of the manifold of FIG. 11A when fluids and/or other materials are being transferred from the syringe or other reservoir to the outlet of the manifold according to one embodiment.

FIG. 11C schematically illustrates the manifold 330 of FIG. 11A as fluids and/or other materials are being delivered through the combination duckbill-umbrella valve 350 to the downstream cavity 348. As shown, if sufficient positive backpressure is applied to the upstream cavity 348, fluids and/or other materials may be transferred through the duckbill portion 352 of the combination valve 350 in a direction generally represented by arrow B. As discussed, in some embodiments, the necessary backpressure may be generated by moving the inner plunger within the outer barrel of the syringe positioned along the inlet 340 of the manifold 330 in order to expel the fluids and/or other materials contained within the syringe. As a result, such fluids and/or other materials can pass through the duckbill portion 352 of the valve 350 to the downstream cavity 348. At the same time, the positive backpressure within the upstream cavity 348 can cause the umbrella portion 356 of the valve to seat against the void 334, thereby ensuring that no fluids and/or other materials enter the void 334 and the main needle 332. Consequently, as discussed herein with reference to FIGS. 7B and 8, a desired volume of fluids and/or other materials exiting the manifold 330 can be delivered to a handpiece assembly through an outlet coupling 390 and a delivery line 250.

Figure 12A:
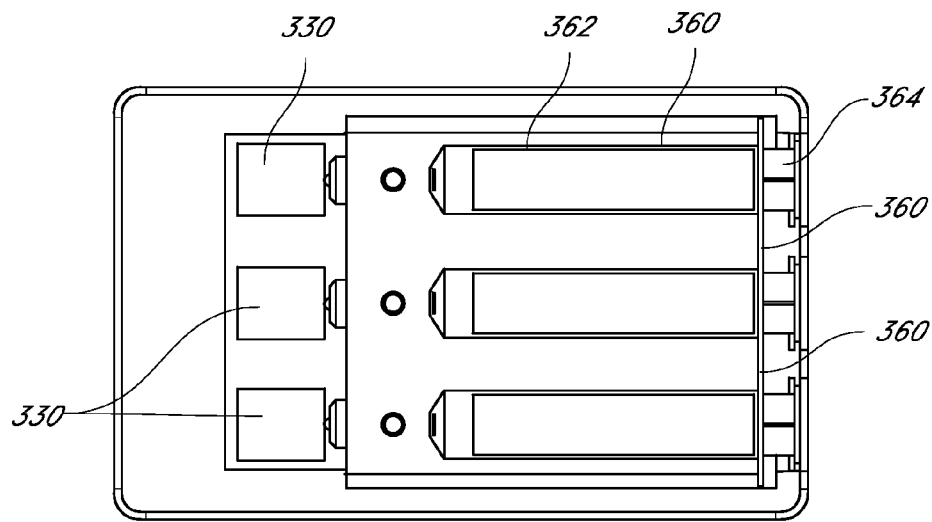
FIG. 12A illustrates a top view of the syringes or other reservoirs of a cassette in a first position.
Figure 12B:
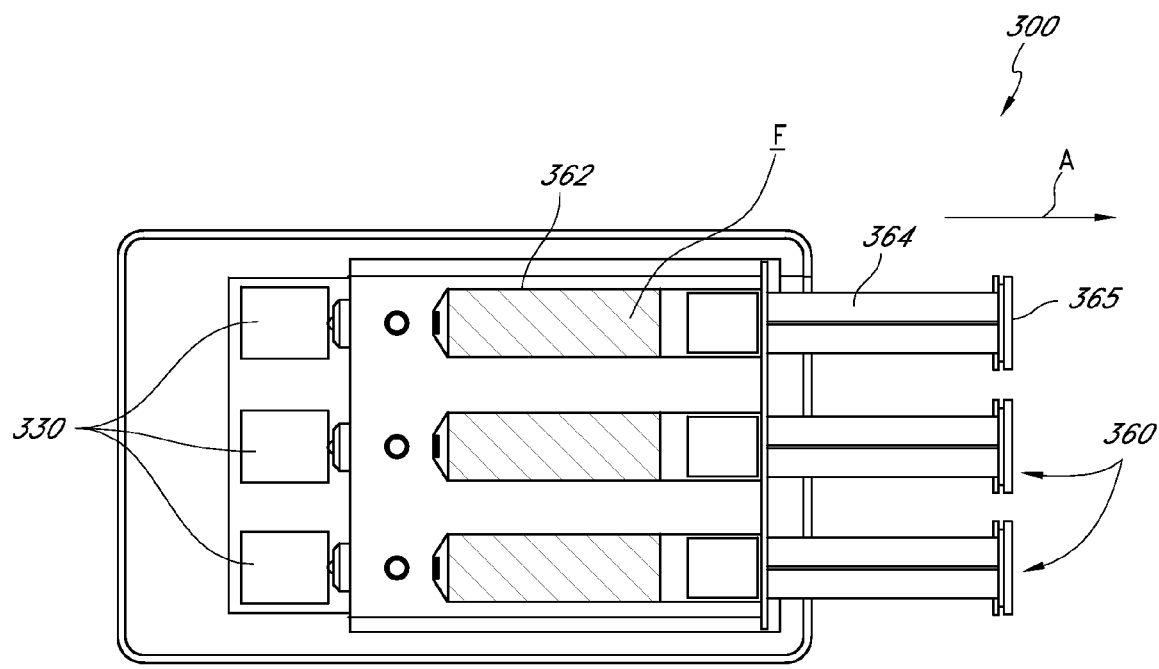
FIG. 12B illustrates a top view of the syringes or other reservoirs of a cassette in a second position.

FIGS. 12A and 12B schematically illustrate the filling of syringes 360 positioned within a cassette 300. In FIG. 12A, each of the three syringes 360 is empty or substantially empty, as the inner plunger 364 is positioned completely within the outer barrel 362. As the inner plungers 364 are drawn rearwardly away from the respective manifolds 330 (e.g., in a direction generally represented by arrow A), fluids F and/or other substances from the vials or other containers secured to the cassette (e.g., nests, loading areas, other receiving areas, etc.) can be drawn through the manifolds 330 and into the syringes 360. As discussed, such fluids F and/or other substances can be subsequently delivered to a downstream handpiece assembly from one or more of the syringes 360. Accordingly, one, two or more different medications, formulations, other fluids and/or other materials can be accurately and conveniently delivered into the anatomy through a single needle positioned at the distal end of the handpiece assembly. Once a syringe 360 has been partially or fully emptied, the inner plunger 364 can once again be moved to fill the interior of the syringe 360 with additional fluids and/or other materials from the corresponding vial or other container positioned on the cassette. For example, once a spent vial positioned on the cassette is replaced with the a filled vial, a motor, actuator and/or other device within the fluid delivery module can move the inner plunger 364 relative to the outer barrel 362 of the syringe 360 in order to refill the syringe or other reservoir.

According to some embodiments, the syringes 360 (or other reservoirs positioned within a cassette) are filled and emptied with the assistance of a stepper motor or other mechanical or pneumatic device. For example, such a device can be configured to slidably move the inner plunger 364 of each syringe 360 relative to the outer barrel 362. As discussed in greater detail herein with reference to FIGS. 8 and 11A-12B, fluids and/or other materials contained within a vial or other container can be selectively loaded into the syringe 360 or discharged from the syringe 360 toward a needle at the distal end of a handpiece assembly. Preferably, such a mechanical device, pneumatic device and/or the like can be configured to precisely move the inner plunger 364 into or out of the outer barrel 362 (or otherwise fill and/or empty the syringe 360 or other reservoir) to help ensure that a desired volume of fluids and/or other materials is accurately delivered to the anatomy.

Figure 13A:
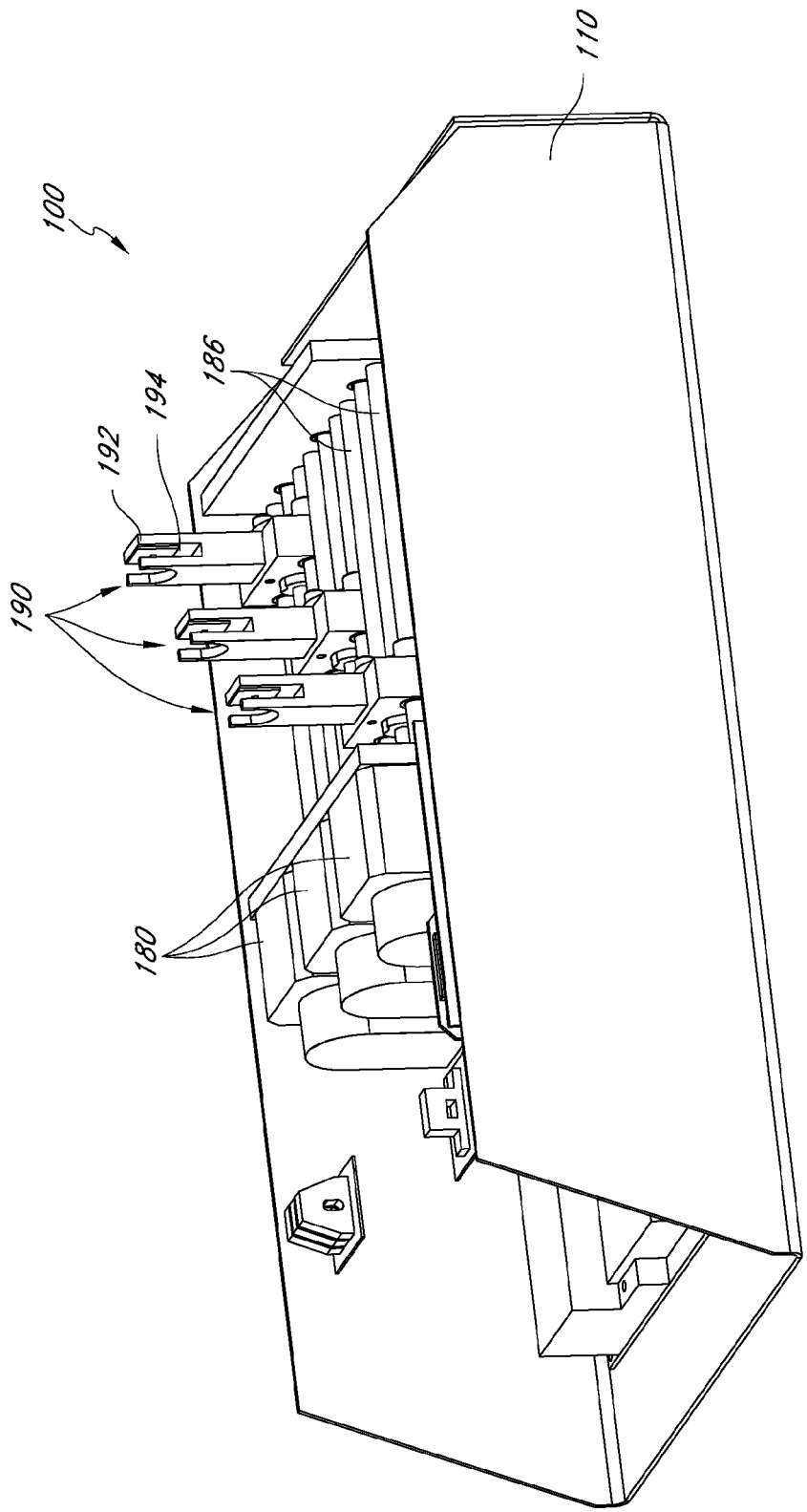
FIG. 13A illustrates a perspective view of a motor and accompanying components of a fluid delivery module according to one embodiment.
Figure 13B:
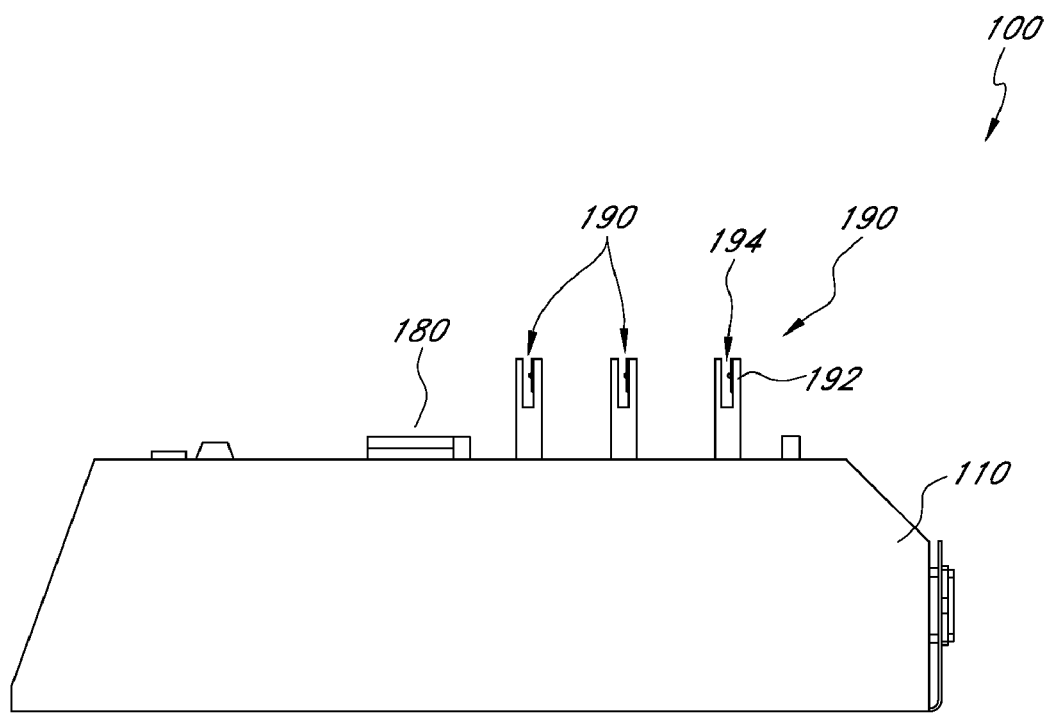
FIG. 13B illustrates a side view of the fluid delivery module of FIG. 13A.

One embodiment of a fluid delivery module 100 configured to accurately adjust the position of the syringes' inner plungers 364 relative to their respective outer barrels 362 is illustrated in FIGS. 13A and 13B. As shown, an interior of the fluid delivery module 100 can comprise one or more stepper motors 180 or other devices (e.g., pumps, another mechanical or pneumatic device, etc.) configured to move fluids and/or other materials between vials (or other containers), syringes 360 (or other reservoirs), a handpiece assembly and/or other components of an articular injection system.

With continued reference to FIGS. 13A and 13B, the fluid delivery module 100 can comprise a stepper motor 180 or other device for each syringe or other reservoir positioned within a cassette (not shown). Alternatively, a stepper motor or other device can be configured to control two or more syringes or other reservoirs. As shown, each stepper motor 180 may be adapted to selectively move a corresponding pusher block 190 along one or more guide rails 186. In the depicted embodiment, each pusher block 190 is configured to move linearly relative to two guide rails 186. However, in other arrangements, a pusher block 190 may be configured to move in two or more directions, along more or fewer guide rails and/or in a completely different manner, as desired or required.

In the illustrated embodiment, each pusher block 190 includes a vertical portion 192 that is sized, shaped and otherwise adapted to engage the end portion 365 of a syringe's inner plunger 364 (FIG. 12B). As discussed herein with reference to FIGS. 7A and 7B, a cassette 300 can include one or more openings 324 adjacent to the syringes 360. Accordingly, the vertical portion 192 of each pusher block 190 can be configured to extend through such an opening 324 of the cassette 300 in order to engage a movable portion of the syringe 360 (e.g., the end portion 365 of the inner plunger 364).

In FIG. 13A, the vertical portion 192 of the pusher block 190 comprises a slot 194 that is sized, shaped, positioned and otherwise configured to securely receive the end portion 365 of the inner plunger 364. Thus, as the pusher block 190 is moved along the guide rails 186, the position of the inner plunger 364 relative to the outer barrel 362 can be selectively modified. As discussed, this permits fluids and/or other materials to be loaded into the cassette and/or accurately delivered to a targeted anatomical location through a handpiece assembly. In order to ensure that the position of the pusher blocks 190 is being accurately controlled, the fluid delivery module 100 can comprise one or more sensors (e.g., optical sensors), other position detection devices and/or the like. It will be appreciated that different methods and/or devices for controlling the loading of vials or other containers and/or the subsequent delivery of fluids and/or other substances may be alternatively used.

Figure 14B:
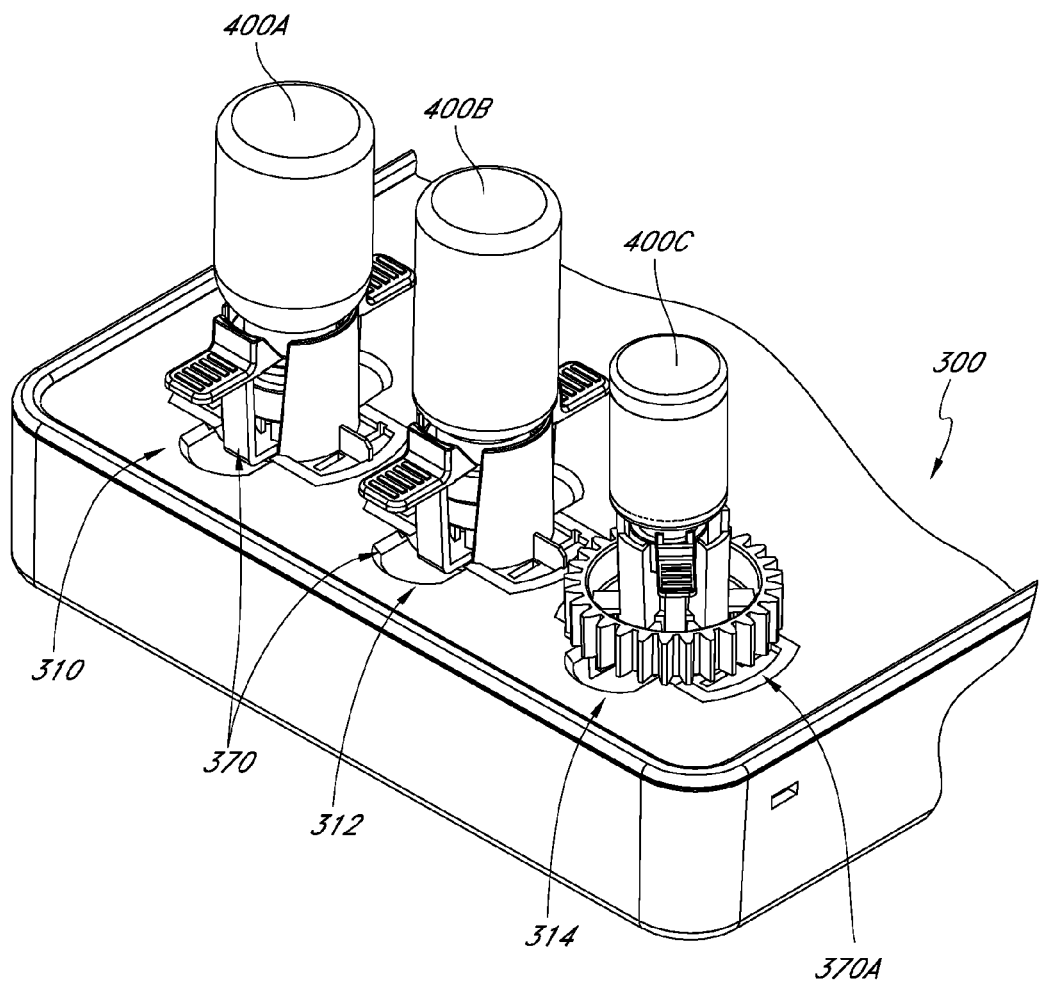
FIG. 14B illustrates a perspective view of a cassette comprising two different types of nests or loading areas according to one embodiment.

As discussed, medicaments and/or other fluids or materials to be delivered to a targeted anatomical location (e.g., a toe, ankle, knee, other joint, organ, etc.) are typically provided to clinicians and other users of an articular injection system in standard or non-standard drug vials. The size or capacity (e.g., 5 ml, 10 ml, 50 ml, etc.), shape, material type (e.g., glass, plastic, acrylic, etc.) and/or characteristics of such vials can vary. As discussed herein with reference to various embodiments of a cassette (e.g., FIGS. 3A and 4A), it may be desirable to secure such a vial 400A-400B to a loading area 370, 370A, 370' or other portion of the cassette 300 or fluid delivery module 100. This can facilitate delivery of the internal contents of the vials to the anatomy using an injection system. Accordingly, as illustrated in FIGS. 14A and 14B, a nest 370, 370A or loading area can be configured to receive one or more nonspecific containers (e.g., vials of varying sizes, shapes, capacities, etc.) 400, 400', 400", 400'''.

Vial Adapters

According to certain embodiments, a vial adapter is used as an interface between a vial and the nest or other portion of the cassette or fluid delivery module. As discussed in greater detail herein, such adapters can make it easier and safer to load the desired medications, formulations and/or other fluids or materials to the injection system and to selectively deliver them within the anatomy.

In some arrangements, a loading area or nest of a cassette (or another portion of a fluid delivery module) is configured to receive a nonspecific container. Regardless of their exact size, shape, capacity and/or other characteristics, nonspecific containers can be secured to the loading areas or nests using the various adapter embodiments disclosed herein. Thus, in one embodiment, the two or more vials or other nonspecific containers secured to a fluid delivery module may be different from each other (e.g., in size, shape, capacity and/or the like).

The ability to mount or otherwise secure nonspecific containers (e.g., vials of varying sizes, shapes, capacities, etc.) to a loading area of a cassette or other portion of the fluid delivery module can provide certain advantages. Such configurations can eliminate the need for two or more different fluid and/or other material streams to be premixed in preparation for an injection procedure. For example, where two, three or more different types of medicaments and/or other substances are needed in a particular injection protocol, a physician, nurse or other clinician may need to combine such fluids and/or other materials in a single syringe or other container in advance of the injection procedure. As a result, such a preliminary step can lead to errors, waste, potentially unsafe conditions for the patient or other problems. For example, one or more of the medications, formulations and/or other substances can be contaminated as they are exposed to the environment while being transferred to a different container. In addition, increased probability of human error associated with performing such pre-injection transfers can increase the likelihood that the subsequent injection procedure will be ineffective and/or harmful for the patient. For instance, the type, volume or other amount, dosage, relative proportion and/or other properties of each of the medicaments and/or other materials being combined may be incorrect or inaccurate.

Further, it may not be advisable to combine certain medications and/or other substances with each other too far in advance of their injection into the anatomy. For instance, one or more of these fluids and/or materials may undesirably degrade or otherwise transform (e.g., chemically, biologically or otherwise) as a result of the premixing. Likewise, certain fluid and/or other material streams may not be physically compatible with each other (e.g., due to differences in densities, viscosities, affinities to certain substances, etc.). Moreover, having to transfer the contents from one container (e.g., the vial in which a particular medicament was supplied) to another (e.g., an injection syringe) can lead to waste, as a residual volume of the contents of the supply vial or other container is wasted. This can be particularly significant when a medication and/or other material is relatively expensive. Further, the need of transferring fluids and/or other materials from separate vials or other container into a single container that will be used to administer a desired formulation during a subsequent injection procedure can be labor and cost intensive.

Accordingly, the various embodiments disclosed herein that permit nonspecific containers (e.g., drug vials) to be secured to a cassette or another portion of a fluid delivery module can be safer, more cost efficient, more effective and reliable, less wasteful, less burdensome on labor and other resources and/or the like. Thus, the injection systems, devices and methods discussed and illustrated herein, and equivalents thereof, can permit two or more different types of medications, formulations and/or other fluids or materials to be delivered to an anatomy without the need for premixing or combining such substances prior to loading the nonspecific containers in which such substances were supplied onto a fluid delivery module.

Figure 15A:
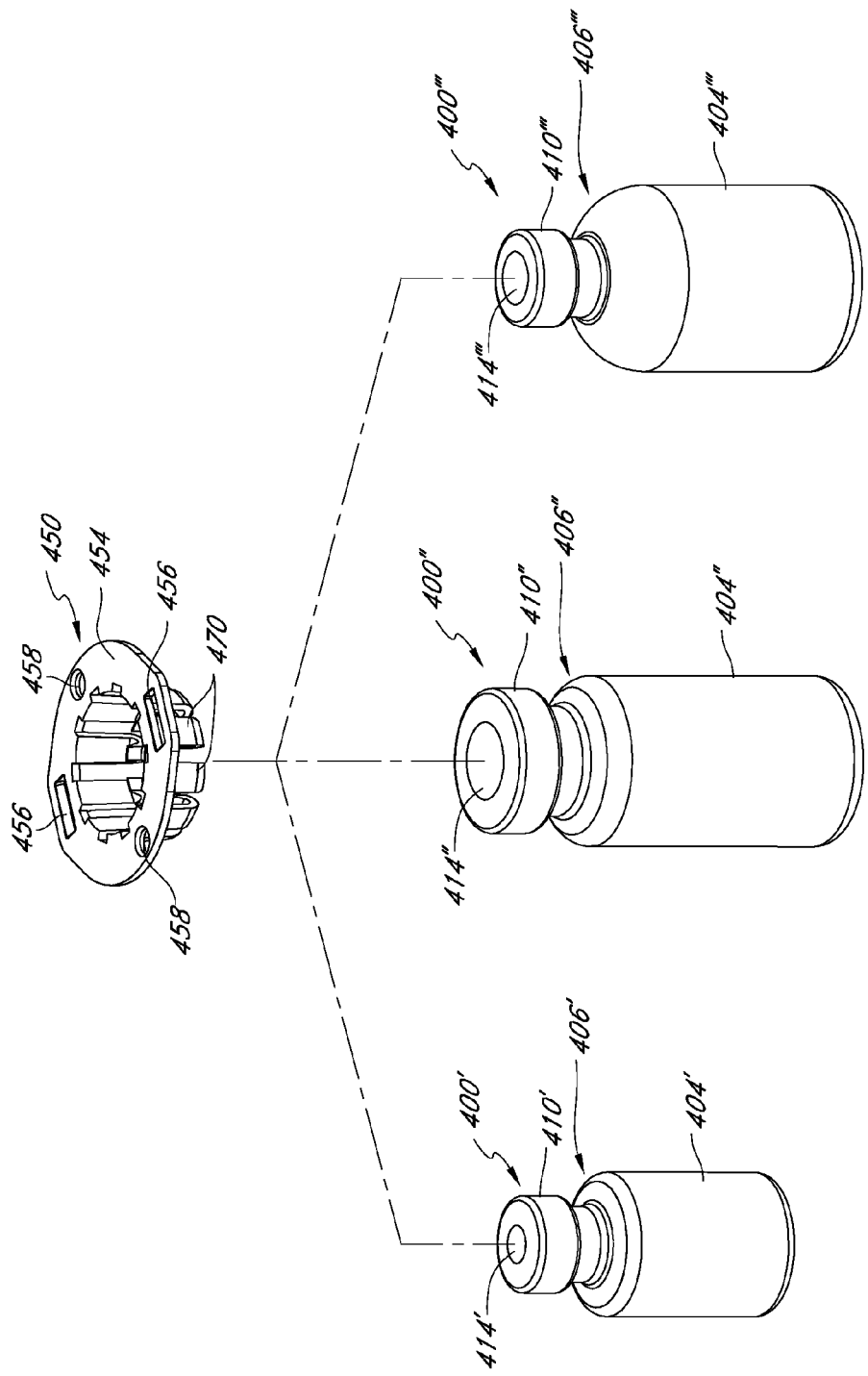
FIG. 15A illustrates a perspective view of an embodiment of a vial adapter and three different vials onto which the adapter may be secured.

One embodiment of a vial adapter 450 is illustrated in FIG. 15A. As shown, the adapter 450 can include a base 454 having a generally circular shape. In the depicted arrangement, the base 454 of the adapter 450 comprises two rectangular openings 456 and two circular openings 458. These openings 454, 458 can be sized, shaped and otherwise configured to receive one or more portions of a nest or other component of the cassette. The adapter 450 can also preferably include a plurality of arms 470 or other members that extent outwardly from the base 454. According to some arrangements, the base, arms and/or other portions of the adapter 450 comprise one or more resilient, rigid, semi-rigid and/or flexible materials, such as, for example, plastic, other polymeric materials, rubber, metal, other synthetic or natural materials and/or the like.

As illustrated in FIG. 15A, regardless of its exact shape, size and/or other characteristics, the adapter 450 can be advantageously configured to be secured to any one of a number of different types and sizes of vials or other containers. Specifically, vials 400', 400", 400''' or other containers can have a different in size (e.g., diameter), shape, type of closure and/or the like. For example, in the depicted arrangement, the size and shape of the vessel portion 404', 404", 404''' of the vials 400', 400", 400''' vary from each other. There may also exist variations in the diameter, height and other characteristics of the neck portions 406', 406", 406''', closures 410', 410", 410''' and other areas of the vials. Thus, it may be desirable to provide a single vial adapter design that can be used with a large number of different vials 400', 400", 400''' or other containers.

Figure 15B:
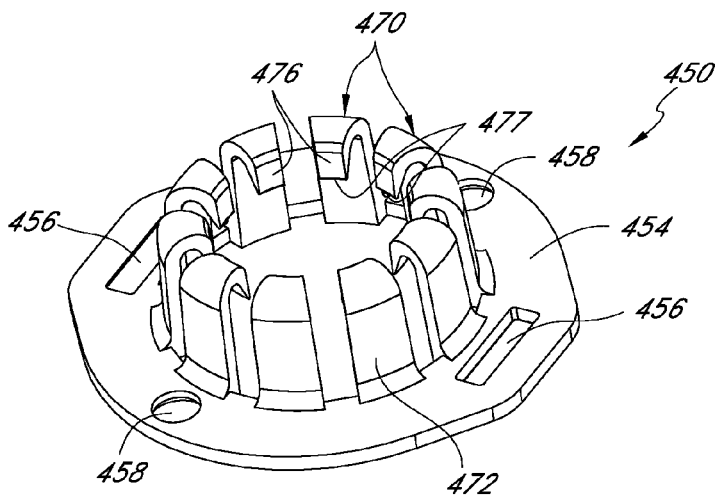
FIG. 15B illustrates a perspective view of the vial adapter of FIG. 15A.
Figure 15C:
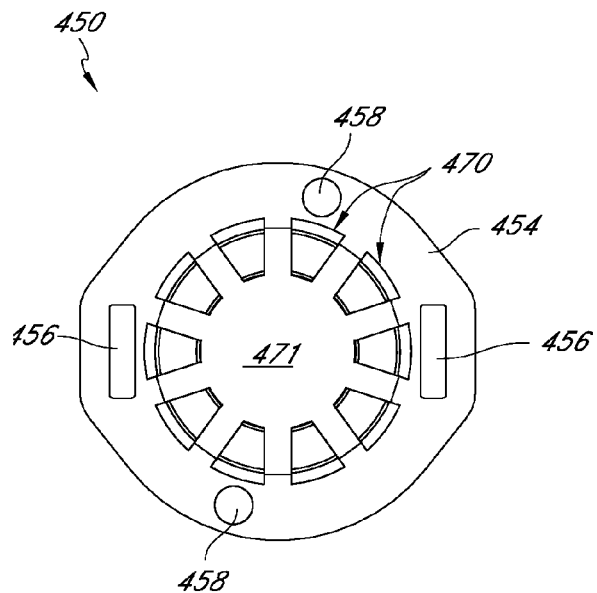
FIG. 15C illustrates a top view of the vial adapter of FIG. 15A.
Figure 15D:
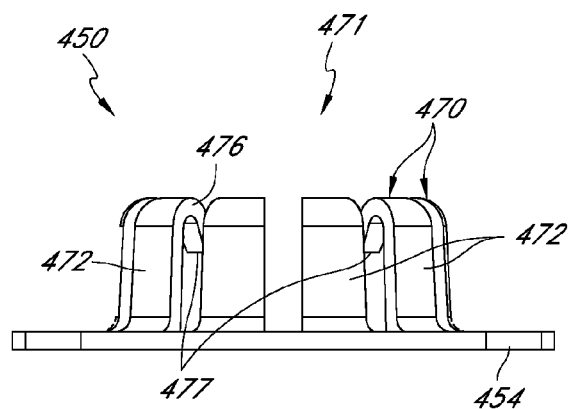
FIG. 15D illustrates a side view of the vial adapter of FIG. 15A.

FIGS. 15B-15D provide detailed views of the vial adapter 450 illustrated in FIG. 15A. As shown, the arms 470 can be arranged in a generally circular pattern to define a center opening 471 through which the top of the vial (e.g., the closure) can be inserted. The arms 470 extend from the base 454 and include a main portion 472 that is generally perpendicular to the base 454. In some arrangements, the arms 470 terminate with a grasping portion 476 located at the ends of the respective main portions 472. In FIGS. 15B-15D, the grasping portions 476 have a generally curved shape that face inwardly toward each other. However, in other embodiments, the shape, size and/or other characteristics of the arms 470 of the adapter 450 can be modified, as desired or required.

According to some embodiments, the arms 470 of the adapter 450 are configured to be resilient or substantially resilient (e.g., configured to flex in a radial direction when an outwardly-oriented force is exerted on them). Thus, as the closure 410', 410", 410''' (FIG. 15A) of a vial is inserted into the center opening 471 of the adapter 450, the arms 470 may be forced outwardly if the outer diameter of the closure is greater than the diameter of the center opening 471 defined by the plurality of arms 470. Consequently, the outer diameter of the closure 410', 410", 410''' is advantageously permitted to slide within the opening 471 and past the grasping portions 476 of the flexed arms 470. Once the entire height of the closure 410', 410", 410''' has cleared the edges 477 of the grasping portions 476, the arms 470 can resiliently retract inwardly (e.g., to or near their original non-biased position). In such embodiments, since the closure 410', 410", 410''' of the vial is trapped underneath the plurality of arms 470, the vial can be confidently secured to the adapter 450.

Figure 15F:
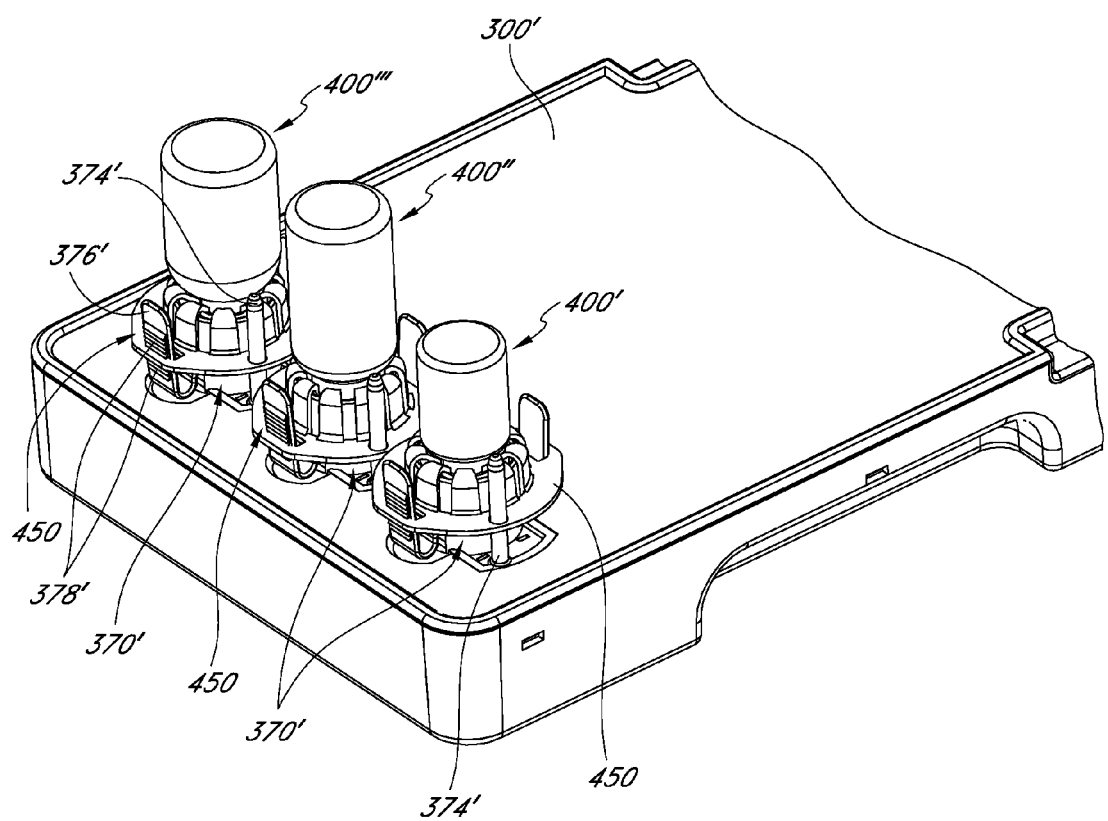
FIG. 15F illustrates a partial perspective view of three vials secured to corresponding loading areas or nests along the top surface of a cassette according to one embodiment.

Accordingly, the adapter 450 can be configured to engage many different types of vials or other containers. In some embodiments, the adapter 450 is sized, shaped and otherwise adapted to be secured to and be used with some, most or all types of vial designs and configurations. For example, FIG. 15E illustrates the adapter 450 of FIGS. 15A-15D secured to three different types of vials 400', 400", 400'''. Such adapters 450 can be used to account for the different types of vials or other containers in which various medications, formulations, other fluids and/or other materials typically injected into the anatomy (e.g., joints) are provided to clinicians. In some embodiments, the adapters 450 are configured to mate with the loading areas or nests 370 of the cassette 300 (FIG. 15F). Consequently, the adapters 450 can facilitate the proper loading of a vial or other container onto the cassette or other portion of the fluid delivery module.

In some embodiments, once an adapter 450 is secured to a vial, the adapter 450 cannot be removed without irreversibly damaging one or more portions of the adapter 450 or vial 400. For instance, it may be necessary to break one or more arms 470 of the adapter 450 and/or remove the closure 410 of the vial in order to separate the vial 400 from the adapter 450. According to some arrangements, vials are supplied to clinicians or other end users with the adapters 450 already attached. In other embodiments, the adapters 450 are supplied without the adapters. Thus, a clinician, nurse, other user or other party within the supply stream may need to secure the adapters 450 to the vials prior to use with an injection system.

FIG. 15F illustrates one embodiment of an adapter 450 that serves as an interface between the loading areas or nests 370' of a cassette 300 and three different types of vials 400', 400", 400'''. Thus, the adapters 450 can help secure the various vials that may be necessary for a particular injection procedure to the cassette 300. In some arrangements, one or more devices and/or methods are used to help lock or otherwise secure a vial/adapter combination to a nest 370' or loading area. For example, as illustrated in FIGS. 15B-15D, the adapter 450 can comprise one or more openings 456, 458 along its base 454. Such openings 456, 458 can be configured to receive corresponding features or components of a nest 370'.

By way of example, the embodiments of the loading area or nest 370' depicted in FIGS. 5A-5E comprise a pair of generally cylindrical posts 374' and a pair of wings 376'. Accordingly, the circular and rectangular openings 458, 456 of the adapter disclosed in FIGS. 15B-15D may be advantageously sized, shaped and otherwise configured to receive the posts 374' and wings 376' of the nest 370'. As best shown in FIG. 5B, the posts 374' can be offset relative to the adjacent wings 376'. Likewise, as illustrated in FIG. 15C, the circular openings 458 can be offset relative to the adjacent rectangular openings 456. Consequently, the posts 374' of the nest 370' and the corresponding circular openings 458 of the adapter 450 can help ensure that the adapter 450 is properly aligned with the nest 370' when a vial is being mounted to a cassette 300 or another portion of a fluid delivery module.

In the embodiment illustrated in FIG. 15F, when the vial/adapter combination is being secured to the cassette 300, the wings 376' of the nest 370' extend through the corresponding rectangular openings 456 (FIGS. 15B-15D) of the adapter 450. As shown, at least a portion of the wings 376' can include one or more teeth 378' or other surface features that are sized, shaped and otherwise adapted to engage the rectangular openings 456 in a ratchet-type manner. For example, the teeth 378' or other surface features of the wings 376' can be sloped in a manner that permits the vial/adapter combination to be advanced only in one direction (e.g., toward the top surface of the cassette 300). This can ensure that the vials 400', 400", 400''' are maintained in a desired vertical orientation relative to the respective loading areas or nests 370' of the cassette 300. In some embodiments, the ratchet-type lock between the teeth 378' of the wings 376' and the rectangular openings 456 can be released by squeezing the wings 376' closer to each other. This can permit the teeth 378' to disengage from the adjacent surfaces of the openings 456, thereby allowing the vial/adapter combination to be selectively moved away from the cassette 300. Consequently, when the internal contents of a vial 400', 400", 400''' have been emptied, a user can remove the vial/adapter combination and load another one on the respective nest 370'.

Figure 15G:
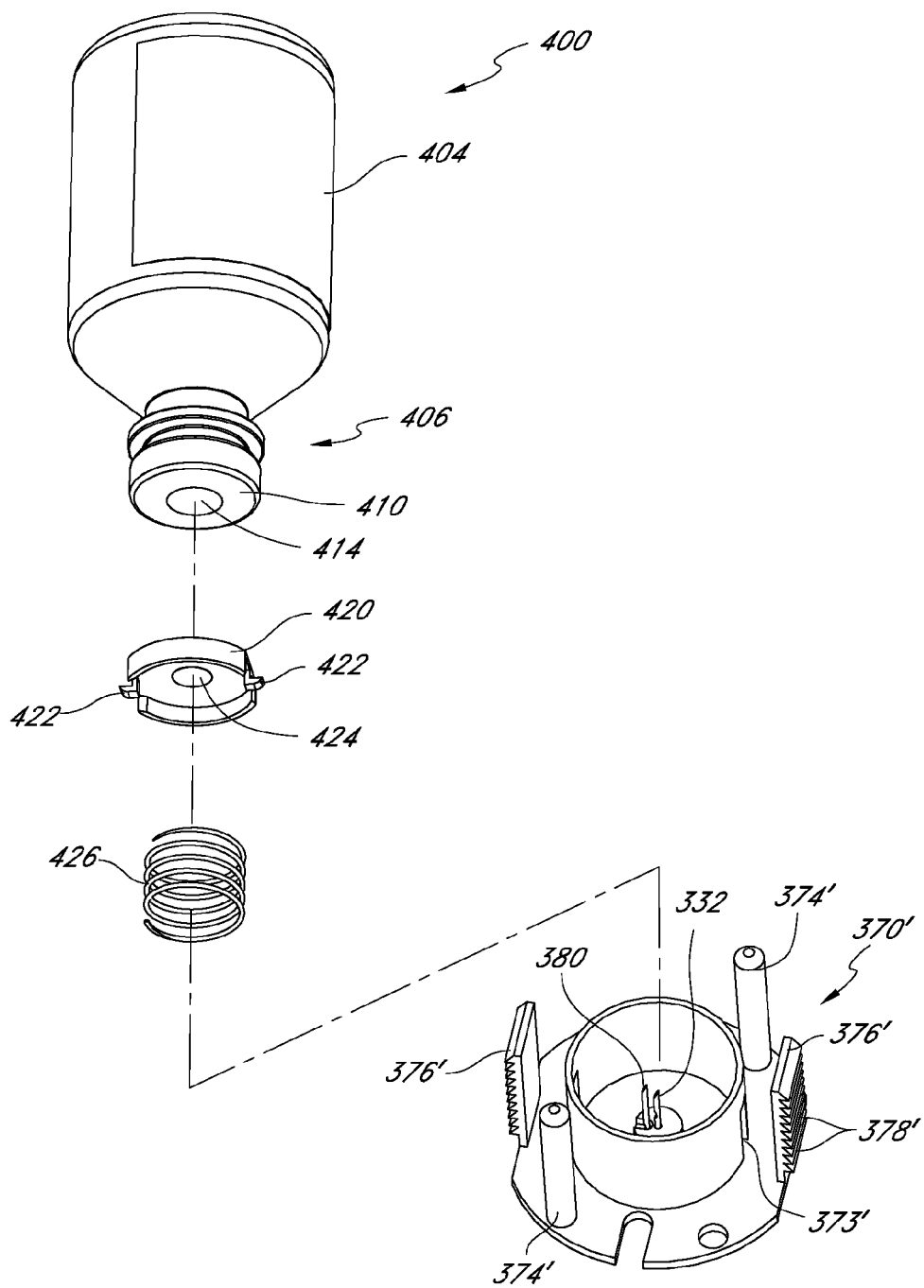
FIG. 15G illustrates an exploded perspective view of a vial and a loading area or nest into which the vial may be inserted according to one embodiment.
Figure 15H:
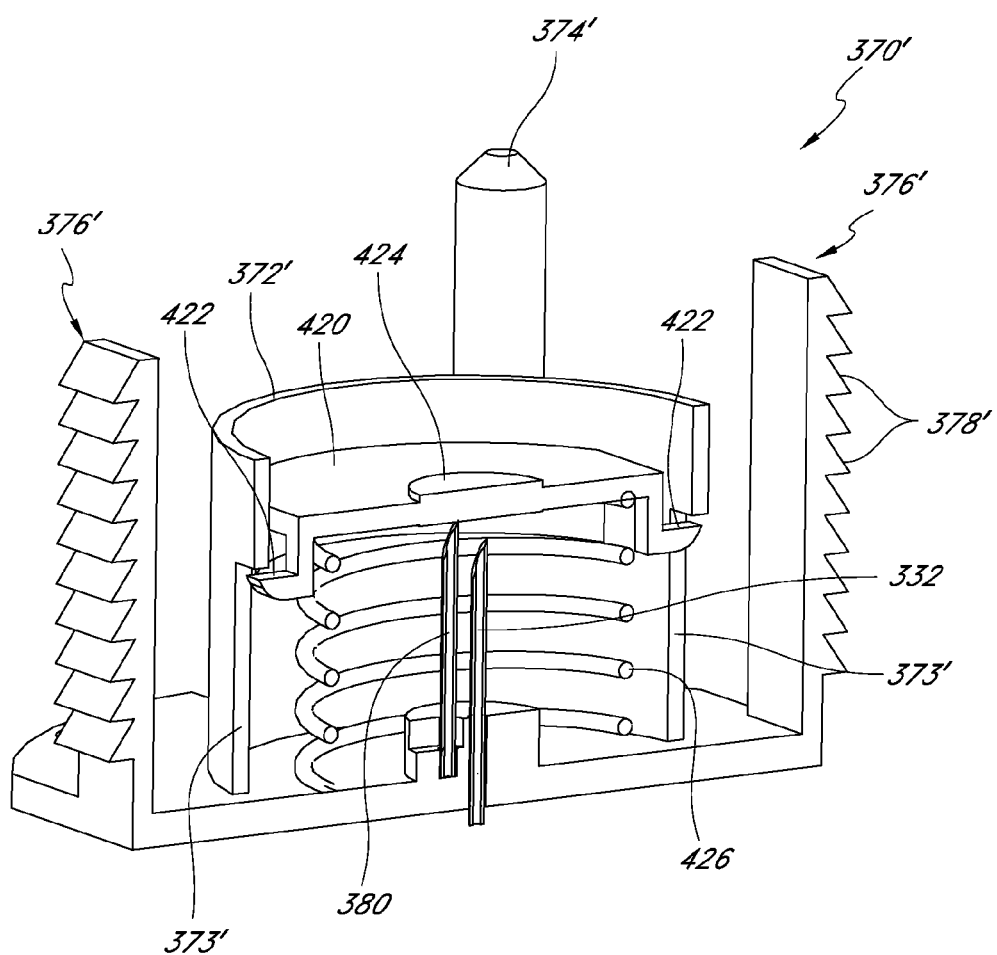
FIG. 15H illustrates a perspective cross-sectional view of the nest of FIG. 15G.
Figure 16A:
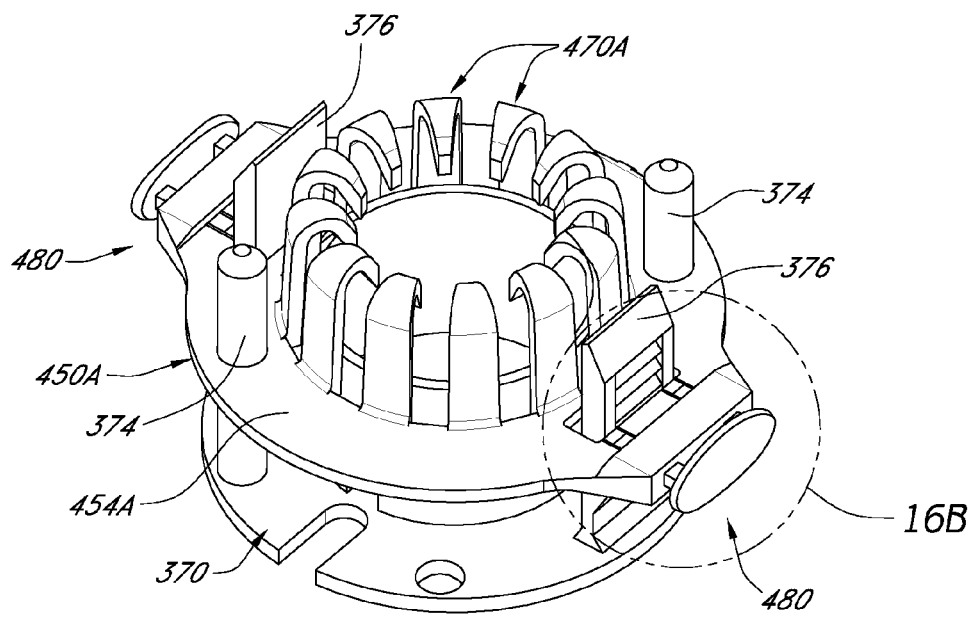
FIGS. 16A-16D illustrate various views of a vial adapter secured to a loading area or nest according to another embodiment.
Figure 16B:
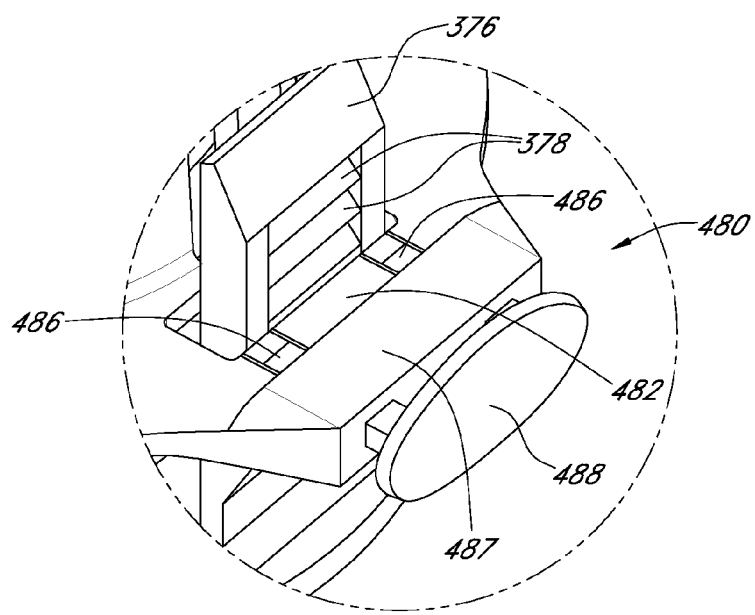
Figure 16C:
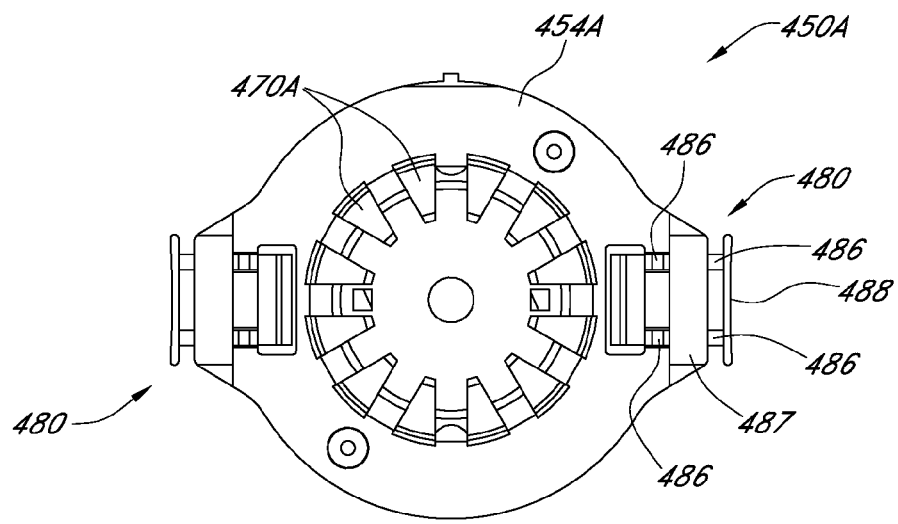
Figure 16D:
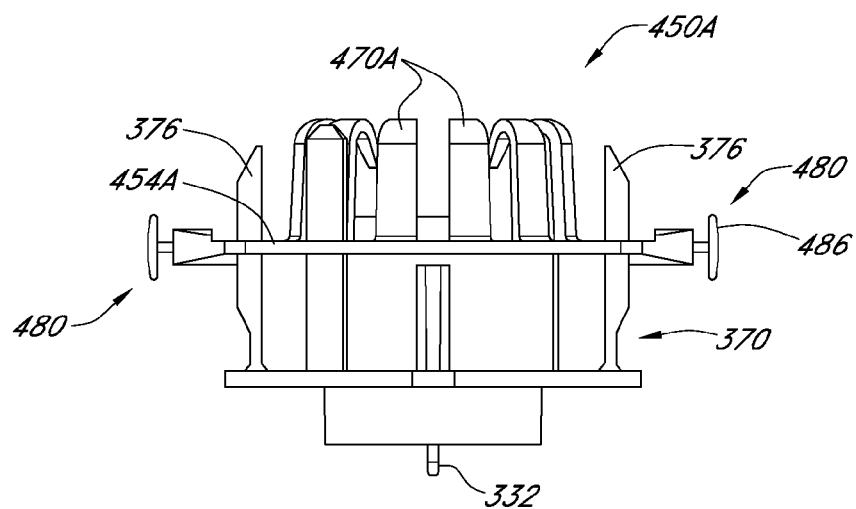

FIG. 15G illustrates an exploded perspective view of a vial 400 configured to be positioned within a loading area or nest 370' of a cassette. The adapter that would normally be secured to the neck 406 and closure 410 of the vial 400 has been omitted from the depicted arrangement for purposes of clarity. As shown, the nest 370' can include one or more vertical slots 373' along its cylindrical portion 372'. In the depicted embodiment, the cylindrical portion 372' comprises a total of two vertical slots 373' that are oriented opposite of each other. However, in other configurations, the quantity, shape, size, position, spacing and/or other details of the slots 373' can vary as desired or required.

As illustrated in FIG. 15G, an intermediate member 420 and a spring 426 can be positioned within the interior of the cylindrical portion 372' of the loading area or nest 370'. In some embodiments, the intermediate member 420 includes a pair of protrusions 422 that are sized, shaped, spaced and otherwise configured to fit within the vertical slots 373' of the nest 370'. A spring 426 or other resilient member can be used to ensure that the intermediate member 420 is normally urged upwardly, generally toward the top of the vertical slots 373'. FIG. 15C illustrates a cross-sectional view of one embodiment in which the intermediate member 420 and the spring 426 are positioned within the cylindrical portion 372' of the nest 370'.

With continued reference to FIGS. 15G and 15C, the intermediate member 420 can include a septum 424, membrane or other portion that is configured to be selectively pierced by the main needle 332 and/or the vent needle 380. In some arrangements, the septum 424 comprises a generally circular shape and is located near the center of the intermediate member 420. Preferably, the septum is adapted to be re-sealable or substantially re-sealable once one or more needles 332, 380 have been removed from it. Accordingly, the inclusion of such an intermediate member 420 and spring 426 within the loading area or nest 370' can help ensure that the needles 332, 380 are shielded from contamination when a vial 400 is not positioned within a nest 370'.

When a vial/adapter combination is loaded onto a loading area or nest 370', the top surface of the vial's closure 410 will initially contact the intermediate member 420. As the vial/adapter combination is lowered toward the cassette, the intermediate member 420 can be urged against the resilient force created by the spring 426. During this process, the protruding members 422 of the intermediate member 420 can slide within the vertical slots 373' of the nest 370'. Eventually, according to some arrangements, the main needle 332 and the vent needle 380 will penetrate both the septum 424 of the intermediate member 420 and the septum 414 of the closure 410 in order to access the interior of the vial 400. Likewise, when the vial/adapter combination is removed from the loading area or nest 370', the spring 426 can help return the intermediate member 420 to its normal position illustrated in FIG. 15C. Consequently, when a nest 370' does not have a vial 400 loaded therein, the needles 332, 380 can be advantageously protected from the outside environment by the intermediate member 420. As discussed, such an intermediate member, cover or other protective member can be used with any nest embodiment disclosed herein or equivalent thereof.

FIGS. 15A-15F illustrate only one embodiment of releasably securing a vial adapter 450 to a loading area or nest 370'. Alternative arrangements for doing so are discussed herein with reference to FIGS. 16A-18D.

FIGS. 16A-16D illustrate an alternative configuration of securing a vial adapter 450A to a loading area or nest 370'. Similar to the arrangement of FIGS. 15A-15F, the depicted vial adapter 450A comprises a base 454A and a plurality of arms 470A extending perpendicularly therefrom. In addition, the adapter 450A can include one or more openings (e.g., circular openings, rectangular openings, etc.) that are sized, shaped and otherwise configured to receive posts 374', wings 376' and/or other features of the nest 370'. As shown, the vial adapter 450A can include two push button assemblies 480 that, when pushed inwardly, are configured to release the vial adapter 450A from the nest 370'. Thus, a user can easily remove a vial from the loading area or nest when the internal contents of such a vial have been transferred to the cassette.

With continued reference to FIGS. 16A-16D, the push button assembly 480 can include a button 488 that is connected to one or more struts 486. In one embodiment, as the button 488 is depressed, the struts 486 exert a force on the adjacent wing 376' of the nest 370'. Accordingly, the wing 376' is urged inwardly (e.g., toward the center of the nest 370') so that the teeth 378' of the wings 376' move out of engaging contact with an adjacent lip 482 of the adapter 450A.

Figure 17A:
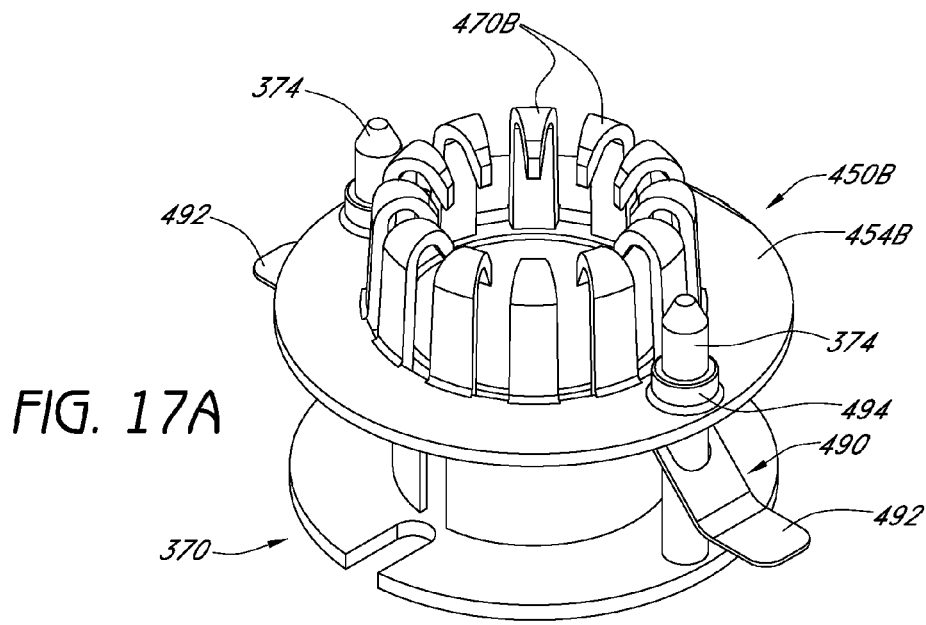
FIGS. 17A-17C illustrate various views of a vial adapter secured to a loading area or nest according to another embodiment.
Figure 17B:
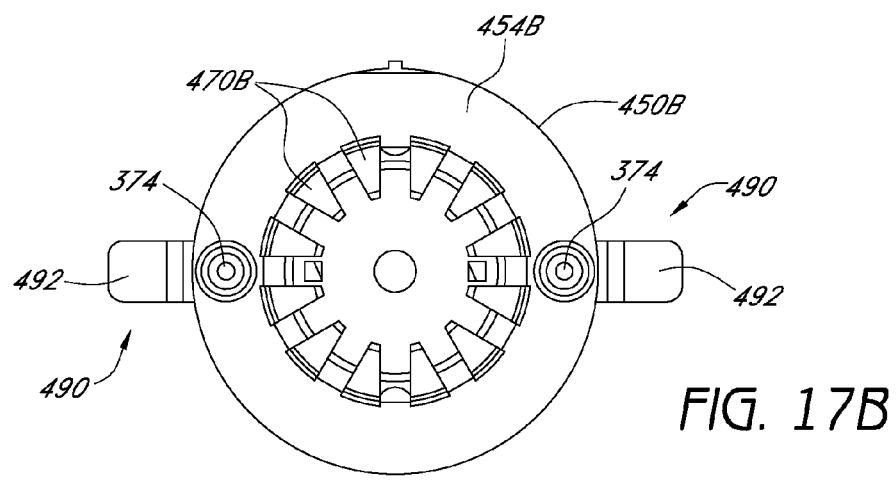
Figure 17C:
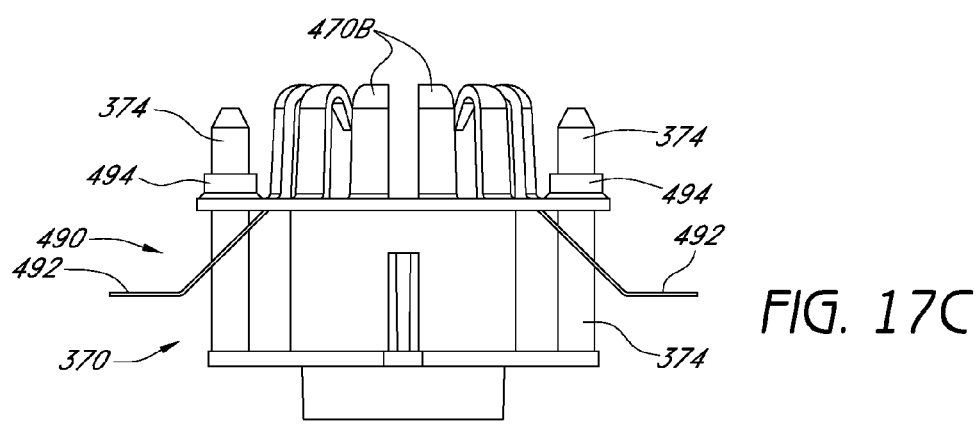
Figure 18A:
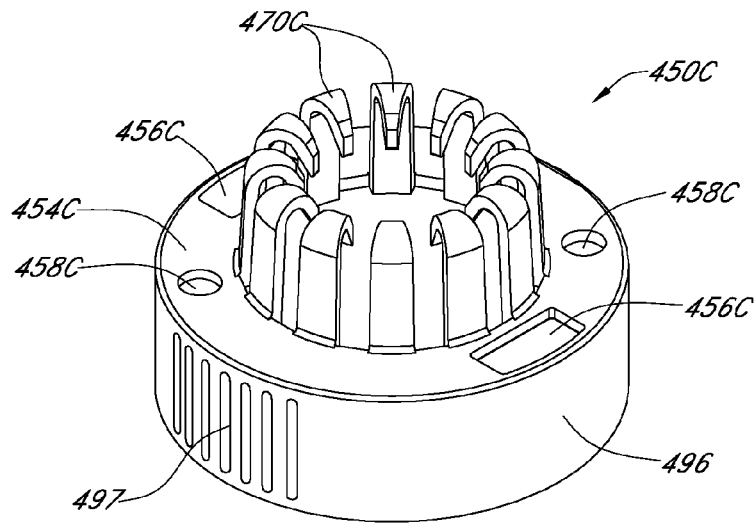
FIGS. 18A-18D illustrate various views of a vial adapter secured to a loading area or nest according to another embodiment.
Figure 18B:
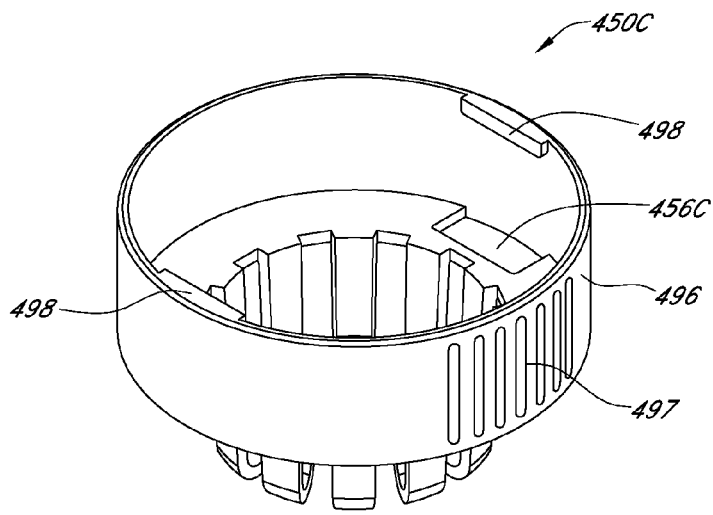
Figure 18C:
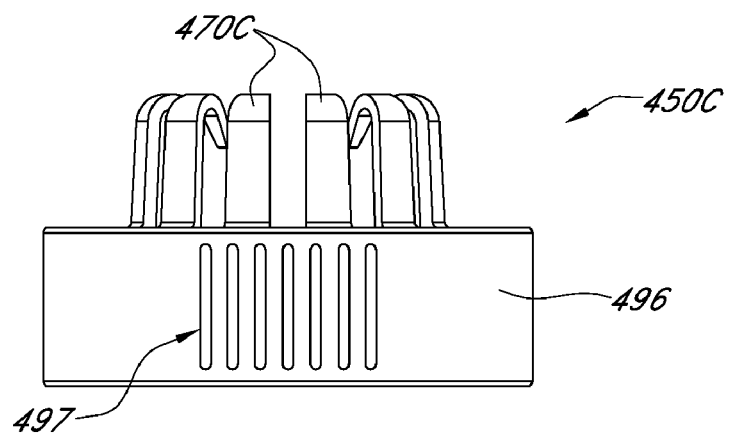
Figure 18D:
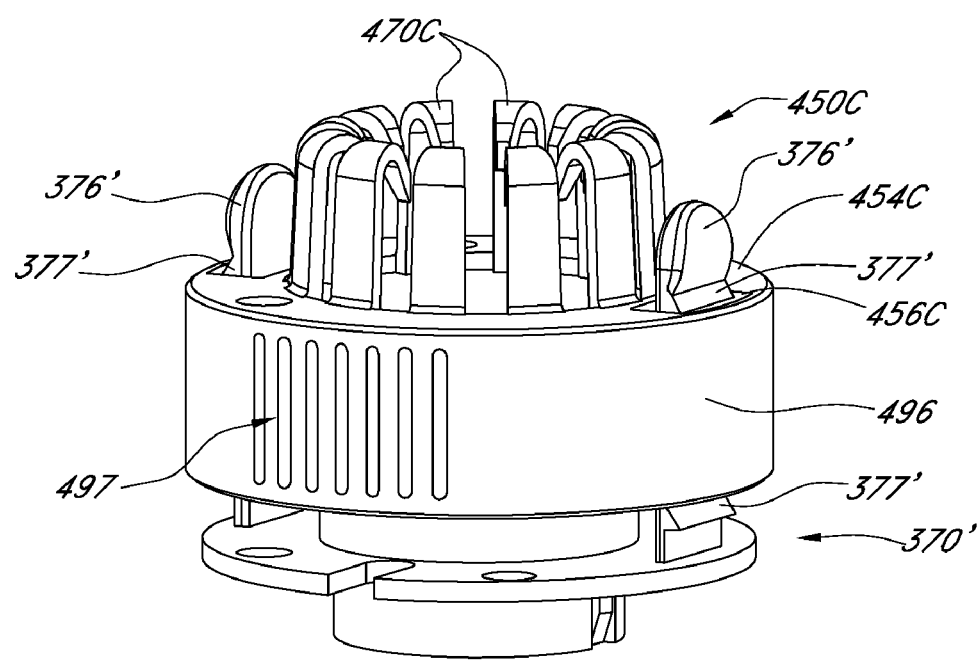

Another embodiment of a vial adapter 450B is illustrated in FIGS. 17A-17C. As shown, the adapter 450B can comprise one or more holders 494 along its base 454B. In some arrangements, such holders 494 are sized, shaped and otherwise configured to securely receive posts 374' and/or other features of a nest 370'. In some arrangements, the holders 494 are adapted to normally prevent movement between the adapter 450B and the nest 370' in one or both directions. For example, the posts 374' of the nest 370' can be permitted to slide relative to the holders 494 only in a direction that moves the adapter 450B closer to the nest 370'. The adapter 450B can include one or more release levers 492 that when properly actuated (e.g., upwardly) can allow the posts 372' to slide relative to the holders 494 in either vertical direction so that the vial/adapter combination can be removed from the nest 370'.

Various views of yet another embodiment of a vial adapter 450C are provided in FIGS. 18A-18D. As shown, the adapter 450C can include a lower portion 496 that extends below a base 454C. In some arrangements, such a lower portion 496 can include one or more lips 498 along its interior surface that are sized, shaped and otherwise configured to mate with a corresponding engagement feature 377" of a nest wing 376". As with other arrangements discussed and illustrated herein, the base 454C of the adapter 450C can include one or more openings (e.g., rectangular openings 456C, circular openings 458C, etc.) that are configured to receive wings 376", posts or other features of the nest 370" or loading area. Once a vial (not shown) is secured to the adapter 450C, the rectangular openings 456C can be aligned with the wings 376" of the nest 370" and urged toward the cassette. When the adapter is moved sufficiently far relative to the nest 370", the lips 498 along the interior of the adapter 450C can come into locking contact with the corresponding engagement features 377" of the wing 376". Thus, the vertical position of the adapter 450C relative to the nest 370" or loading area can be advantageously maintained. Once the user desires to remove the vial/adapter combination from the nest 370" (e.g., in order to discard a spent vial, replace a spent vial with a new vial, etc.), he or she can depress the sides of the adapter's lower portion 497 (e.g., along the textured region 497) so that the overall shape of the adapter 370" is modified. If the sides 497 of the adapter 450C are squeezed with sufficient force, the lips 498 and the corresponding features 377" can be disengaged, thereby allowing the adapter to be removed from the nest 370". It will be appreciated that one or more other methods or devices for releasably locking an adapter to a loading area, nest or other portion of a cassette or fluid delivery module can be used, either in lieu of or in addition to the specific embodiments discussed and illustrated herein.

In some embodiments, as illustrated in FIGS. 19A-19C, vial adapters 450D comprise one or more identification flags 460 or other members that include a machine readable code or pattern 462. In the illustrated arrangement, the flag 460 extends upwardly from the base 454D of the adapter 450D in a direction generally opposite of the vial 400 to which the vial 400 is secured. The identification code or pattern 462 on the flag 460 can include a barcode, an identifiable graphical or color pattern, a numerical code, an RFID or other radio frequency code and/or the like. For example, in some embodiments, the identification flag 460 or other member comprises the National Drug Code (NDC) number of the particular medication or other formulation contained within the vial 400 to which the adapter 450D is secured.

With continued reference to FIG. 19C, the loading area or nest 370' can include an opening 375' through which the identification flag 460 of the adapter 450D may pass as the adapter 450D is secured to the nest 370' or other portion of the cassette or fluid delivery module. In some embodiments, the cassette or other portion of the fluid delivery module includes a reader (e.g., barcode scanner, RFID reader, etc.) that is configured to automatically detect the identifiable pattern 462 of the flag 460 when the adapter is secured to the nest 370'. Accordingly, assuming the correct adapter 450D is secured to a vial 400, the fluid delivery module can be advantageously configured to automatically detect the various medications, formulations, other agents and/or other fluids or materials that are being loaded into the cassettes. This can help improve the safety of the articular injection system as the likelihood of potentially dangerous errors can be eliminated or reduced.

Vials containing medications and/or other materials used during an injection procedure can be supplied with such vial adapters 450D already attached to them. In other arrangements, a clinician, another user and/or someone higher in the supply chain to the end users may be responsible for securing the correct vial adapters 450D to the vials 400.

In some embodiments, the internal contents of a vial or other container to be loaded onto a fluid delivery module can be detected, either manually or automatically, using one or more other identification devices. For example, the fluid delivery module and/or another portion of the injection system can include a barcode reader, RF reader or other type of identification device (not shown). In one arrangement, a scanner is positioned along an exterior surface of the fluid delivery module housing. Such an identification device can be adapted to read a barcode, RFID patch and/or any other label, signal or the like of a vial (or other container of anesthetics or other pain-relieving medication, steroid, saline, pharmaceutical compositions, hyaluronic acid, other medications or drugs, cells, liquid and non-liquid fluids and flowable materials, nanoparticles, cement, microbeads, etc.).

An vial identification device can permit a user to quickly, easily and securely verify the type, dosage, strength and other details of the medication, fluid and/or other material that will be delivered to the targeted anatomical location by the injection system. Thus, in some embodiments, once a particular treatment or delivery sequence is selected, a clinician or other user can confirm that the correct medications, fluids and/or other materials are loaded into the fluid delivery module using such an identification device (e.g., scanner, RF reader, etc.). For example, once a particular joint treatment is selected, the required vials or other containers of anesthetics, steroids or other therapeutics (such as hyaluronic acid and/or the like) can be confirmed using a scanner or other identification device before loading the corresponding vials into the cassette or other portion of the fluid delivery module.

As discussed, it may be desirable or necessary to maintain the internal contents of a vial or other container mixed while such vial or other container is positioned on the cassette. For example, certain types of steroids or other formulations that include a relatively high solids concentration may need to be mixed to ensure that a consistent and homogeneous dose is provided to the patient during an injection procedure. Thus, one or more devices or methods of agitating the internal contents of a vial or other container can be advantageously provided. One embodiment of such an agitation system is discussed herein with reference to the nest 370A or loading area illustrated in FIGS. 3K-3S.

Another arrangement configured to mix the contents of a vial or other container secured to a fluid delivery module is illustrated in FIGS. 20A-20C. Similar to other standard or non-standard vials or other containers discussed and illustrated herein, the depicted mixable vial 430 comprises a neck portion 434 and a closure 436 to which an adapter (not shown) may be selectively secured. As shown, a stopper 440 can be positioned at the opposite end of the vessel 432 to define a sealed interior space 433 into which steroids and/or other fluids or materials may be placed. In order to ensure that the interior space 433 is properly sealed, one or more O-rings 435 or other sealing members can be used between the vessel 432 and the stopper 440.

With continued reference to FIGS. 20A-20C, the vial 430 can include one or more agitators 444 configured to continuously or intermittently stir the interior space 433. In the illustrated embodiment, the vial comprises a single agitator 444 that includes a corkscrew shape and extends throughout most or all of the length of the vessel 432. However, in other arrangements, the quantity, shape, size and other details of the agitator 444 can vary, as desired or required. The agitator 444 can be mechanically coupled to a gear 448 using a pin 449 or other connection device or method. In some embodiments, the gear 448 is coupled to a motor (not shown) that can cause the agitator 444 to rotate or otherwise move in order to mix the internal contents (e.g., steroids) of the vial 430.

When injecting fluids and/or other materials into the anatomy that require continuous or intermittent mixing, it may be desirable to transfer such fluids and/or other materials from the vial 430 to the cassette 300 on as needed basis. For example, the fluids or materials can be maintained in an agitated state within a mixable vial 430 or within a rotatable nest 370A or loading area (FIGS. 3K-3S) until immediately before the injection procedure is commenced. Otherwise, if such fluids and/or other materials are permitted to become non-homogeneous, the effectiveness of the injection procedure may be negatively affected. It will be appreciated that other devices and/or methods of agitating the contents of a vial 430 can be used, either in addition to or in lieu of the specific embodiments disclosed herein. Further, it may be necessary to provide temperature control to one or more of the vials, the cassette and/or another portion of the articular injection system. For example, temperature control may be needed to prevent degradation or decomposition of a particular medication, composition or other material being delivered during an injection procedure. Accordingly, the fluid delivery module, the handpiece assembly and/or another portion of the injection system can be selectively temperature controlled. Such climate control can be accomplished using heating, refrigeration and/or other techniques known to those of skill in the art. For example, one or more components of the injection system can include refrigeration or heating units, thermostats, necessary controls and/or the like.

C. Handpiece Assembly

General

As discussed herein with reference to FIGS. 1 and 2, an articular injection system 10 can include a handpiece assembly 200 that serves as an interface between the fluid delivery module 100 and the targeted anatomical location T to which one or more fluids and/or other materials are to be delivered. One embodiment of such a handpiece assembly 200 is illustrated FIGS. 21A and 21B. As shown, the handpiece assembly 200 can include several different portions that are selectively removable from and attachable to each other. This can help reduce or minimize the number of items that need to be discarded and/or cleaned (e.g., sterilized) over time and/or between procedures. As a result, material and operational costs, as well as the amount of waste that is generated over time, can be advantageously reduced. In addition, the efficiency with which the system is operated and maintained can be improved.

As discussed in greater detail herein, the handpiece assembly permits a user to selectively deliver one, two or more different medicaments, other fluids and/or other materials into a patient's anatomy through a single needle positioned at the distal end of the device. In some embodiments, a clinician uses buttons and/or other controllers positioned on the handpiece assembly to control the delivery of the various fluids and/or other materials through the assembly. A user can manipulate such buttons or other controllers to modify one or more aspects of the injection procedure (e.g., which fluids are being delivered, sequence of delivery, flowrate, etc.) while continuing to grasp and manipulate the handpiece assembly. Accordingly, in some embodiments, a user executes a desired procedure without taking his or her hands off the handpiece assembly.

Moreover, at least some of the various embodiments of the handpiece assembly discussed herein permit two or more different fluids and/or other materials to be transferred to or near a needle without prior mixing or cross-contamination of the various streams. Thus, in some embodiments, the different fluids and/or other substances are mixed just prior to entering the needle. As discussed in greater detail herein, the various fluid or other material streams can be mixed at a distal end of the clip (e.g., a common or collection area), at or near the interface between the clip and the disposable tip and/or at any other location. In certain situations, the effectiveness of an injection may be enhanced if the contact time between the various fluids and/or other substances being delivered into a patient is reduced or minimized (e.g., for various chemical, biological and/or other reasons). Relatedly, the handpiece assembly can be adapted to prevent backflow of fluids and/or other materials being transferred therethrough. This can help reduce the likelihood of cross-contamination or inadvertent mixing of the various medicaments and other substances. For example, as discussed, the handpiece can include various valves (e.g., duckbill valves, combination duckbill/umbrella valves, other check valves, etc.) and/or other backflow prevention devices.

In some embodiments, the handpiece assembly includes buttons and/or other controllers that are used to operate another device, such as, for example, an ultrasound device or another imaging system. Such buttons or other controllers can be included either in lieu of or in addition to the buttons and controllers on the handpiece for the operation of the injection system itself. Thus, a clinician or other user can advantageously control the operation of an ultrasound or other imaging device and/or any other system using only the handpiece assembly. As a result, the clinician can control and complete an injection procedure while continuing to hold the handpiece assembly (e.g., without the use of any other device or system). Accordingly, this can help improve the safety and accuracy of a procedure as the user is permitted to operate various systems during an injection while continuing to hold and manipulate the handpiece assembly.

In addition, as discussed in greater detail herein, configuring different devices and systems to interface with one another during an injection procedure can provide additional benefits. For example, information about the delivery of fluids and/or other substances (e.g., the volume of each medicament delivered, the volume of each medicament remaining, the flowrate of medicament through the handpiece, etc.) can be incorporated into the same visual display with the graphics of an ultrasound or other imaging technology. As discussed in greater detail herein, this can further facilitate the execution of an injection procedure. In addition, such a configuration can improve record-keeping, billing and other functions that are related to the administration of a medical procedure.

For example, in one embodiment, the handpiece assembly 200 comprises a core 210, a clip assembly 240 and a tip 280 having a needle 290 along its distal end. A delivery line 250 comprising one or more different conduits 251 (FIG. 7B) can be used to place the handpiece assembly 200 in fluid communication with the cassette 300 and/or another portion of the fluid delivery module 100. In one embodiment, the tip 280 is replaced after each injection (e.g., immediately following removal of the needle 290 from the anatomy). Further, the clip assembly 240 can be replaced when the type and/or dosage of the medications, formulations and/or other materials being delivered through the handpiece assembly 200 are modified. As discussed, in some embodiments, the clip assembly 240, the delivery line 250 and the cassette 300 can be supplied and replaced as a single system or kit as desired or required.

The handpiece assembly 200 can be adapted to allow a clinician or other user to easily grasp and manipulate it during an injection procedure. As such, the diameter, length, other dimensions and/or other characteristics of the handpiece assembly 200 can be advantageously selected to achieve the desired functional and/or aesthetic goals. Further, the handpiece assembly 200 can include a shape, other features (e.g., finger grooves, tactile members or outer surface, etc.) and/or the like to further enhance its ergonomic and/or other properties. According to some arrangements, the approximate diameter and total length (e.g., not including the needle 290) of the handpiece assembly 200 are approximately 5 to 6 inches and approximately 0.5 to 0.7 inches, respectively. In addition, the various components of the handpiece assembly 200, including the core 210, clip 240, tip 280 and the like, can be manufactured using one or more materials that are durable and otherwise suitable to withstand the forces and wear and tear to which the handpiece assembly 200 may be exposed.

For example, in several embodiments, the handpiece assembly 200 comprises plastics, other polymeric materials, metals, alloys and/or any other synthetic or natural materials.

In some embodiments, the clip assembly 240 is replaced according to a particular schedule or protocol. For instance, the clip assembly 240 (and, in certain arrangements, the delivery line and the cassette together with the clip assembly) can be replaced following a predetermined number of injection procedures, following a predetermined volumetric amount of fluids and other materials passing through the clip assembly 240, based on a predetermined time frequency (e.g., once a day, once every four hours, etc.) and/or according to some other set of rules, as desired or required by the particular application or use. In some arrangements, the core 210 is advantageously configured to not contact any fluids and/or other materials being conveyed through the handpiece assembly 200. As a result, the same core 210 can be used repeatedly without the need to replace or clean it. However, it will be appreciated that even such a core 210 may need to undergo frequent cleaning (e.g., sterilization), calibration and/or other maintenance procedures. Each component of such a handpiece assembly 200 is discussed in greater detail herein.

Handpiece Core

Figure 21A:
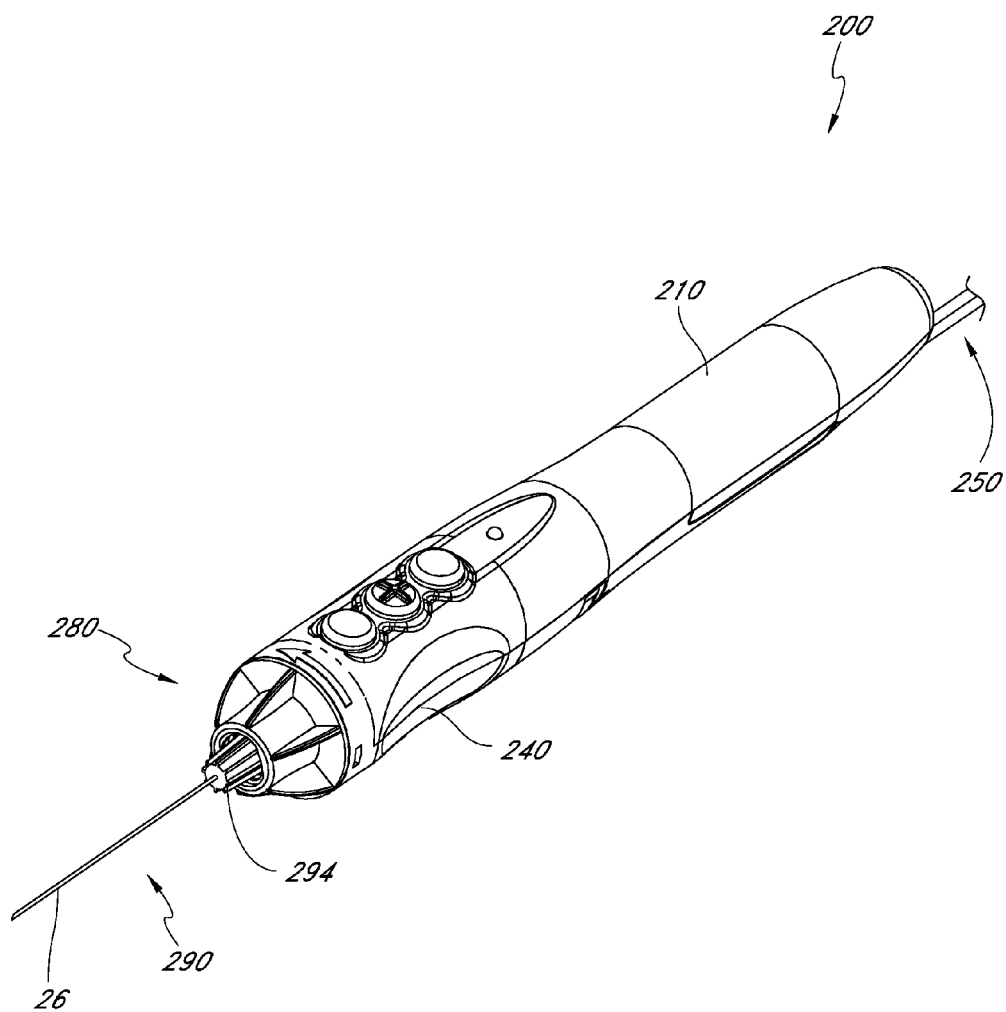
FIG. 21A illustrates a perspective view of a handpiece assembly configured for use with an articular injection system according to one embodiment.
Figure 22A:
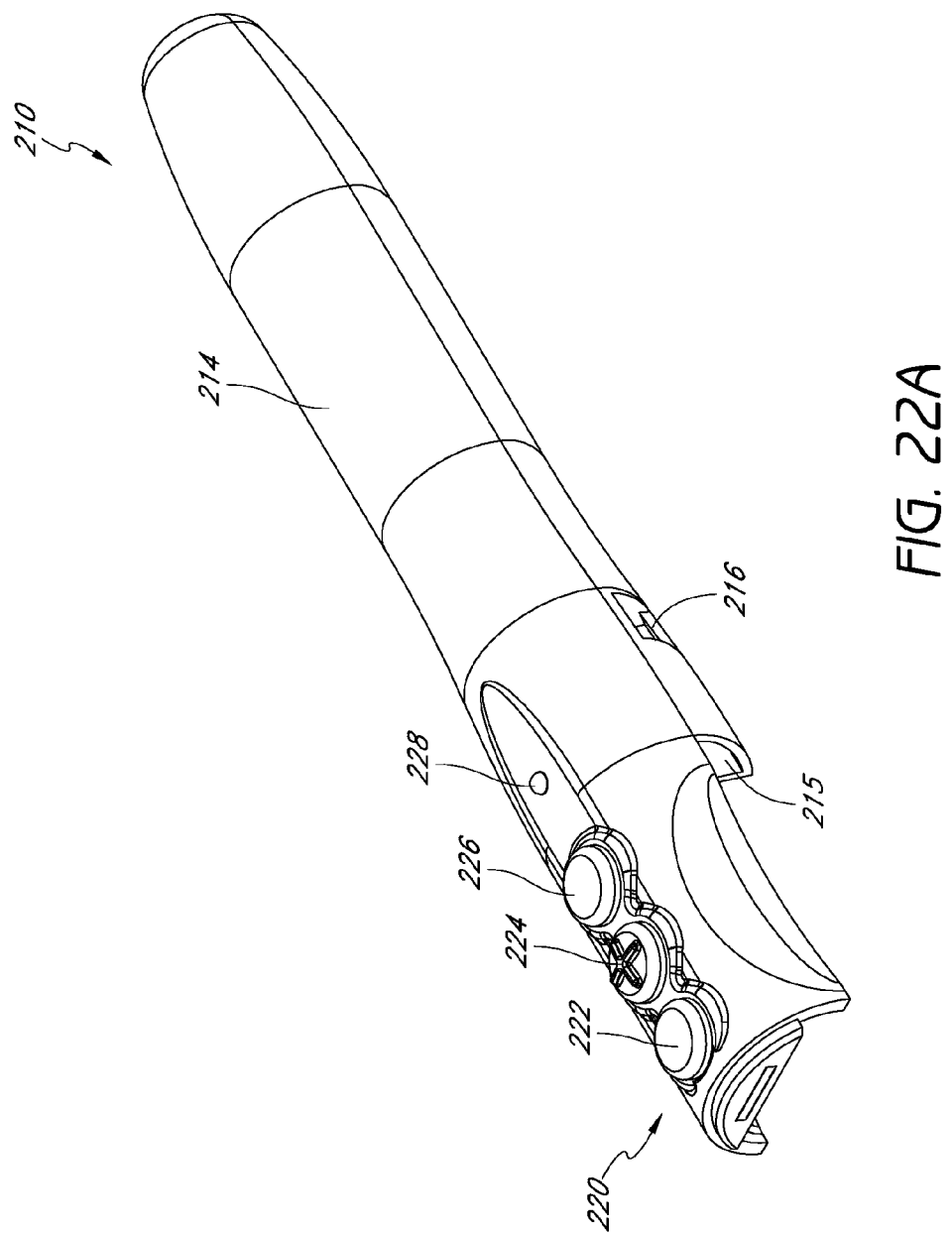
FIG. 22A illustrates a perspective view of a core of a handpiece assembly according to one embodiment.
Figure 22B:
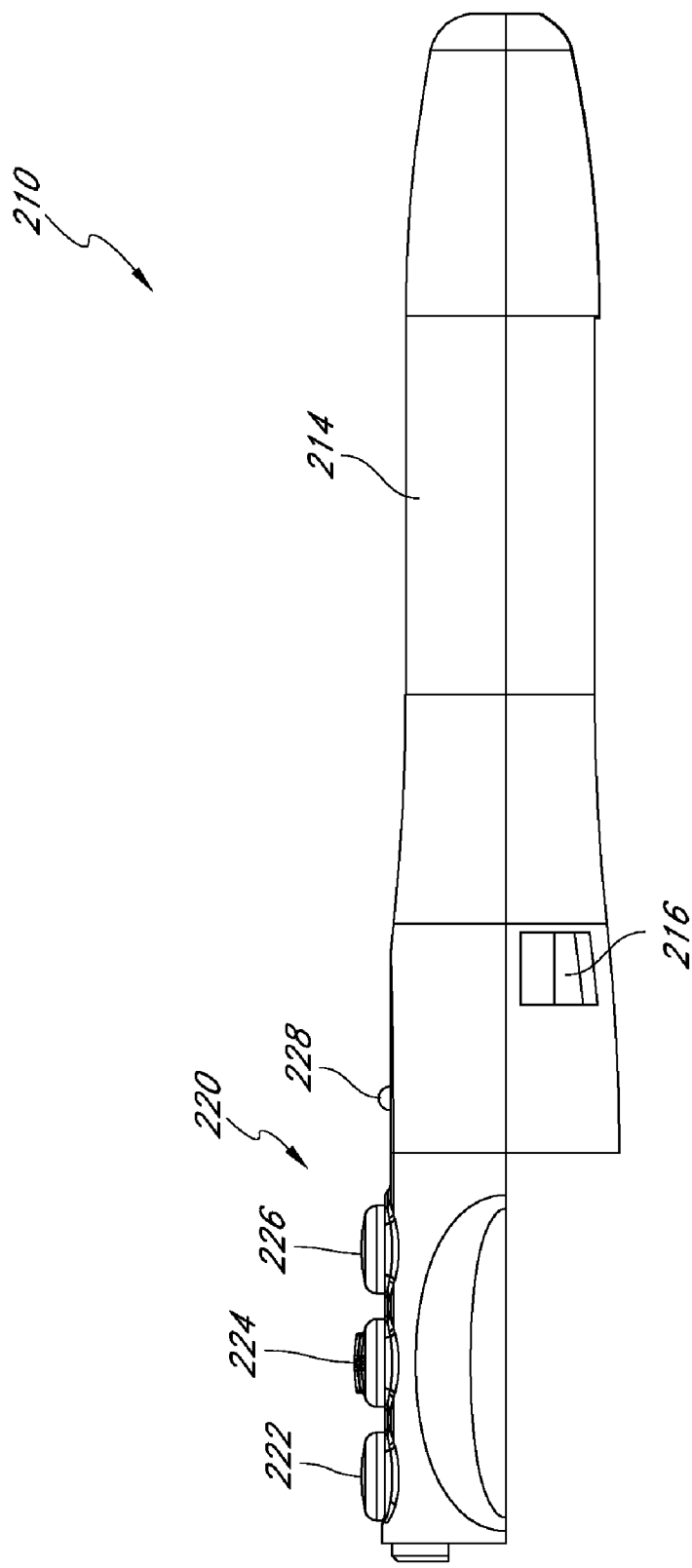
FIG. 22B illustrates a side view of the core of FIG. 22A.

FIGS. 22A and 22B illustrate different views of the core 210 included in the handpiece assembly 200 of FIGS. 21A and 21B. As shown, the core 210 can comprise a control portion 220 having one or more buttons 222, 224, 226, controllers and/or other adjusting devices (e.g., knobs, dials, switches, etc.). In addition, the control portion 220 can include one or more indicator lights 228 and/or any other feature that provides information to the user regarding the operation of the assembly 200 and/or the injection system.

The buttons 222, 224, 226 and/or other control features of the core 210 can help regulate the delivery of various fluids and/or other materials through the handpiece assembly 200. For example, such buttons 222, 224, 226 can be used to activate or deactivate (e.g., ON/OFF) the supply (and/or withdrawal) of fluid or other substances to or from an intraarticular space or other anatomical location. In certain arrangements, the buttons or other controllers are manipulated to regulate the rate of delivery (e.g., flowrate) of one or more medicants and/or other materials being transferred through the handpiece assembly. As discussed, in other embodiments where the fluid delivery module is in data communication with one or more other components or devices (e.g., ultrasound devices, radio frequency spectroscopy devices, other imaging devices or systems, etc.), buttons or other controllers can be used to also regulate the operation of such systems. For example, as discussed in greater detail herein, the buttons or other controllers of a handpiece assembly can be used to capture an ultrasound image or video while a target anatomical space (e.g., a joint, organ, etc.) is being located and/or while one or more fluids or other materials are being injected into a target anatomical location. Alternatively, the buttons or other controllers can be used to vary one or more other aspects of an imaging system, such as, for example, zoom, resolution, contrast, brightness and/or the like. In some embodiments, a handpiece assembly includes additional, fewer and/or different buttons, knobs, levers and/or other control devices that permit a user to control one or more aspects of the system.

With continued reference to FIG. 22A, each of the buttons 222, 224, 226 along the outside of the core 210 can be configured to correspond to one of the medications and/or other materials which are loaded onto the fluid delivery module 100 and which can be selectively delivered from to the handpiece assembly 200. For instance, each such medication, other fluid or the like can be associated with a particular color, shape, pattern, design, scheme, texture, other identifying feature and/or the like. Thus, in some embodiments, the color, shape or pattern of the buttons 222, 224, 226 is configured to match a corresponding characteristic of the medications and/or other materials that are loaded onto the fluid delivery module (e.g., positioned on the nests or loading areas of the cassette). By way of example, one of the buttons 222 on the core can be yellow. In addition, the user may have selected yellow to also correspond to a particular type of therapeutic agent (e.g., steroid) which is loaded onto the cassette and which may be selectively delivered from the fluid delivery module to the handpiece assembly 200 (see FIGS. 48A-48D and 49A-49D for additional information regarding matching a particular medication and/or other material to a button of the handpiece assembly). In another embodiment, the buttons are textured in a manner that permits a clinician or other user who handles the handpiece assembly to identify the various buttons without having to look at them. For example, the buttons can include a raised or recessed pattern (e.g., a "plus" or "minus" sign, dots, a rectangle, circle, other geometric design, other discernable pattern and/or the like). Thus, by pressing the appropriate button 222, the user can commence, terminate, speed up, slow down and/or otherwise adjust the delivery of a therapeutic agent and/or other fluid or substance to the patient.

According to certain embodiments, a handpiece assembly 200 comprises one or more two-mode or other multi-mode buttons and/or other controllers. Pressing or otherwise manipulating such a button can alternately commence or terminate the delivery of one or more fluids and/or other materials through the assembly. Alternatively, the handpiece assembly 200 can include one or more other types of buttons or controllers. In some arrangements, the buttons are configured to permit the user to select between two, three or more different settings. In other embodiments, a button is of the multi-depth type (e.g., dual-depth, tri-depth, etc.), enabling a user to selectively press the button to two or more distinct depths or other levels. Each distinct depth or level can correspond to a particular setting (e.g., flowrate, selection of which fluids or other materials to deliver, etc.). For example, pressing the button to the first level can cause the desired fluid and/or other material to be conveyed at the maximum or minimum rate. Further, continuing to press the button to subsequent lower levels can cause the rate of delivery to increase, decrease or terminate. In other embodiments, the handpiece assembly comprises multi-depth buttons that do not include distinct depths, such as, for example, a rheostat. Thus, a particular setting (e.g., flowrate) can be varied based on the depth to which a button is depressed.

In other arrangements, the core 210 of the handpiece assembly comprises one or more buttons that have only two positions, but which are configured to permit a user to select between three or more different settings. For example, an injection system can be adapted to sequentially move between different flowrate settings (e.g., high-medium-low-off, vice versa, etc.) every time such a button is pressed.

As discussed, a core 210 or other portion of a handpiece assembly can comprise other types of controllers, either in lieu of or in addition to the buttons. For example, the handpiece assembly 200 can include a roller ball, a roller wheel, a dial, a knob, a modulating switch or other device and/or the like. Regardless of their exact configuration and design, such control devices can enable a clinician or other user to regulate the delivery of fluids and/or other materials from the fluid delivery module to a patient. As discussed, the various fluids and/or other materials can be delivered through the handpiece assembly simultaneously or sequentially, as desired or required. For example, the buttons and/or other controllers can be used to select which fluids or other materials, or combinations thereof, are to be directed through the handpiece assembly. In other embodiments, the controllers are configured to control the rate of delivery (e.g., flowrate) of such fluids and/or other substances to a patient. In still other arrangements, the buttons control one or more other aspects of the injection procedure (e.g., the sequence of delivery, an ultrasound or other imaging device that is in data communication with the injection system, etc.).

In other arrangements, the buttons 222, 224, 226 on the handpiece assembly 200 are adapted to guide the user through one or more user-interface screens on the display or graphic user interface (GUI) 130 (FIG. 2A) on the fluid delivery module 100. Thus, the buttons 222, 224, 226 can be used to make selections through one or more menus or the like.

According to some embodiments, the handpiece assembly 200 is connected to the fluid delivery module 100 of the injection system 10 using one or more hardwired connections. However, the handpiece assembly 200 can be configured to communicate with the fluid delivery module 100 and/or any other component of the injection system using a wireless connection, such as, for example, radio frequency (RF), Wi-Fi, Bluetooth and/or like, either in addition to or in lieu of a hardwired connection. As discussed herein with reference to FIG. 2A, the handpiece assembly 200 can comprise a battery that is configured to be recharged when the handpiece assembly is positioned within a corresponding docking station 116 of the fluid delivery module 100. Such a battery (not shown) can be positioned within an interior portion of the core 210. The docking station 116 can be adapted to recharge the battery using electromagnetic induction, simple charging (e.g., using a DC or AC connection), pulse charging and/or any other charging method or device. Thus, in some arrangements, the battery within the core is permitted to recharge when the handpiece assembly is positioned within a docking station 116 of the fluid delivery module. Alternatively, the handpiece assembly 200 may draw its power from one or more other sources, such as, for example, a DC or AC hardwired connection and/or the like.

As discussed, an interior portion of the core 210 can include a battery, circuitry, indicator light 228 (e.g., LED) and/or any other component or feature. As illustrated in FIGS. 22A and 22B, the core 210 can include one or more indicator lights 228 that provide information to the clinician or other user of the assembly prior to, during and/or following an injection procedure. For example, the light 228 can be configured to light up when the battery of the assembly is above or below a particular threshold level (e.g., adequately charged, in need of charging, etc.). Alternatively, the brightness, color and/or other characteristics of the indicator light 228 can be configured to change in response to certain conditions. For instance, the properties of the light 228 can vary based on the strength of the battery, on the signal strength of the wireless connection (e.g., radio frequency, RF, Bluetooth, etc.) between the handpiece assembly and the fluid delivery module or other component of the system and/or the like.

In other embodiments, an indicator light 228 is activated (e.g., lights up, begins to flash, changes color, etc.) as a warning to the user. For example, the triggering event for such an activation can include a low battery level, the presence of air or other gas within a fluid delivery conduit, excessive back-pressure encountered during the delivery of a fluid or other material within the anatomy, low fluid level within a reservoir of the fluid delivery module, some other breach and/or the like. According to certain embodiments, the core 210 or other portions of the handpiece assembly 200 includes a small display (e.g., LCD) that is configured to provide information to the user in the form of text, graphics and/or the like, either in addition to or in lieu of one or more indicator lights 228.

Consequently, the inclusion of the various electronic and/or other components and features within a single core 210 or other portion of the handpiece assembly 200 provides a number of benefits. As discussed, such configurations can permit a clinician or other user to control some or all aspects of an injection procedure without having to take his or her hands off the handpiece assembly 200. In addition, a single handpiece assembly 200 can be adapted to control one or more other devices or systems which are used during the execution of injection procedures. For example, the buttons or other controllers of the handpiece assembly can be used to advantageously regulate an ultrasound device or other imaging system. Although the inclusion of electrical and control components within the relatively limited space of a core 210 is challenging, the convenience and other benefits associated with using a single handpiece to control some, most or all aspects of an injection procedure can be beneficial.

As described in greater detail herein, a touchscreen display 130 or other graphic user interface which is either attached to the fluid delivery module 100 (FIG. 2A) or operatively connected to it can be used to regulate, at least in part, the function of the handpiece assembly 200 and/or other components of the articular injection system 10. In other embodiments, a separate handheld device, instrument and/or other device or system can be used to control the handpiece assembly 200 and/or other components of the injection system. For example, such a control device or other instrument can include separate power, control and/or instrumentation wires that are molded within or otherwise positioned relative to the separate device. In some embodiments, the separate control device is configured to attach to (e.g., snap or otherwise mount to) or otherwise secure to the handpiece assembly 200 using one or more types of connection devices and/or methods.

Moreover, other devices and methods of controlling one or more aspects or components of the injection system can be used, either in addition to or in lieu of the devices and methods specifically disclosed herein. In some embodiments, the injection system includes a foot pedal or other user-actuated lever or control. Alternatively, the injection system can comprise control features that are configured to respond to a clinician's or other user's voice commands or prompts, such as, for example, "START," "STOP," "INJECT/DELIVER," "ASPIRATE," "INCREASE FLOWRATE," "DECREASE FLOWRATE," "CHANGE MODE/SEQUENCE" and/or the like. It will be appreciated that an articular injection system can include any combination of controls or other features described herein, as desired by the user or required by a particular application.

In some embodiments, the shape of the core housing 214 and other graspable portions of the handpiece assembly 200 are configured to be ergonomically correct or are otherwise designed to facilitate the handling and manipulation of the handpiece assembly 200. Further, as discussed in greater detail herein, the core 210 can be configured to quickly and easily attach to and detach from one or more other subcomponents of the handpiece assembly 200, such as, for example, the clip assembly 240 and the tip 280.

Clip Assembly

FIGS. 23A-23D illustrate various views of one embodiment of a clip assembly 240 configured to be used in a handpiece assembly 200. As shown, the clip assembly 240 can include a ring 242 at or near its distal end. In some arrangements, the distal end of the clip assembly 240 comprises a recessed surface 243 to which a tip 280 can be removably secured (FIGS. 21A and 21B). Further, a central portion of the recessed surface 243 can include an outlet opening 248 into which an inlet portion of the tip 280 may be positioned. In addition, the interior and/or exterior of the ring 242 can comprise one or more tabs 246 and/or recesses 244 to help secure the clip assembly 240 to the tip 280, the core 210 and/or any other portion of the handpiece assembly 200. Additional details regarding various tip embodiments are discussed in greater detail herein with reference to FIGS. 28A-34.

With continued reference to FIGS. 23A-23D, the clip assembly 240 can include a main body 256, which in some embodiments is configured to at least partially define an exterior surface of the handpiece assembly 200. At the proximal end of the main body 256, the clip 240 can include one or more elongate members 258 that are sized, shaped and otherwise adapted to mate with corresponding portions of the core 210 (FIGS. 22A and 22B). For example, the elongate members 258 can slide within corresponding slots 215 (FIG. 22A) of the core 210. In the illustrated arrangement, at least one of the elongate members 258 comprises a locking tab 259 that is adapted to snap into a matching hole 216 (FIG. 22A) along the outer surface of the core 210. Thus, if the elongate members 258 are inserted sufficiently far into the corresponding slots 215 of the core 210, the locking tab 259 of the clip 240 will resiliently engage the matching hole 216 of the core 210. Consequently, the clip 240 can be advantageously locked relative to the core 210. In order to separate the clip 240 from the core 210, the locking tab 259 can be pressed inwardly so that the tab 259 disengages from the matching hole 216.

Figure 23A:
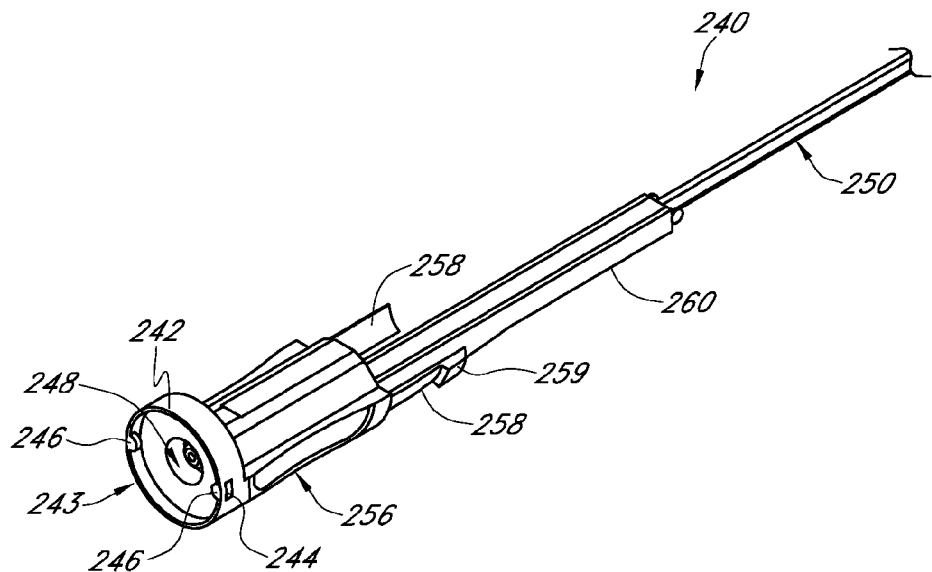
FIG. 23A illustrates a perspective view of a clip of a handpiece assembly according to one embodiment.
Figure 23B:
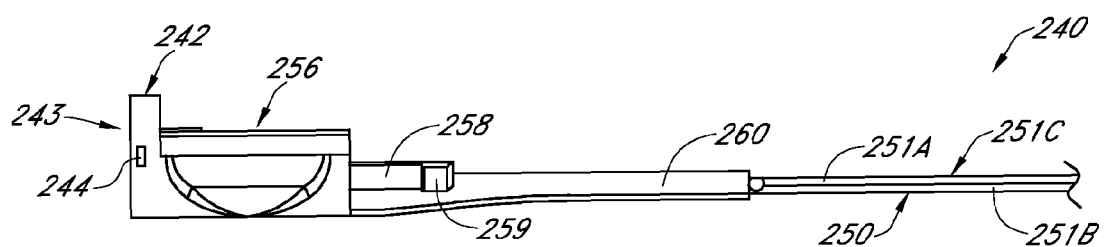
FIG. 23B illustrates a side view of the clip of FIG. 23A.
Figure 23C:
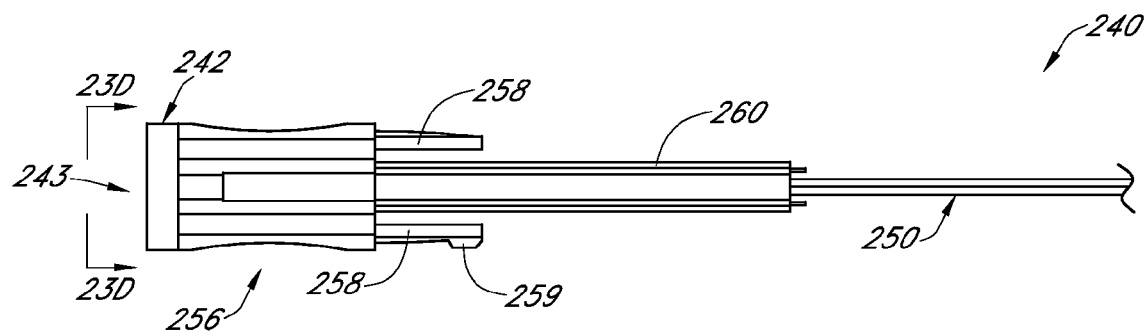
FIG. 23C illustrates a top view of the clip of FIG. 23A.
Figure 23D:
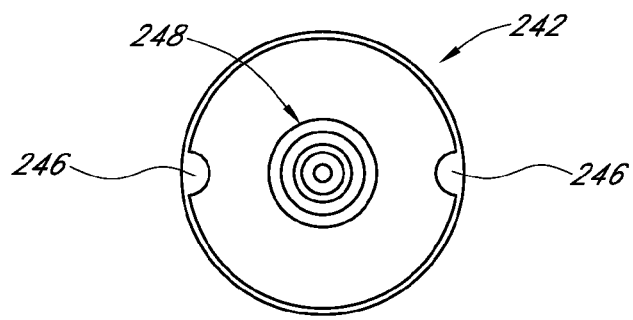
FIG. 23D illustrates a front view of the clip of FIG. 23A.

As illustrated in FIGS. 23A-23C, the clip 240 can include a channel 260 or other portion that is configured to receive the delivery line 250. As discussed herein with reference to other components, the delivery line 250 can include one, two or more of the individual conduits 251A-251C that are in fluid communication with the outlets of the various cassette manifolds (FIG. 7B). Thus, in some arrangements, the channel 260 of the clip 240 is preferably sized and shaped to accommodate all the individual conduits 251A-251C of the delivery line 250.

Figure 24A:
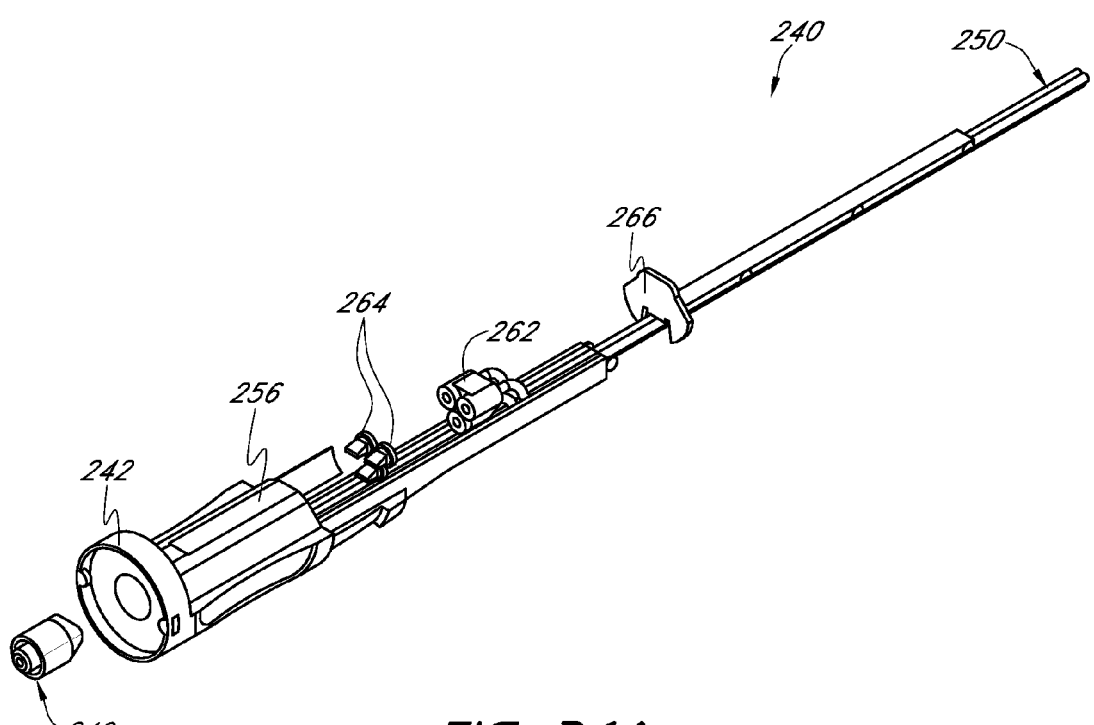
FIGS. 24A-24C illustrate perspective views of a clip of a handpiece assembly according to another embodiment.
Figure 24B:
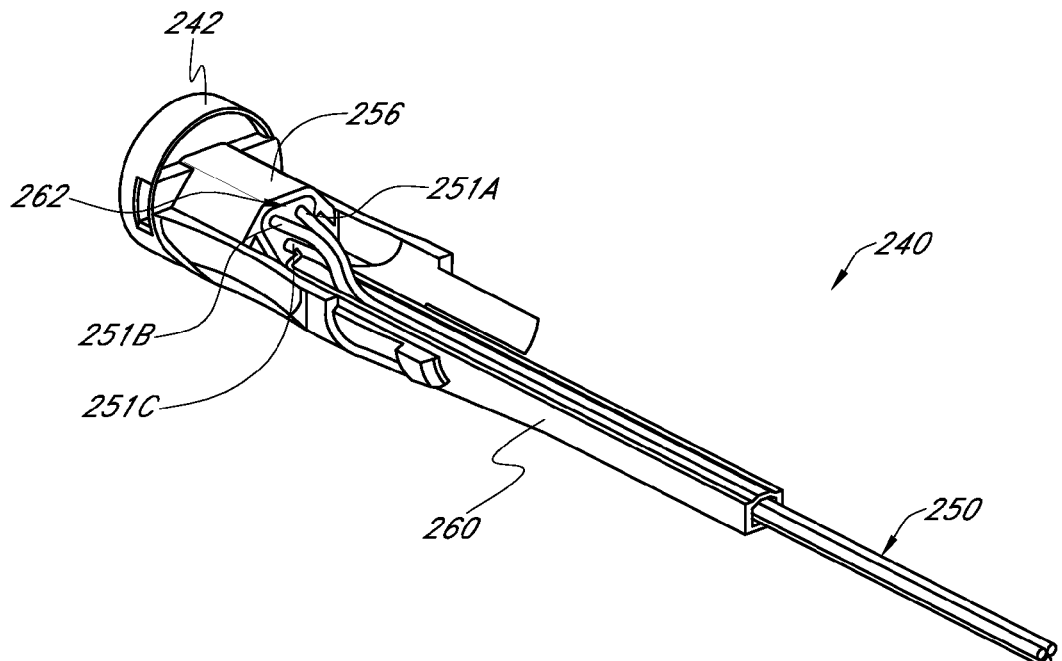
Figure 24C:
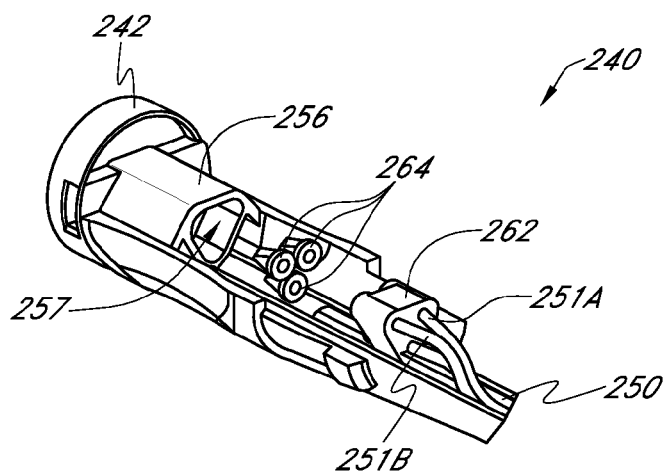

One embodiment of the manner in which the individual conduits 251A-251C of the delivery line 250 are attached to the clip 240 is illustrated in FIGS. 24A-24C. As shown, the conduits 251A-251C can be routed to a main coupling 262. In the depicted arrangement, the main coupling 262 comprises a generally triangular shape and is adapted to fit within a corresponding recessed area 257 of the main body 256. As best illustrated in FIGS. 24A and 24C, a duckbill valve 264 (or other type of backflow prevention valve or device) can be positioned immediately downstream of the main coupling 262. Thus, fluids and/or other materials passing through the passages of the main coupling 262 are not permitted to reverse direction through the main coupling 262. This helps ensure that there is no cross contamination of the individual conduits 251A-251C upstream of the main coupling 262.

Figure 25A:
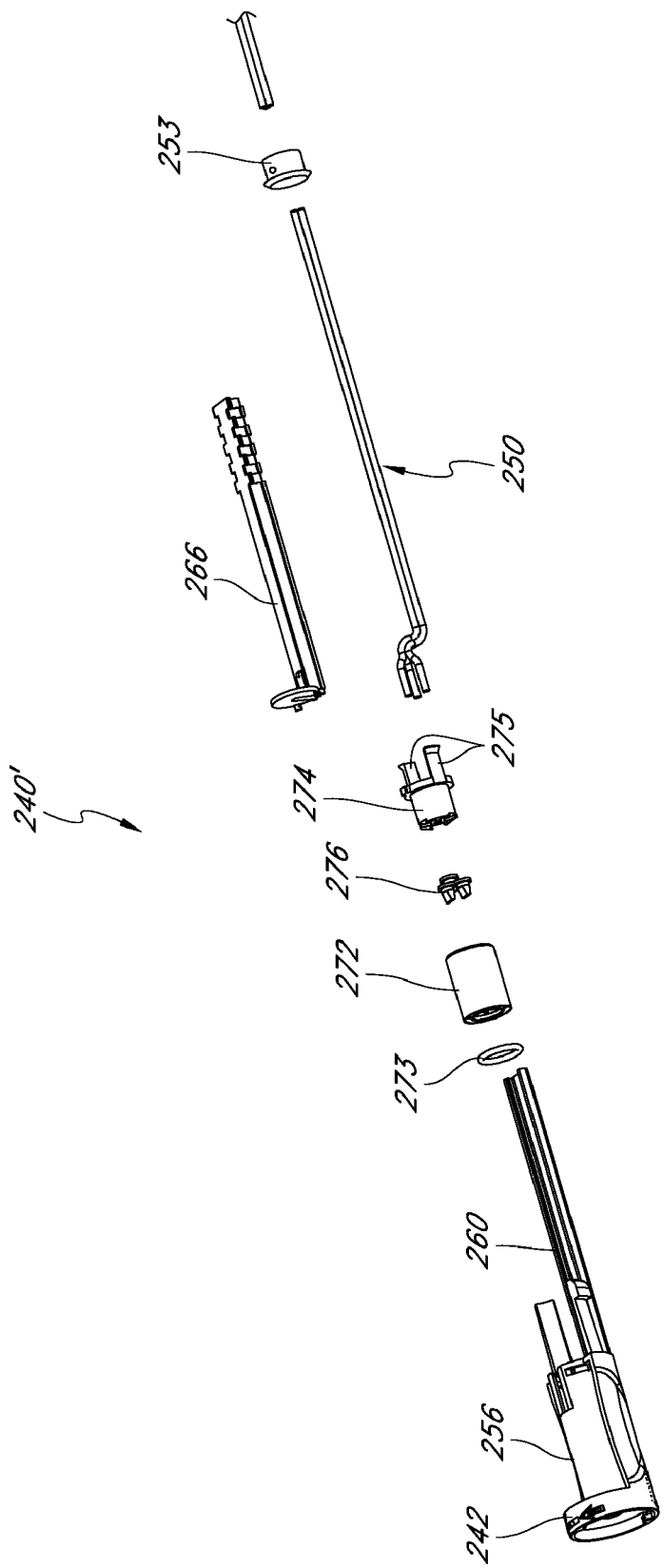
FIG. 25A illustrates an exploded perspective view of a clip of a handpiece assembly according to another embodiment.
Figure 25B:
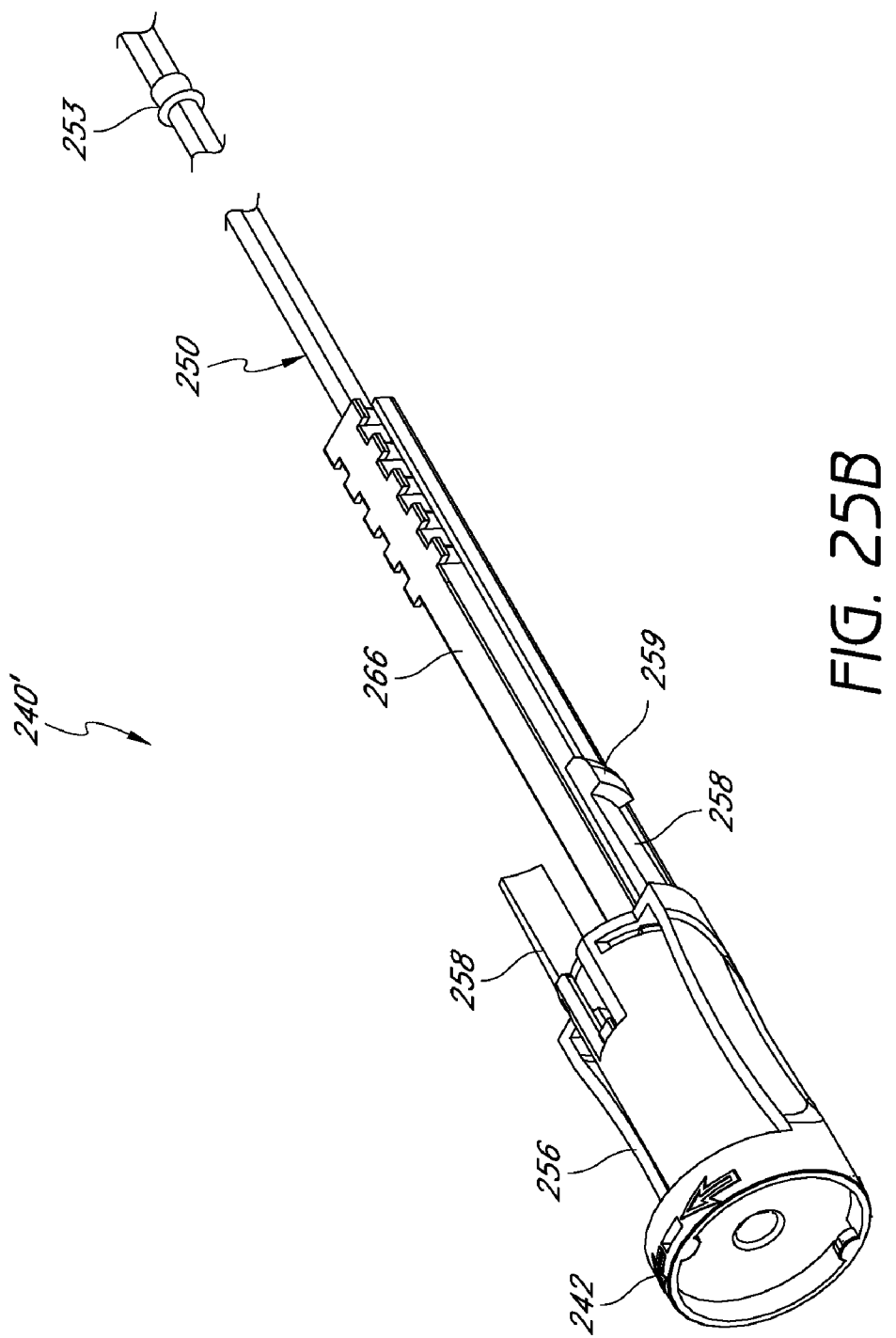
FIG. 25B illustrates a perspective view of the clip of FIG. 25A.
Figure 26A:
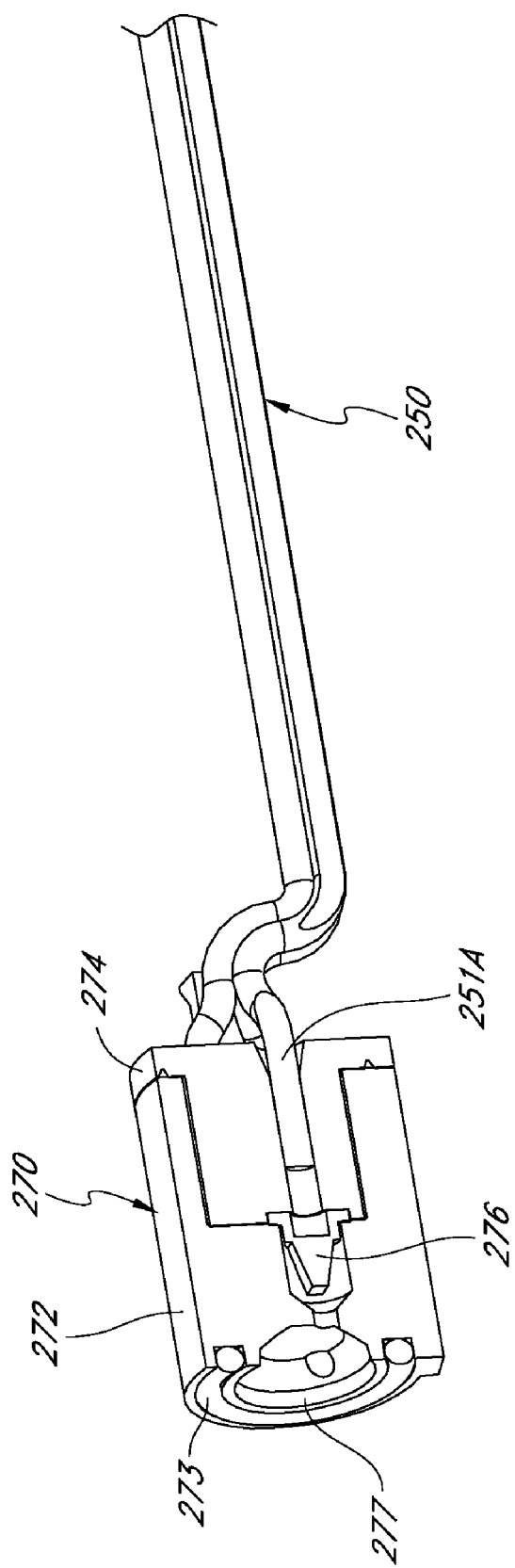
FIGS. 26A-26C illustrate various perspective views of the delivery line and portions of the clip of FIG. 25A.
Figure 26B:
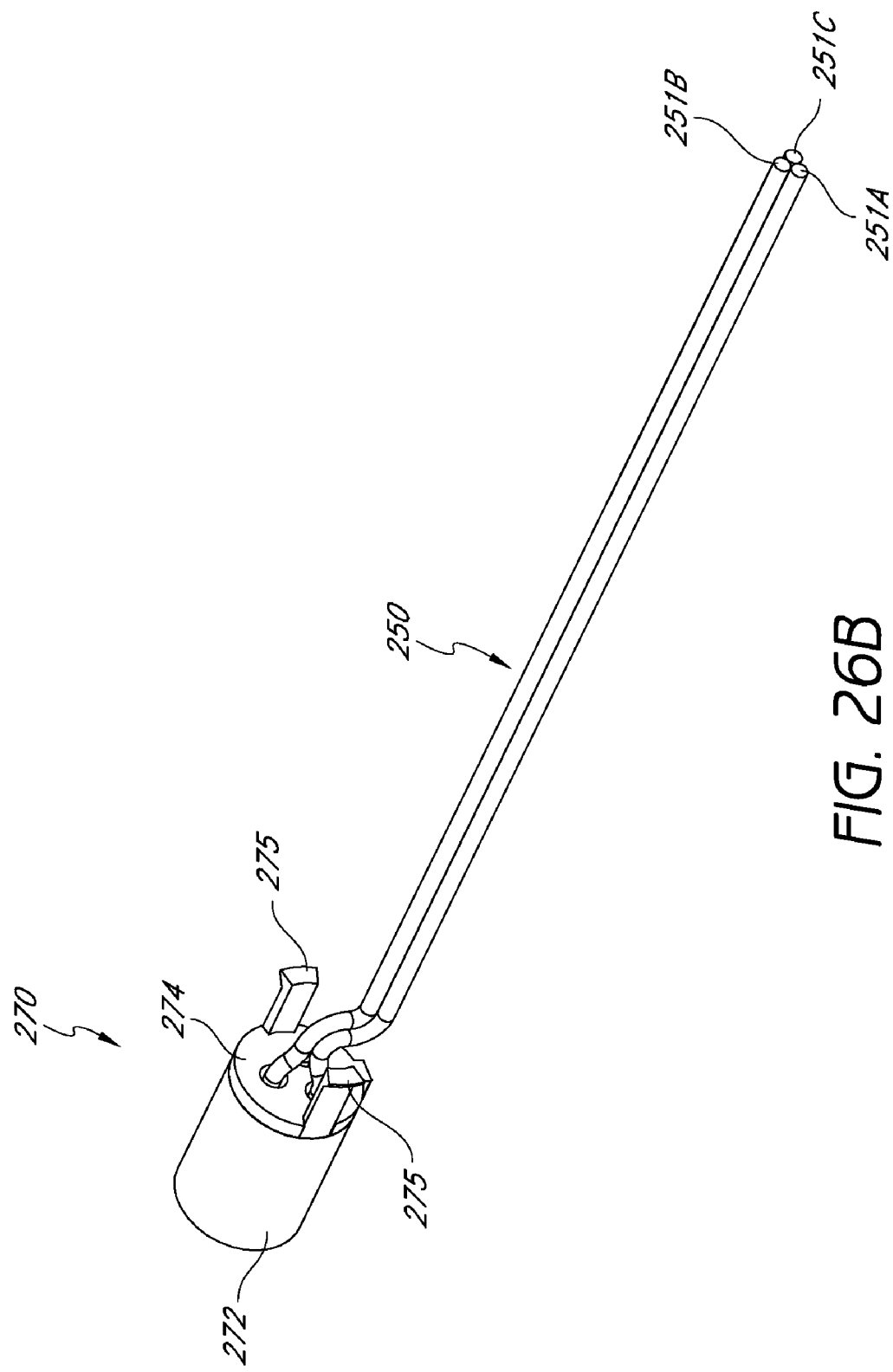
Figure 26C:
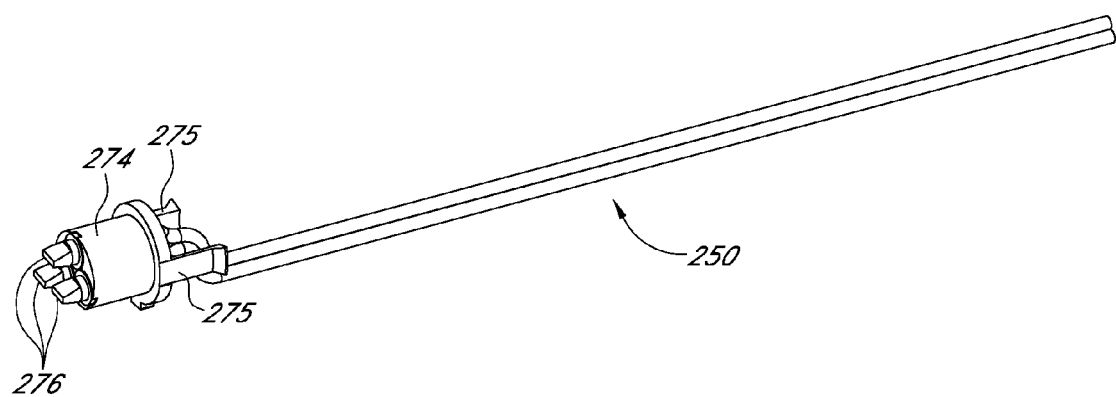
Figure 29A:
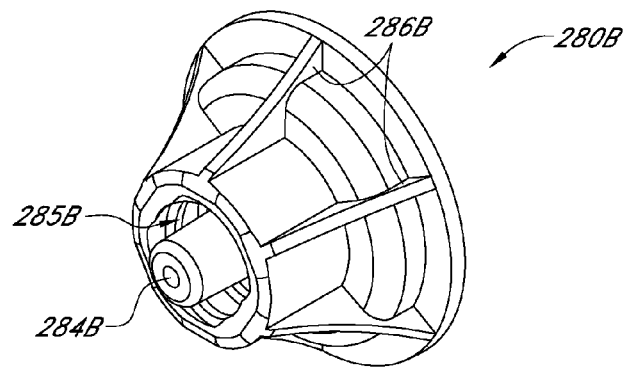
FIG. 29A illustrates a front perspective view of a tip configured for use in a handpiece assembly according to another embodiment.
Figure 29B:
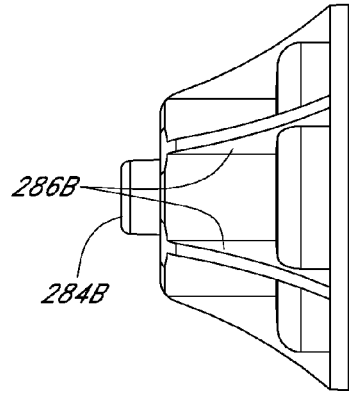
FIG. 29B illustrates a side view of the tip of FIG. 29A.
Figure 29C:
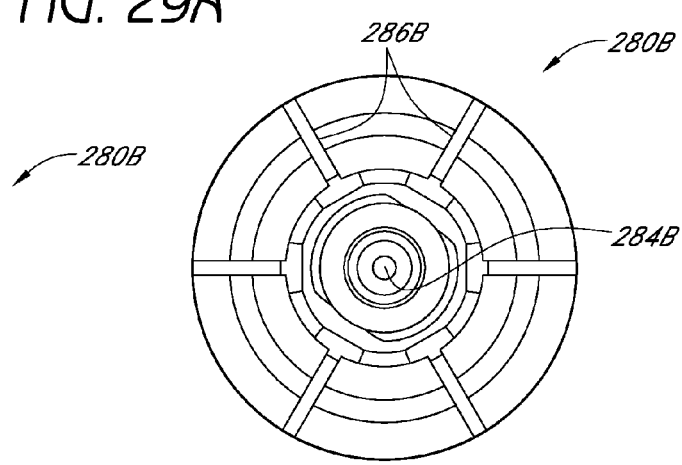
FIG. 29C illustrates a front view of the tip of FIG. 29A.
Figure 29D:
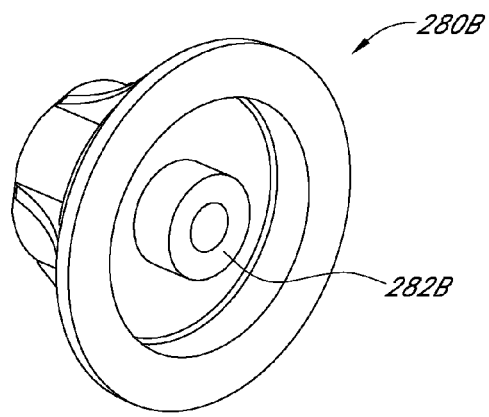
FIG. 29D illustrates a rear perspective view of the tip of FIG. 29A.
Figure 29E:
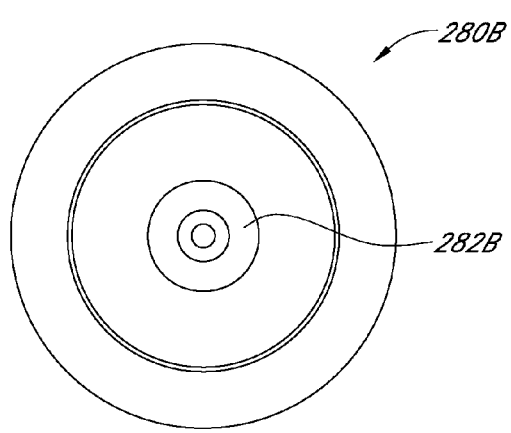
FIG. 29E illustrates a rear view of the tip of FIG. 29A.
Figure 31A:
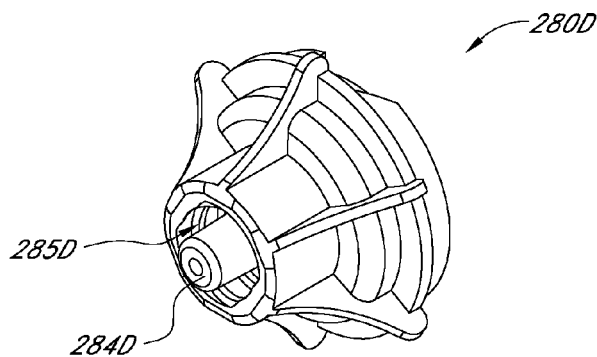
Figure 31B:
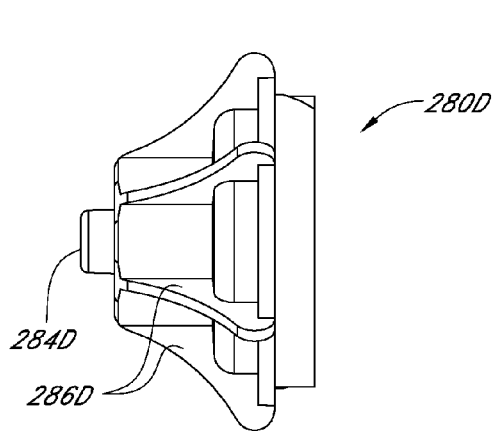
Figure 31C:
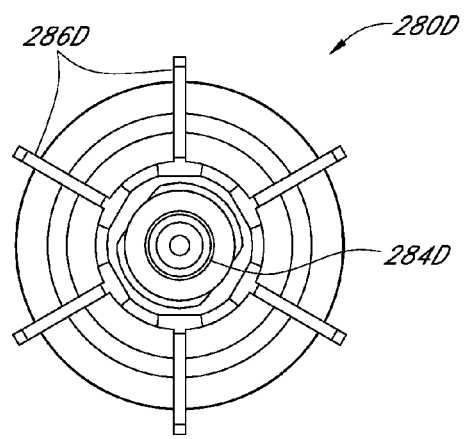
Figure 31D:
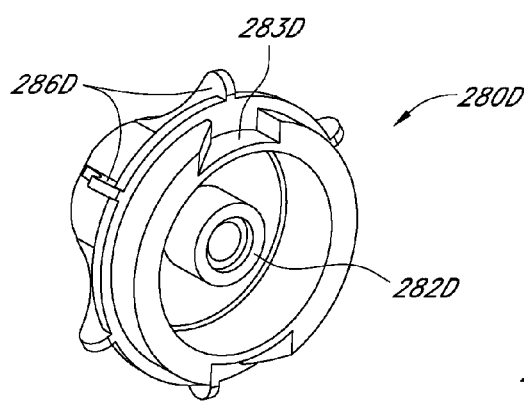
Figure 31E:
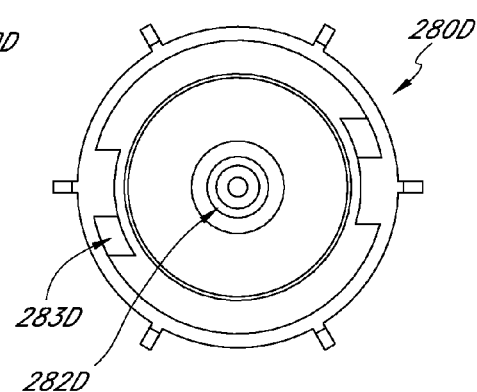
Figure 32A:
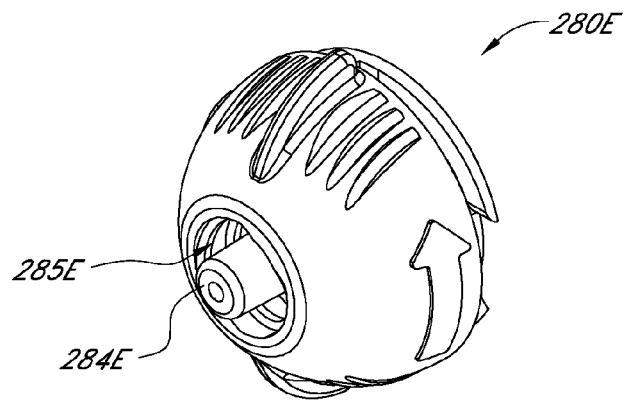
FIG. 32A illustrates a front perspective view of a tip configured for use in a handpiece assembly according to another embodiment.
Figure 32B:
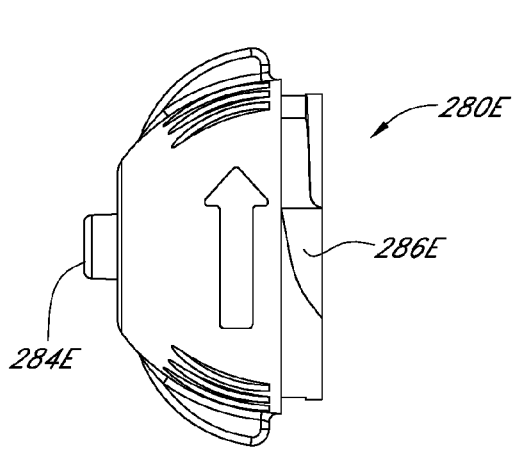
FIG. 32B illustrates a side view of the tip of FIG. 32A.
Figure 32C:
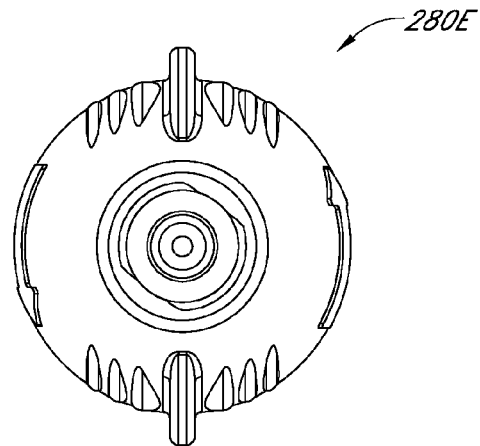
FIG. 32C illustrates a front view of the tip of FIG. 32A.
Figure 32D:
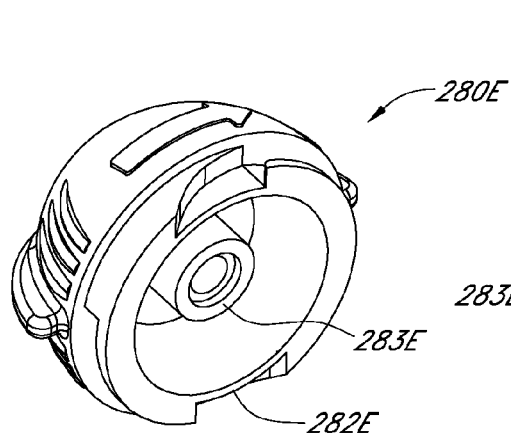
FIG. 32D illustrates a rear perspective view of the tip of FIG. 32A.
Figure 32E:
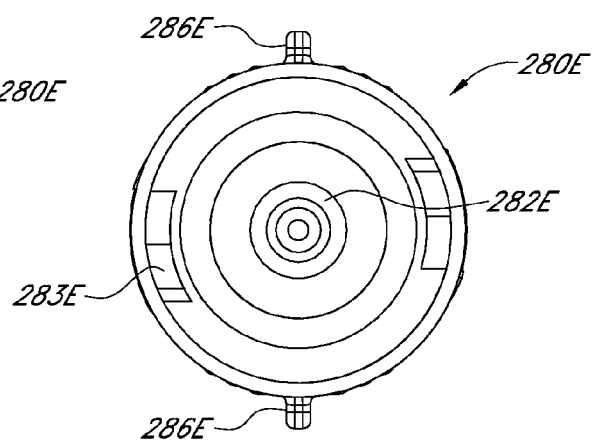
FIG. 32E illustrates a rear view of the tip of FIG. 32A.

Another embodiment of the connection of individual conduits 251A-251C in the clip 240' is illustrated in FIGS. 25A-26C. As with the clip 240 of FIGS. 24A-24C, the depicted arrangement includes a main body 256 that can be selectively attached to and/or removed from the core 210. However, as discussed in greater detail below, there are some variations in the manner in which the conduits 251A-251C are connected to the distal end of the clip 240'. As best illustrated in the views of FIGS. 26A-26C, the conduits 251A-251C can separate from each other a short distance upstream of a multipiece coupling 270. The coupling 270 can include an inner portion 274 fitted within an outer portion 272 located immediately downstream of the inner portion 274. According to some embodiments, a duckbill valve 276 or other backflow prevention valve or device can be positioned in the fluid path of each conduit 251A-251C, generally between the outer and inner portions 272, 274. Thus, as discussed above with reference to FIGS. 24A-24C, the valves 276 can help prevent cross-contamination of the individual conduits 251A-251C when fluids and/or other materials are moving through the clip 240'. In the illustrated embodiments, once they have passed through the duckbill valves 276, such fluids and/or other materials enter a common chamber 277 or collection chamber 277 located at the distal end of the outer portion 272. Accordingly, fluids and/or other materials can exit the outlet opening 248 (FIGS. 23A and 23D), toward a tip 280 attached at the distal end of the ring 242.

According to some configurations, the inner portion 274 comprises one or more prongs 275 that are adapted to secure to corresponding areas of the main body 256. Thus, the inner portion 274 and other components of the coupling 270 can be conveniently attached to the rest of the clip 240. It will be appreciated that one or more other devices or methods can be used to secure the coupling 270 to the clip 240. Further, as shown in FIGS. 25A and 25B, a closure 266 can be used to completely or partially cover the interior of the channel 260 through which the delivery line 250 is routed.

FIGS. 27A-27E illustrate cross-sectional views of various embodiments of a delivery line 250A-250E configured for use with an articular injection system. As shown, each delivery line 250A-250E can include two or more different conduits 251 or lumens. Accordingly, the depicted arrangements can advantageously provide a simple design for conveying two or more different types of fluids and/or other materials through a single member. For example, the handpiece assembly 200 in fluid communication with the fluid delivery module using only a single multi-lumen tubular member. In addition, the internal configuration and overall design of the clip 240 and/or other portions of the handpiece assembly 200 can be improved by using such a multi-lumen delivery line 250A-250E, especially where available space within the clip or other portion of the handpiece assembly is limited.

Multi-lumen delivery lines 250A-250E, such as those illustrated in FIGS. 27A-27E, can be manufactured using one or more methods (e.g., extrusion, injection molding, etc.) and/or one or more suitable materials (e.g., rubber, polymeric materials and/or the like). In some embodiments, the delivery lines are at least partially transparent or translucent so that an optical sensor can detect the presence of undesirable air or other gas bubbles passing therethrough (see FIGS. 7C and 7D). The materials used in the manufacture of the delivery lines 250A-250E and other portions of the articular injection system that may come into contact with medications, formulations and/or any other materials being injected into the anatomy preferably satisfy all regulatory standards and requirements (e.g., medical-grade quality, FDA regulations, etc.). According to some embodiments, the inner diameter of each lumen of the delivery line is approximately 0.01-0.04 inches (e.g., 0.030 inches). However, the inner diameter can be greater than 0.04 or smaller than 0.01, as desired or required.

The structural integrity, diameter, other dimensions, materials of construction, durability, flexibility, pH resistance, chemical/biological resistance, temperature resistance and/or other characteristics of the delivery line or other conduits used in the injection system can be advantageously selected for the particular application. For example, the delivery line or other conduit can be manufactured from medical-grade silicone, polymers, glass, stainless steel, copper and/or the like.

Further, the delivery line or other conduit can be configured so it adequately resists the fluids and/or other materials which it may contact. Further, such delivery lines or conduits can be advantageously adapted to withstand the pressures (e.g., positive, negative/vacuum, etc.) to which they may be exposed. Also, in some embodiments, the lines or conduits are configured to withstand a minimum of 2 pounds of joint tensile strength. However, in other embodiments, the structural characteristics of the delivery lines, conduits and/or other components of the system can be different. As discussed, some or all of the conduits used in the injection system can be constructed or otherwise assembled as a single unit. For hygienic, regulatory and/or other purposes, the delivery lines and other conduits can be sterile and disposable.

Tip

As discussed, in some embodiments, the handpiece assembly 200 preferably includes a disposable tip that can be easily and quickly discarded and replaced between injection procedures. One embodiment of a tip 280A configured to be positioned at the distal end of the handpiece assembly 200 is illustrated in FIGS. 28A-28E. The tip 280A can include a tip inlet 282A and a tip outlet 284A. As illustrated in FIGS. 28A and 28C, the distal end of the tip 280A can include an annular opening 285A around the tip outlet 284A. In some arrangements, this annular opening 285A includes interior threads that are adapted to engage corresponding a thread pattern (e.g., standard or non-standard) of a needle hub 294 (FIGS. 21A and 21B). For example, the needle hub 294 can be attached to the annular opening 285A using a standard luer lock connection. Thus, a needle 290 can be easily secured to and removed from the distal end of the tip 280. The tip outlet 284A can be sized, shaped and otherwise configured to fit within the cavity of a needle hub 294.

The type, size (e.g., gauge), length and/or other details of the needle 290 can be selected according to a particular application. For example, in some embodiments, the needle has a gauge of approximately 18 G-30 G and a length of approximately 0.5 to 5.0 inches (e.g., 1.0 to 1.5 inches). However, that the gauge, length and/or other details of the needle can be greater or smaller than the range indicated herein, as desired or required by a particular application.

With continued reference to FIGS. 28A-28E, the tip 280A can include an engagement feature 283A (e.g., locking ring) along one or more of its proximal surfaces. Such engagement features 283A can be used to enhance the connection between the tip 280A and the clip ring 242 (FIGS. 23A-24C). In some embodiments, an engagement feature 283A of the tip 280A is adapted to rotatably connect to a corresponding feature of the ring 242 or other portion of the clip 240. It will be appreciated that any other attachment device or method can be used to removably mate the tip 280A with the distal end of the clip 240.

In some arrangements, the tip inlet 282A extends outwardly (e.g., along a proximal direction) so that it can fit within the outlet opening 248 of the clip 240 (FIGS. 23A and 23D) when the tip 280A is secured to the clip 240. Thus, as fluids and/or other materials are discharged from the individual conduits 251A-250C into the collection chamber 277 at the distal end of the clip 240, they can be directed into the tip inlet 282A.

In addition, according to some arrangements, the tip 280A comprises a plurality of ribs 286A or other reinforcing members along its outer surface. The ribs 286A can be configured to enhance the structural integrity of the tip 280A, enhance the appearance of the tip 280A and/or facilitate handling of the tip 280A (e.g., attaching or removing the tip to or from the adjacent portion of the handpiece assembly 200). Further, the tip 280A may include one or more other functional or aesthetic features, as desired or required. Additional embodiments of disposable tips 280B-280E configured to receive a needle 290 and to connect to the clip 240 or other portion of the handpiece assembly 200 are illustrated in FIGS. 29A-32E. As shown, the shape, size and/or other design considerations of the tips 280B-280E can be modified, as desired or required. For example, the quantity, shape, size, method of connection and/or other details of the tip inlet, tip outlet ribs and other components of the tip can modified according to the individual needs or preferences of particular clinician or other user of the injection system.

Figure 33A:
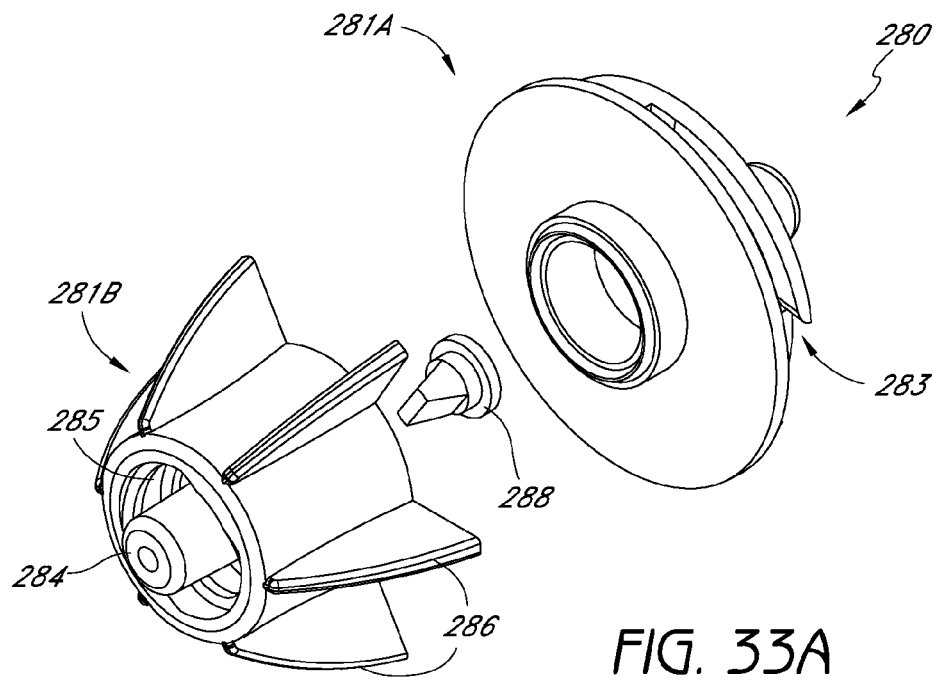
FIGS. 33A and 33B illustrate different exploded perspective views of tip comprising a backflow prevention valve according to one embodiment.
Figure 33B:
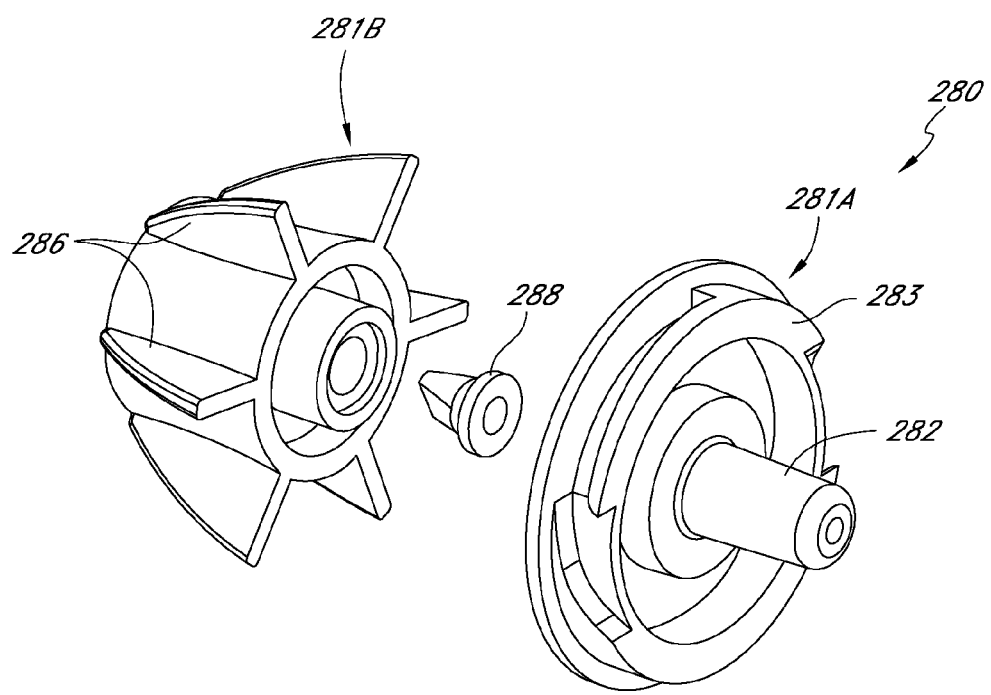
Figure 34:
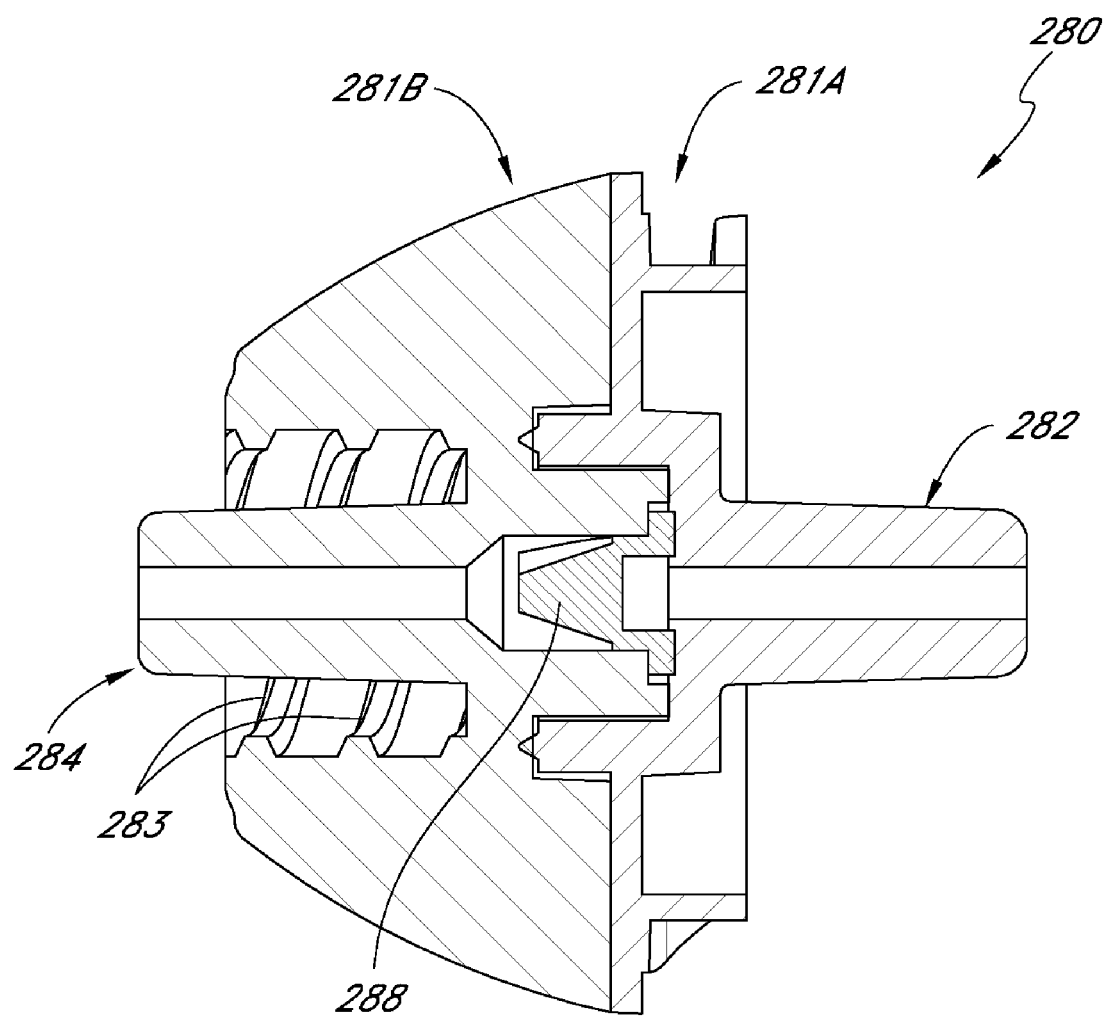
FIG. 34 illustrates a cross-sectional view of the tip of FIGS. 33A and 33B.
Figure 35:
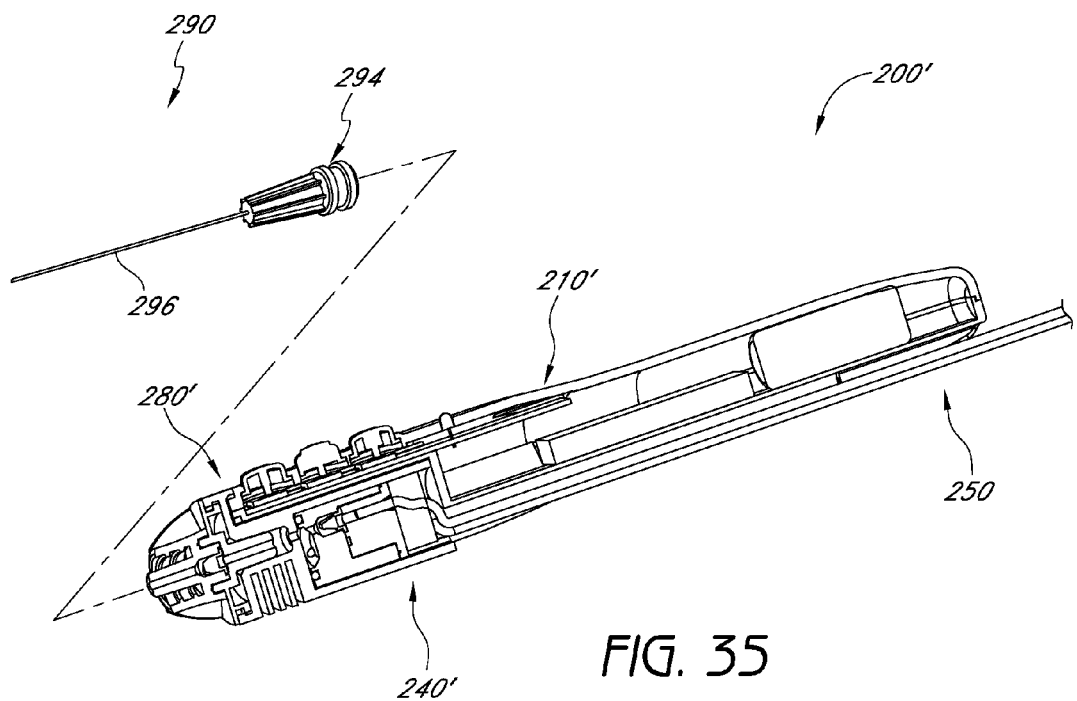

In some embodiments, as illustrated in FIGS. 33A and 33B, the tip 280 includes a backflow prevention valve or device 288, such as, for example, a duckbill valve, another type of check valve and/or the like. Such a valve 288 can help ensure that fluids and/or other materials do not travel backwards through the tip 280 toward the clip 240 and/or other upstream components of the injection system. In other embodiments, the tip 280 comprises a combination duckbill-umbrella valve 288 that may permit fluids and/or other materials to travel backwards toward the tip inlet 282 only under certain conditions. For example, as discussed herein with reference to aspiration procedures (FIG. 44), such a combination valve 288 may be configured to permit retrograde flow only when a threshold vacuum force is applied to the tip inlet 282 (e.g., when a syringe or other vacuum device is placed in fluid communication with the tip inlet 282). Thus, a combination valve 288 can help prevent accidental backflow of fluids and/or other materials toward the tip inlet 282 under typical operating conditions. Accordingly, the various fluid and/or other streams being delivered through the handpiece assembly 200 can be maintained separate of each other upstream of such a valve 288 or other flow control device.

With continued reference to FIGS. 33A and 33B, the tip 280 can include a proximal portion 281A and a distal portion 281B attached thereto. In some arrangements, a flow-regulating valve (e.g., duckbill valve, other check valve, combination duckbill-umbrella valve, etc.) is positioned within the tip's flow path generally between the proximal and distal portions 281A, 281B. A cross-sectional view of such an embodiment is provided in FIG. 34. As shown, the valve 288 can be advantageously positioned immediately between the tip inlet 282 and tip outlet 284 so that no fluids and/or other materials being conveyed through the tip 280 can short-circuit the valve 288.

Figure 35:
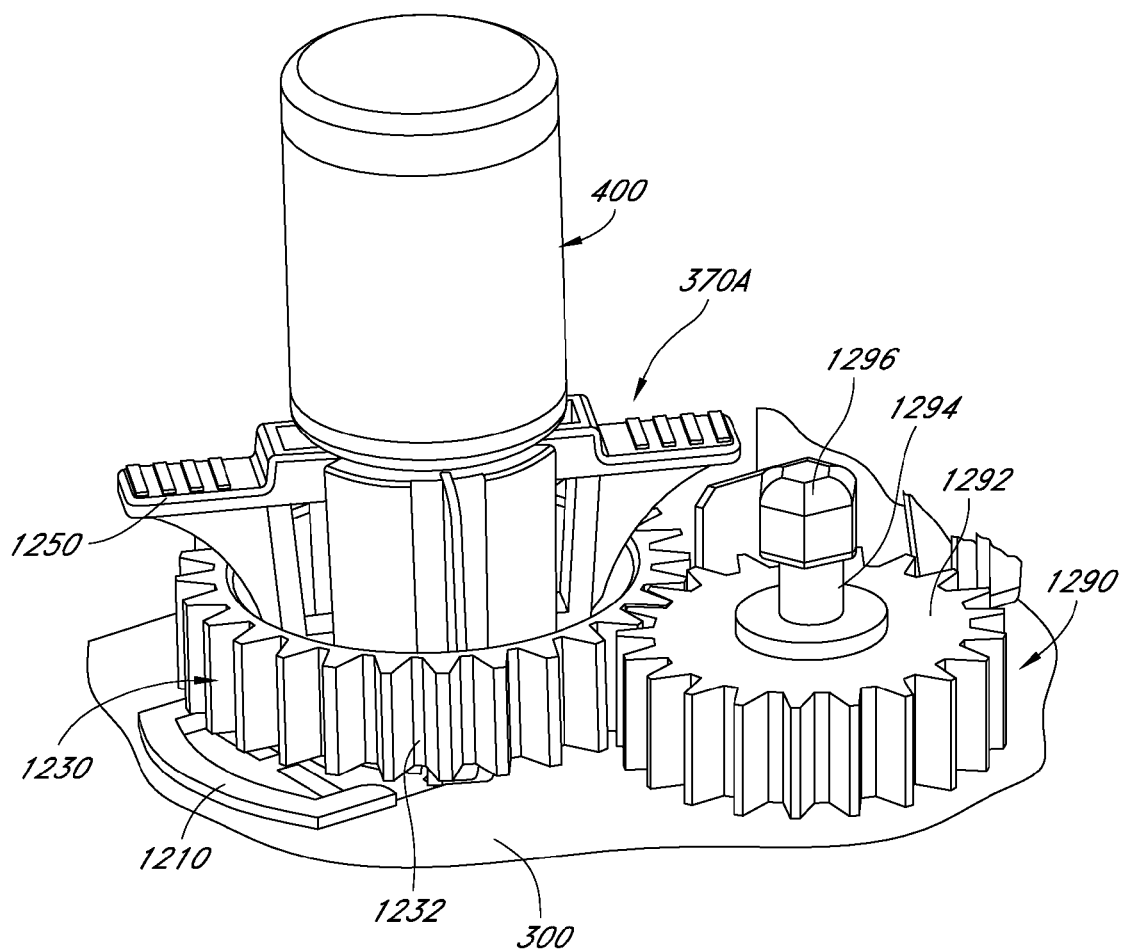
FIG. 35 illustrates a cross-sectional view of a handpiece assembly according to one embodiment.

A cross-sectional view of one embodiment of a completely assembled handpiece assembly 200' is illustrated in FIG. 35. As discussed herein with reference to other arrangements, the core 210' and the clip 240' can be secured to each other prior to using the assembly 200'. Further, as discussed, the core 210' can be advantageously configured so that it does not contact any fluids and/or other materials flowing through the handpiece assembly 200'. As a result, there is ordinarily no need to periodically replace or clean the core 210'. Unlike the core 210', the clip 210' may be configured to be periodically replaced, as one or more of its components (e.g., its internal coupling 270, the delivery line 250, etc.) contact the fluids and/or other materials that are being transferred through the handpiece assembly 200'. According to some arrangements, the clip 240' is replaced when the type, dosage and/or other characteristics of the fluids and/or other materials loaded into the injection system are altered. The clip 210' can also be replaced according to some predetermined time frequency, schedule, protocol or the like, even when the characteristics of the medications or other formulations being injected through the handpiece assembly 200' are not modified. In some embodiments, the clip 210' is replaced together with the cassette and the delivery line placing the cassette in fluid communication with the clip 210'.

With continued reference to FIG. 35, the handpiece assembly 200' can additionally include a tip 280' that is removably secured to the core/clip combination. For example, in the depicted embodiment, the tip attaches to the distal end of the clip 240' and is placed in fluid communication with the delivery line 250 routed through the clip 240'. Moreover, as illustrated, a needle 290 can be configured to attach to the distal end of the tip 280'. A threaded hub 294 of the needle 290 can be configured to engage corresponding threads at the distal end of the tip 280'. In some embodiments, the hub 294 attaches to the distal end of the tip 280' using a standard or non-standard luer lock connection. Alternatively, one or more other types of connection devices or methods can be used.

Figure 36:
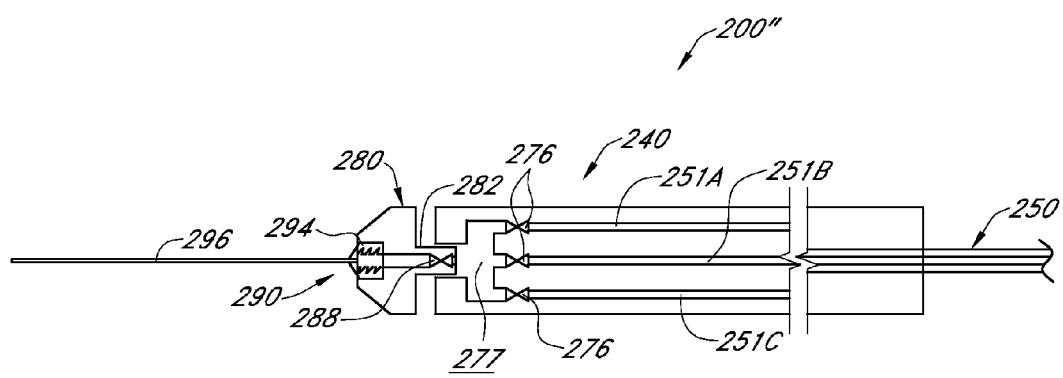
FIG. 36 illustrates a schematic cross-sectional view of a handpiece assembly according to one embodiment.

The schematic of FIG. 36 illustrates one embodiment of fluids and/or other materials being conveyed through a handpiece assembly 200". As discussed in greater detail herein, medications and/or other substances that are desired for a particular injection procedure can be selectively and accurately delivered from a fluid delivery module to a downstream handpiece assembly 200" via a delivery line 250. In some embodiments, the delivery line 250 comprises one, two, three or more different conduits 251A-251C, each of which is in fluid communication with a particular medication, other composition and/or the like that has been loaded onto the fluid delivery module.

With continued reference to FIG. 36, once the delivery line 250 enters the clip 240 of the handpiece assembly 200", each of the various conduits 251A-251C can be placed in fluid communication with a dedicated backflow prevention valve 376 (e.g., duckbill valve, other check valve or device, etc.) to prevent cross-contamination of the various conduits 251A-251C and to prevent fluids and/or other materials from undesirably moving in the reverse direction toward the fluid delivery module. As shown, once fluids and/or other materials pass through the respective valves 276, they can enter into a common chamber 277. From there, such fluids and/or other materials can be delivered to a desired anatomical location through a needle 290 positioned at the distal end of a tip 280. As shown, the tip 280 can include an internal passage that places the needle 290 in fluid communication with the common chamber 277 of the clip 240.

In some embodiments, the tip 280 comprises a backflow prevention valve 288 (e.g., duckbill valve, other check valve, etc.) that is configured to prevent fluids and/or other materials from moving backwards therethrough under normal operating conditions. In other arrangements, the valve 288 is configured to also permit flow in the reverse direction (e.g., from distal end of the tip 280 toward the clip 240) when a vacuum pressure applied to the tip inlet 288 reaches or exceeds a particular threshold level. This can permit a user to aspirate a volume of fluids and/or other substances from a desired anatomical location using the tip 280 as an interface between the needle 290 and a vacuum-generating device (e.g., syringe, pump, etc.). Additional details regarding such aspiration procedures are provided herein with reference to the FIG. 44.

Depending on the types of medications, other fluids and/or other materials being delivered through the handpiece assembly during an injection procedure, it may be desirable or necessary to ensure that such formulations are sufficiently mixed before they are injected into the anatomy. Thus, one or more internal conduits or other passages of the handpiece assembly can be adapted to provide such mixing. For example, in the schematic illustrated in FIG. 37, a clip 240' comprises two individual conduits 251A, 251B that are placed in fluid communication with a common chamber 277' located at or near the distal end of the clip 240'. As discussed, a clip 240' can include more or fewer conduits as desired or required. Under certain circumstances, the fluids and/or other materials being conveyed through each conduit 251A, 251B are traveling with sufficient velocity and energy that the two streams will effectively mix with one another upon entering into the chamber 277'. However, in other arrangements, it may be desirable or necessary to further enhance the mixing of the various fluids and/or other materials upstream of the needle 290'. For example, such mixing may be helpful when the various fluid and/or other material streams have varying physical (e.g., viscosity, density, affinity to water, etc.), chemical (e.g., pH) or other properties.

Figure 37:
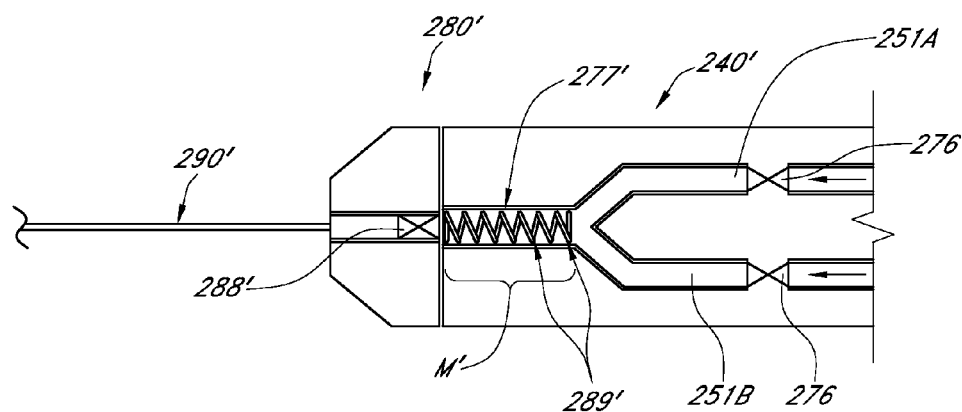
FIG. 37 illustrates a schematic cross-sectional view of a handpiece assembly configured to mix various fluid and/or other material streams passing therethrough according to one embodiment.

With continued reference to FIG. 37, the common chamber 277' at or near the distal end of the clip 240' can include a plurality of flow diverters 289' or other obstructions that extend into the flow path. As a result, the various streams entering the chamber 277' from each of the upstream conduits 251A, 251B can experience turbulent or substantially turbulent conditions, thereby facilitating the desired mixing. In some embodiments, the diverters 289' or other flow obstruction members are arranged to direct the fluids and/or other materials entering the mixing zone M' in a particular pattern. For example, the diverters 289' can be arranged so the fluids and/or other materials passing therethrough are conveyed in a spiral or helical pattern. In one embodiment, the mixing zone M' comprises a series of helices or other diverters 289' that are skewed relative to each other. In other arrangements, the mixing zone M' includes a plurality of diverters 289' (e.g., square or rectangular elements) that are shaped, spaced, oriented and otherwise configured within the chamber 277' to cause the fluids and/or other materials passing therethrough to change direction (e.g., left and right, up and down, etc.). Although specific examples of diverters 289' and methods of mixing the various streams are disclosed herein, it will be appreciated that the desired level of mixing may be accomplished in any other manner.

Figure 38A:
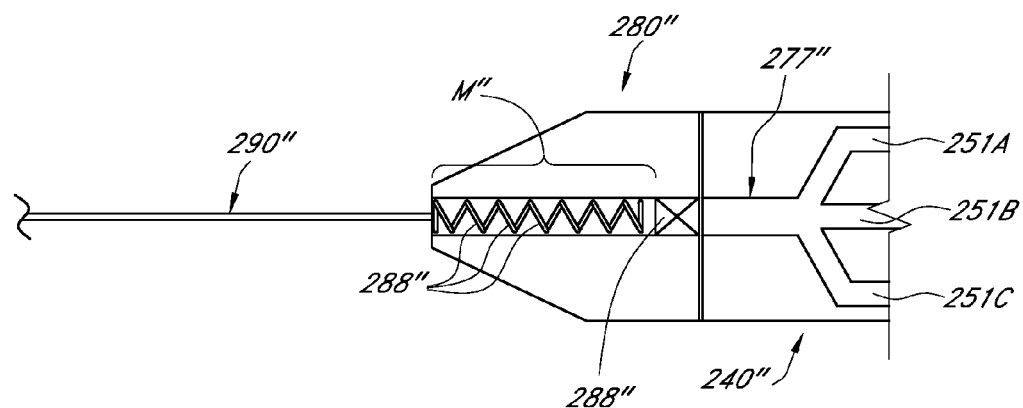
FIG. 38A illustrates a schematic cross-sectional view of a tip of a handpiece assembly configured to mix various fluid and/or other material streams passing therethrough according to another embodiment.

In FIG. 38A, mixing of the various fluid and/or material streams occurs within the tip 280" of the handpiece assembly. This can advantageously permit the mixing zone M" to be situated in a component of the handpiece assembly that is replaced between injection procedures. In the depicted embodiment, the mixing zone M" is located immediately downstream of a valve 288" (e.g., duckbill valve, combination duckbill/umbrella valve, etc.). However, the orientation of the mixing zone M" relative to the valve 288" and/or any other component of the tip 280" can be modified, as desired or required. As discussed herein with reference to FIG. 37, one or more diverters 289" or flow obstructing or directing members can be positioned within the mixing zone M" to achieve the desired mixing scheme.

Figure 38B:
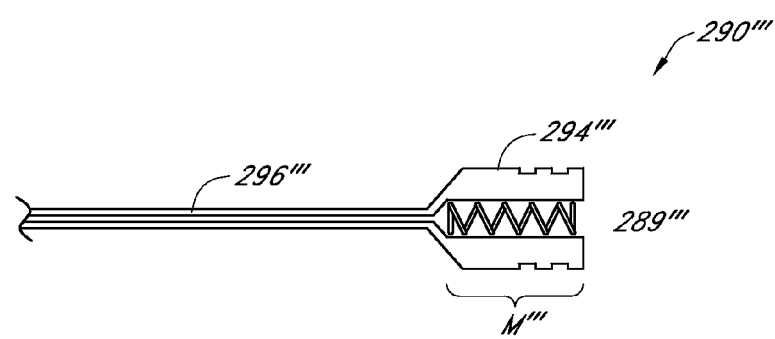
FIG. 38B illustrates a schematic cross-sectional view of a needle for use in a handpiece assembly configured to mix various fluid and/or other material streams passing therethrough according to another embodiment.

In other embodiments, as illustrated in FIG. 38B, the mixing zone M'" is included within the needle assembly 290'". For example, in FIG. 38B, the diverters 289'" are positioned within the hub 294'" portion of the needle assembly 290'" (e.g., immediately upstream of the needle 296'"). Such a configuration can eliminate the need to provide the required or desired mixing within the tip 280, the clip 240 or other upstream component or portion of the handpiece assembly. As a result, the overall design of the handpiece assembly can be simplified. In addition, the costs of providing a handpiece assembly configured to adequately mix the various fluid and/or other material streams passing therethrough can be advantageously reduced.

Additional Handpiece Assembly Features/Alternative Designs

Other embodiments of a handpiece assembly are illustrated in FIGS. 39-43B. The shape, size and/or other characteristics of the handpiece assembly can be modified to achieve a particular feel, comfort or other functional objective. In addition, the configuration of the handpiece assembly can be modified for other functional and/or aesthetic reasons.

As illustrated in FIG. 38, a handpiece assembly 200A can include a site light 202 or other source of light to facilitate the clinician or other user during an injection procedure. In the depicted arrangement, the site light 202 is positioned at the distal end of the handpiece assembly 200A. However, the location, size, shape and/or other details of the site light 202 can vary to suit a particular application or use. In addition, a handpiece assembly can include two or more site lights 202 or other light sources, as desired or required.

As illustrated in FIG. 38, the handpiece assembly 200A can also comprise an optical ring 204 that is adapted to light up during an injection procedure. In some embodiments, each type of medication and/or other formulation loaded within the fluid delivery module is associated with a particular color. The color assigned to each medication or other formulation (or a combination of two or more of such medications and/or formulations) can match or substantially match the color of a button 222, 224, 226 or other control device (e.g., knob, switch, etc.) which is positioned along the outside of the handpiece assembly (FIG. 22A) and is used to selectively regulate the transfer of such medication or other formulation through the handpiece assembly.

In other embodiments, the color assigned to each medication or other formulation (or a combination of two or more of such medications and/or formulations) generally coincides with a color assigned to that medication or formulation by the graphic user interface (FIGS. 48A-51) and shown on the display 130 of the fluid delivery module 100 (FIG. 2A). Accordingly, the optical ring 204 of the handpiece assembly 200A can be adapted to light up with the color of the medication or other formulation (or a combination of two or more of such medications and/or formulations) being delivered through the handpiece 200A at any particular moment in time. Thus, the clinician or other user performing the injection procedure can be continuously and conveniently informed about what is being injected into the patient's anatomy.

Figure 39:
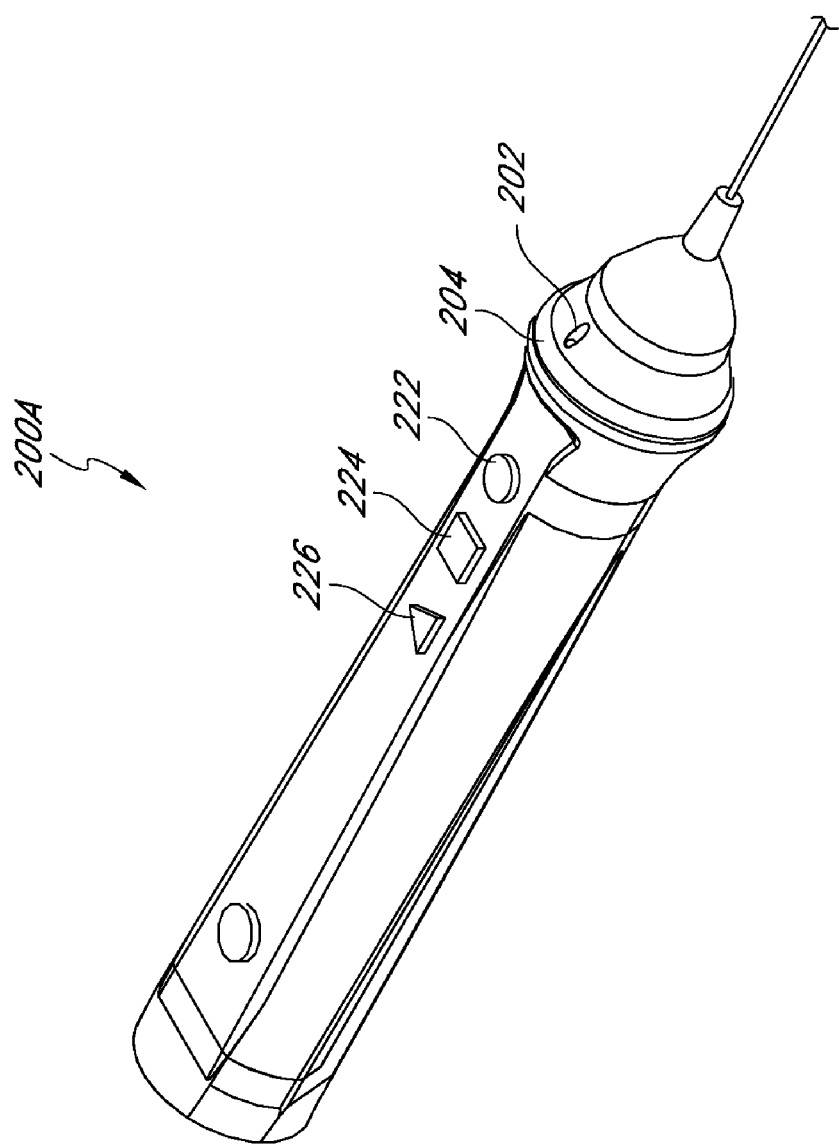
FIG. 39 illustrates a perspective view of a handpiece assembly comprising a site light and an optical ring according to one embodiment.

As illustrated in the embodiment of FIG. 39, the optical ring 204 is positioned near the distal end of the handpiece assembly 200A. For instance, the optical ring 204 can be positioned, either partially or completely, around the distal end of the core and/or clip portion. However, the optical ring 204 can be positioned in any other location of the handpiece assembly 200A, such as, for example, near the buttons 222, 224, 226, at or near the proximal end of the assembly 200A or the like. Further, the optical ring 204 can have a different shape, size and/or other characteristic than illustrated in FIG. 39. For example, the optical ring 204 can be a relatively small light having a circular, oval, rectangular or any other shape (e.g., similar to the indicator light 228 illustrated in FIG. 22A). Moreover, the optical ring 204 may comprise LEDs, fiberoptics and/or any other technology to permit it to emit one or more colors. In other embodiments, the handpiece assembly 200A comprises a small display (e.g., LCD) that provides the name of the medication or formulation (or combination thereof) being conveyed and/or any other information regarding the injection procedure being performed.

Although the site light 202 and the optical ring 204 are discussed with specific reference to FIGS. 38 and 39, those of skill in the art will appreciate that one or both of these features (or equivalents thereof) can be provided on any other handpiece assembly disclosed herein. Therefore, the handpiece assembly 200 discussed herein with reference to FIGS. 21A-26C can be modified to incorporate one or more site lights 202 and/or optical rings 204, as desired or required.

Figure 40:
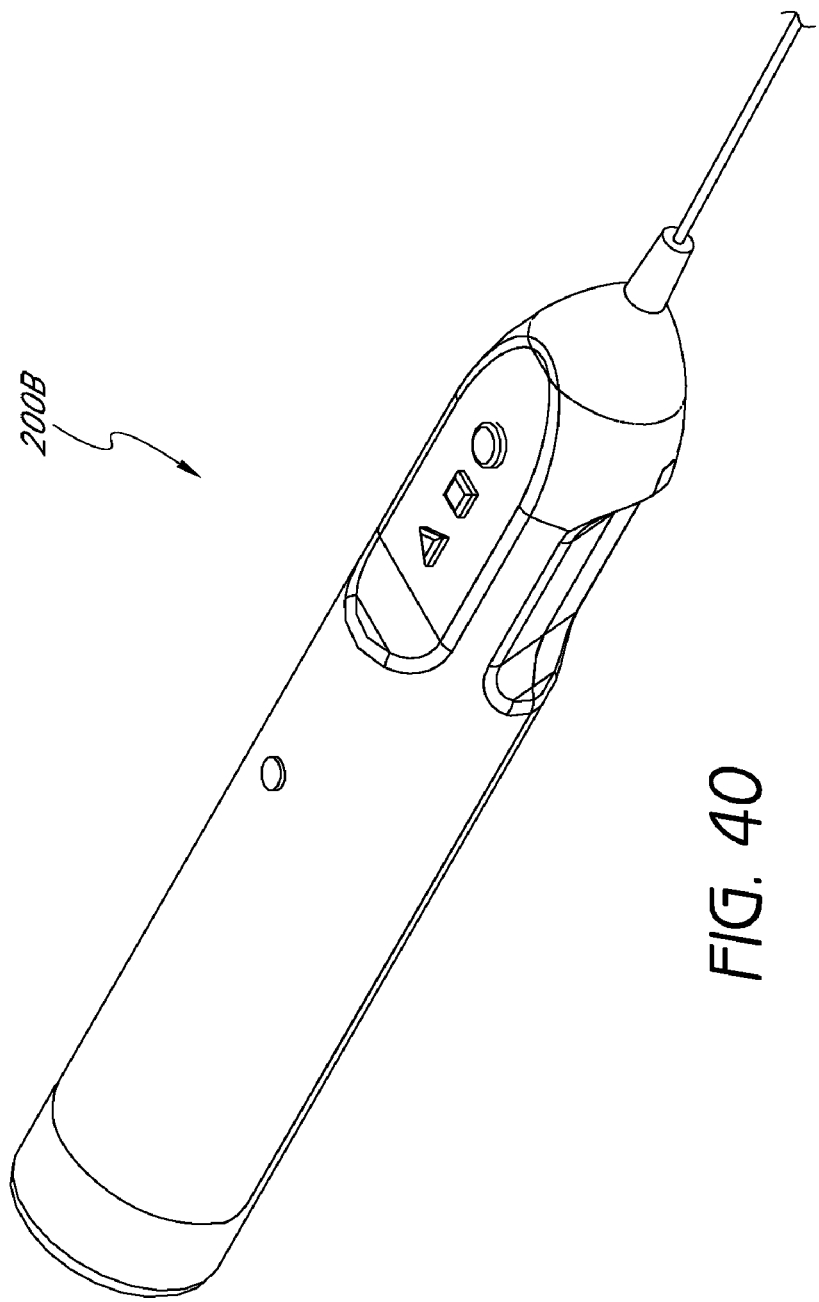

Another embodiment of the handpiece assembly 200B is provided in FIG. 40. The depicted assembly 200B is generally similar to other configurations disclosed herein. However, the illustrated handpiece assembly 200B includes a larger outer diameter to facilitate handling and manipulation during use. As discussed, the handpiece assembly 200B can also include one or more other ergonomic, functional and/or aesthetic features or advantages, as desired or required.

Figure 41:
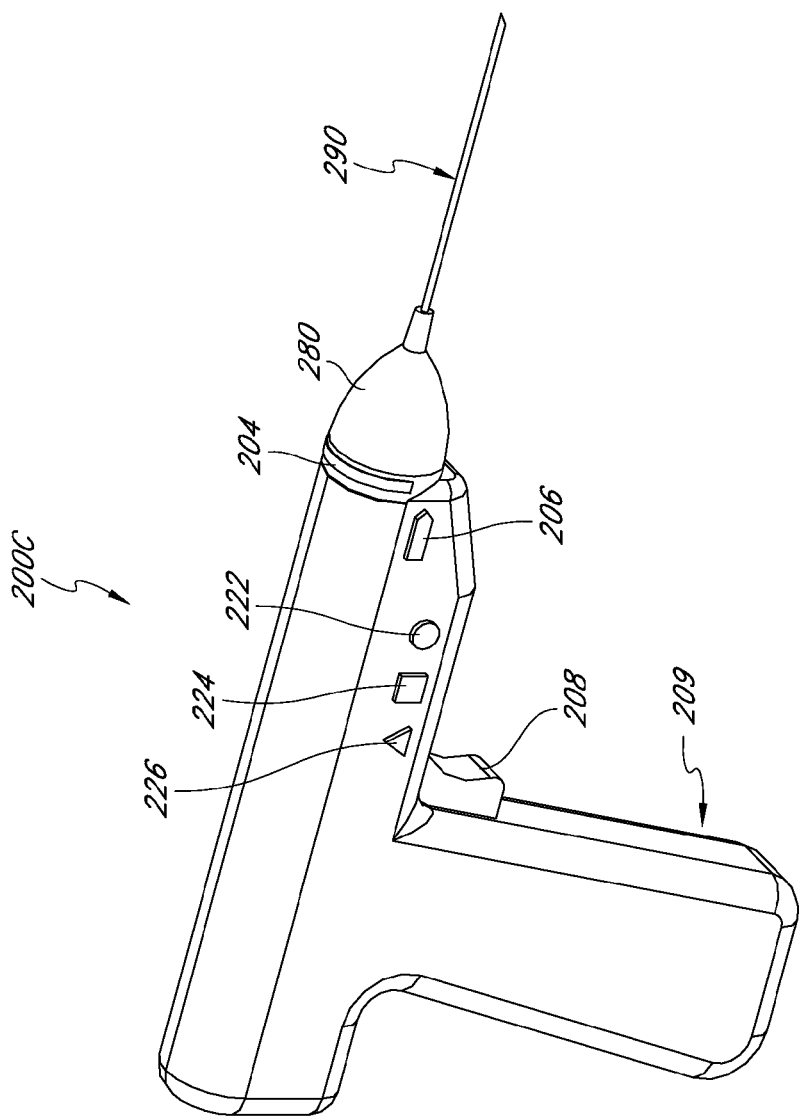

FIG. 41 illustrates yet another embodiment of a handpiece assembly 200C adapted for use in an articular injection system. As shown, the handpiece assembly 200C can have a pistol-shape with a lower handle portion 209. As with other arrangements disclosed herein, the depicted handpiece assembly 200C comprises a tip 280 and a needle 290 along its distal end. Further, the assembly 200C can include a plurality of buttons 222, 224, 226 that help the user control one or more aspects of the operation of the injection system. In some embodiments, the handpiece assembly 200C comprises one or more triggers 208 (or other buttons, levers, knobs or the like) that are adapted to help regulate the operation of the injection system (e.g., deliver one or more fluids, make selections on the display of the fluid delivery module, etc.). Such a trigger 208 can be strategically positioned to allow a user to conveniently manipulate it with his or her index finger while grasping the lower handle portion 209.

With continued reference to FIG. 41, the handpiece assembly 200C can include a tip release button 206 strategically positioned along its outer surface. In some embodiments, pressing the release button 206 causes the tip 280 to detach from the remainder of the handpiece assembly 200C (e.g., the clip). Thus, the tip 280 can be conveniently, quickly and safely discarded after an injection procedure. The shape, size, location and/or other details of the tip release button 206 can be different than illustrated herein. In addition, such a release button 206 for the tip 280 or any other portion of the handpiece assembly 200 can be included in any other embodiment of a handpiece assembly disclosed herein or equivalent thereof.

Figure 42:
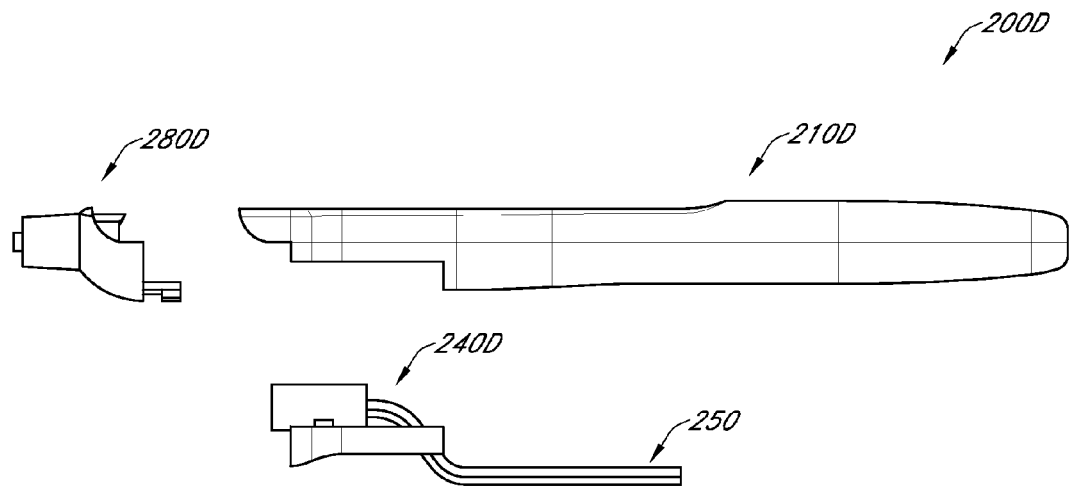

FIG. 42 illustrates an exploded side view of a handpiece assembly 200D according to a different arrangement. Like the handpiece assembly 200 of FIGS. 21A-26C, the depicted embodiment includes a core 210D, a clip 240D and a tip 280D that can be separated from each other.

Figure 43A:
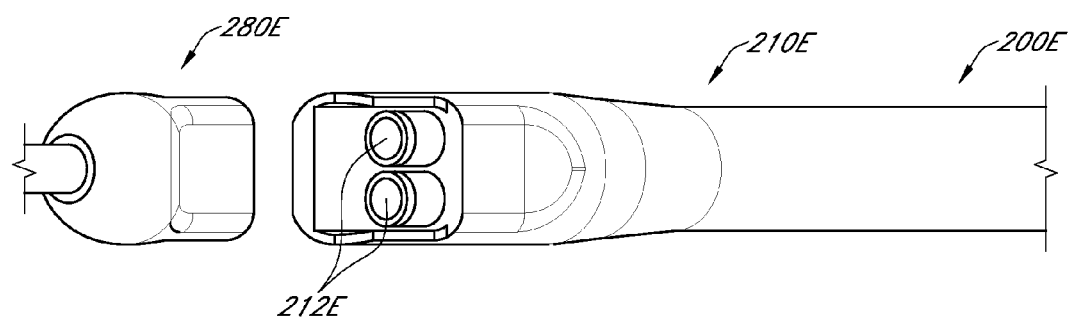
Figure 43B:
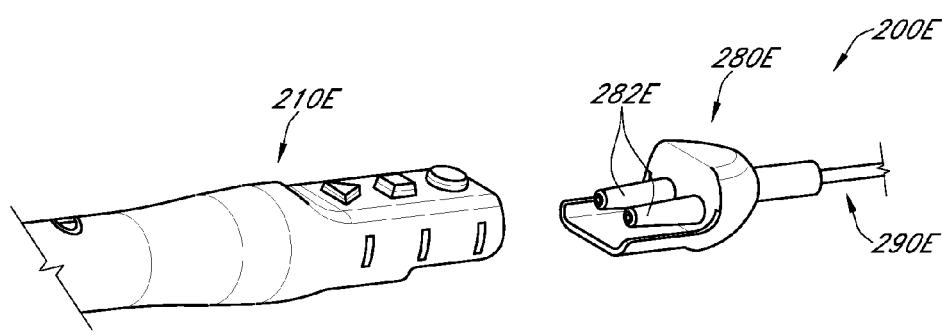
Figure 44:
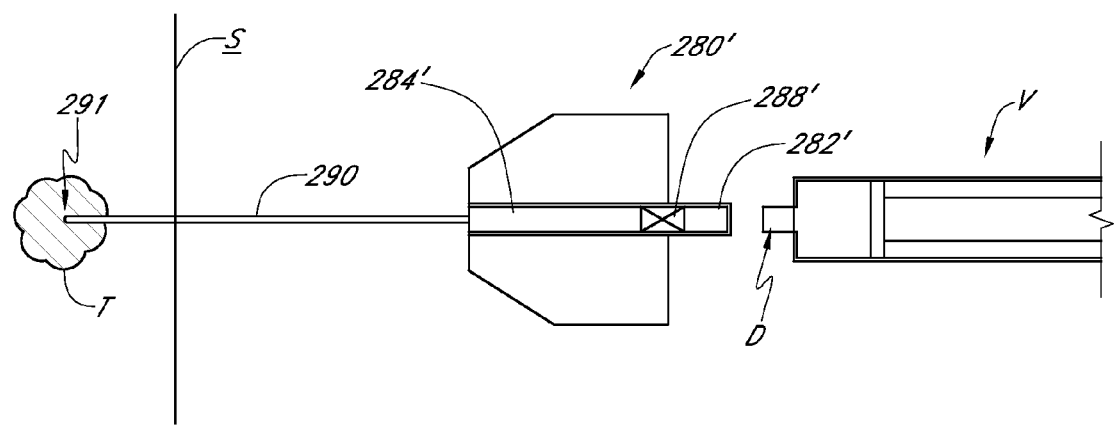

The handpiece assembly 200E illustrated in FIGS. 43A and 43B includes a proximal main portion 210E and a distal tip portion 280E that are configured to removably attach to each other. As shown in FIG. 43A, the main portion 210E can comprise one or more passages 212E through which fluids and/or other materials can be selectively transferred. For example, such passages 212E can be placed in fluid communication with one or more components of an articular injection system (e.g., a cassette, a fluid delivery module, a delivery line, etc.). In some embodiments, as illustrated in FIG. 43B, the tip portion 280E includes one or more conduits 282E that are sized, shaped and otherwise configured to mate with the passages 212E when the tip portion 280E is properly secured to the main portion 210E. Thus, fluids and/or other materials can be conveyed through the passages 212E and the conduits 282E toward a needle 290E positioned at the distal end of the tip portion 280E. In some arrangements, the passages 212E, the conduits 282E and/or any other portion of the handpiece assembly 200E that may in contact with the fluids and/or other materials passing therethrough are configured to be replaced between injection procedures or in accordance with some other protocol or schedule.

Aspiration

As discussed, any of the configurations of the articular injection system and its various components disclosed herein can be adapted to also aspirate fluids and/or other materials from the anatomy. One embodiment of a tip 280' designed to be used during both an injection procedure and an aspiration procedure is schematically illustrated in FIG. 44A. For example, such a tip 280' can be positioned at the distal end of a clip 240 or other portion of a handpiece assembly 200 (FIGS. 21A and 21B). Thus, fluids and/or other materials can be conveyed from the clip 240, through the tip 280' and into a needle 290 secured to the distal end of the tip 280'. As discussed, the various configurations of an injection system disclosed herein can advantageously permit two or more different types of medications and/or other formulations to be delivered into the anatomy (e.g., intra-articular location) with only a single needle penetration. This can facilitate the injection procedure and reduce the pain and discomfort for the patient.

In some arrangements, the same tip 280' can be utilized when fluids and/or other materials need to be removed from the anatomy. In the schematic of FIG. 44A, a needle 290 is secured to the outlet 284' of the tip 280'. As shown, with the distal end 291 of the needle 290 accurately positioned through a patient's skin S and within a target anatomical location T, the tip 280' can be separated from the proximal components (e.g., clip, core, etc.) of the handpiece assembly 200. In some embodiments, as discussed herein with reference to FIG. 41, the handpiece assembly includes a release button 206 to facilitate isolation of the tip 280'. Alternatively, the tip 280' can be manually removed from the clip or other components of the handpiece assembly (e.g., by turning, pulling or otherwise moving the tip 280' relative to the clip).

In some embodiments, the tip 280' comprises a combination duckbill/umbrella valve 288' or other type of flow control device that is configured to permit flow in both directions under certain circumstances. As a result, fluids may not be permitted to be prematurely removed from the anatomy through the tip inlet 282' when the tip is separated from the proximal portions of the handpiece assembly. When the clinician or other user is ready to aspirate fluids and/or other materials from the target anatomical location (e.g., joint), he or she can attach a vacuum source V to the tip inlet 282'. The vacuum source V can comprise a syringe, a pump and/or the like (e.g., a mechanical, pneumatic or other type of device). In the illustrated embodiment, the tip inlet 282' is sized, shaped and otherwise configured to receive a distal tip D of a standard syringe V. For example, the tip inlet 282' and the distal tip D of the syringe V can be connected using a luer connection, another type of threaded connection or the like. Once the syringe or other vacuum source V is properly attached to the tip inlet 282', a suction force can be generated at the tip inlet 282' (e.g., by pulling the inner plunger of the syringe rearwardly relative to the outer barrel, by activating a pump or other device, etc.). If the suction force meets or exceeds a particular threshold, fluids and/or other materials from the distal end 291 of the needle 290 can be permitted to pass through the valve 288'. Accordingly, such fluids and/or other materials can be advantageously removed form the anatomy.

In other embodiments, the tip 280' can be configured to permit aspiration of fluids and/or other materials from the anatomy without having to disconnect the tip 280' from the clip, core or any other proximal portion of the handpiece assembly. For example, the tip 280' can include a side branch that is in fluid communication with the main fluid passage connecting the tip inlet 282' and tip outlet 284'. Such a branch can include a flow control valve that is configured to prevent flow therethrough when fluids and/or other materials are being injected, while allowing fluids and/or other materials to be removed from the anatomy when a vacuum source (e.g., syringe, pump, etc.) is connected thereto. In some embodiments, such a branch terminates at the side of the tip 280' with a luer connection, other threaded connection and/or the like.

D. Injection System with Imaging

In some embodiments, an articular injection system 10 can be configured to locate a targeted intra-articular or other anatomical site before delivering fluids thereto (or aspirating fluids therefrom). According to some embodiments, a target anatomical location can be located using one or more imaging, scanning and/or other locating devices or techniques. For example, as discussed in greater detail herein, an ultrasound device can be used to locate the targeted intra-articular space or other anatomical location prior to transferring medications, fluids and/or other materials to or from a handpiece assembly 200. In some embodiments, the ultrasound device, radio frequency spectroscopy device or other locating apparatus can be connected to and/or configured to work in combination or otherwise interface with a fluid delivery module.

Figure 45:
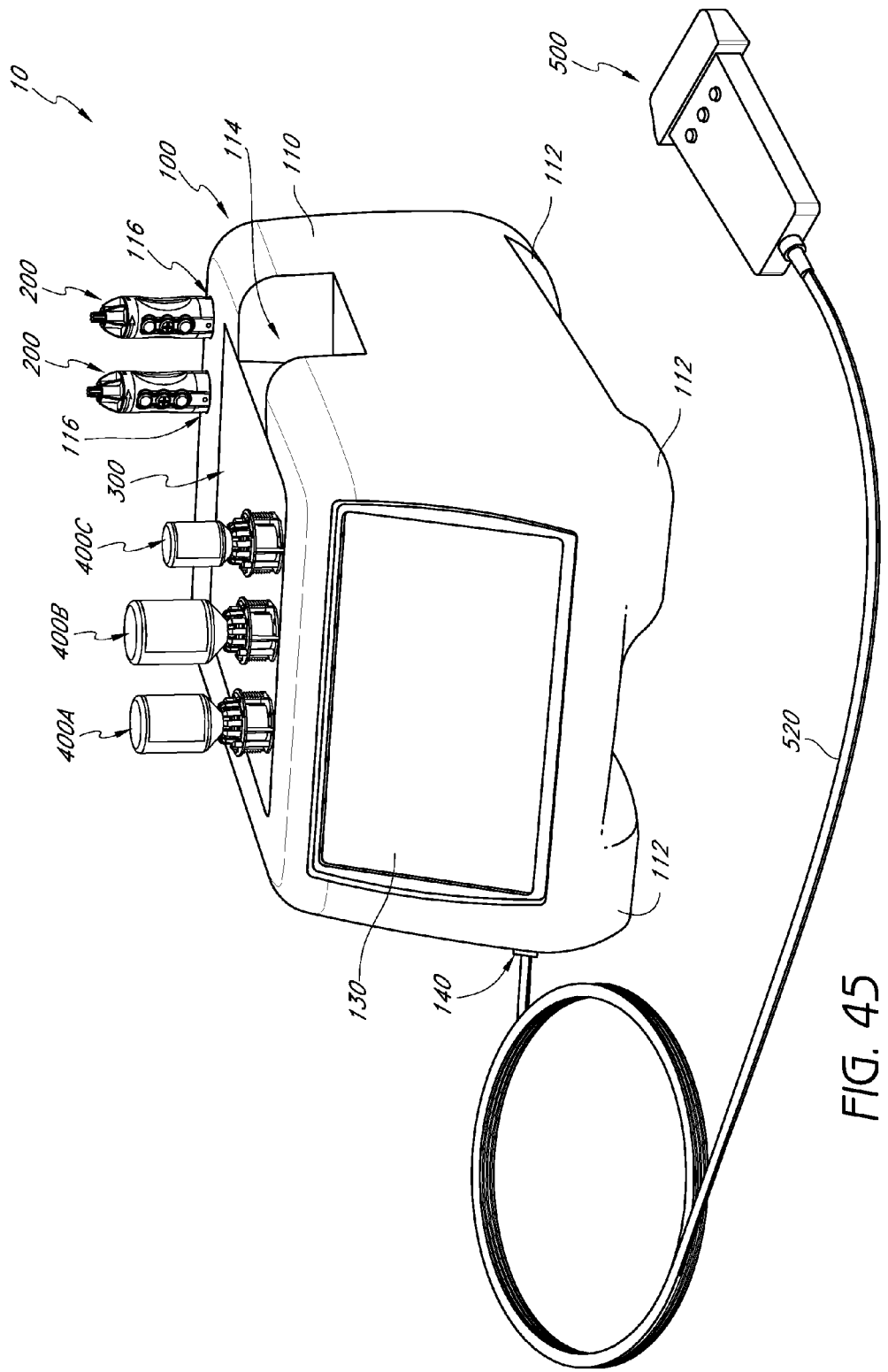

FIG. 45 illustrates an embodiment of an injection system 10 that comprises imaging devices or components that are configured to assist in locating a target anatomical location. As shown, the fluid delivery module 100 can include a cassette 300 that is adapted to receive one or more vials 400 or other containers. As discussed with reference to other embodiments herein, such vials 400 can comprise anesthetics (e.g., Lidocaine), other pain-relieving medications, steroids (e.g., Depo-Medrol®, methylprednisolone acetate, etc.), hyaluronic acid, saline, pharmaceutical compositions, other medications or drugs, cells, liquid and non-liquid fluids and flowable materials, nanoparticles, cement, microbeads and/or any other material. In addition, as with other embodiments disclosed herein, the cassette 300 or another portion of the fluid delivery module 100 can be in fluid communication with a handpiece assembly 200 that is configured to transfer one or more fluids and/or other materials to and/or from a targeted anatomical location with a single needle penetration.

As discussed, the articular injection system 10 can comprise ultrasound, radio frequency spectroscopy or other imaging capabilities. For example, the fluid delivery module 100 can be in data communication with an ultrasound wand 500 and/or any other component or feature of an imaging system. As illustrated in FIG. 45, the processors and other components that enable the fluid delivery module 100 to comprise the desired imaging capabilities can be generally incorporated within the wand 500 and/or the fluid delivery module 100. However, in other embodiments, one, some or all of the necessary components of the imaging system are included in other devices or other components of the injection system 10. Such separate devices can be adapted to be selectively placed into and out of data communication with the fluid delivery module 100 using one or more connection devices or methods (e.g., hardwired connections, wireless connections, etc.). For example, as discussed in greater detail herein, a core 210 or other portion of a handpiece assembly 200 can include buttons, other controller, circuitry, processors and/or other electrical and control features that are configured to regulate the operation of an ultrasound device or other imaging system.

With reference to FIG. 45, the ultrasound wand 500 can be connected to the fluid delivery module 100 using a cord 520 or other hardwired connection. However, as discussed, the wand 500 can be configured to communicate with the fluid delivery module 100 wirelessly (e.g., using RF, Bluetooth and/or the like). As shown, the connection cord 520 can be inserted into a port 140 positioned along the outer housing of the fluid delivery module 100.

Figure 46:
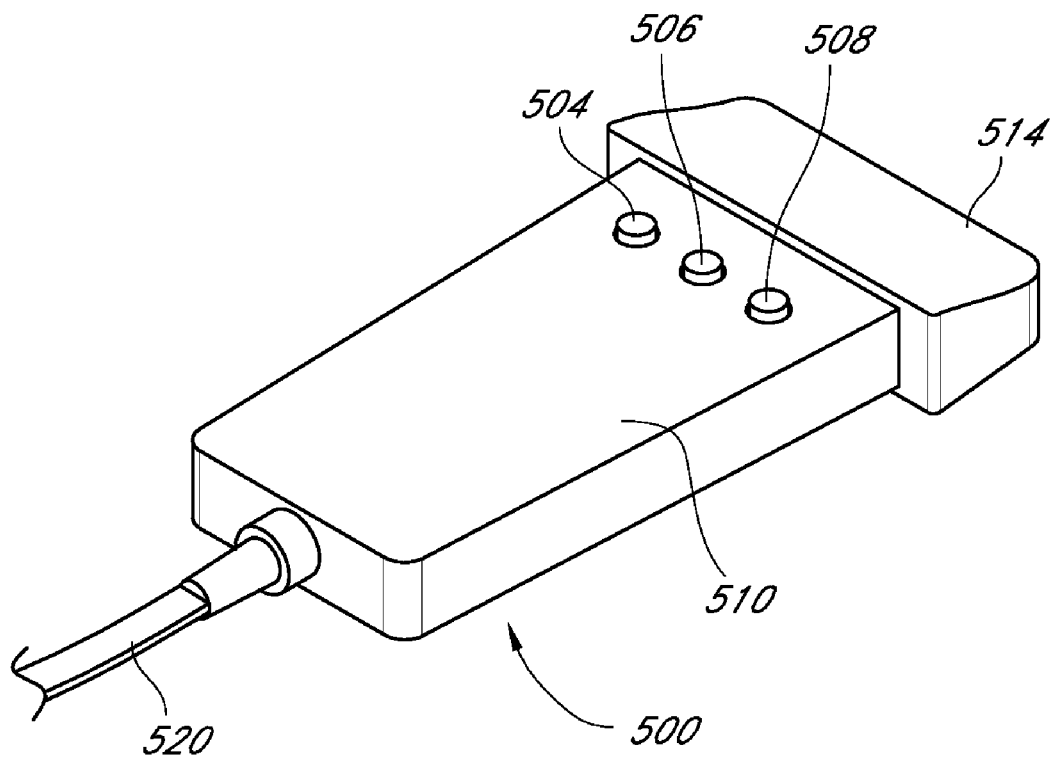

A detailed perspective view of the ultrasound or other imaging wand of FIG. 45 is provided in FIG. 46. As shown, the wand can include a main body 510 and a head 514 that is configured to contact the patient's skin during the imaging procedure. In addition, the wand 500 can include a plurality of buttons 504, 506, 508, knobs, levers, switches and/or other controllers that allow the clinician to operate one or more aspects of the imaging system and/or the injection system. For example, the buttons 504, 506, 508 can be configured to adjust or capture an ultrasound or other type of image. In some embodiments, the buttons 504, 506, 508 are configured to regulate the injection of fluids and/or other materials through the handpiece assembly 200. Thus, the clinician or other user can control all aspects of a procedure through a single device. Alternatively, the handpiece assembly 200 can include the buttons, knobs and other adjustment devices that are necessary to control both the delivery of fluids and/or other materials through the handpiece assembly 200 and the operation of an imaging system. As discussed, this can advantageously permit a user to locate a targeted anatomical space (e.g., a joint), control the delivery of one, two or more different fluids and/or substances to such a targeted space and/or regulate one or more other aspects of an injection procedure without having to remove his or her hands from the handpiece assembly. In other embodiments, both the injection and imaging systems are controlled by buttons or other adjustment devices located on the fluid delivery module 100 (e.g., touchscreen display), another portion of the injection system and/or a separate device, either in lieu of or in addition to buttons located on the handpiece assembly and/or the imaging wand 500.

Figure 47:
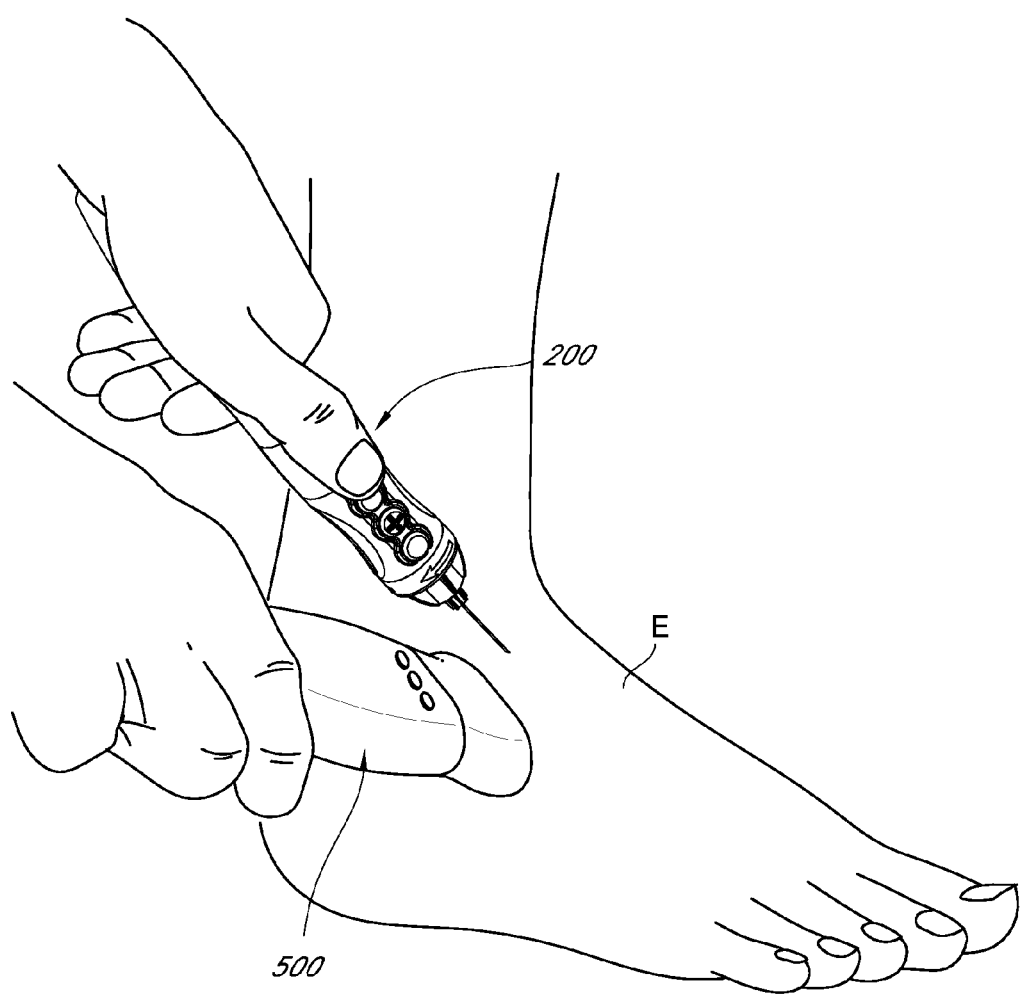

Incorporating imaging technologies (e.g., ultrasound, radio frequency spectroscopy, CT, MRI, etc.) into an articular injection system 10 that is also configured to selectively transfer fluids and/or other materials into or out of a targeted anatomical location can facilitate the injection/aspiration procedures for a clinician or other user. In some embodiments, an imaging-enabled injection system 10 can facilitate execution of a particular injection procedure. In addition, such systems 10 can enable an injection procedure to be completed with fewer clinicians and other resources. For example, when a separate imaging device is utilized, two or more physicians or clinicians are typically needed to properly and safely complete the procedure. As illustrated in the embodiment of FIG. 47, a clinician or other user can perform an injection procedure by manipulating an imaging (e.g., ultrasound, radio frequency spectroscopy, etc.) wand 500 in one hand to locate the targeted anatomical location (e.g., toe, foot, knee, other joint, etc.), while simultaneously handling the handpiece assembly 200 in the other hand to selectively transfer fluids or other materials to (or from) such location.

Consequently, incorporating imaging technologies into the articular injection system 10 can offer a number of advantages. For example, such a combination unit can be operated using a single power supply. In addition, such a configuration can be operated using a single logic board, computer chip or other processor. Further, as discussed, the combination unit can allow a clinician to use "multi function" buttons and controls. For instance, a button, soft key or other adjustment device can be used to control both an ultrasound unit (or other imaging or location device) and the injection system.

As discussed, in any of the embodiments disclosed herein, a target intra-articular location or other anatomical space can be located using one or more imaging techniques, such as, for example, ultrasound, fluoroscopy, CT, MRI and/or the like. Ultrasound technology uses sound waves of a particular frequency to image internal structures (e.g., tissue, organs, joints, etc.). In some arrangements, pulsed and/or continuous sound waves can be directed to the area of interest using one or more transducers. Redirected sound waves that bounce off anatomical structures are detected by the transducers or other devices (e.g., the wand 500 of FIG. 45). These data can then be processed to generate an image or other visual display of the targeted area.

Ultrasound transducers and other components used to locate a desired anatomical location can be directly or indirectly incorporated into a fluid injection system. For example, in some embodiments, a separate ultrasound probe or wand is used to visually confirm the location of the needle relative to the target location (e.g., an intra-articular space). The ultrasound equipment can be configured to operate either continuously or intermittently during the course of the procedure, as desired or required. In other embodiments, an ultrasound transducer and/or other ultrasound devices is incorporated directly into one or more components of an injection system. For instance, a small ultrasound transducer can be positioned at or near the tip of the delivery or aspiration needle. The ultrasound transducer can be placed in data communication with a processing apparatus and/or other components using one or more hardwired and/or wireless connections. In addition, the injection system can be configured so that the imaging results are advantageously viewed on the display 130 of the fluid delivery module.

Thus, as the needle is inserted into the body, a physician or other clinician can accurately detect the position of the distal end of the needle. Such imaging techniques can be used alone or in conjunction with one or more other locating methods or devices. For example, in one embodiment, tissue response measurements can be used to locate a target intra-articular space. In other embodiments, ultrasound and/or other imaging technologies are used to locate a targeted intra-articular space. In other embodiments, both tissue response measurements and ultrasound and/or other imaging technologies are used to locate a joint space. In still other embodiments, one or more other joint locating methods or devices can be used, either in lieu of or in addition to methods, systems and methods disclosed herein.

In one embodiment, ultrasound imaging is particularly advantageous because it permits real-time visualization of a joint or other target location. By way of example, in one embodiment, the delivery module and system include an ultrasound device using a broadband curved array transducer working at about 2-5 MHz and a broadband linear array working at about 4-7 MHz. Imaging errors can be kept at a minimum by taking the linear array for measurements. Curved array may be desirable and used for better penetration depth.

The use of ultrasound to guide injection of fluid into small joint spaces is particularly useful. Researchers have used ultrasound guide for the aspiration of fluid from joint spaces (see Ultrasound guidance allows accurate needle placement and aspiration from small joints in patients with early inflammatory arthritis, Rheumatology 2003; 42: 976-979, herein incorporated by reference). However, several embodiments of the present invention provide a system and method of using ultrasound guidance to inject fluids into small joint spaces.

Ultrasound can assist in the visualization of internal structures (e.g., bones, joints, organs, other tissue, etc.) within the anatomy. As such, ultrasound technologies can be used to visually display the orientation of the needle with respect to such internal structures. Consequently, ultrasound can assist a user in correctly positioning and directing the needle during an injection and/or aspiration procedure.

In addition, a contrast media can be used with the ultrasound devices and methods described herein to further enhance the user's ability to verify the location of the needle tip relative to the targeted anatomical location (e.g., intra-articular location, organ, etc.). This can provide additional assurances that the medication, other fluid and/or other substances are being delivered to the desired location within the patient being treated. A contrast media can also be used in embodiments where aspiration of a fluid or other material is desired. For example, if acceptable, a contrast media can be delivered to or near the desired location. Then, once placement of the aspiration needle has been confirmed, the fluid module can be used to aspirate as required. In some embodiments, if the aspiration procedure is therapeutic in nature (e.g., being used to relieve pressure within the targeted anatomical location), the use of contrast media may be acceptable. However, in one or more other circumstances, the use of contrast media may not be acceptable or desirable. For example, if the purpose of the aspirating is to withdraw a fluid for diagnostic reasons (e.g., testing the extracted fluid sample), initially injecting a contrast media or other substance may contaminate the desired sample.

The incorporation of an ultrasound or other imaging device or system into an injection system can provide additional benefits to a facility, a clinician or other user. In some arrangements, such a configuration helps with the generation of accurate reports for billing, recordkeeping and/or other purposes. For example, data regarding which ultrasound and/or other imaging devices or systems were utilized and to what extent they were used during a particular injection procedure can be automatically stored within a memory (e.g., hard disk, other fixed or removable drive, etc.) of the fluid delivery module or other component of the injection system (or other system operatively connected to the injection system, e.g., a separate computer, processor and/or the like). Consequently, such accurate information can be retrieved and processed to generate bills or other summaries of work performed. Thus, a provider can accurately charge and be reimbursed for the ultrasound or other imaging technology utilized in a particular procedure.

Further, ultrasound or other imaging technologies can be incorporated into an articular injection system for evidentiary purposes. For instance, physicians, other clinicians, their employers, the facilities in which such injection procedures are executed, insurance companies and/or any other interested parties can be provided with an accurate summary of an entire injection procedure. Information that can be saved may include, without limitation, the date, time and duration of a procedure, the name(s) of the patient, physician, clinician or other party executing or assisting with the execution of the procedure, the steps taken to locate a joint or other target location, the amount of each medicament or other substance delivered into a patient, the sequence, flowrate and other details related to the delivery of the various injected materials and/or the like. In addition, ultrasound or other images captured during the procedure can also be saved for later processing or retrieval. In some embodiments, time-sequential images can be captured and saved prior, during or following the various steps of a procedure (e.g., locating a joint or other anatomical location, injecting a first fluid or other substance, injecting a second or additional fluids or other substances, removing the needle, etc.). This can be particularly useful when color Doppler or other technologies are used that permit for the various fluid and/or material streams to be visually distinguished.

In some embodiments, such data collection is important to determine whether a patient has satisfied certain prerequisites for subsequent treatment procedures. For instance, certain health insurance plans or managed care organizations (e.g., HMOs) require that a subscriber undergo certain preliminary procedures (e.g., injections) before becoming eligible for more expensive and complicated treatments, such as, for example, surgery.

E. Graphic User Interface

According to some embodiments, the display 130 on the fluid delivery module 100 or any other component of the system 10 (FIG. 2A) can be advantageously configured to facilitate the user in customizing and executing a particular injection procedure. For example, the display 130 can include a touchscreen that is adapted to provide information to and receive instructions from a clinician or other user. In other arrangements, the fluid delivery module 100 and/or another component of the injection system 10 can include a data input device (e.g., a keypad, keyboard, etc.) that is separate from the display 130.

The various embodiments of an injection system disclosed herein can be configured to selectively deliver one, two, three or more different medications, formulations and/or the like into a targeted anatomical location. In some arrangements, such fluids and/or other materials are delivered simultaneously (e.g., mixed with one another) during delivery. Alternatively, such fluids and/or other materials can be delivered sequentially, according to some predetermined sequence or protocol, as desired or required. As discussed with reference to FIGS. 22A and 22B, the handpiece assembly 200 of the injection system can include one or more buttons 222, 224, 226, levers, knobs and/or other control features to allow the user to regulate the transfer of fluids to the distal end of the needle 290. For instance, each button 222, 224, 226 can be configured to control the delivery of a medication, formulation or other fluid or material from a corresponding vial 400 or other container loaded onto the fluid delivery module 100. As discussed in greater detail herein, a button 222, 224, 226 can be adapted to simultaneously deliver the contents of two or more vials 400 or other containers.

FIGS. 48A-48D illustrate various screenshots 600A-600D of a touchscreen display 130 of the fluid delivery module 100 that can be advantageously configured to permit a clinician or other user to control the delivery of the medications and/or other fluids or materials loaded onto the fluid delivery module. In the embodiment illustrated in FIGS. 48A-48D, the fluid delivery module is adapted to receive up to three vials or other containers, the contents of which may be selectively delivered through a handpiece assembly as described in greater detail herein. However, in other embodiments, the articular delivery system may include more or fewer vials or other containers, as desired or required.

Figure 48A:
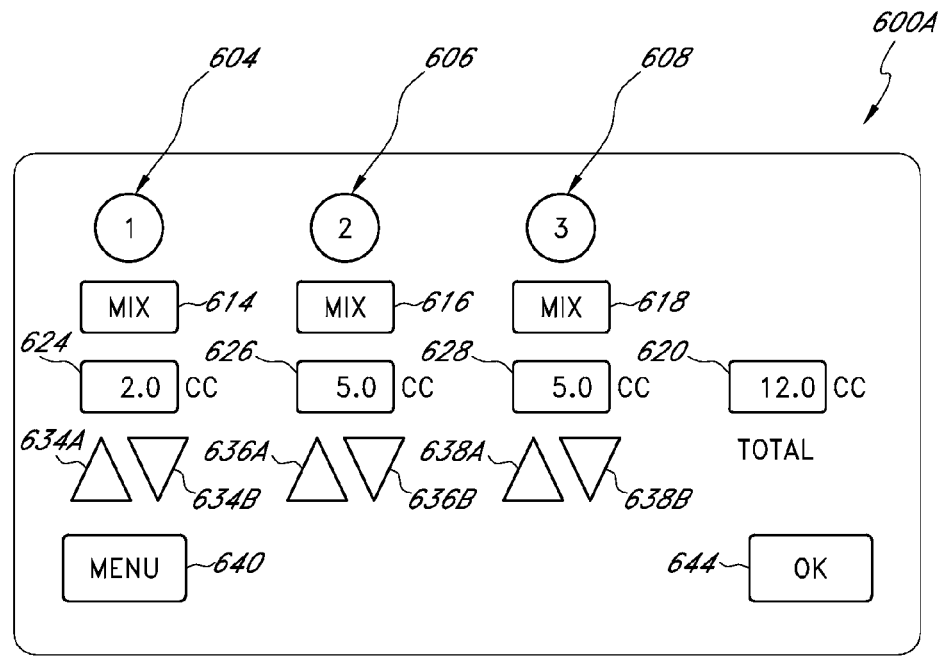

With reference to the screenshot 600A illustrated in FIG. 48A, the touchscreen display can provide flowrate and other data for each type of medication, formulation and/or other fluid or material loaded onto the fluid delivery module. For example, the contents of the vial or other container positioned on a first nest or loading area of the fluid delivery module (and subsequently placed in fluid communication with the handpiece assembly as discussed herein) can correspond to one of the numbered headings 604, 606, 608 depicted on the display. As discussed in greater detail herein, these numbered headings 604, 606, 608 can also correspond to the buttons 222, 224, 226 or other controllers provided on the handpiece assembly 200 or other component of the injection system (FIGS. 22A and 22B).

In some embodiments, other information about the fluids and/or other materials that are loaded within a fluid delivery module can be provided on the screenshots 600A-600D. For example, information about the name of the composition and/or other fluid or material can be provided. In other arrangements, a code (e.g., NDC) and/or other identifier about the particular medication or formulation loaded onto the fluid delivery module can be displayed. Further, as discussed with reference to FIGS. 19A-19C, the vials 400 or other containers being secured to the fluid delivery module can be configured to be automatically or manually identified (e.g., using an identification flag 460 or other member secured to a vial adapter 450D, using a barcode scanner or other identification device positioned along the outside of the fluid delivery module, etc.). Thus, information detected by these types of devices (e.g., type of medication, dosage or concentration, manufacturer, expiration date, etc.) can be advantageously provided on the display of the fluid delivery module. In addition, other data or other information can also be included on the display, such as, for example, imaging data for locating the distal end of the needle, date, time, name of the patient, name of the physician or other clinician performing the procedure and/or the like, as desired or required.

With continued reference to FIG. 48A, the touchscreen display can include up and down arrows 634A, 634B, 636A, 636B, 638A, 638B associated with each type of medication, formulation and/or other fluid or material. Thus, a clinician or other user can select the volume, mass and/or other amount of a particular substance that should be delivered within a targeted anatomical location for an injection procedure. The volume or other amount selected at any particular time can be displayed in a corresponding area 624, 626, 628 of the display. In addition, the total 620 volumetric or other amount of fluids and/or other materials to be delivered within an anatomy for a particular injection procedure can also be displayed.

By way of example, in FIG. 48A, the user has selected to inject 2.0 cc, 5.0 cc and 5.0 cc of a first, second and third medication or other formulation, respectively. Thus, as shown, the total volume of fluids to be delivered during this procedure is 12.0 cc (e.g., displayed on summation window 620). Further, the touchscreen display can offer a convenient way of modifying a particular protocol using the up and down arrows 634A, 634B, 636A, 636B, 638A, 638B. As illustrated, a screenshot 600A of the touchscreen display can include one or more softkeys or other buttons (e.g., "MENU", "OK", etc.) that enable a user to input desired settings (e.g., maneuver through the various screens) and/or adjust the details associated with a specific injection procedure.

Once the details of a desired injection protocol have been entered, a user can use the buttons 222, 224, 226 or other control devices positioned along the exterior of the handpiece assembly 200 (FIGS. 22A and 22B) or other component of the system to selectively deliver one or more of the medications, formulations and/or other fluids or materials to a patient. For example, in one arrangement, a physician or other user presses a button 222 of the handpiece assembly 200 to deliver the internal contents of a first vial or other container secured to the fluid delivery module. In the depicted screenshot 600A, the button 222 that is assigned to control the delivery of such fluids and/or other materials can be generally represented by a number 604 (e.g., "1," "2," or "3"). Such a number or other identifier (e.g., shape, color, graphic, etc.) can match or substantially match the number or other identifier on or near the corresponding button 222 of the handpiece assembly. Thus, a clinician or other user can easily determine which button 222, 224, 226 or other controller of the handpiece assembly 200 is used to deliver a particular medication, formulation and/or other fluid or material.

In order to stop delivering such a fluid or other material to the patient, the physician can release the corresponding button 222 or other controller (or press such a button 222 again). In some embodiments, the amount of a medication or other formulation is not permitted to exceed the amount selected using the corresponding up and down arrows 634A, 634B and displayed in the corresponding area 624 of the display. Other buttons 224, 226 of the handpiece assembly 200 can be manipulated to selectively deliver other fluids and/or materials (e.g., generally corresponding to buttons "2" and "3" on FIG. 48A).

Accordingly, the screenshot information provided on the display can be used to control the manner in which medications, formulations and/or other fluids or materials are delivered to an articular space or other anatomical location. As discussed herein with reference to FIGS. 49A-49D, the display can change to a different screenshot during the delivery of the various fluids and/or other materials. Thus, in some arrangements, the screenshots 600A-600D illustrated in FIGS. 48A-48D are primarily used to enter the details regarding a desired injection procedure.

In some embodiments, two or more medications, formulations and/or other fluids or materials can be combined and delivered together through the handpiece assembly by pressing a single button 222, 224, 226 of the handpiece assembly 200. For example, the fluids and/or other materials associated with buttons "1" and "2" 604, 606 in FIG. 48A can be concurrently delivered to a targeted anatomical location by activating a single button (e.g., button "1") of the handpiece assembly 200. In some embodiments, a user can use the "MIX" buttons 614, 616, 618 of the touchscreen display to program the injection system so that two or more medications or other formulation are concurrently delivered using a single button 222, 224, 226 or other controller.

Figure 48B:
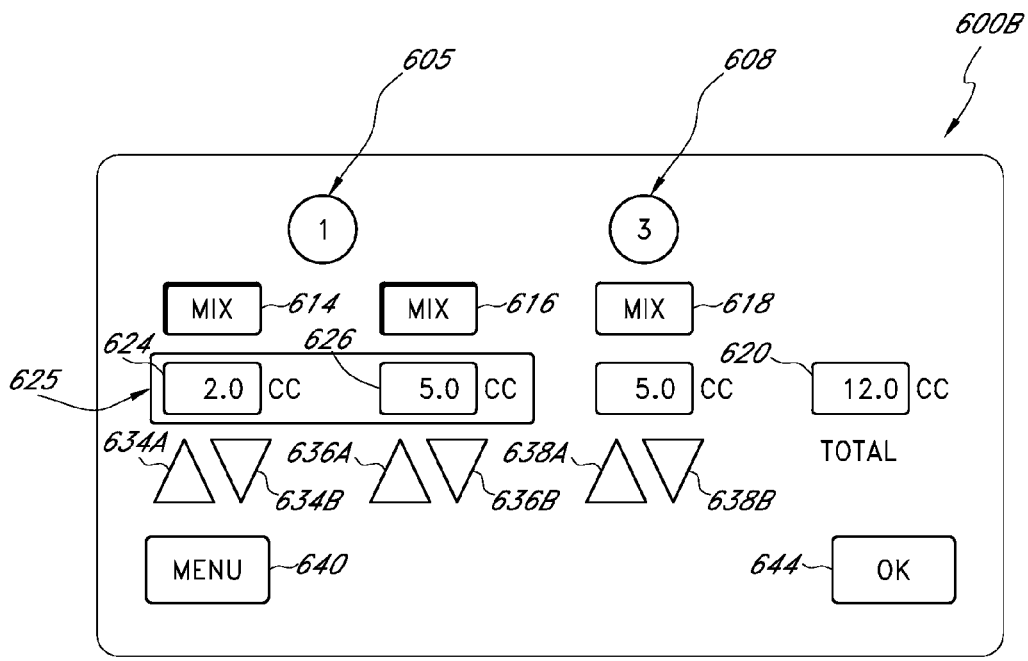

With continued reference to FIG. 48B, once a user chooses to deliver two or more different medications, formulations and/or other fluids or materials using a single button or other controller, the display can be configured to visually assign a single button number 605 (e.g., "1") to such a combination. Further, the windows 624, 626 or other portions of the screenshot 600B displaying the volume or other amount of the corresponding medications, formulations and/or the like can be visually combined (e.g., using a larger window or area 625) in order to make it clear that such materials will be delivered simultaneously.

According to some embodiments, the rate of delivery of the medications, formulations and/or materials being simultaneously delivered (e.g., using a single button as illustrated in FIG. 48B) is adjusted so that the desired volumes or other amounts of such materials expire at the same time for a particular injection procedure. In other words, in the arrangement of FIG. 48B, the rate of delivery of the first fluid can be slow relative to the rate of delivery of the second fluid so that the 2.0 cc of the first fluid and the 5.0 cc of the second fluid are used up at the same time or approximately the same time during an injection procedure. Alternatively, the rate of delivery of the fluids and/or other materials that are simultaneously delivered through the handpiece can be adjusted so that one or some of the fluids or materials are used up before the others.

Figure 48C:
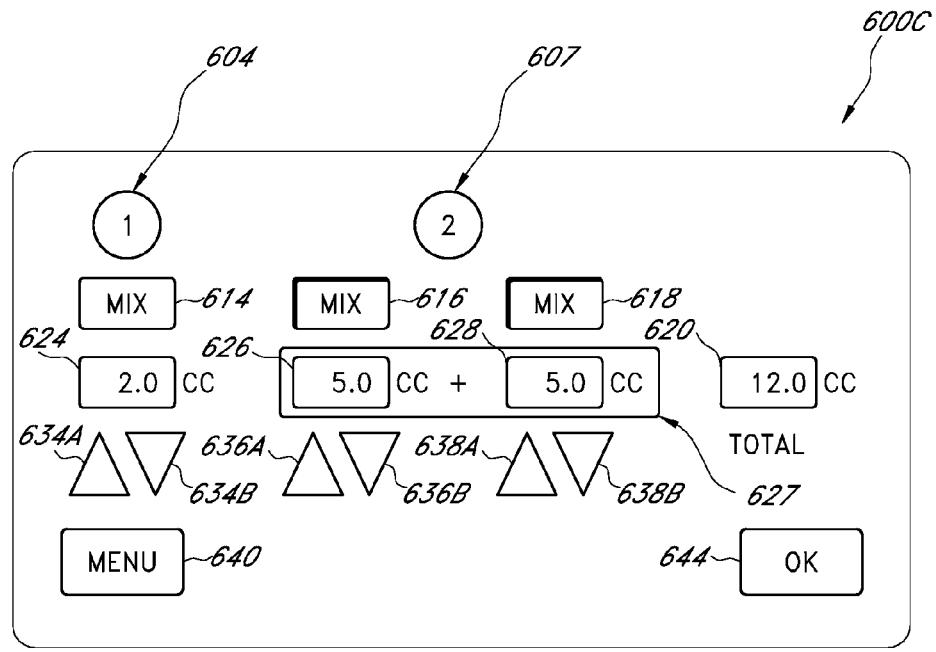

FIG. 48C illustrates another screenshot 600C configured to be displayed on a touchscreen or other display of a fluid delivery module. In the depicted embodiment, the clinician or other user has chosen to deliver the second and third medications, formulations and/or other fluids or materials using a single button (e.g., button "2" of the handpiece assembly). The combination of such fluids and/or other materials is generally represented in the illustrated screenshot 600C by the numeric label "2" 607. Thus, as discussed herein with reference to FIG. 48B, these fluids and/or other materials can be simultaneously delivered by the clinician using a single button 222, 224, 226 of the handpiece assembly 200 that includes a corresponding numeric label (e.g., "2") or other identifier (e.g., color, graphic, etc.).

Figure 48D:
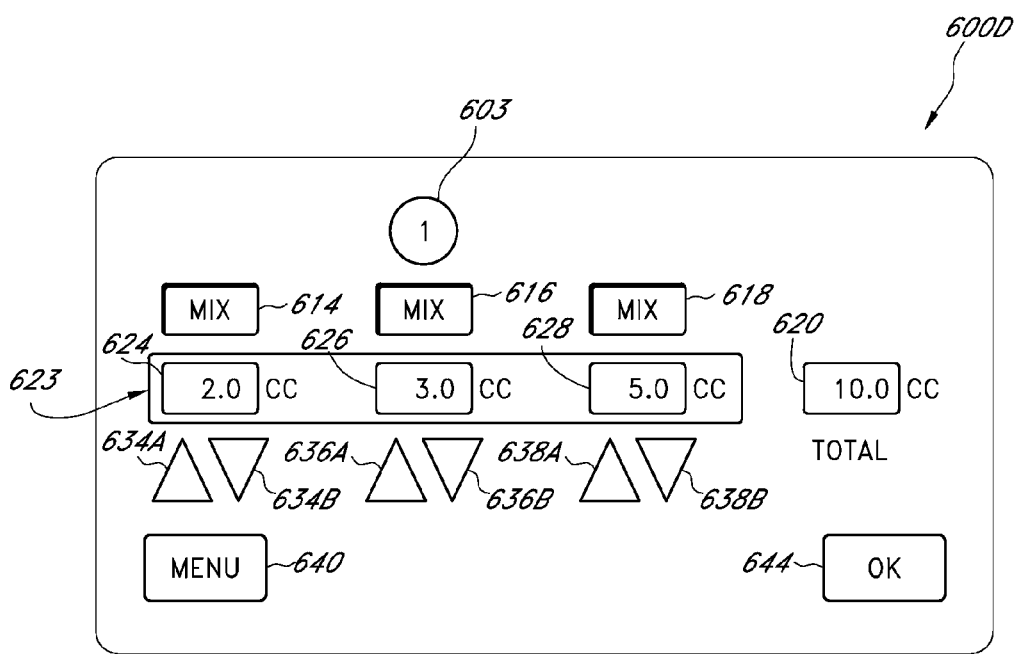

In the embodiment depicted in FIG. 48D, the clinician or other user has programmed the injection system so that all three medications, formulations and/or other fluids or materials loaded onto the fluid delivery module are delivered using a single button 222, 224, 226 of the handpiece assembly 200. In the illustrated arrangement, the simultaneous delivery of all three fluids and/or other materials is generally represented by numeric label "1" 603. Thus, by pressing and releasing the corresponding button 222, 224, 226 of the handpiece assembly, a user can selectively activate and deactivate delivery of all three fluids and/or materials, respectively.

As discussed, in some embodiments, the display is configured to switch to an alternate screenshot once the injection procedure has been commenced. Examples of such delivery screenshots 650A-650D are illustrated in FIGS. 49A-49D. Each screenshot 650A-650D shown in FIGS. 49A, 49B, 49C and 49D generally corresponds with and follows the injection setup screenshot 600A-600D shown in FIGS. 48A, 48B, 48C, 48D, respectively.

Figure 49A:
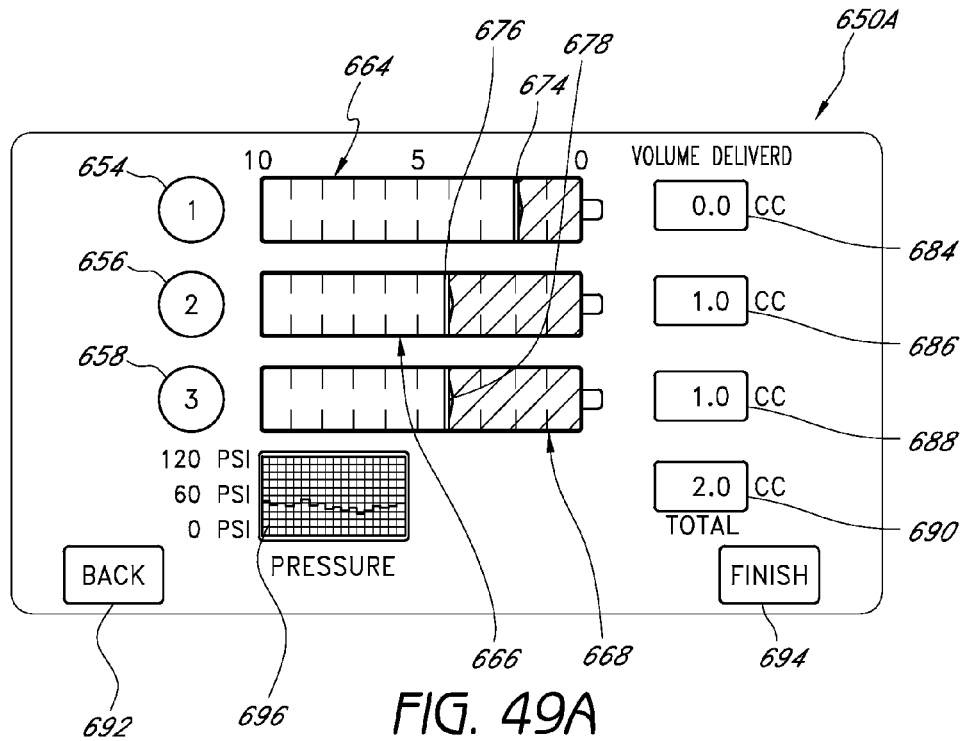

With reference to FIG. 49A, each fluid and/or other material loaded onto the fluid delivery module can be represented by a syringe 664, 666, 668. In the illustrated embodiment, the volume or other amount of each type of medication or formulation remaining within the cassette or other portion of the fluid delivery module for injection into a patient is graphically represented on the screenshot 650A. For example, each syringe 664, 666, 668 can be shown filled with the remaining volume of fluids and/or other materials. As fluids and/or other materials are delivered into an anatomy, a line 674, 676, 678 representing the distal end of a syringe plunger moves within the corresponding syringe 664, 666, 668 (e.g., to the right as illustrated in FIGS. 49A-49D). As a result, the amount of fluid remaining within the corresponding syringe 664, 666, 668 decreases. Accordingly, the user is permitted to conveniently follow the status of the injection procedure.

Figure 49B:
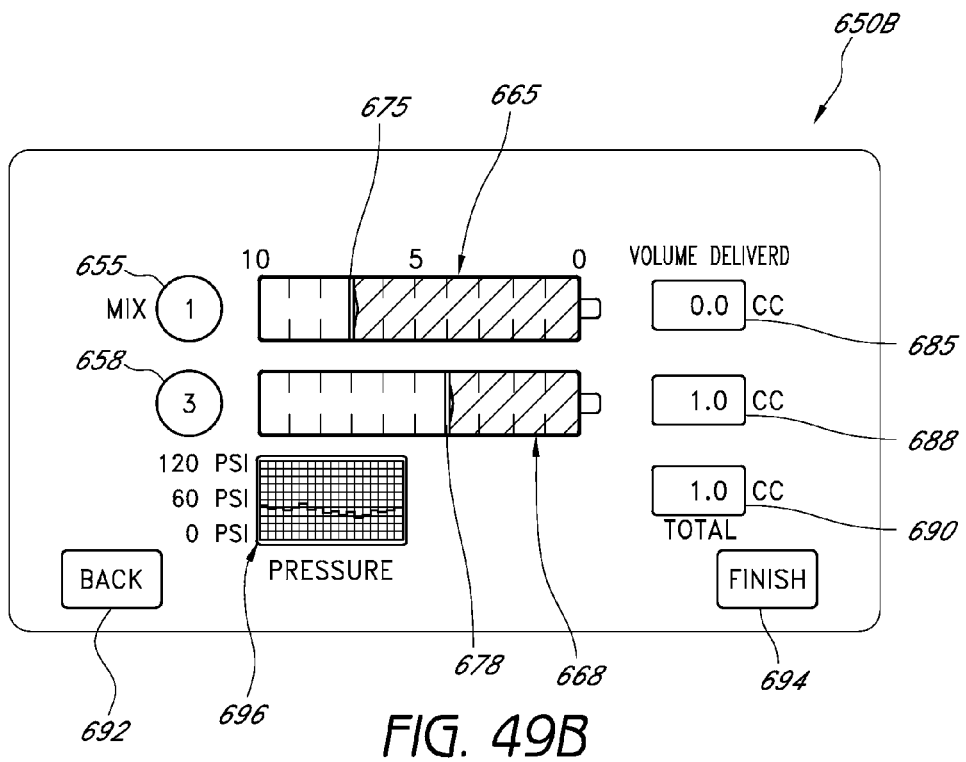
Figure 49C:
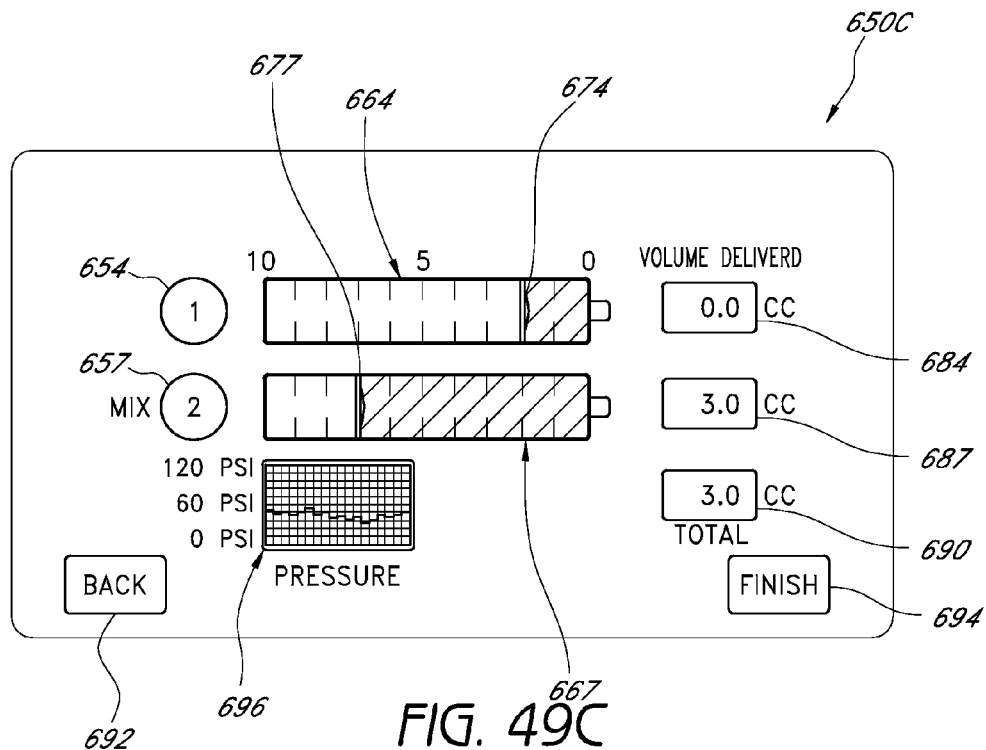
Figure 49D:
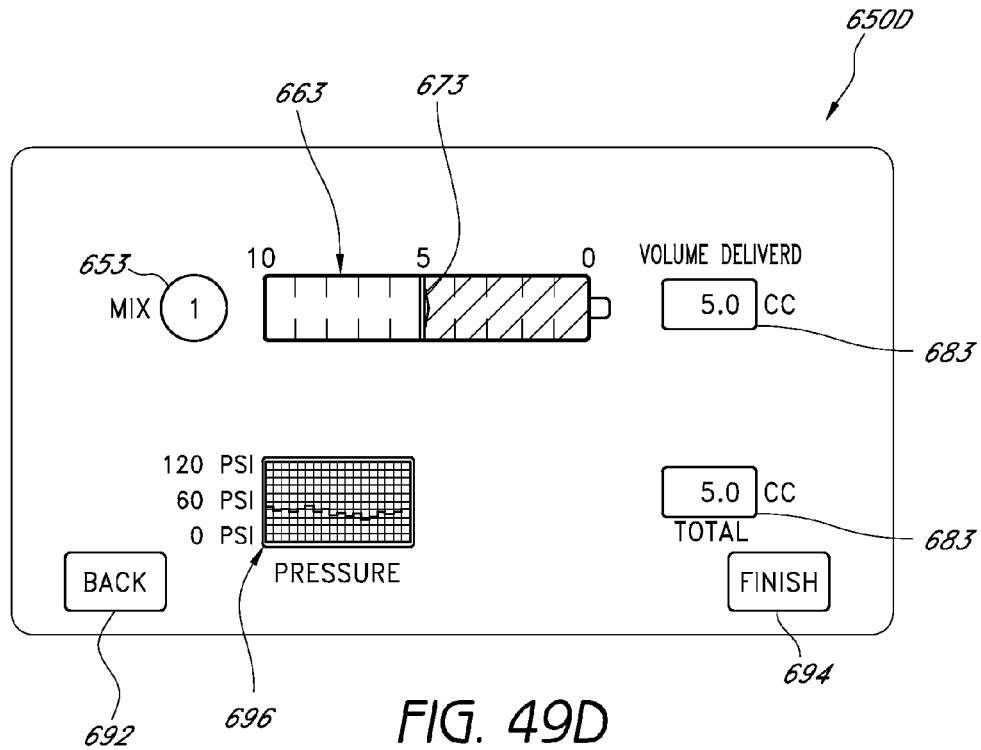

As shown in FIGS. 49A-49D, the volume or other amount of each medication or formulation can also be numerically displayed within corresponding windows 684, 686, 688 of the screenshots 650A-650D. The screenshot may also include a window 690 displaying the total volume of fluids and/or other materials delivered into an anatomy during an injection procedure. In FIGS. 49B-49D, two or more types of medications or formulations are being delivered simultaneously by selectively manipulating a single button 222, 224, 226 or other controller of the handpiece assembly 200. Thus, a single syringe 665, 667, 663 can be used to graphically represent such combined fluids and/or other materials.

With continued reference to FIGS. 49A-49D, the display can be configured to display information regarding the pressure 696 at or near the distal end of the needle 290, either while the needle 290 is being delivered to the target anatomical location (e.g., a joint) or while fluids and/or other materials are being delivered to such a location during the course of an injection procedure.

According to some arrangements, in part for patient safety, the fluid delivery module is configured to accurately measure and regulate the flowrate and/or pressure of a medication, fluid or other material being delivered to the target anatomical location. Thus, the system can comprise pressure and/or flow measurement devices (e.g., pressure transducers, flowmeters, etc.). Pressure sensing devices can be used to ensure that the pressure or vacuum created by the discharge of the medications, compositions, fluids and/or other materials within the anatomy does not exceed a particular threshold level. This can help prevent or reduce the likelihood of damage occurring to the patient being treated using the injection system. Such an internal force measurement system can be configured to automatically shut off the fluid transfer device (e.g., movement of the stepper motor, other pump, etc.) when the discharge pressure exceeds a maximum level (e.g., 3 psi). In other arrangements, the fluid delivery module can include a visual and/or audible alarm or other similar feature to alert the user than a threshold pressure has been attained, either in lieu of or in addition to any automatic shut-off mechanism. For example, the clinician or other user can track real-time pressure and/or flowrate data on corresponding portions 696 of the display during an injection procedure. Other types of feedback that indicates position or placement to a user may also be used (e.g., mechanical or tactile feedback). Such safety features can be included in any of the embodiments of the modules or systems disclosed herein.

Figure 50A:
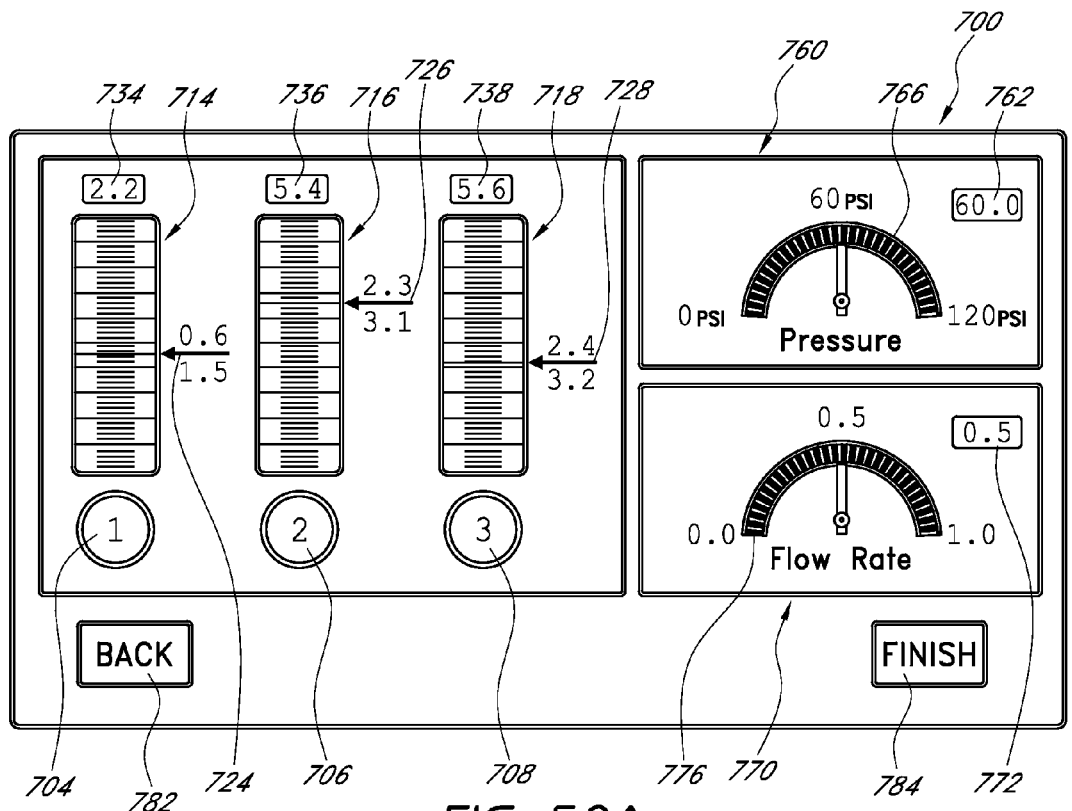
Figure 50B:
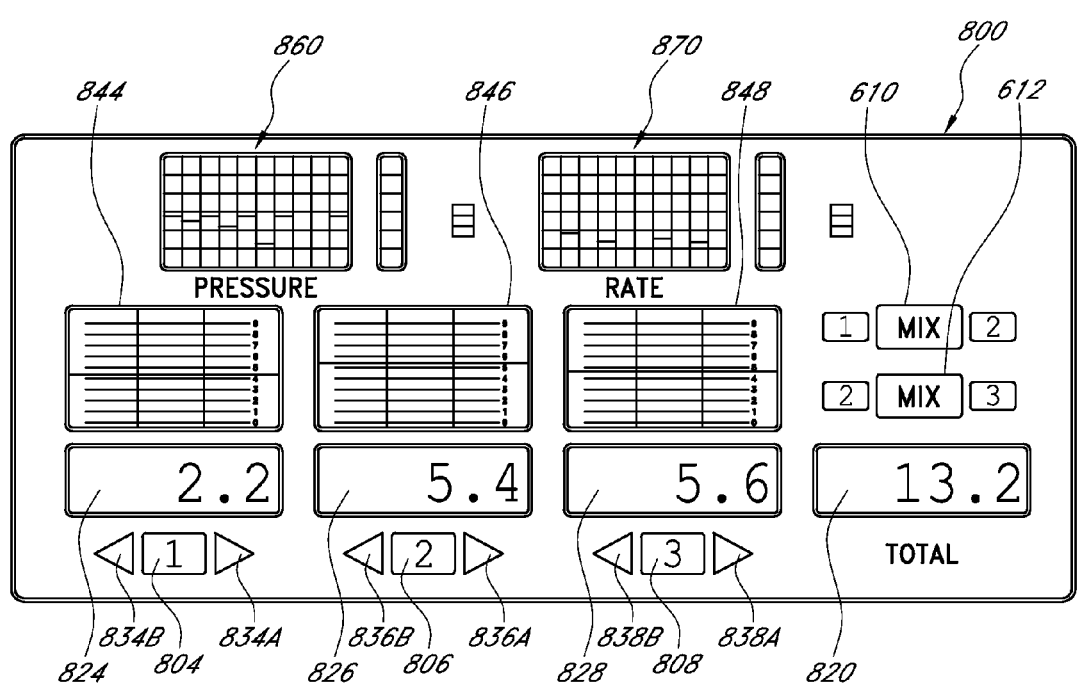

Alternative embodiments of screenshots 700, 800 for a display of fluid delivery module or other component of an injection system are illustrated in FIGS. 50A and 50B, respectively. As shown, the screenshots 700, 800 can comprise various graphical and/or numeric portions that are adapted to provide data and other information to the user, either before or during an injection procedure. In addition, the display can include softkeys, buttons and/or other data input devices that permit a user to adjust and customize an injection procedure as desired or required.

FIG. 51 illustrates one embodiment of a screenshot 880 configured to be shown on a display of a fluid delivery module or other component of or operatively connected to an injection system. As shown, the display can be configured to simultaneously provide information regarding both imaging and the injection of fluids and/or other materials. For example, an upper portion 884 of the screenshot 880 can be adapted to provide a real-time ultrasound image (e.g., to help locate a joint or other target anatomical location). Further, a lower portion 886 of the screenshot 880 can be adapted to provide information regarding the delivery of the various substances into the patient. Thus, a clinician can use a single display of the fluid delivery module or other portion of an injection system to execute an injection procedure. Further, in some embodiments, color Doppler technology can be used to permit a clinician or other user to visualize the various steps of an injection procedure in real time. As discussed in greater detail herein, such screenshots and other images can be saved for billing, recordkeeping and/or other evidentiary purposes.

As discussed, in some embodiments, data and other information regarding the types, volumes or other amounts, dosages and/or other details of the various medications and/or other substances administered during a particular injection procedure, as displayed to the user in a touchscreen or other interface, are automatically stored within a memory of the fluid delivery module, another component or portion of the injection system or an external processor or network with which the injection system is in data communication. In addition data and information related to ultrasound or other imaging procedures that were conducted can also be saved for later processing (e.g., documentation, billing, etc.) or retrieval. Such data and information can include actual ultrasound images, details regarding the imaging equipment used, the extent to which a particular imaging device was used and/or the like. Systems incorporating such a feature can be facilitated by the use of automatically detectable vials or other containers (e.g., FIGS. 19A-19C). In addition, as discussed, other details related to a specific procedure can also be recorded, maintained and linked to a delivery sequence of various medicaments and/or other substances. For example, the injection system can be configured to receive and maintain the name of the patient, the date and time that the procedure was performed, the duration of the procedure, the physicians, clinicians and/or other personnel that participated in the preparation and/or execution of the procedure, the disease or condition being treated, specific treatment codes and other administrative information and/or the like. Such data collection capabilities can assist with billing, patient record keeping, generation of reports, reordering of medicaments and other injectable materials and/or other functions.

F. Cart

FIG. 52 illustrates a cart 900 adapted to support an embodiment of an articular injection system 10 disclosed herein or an equivalent thereof. As shown, the cart 900 can include a top shelf 910 that is sized, shaped and otherwise configured to receive a fluid delivery module 100, one or more handpiece assemblies 200 and any other components of the system 10. In one embodiment, the cart 900 includes a docking station 914 that is configured to receive a handpiece assembly 200 for recharging and storage when not in use. In addition, the cart 900 can include one or more other shelves 926, drawers 930 and/or containers 910 (e.g., waste receptacles for receiving spent needles, tips, etc.), as desired or required. The cart 900 can include one or more wheels 920 so that it can be easily moved to various locations within a facility.

EXAMPLES

Non-limiting examples of injection procedures that may be performed using the various embodiments of systems, devices and methods disclosed herein (or equivalents thereof) are provided below. It should be noted that these examples are provided to simply demonstrate only some of the features and/or other details of injection systems, devices and methods discussed and illustrated herein. As such, the following examples or any other portion of the specification or figures should not be used to limit the present application in any manner.

Example No. 1

The flowchart in FIG. 53 schematically illustrates one non-limiting example of a sequence 1000 for delivering medications, formulations and/or other fluids or substances to a target anatomical site (e.g., a joint, an organ, etc.) using an injection system in accordance with the embodiments disclosed herein. A touchscreen or other visual display of a fluid delivery module or other portion of the system can be configured to initially display 1010 a logo, the time, date, patient and/or physician identifying information, hospital or facility name or logo and/or any other image, design or other alphanumeric text. However, in other embodiments, such a display is configured to not display anything at all. In fact, the fluid delivery module may not include a display at all.

With reference to FIG. 53, it may be necessary for a physician or other clinician to prepare the system 1014 for the subsequent delivery of fluids into a patient. For example, as discussed in greater detail herein, a cassette (or other portion of the fluid delivery module) may be replaced. In some embodiments, used needles, tips, clips, delivery lines, other conduits and/or any other component or portion of the handpiece assembly are removed and replaced with new components or portions. For example, the clinician or other user can secure an appropriately sized (e.g., length, diameter, etc.) sterile needle and/or tip to the distal end of the handpiece device.

As discussed, the needle and tip of the handpiece device can be replaced between injection/aspiration treatments or procedures. Thus, as is standard practice in medical procedures, cross-contamination of fluids between different patients can be prevented. Assuming that there is no need to change the medications or other materials loaded within the delivery module, replacement of only the needle and tip can advantageously permit a physician or other user to quickly and easily perform injection procedures in many different patients. For example, in some embodiments, a physician can perform injection procedures in 30-40 or more different patients per day without having to replace the clip, core or any other portion of the handpiece assembly. Therefore, for practical reasons, a clinician can dedicate a particular delivery module to a specific combination of medications or other substances so that he or she only needs to replace the tip and needle between uses.

In other embodiments, where the type, dosage or other characteristics of the medications or other substances secured within the loading area of the delivery module change, the clinician or other user may also be required to replace the clip, delivery line or other conduits, cassette and/or any component, subcomponent or portion of the injection system that may contact the medications, formulations and/or other fluids or materials being delivered within an anatomy. Thus, as discussed with respect to the various embodiments disclosed herein, certain components and portions of the injection system (e.g., the handpiece assembly, fluid delivery module, etc.) can be advantageously configured to be easily and quickly removed and replaced as desired or required (e.g., between injection procedures, when the characteristics of the medications and/or other materials being injected are modified, according to some predetermined schedule, etc.). The foregoing disclosure regarding the replacement of tips, needles, clips, delivery lines, other conduits and/or the like can be applied to any embodiments disclosed herein or variations thereof.

Once the injection system has been adequately prepped, the clinician can select 1018 the details of the particular injection procedure to be performed. For example, in some embodiments, the clinician uses the interactive menus provided on a display of the fluid delivery module or other component of the system to choose one of various protocols already recognized by the injection system (e.g., saved within the memory of the fluid delivery module). In other arrangements, the clinician enters the details (e.g., types, volumes or other amounts, dosages and/or other information) regarding the medications, formulations and/or other materials to be injected into a patient. Thus, a clinician or other user can customize a particular injection protocol, as desired or required. In some embodiments, the injection system is configured to save the details of the various injection protocols, thereby allowing a clinician or other user to access such information in the future (e.g., for purposes of repeating the same injection protocol, for record keeping and/or for any other purpose). Such data and other information can be shared with another network (e.g., the hospital's or other faculty's main network, the internet, etc.).

Next, the clinician or other user can secure 1022 one or more vials containing the medications, formulations and/or other fluids or materials that are needed to execute a particular injection procedure. For example, each vial or other container can comprise anesthetics or other pain-relieving medications (e.g., Lidocaine, other slow or fast acting anesthetics, etc.) steroids (e.g., Depo-Medrol®, methylprednisolone acetate, etc.), hyaluronic acid, saline, pharmaceutical compositions, other medications or drugs, cells, liquid and non-liquid fluids and flowable materials, nanoparticles, cement, microbeads and/or combinations of such fluids and other materials.

In some embodiments, the required vials or other containers are secured to a nest, loading area or other receiving area of the fluid delivery module (e.g., cassette). Alternatively, the vials can be positioned along a different portion of the fluid delivery module or other component of the injection system, as desired or required.

According to some arrangements, the vials or other containers secured to the fluid delivery module or other portion of the system are verified 1026 to confirm that the characteristics (e.g., type, dosage, volume, expiration date, etc.) of the medications, formulations and/or other fluids or materials that will be delivered into a patient are in accordance with the intended protocol. This can improve the safety and accuracy of the injection procedure, as the likelihood of delivering incorrect substances to a patient is advantageously eliminated or reduced.

Confirmation of the medications and/or other materials contained within the vials secured to the fluid delivery module or other portion of the injection system can be performed manually or automatically. As discussed herein with reference to FIGS. 19A-19C, adapters with flags or identification members can be secured to the vials or other containers. As a result, when a vial is secured to the fluid delivery module, a reader or other identification device can be configured to automatically detect the contents of such a vial. In other arrangements, the fluid delivery module or other portion of the injection system comprises a barcode scanner, RFID reader or other device adapted to identify a machine-readable machine code (e.g., barcode or other textual code, color or graphical pattern, etc.) and/or the like. In still other embodiments, the clinician or other user manually confirms the contents of a vial or other container. For such systems, a user may be required to enter certain data and/or other information about the vials or other containers into one or more components of the injection system. For instance, a user can use a touchscreen, a keypad or keyboard or other data entry device to input the NDC, the name of the medication and/or any other information, to confirm the identity of the vials and/or the like.

With continued reference to the example injection procedure that is schematically illustrated in FIG. 53, the clinician can then transfer 1030 all or some of the medications, formulations and/or other materials contained in the vials to an interior portion of the fluid delivery module or other component of the injection system. For example, as discussed in greater detail herein, the internal contents of such vials or other containers can be conveyed to syringes or other reservoirs within a cassette or other portion of the fluid delivery module. Once within such syringes or other reservoirs, one or more of the various medications and/or other materials can be selectively administered into a patient through a handpiece assembly.

However, before any medications and/or other materials can be injected into a patient, the needle at the distal end of the handpiece assembly must be accurately positioned within the targeted anatomical location (e.g., joint, organ, etc.). In some embodiments, imaging techniques can be used to locate 1034 such a joint or other targeted location. Alternatively, one or more other devices or methods can be used to accurately position the needle within a patient's body. For example, as discussed herein with reference to FIGS. 45-47, the injection system can comprise ultrasound, radio frequency spectroscopy and/or other imaging capabilities to assist in accurately positioning the needle of the handpiece assembly within the anatomy of a patient. Incorporating imaging technologies (e.g., ultrasound, radio frequency spectroscopy, CT, MRI, etc.) into an injection/aspiration system can facilitate the injection and/or aspiration procedures for a physician or other clinician. For example, as noted herein, such injection systems can permit a single user to conduct the entire procedure alone.

In other embodiments, locating the targeted intra-articular space comprises measuring one or more tissue characteristics at or near the tip or distal end of the needle being inserted into the anatomy. Each type of intra-articular space can be associated with a particular tissue response range within which the tissue response value at the distal end of the needle should be. Thus, as the needle is advanced through skin, subcutaneous tissue and/or other anatomical layers, the tissue response value at or near the tip of the needle may fluctuate. In one embodiment, the tissue response value at the needle tip decreases as the needle enters into the desired intra-articular space. Therefore, the system can be configured to instruct the user to advance the needle until the tissue response value drops below a specific threshold level.

In some embodiments, an optical fiber, electrode or other type of sensing device can be located at or near the distal end of the needle. A processor of the delivery module can be programmed or otherwise configured so when a tissue response value is measured, received or detected by the corresponding sensor (e.g., optical fiber, electrode, etc.), the fluid delivery module can determine whether the targeted anatomical area has been reached. The delivery module can be configured to indicate relevant information regarding the needle's position using one or more devices, components or methods, such as, for example, via the touchscreen or other display (e.g., visual readouts, charts, etc.), via audible indicia (e.g., tones, voice commands, etc.) and/or the like.

A display of the fluid delivery module (e.g., touchscreen, LCD screen, other monitor, etc.) can be configured to provide a textual and/or graphic representation of the tissue response value, its rate of change and/or any other details related to locating an intra-articular space. For example, the tissue response value at or near the tip of the needle can be displayed as the actual value (as text) or as a chart or graph (e.g., X-Y plot, a circular target chart, etc.).

After the needle has been properly positioned within a patient, the clinician can initiate delivery 1038 of one or more medications, formulations and/or other fluids or materials, as required by a particular injection protocol. As discussed, the clinician can use the buttons or other controllers on the handpiece assembly or other portion of the injection system to accurately control the delivery of a particular fluid or material stream into the patient. For example, in some arrangements, the clinician initiates delivery of Lidocaine or another anesthetic. As discussed, the delivery of such anesthetics can be initiated as the clinician begins to advance the needle through the patient's anatomy or after the tip of the needle has been accurately positioned within a joint or another targeted anatomical location (e.g., muscle tissue, organ, etc.).

The incorporation of mechanically, hydraulically, pneumatically or differently driven delivery of medications, formulations and/or other fluids or materials from the fluid delivery module to the patient can facilitate the execution of an injection procedure. For example, a physician or other clinician can simply use one or more buttons or other controllers (e.g., on the handpiece assembly, touchscreen of fluid delivery module, imaging wand, etc.) to accurately deliver a volume or other amount of a particular substance to a joint or another targeted anatomical location. This can be particularly helpful when the manual delivery of such fluids and/or other materials could be difficult, strenuous, repetitive or otherwise problematic. A relatively high and persistent force and effort may be required by the physician or other clinician to deliver one or more medicaments and/or other substances to a targeted anatomical location. This can be particularly problematic when attempting to inject dense, viscous or high-solids fluids or other materials to small joints (e.g., toes, fingers, midfoot joints, etc.) or another high back-pressure locations within an anatomy (e.g., to or near bones, certain organs, etc.). Thus, at least some of the embodiments of the injection systems, devices and methods disclosed herein permit the delivery of one or more medicaments and/or other materials from a fluid delivery module to a target anatomical location within a patient without the need to push or exert the necessary force or effort to physically administer such substances. Consequently, the clinician or other user can dedicate more of his or her time and effort in accurately locating a joint or other targeted anatomical location and executing the desired injection procedure.

As discussed, the clinician can selectively deliver 1042 one or more other fluid and/or material streams into a patient, either alone or concurrently with the delivery of another stream. In some embodiments, this is accomplished by pressing or otherwise manipulating buttons or other controller on the handpiece assembly or another portion of the injection system. Further, the injection system can be configured so that operation of such a button or other controller causes two or more different fluid and/or material streams to be simultaneously delivered through the needle. Screenshots (FIGS. 48A-51) visually provided on a display or other output device can assist the clinician with selecting an injection protocol and/or executing an injection procedure.

According to one embodiment, a procedure comprises the injection of a volume of an anesthetic and/or a steroid (Depo-Medrol®) after a volume of a first medication (e.g., Lidocaine or another anesthetic or pain-relieving medication) has been injected into the targeted area. In other arrangements, one or more other fluids and/or other materials (e.g., hyaluronic acid, saline, pharmaceutical compositions, cells, nanoparticles, cement, microbeads, etc.) can be contained within one or more of the vials or other containers loaded onto the cassette or other portion of the fluid delivery module, either in lieu of or in addition to the anesthetics, pain-relieving medications and steroids, as required or desired. According to some embodiments of injection modes or sequences, two or more of the various medications, other fluids and/or other materials loaded onto a fluid delivery module can be delivered simultaneously with one another or sequentially.

Once the desired volumes or other quantities of medications, formulations and/or other substances have been delivered, the clinician can remove the needle from the patient and terminate the procedure 1046. However, in other embodiments, one or more additional treatment steps or procedures may remain after the delivery of the desired medications and/or other substances. The needle, tip and/or any other component of the handpiece assembly (e.g., clip, delivery line, etc.), fluid delivery module (e.g., cassette, vials, etc.) or other portion of the injection system can be properly discarded 1050 to reset 1054 the system in preparation for a subsequent injection procedure.

Example No. 2

FIG. 54 schematically illustrates another example of a injection/aspiration sequence 1100. With the exception of several steps and other details, the depicted embodiment is similar to the sequence 1000 discussed herein with reference to FIG. 53. For example, in the illustrated sequence 1100, once a targeted joint space or other anatomical location has been located 1134, the clinician can detach the tip 1136 from the proximal portion of the handpiece assembly (e.g., the clip, core, etc.). Then, as discussed herein with reference to FIG. 44, a syringe or other vacuum source can be placed in fluid communication with the tip and the needle attached thereto in order to selectively withdraw fluids and/or other substances from the patient. For example, it may be beneficial or desirable to remove excess fluids from a damaged joint before injecting one or more medications or formulations. Once a desired volume or other amount of fluid or other material have been removed from the patient, the clinician can reattach the tip 1138 and initiate delivery of one or more medications, other fluids and/or other substances, as desired or required. For example, in one mode, a volume of a second fluid or other material (e.g., steroids, anesthetics, other pain-relieving medications, hyaluronic acid, saline, pharmaceutical compositions, cells, nanoparticles, cement, microbeads, etc.) is delivered after a volume of a first medication (e.g., Lidocaine, other anesthetic, pain-relieving medication, etc.) has been injected into the targeted area. In other modes or sequences, the various medications, other fluids and/or other materials can be delivered to an intra-articular space simultaneously or according to a different order.

The above disclosure regarding the sequences for delivering medications and/or other materials to a target anatomical location and other related features can be applied to any embodiment of an injection system, device or method disclosed herein or equivalents thereof.

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although several preferred embodiments and examples are disclosed herein, the present invention extends beyond the specifically disclosed embodiments to other alternative embodiments and/or uses of the invention and modifications and equivalents thereof. It is also contemplated that various combinations or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A method of injecting two or more fluids into a joint of a patient using a handpiece assembly of an injection system, the method comprising:
    manipulating at least a portion of a handpiece assembly into an anatomy of a patient, said handpiece assembly comprising a main portion, a needle positioned along a distal end of said main portion, and at least one fluid conduit in fluid communication with said needle;
    wherein a first fluid and at least a second fluid are configured to selectively flow through the at least one fluid conduit and to the needle;
    wherein the first fluid and the second fluid are configured to be delivered through the at least one fluid conduit either simultaneously or sequentially, based at least in part on instructions provided by a user;
    wherein the at least one fluid conduit is at least partially routed through an interior of the handpiece assembly;
    wherein at least one electronic controller is positioned along the main portion of the handpiece assembly, wherein manipulation of the at least one electronic controller is configured to regulate a fluid delivery scheme for selectively delivering the first fluid and the second fluid to and through the needle;
    wherein the fluid delivery scheme comprises an order in which the first and second fluids are delivered through the at least one fluid conduit and a flowrate at which the first and second fluids are delivered through the at least one fluid conduit;
    wherein the at least one electronic controller is configured to be in data communication with a fluid delivery module;
    wherein handpiece assembly is configured such that fluids are prevented from flowing proximally from the handpiece assembly through the at least one fluid conduit, toward the fluid delivery module;
    wherein the needle is configured to be positioned within a joint to selectively deliver at least one of said first fluid and said second fluid to said joint;
    positioning the needle into or near a joint of the patient; and
    delivering a volume of at least one of the first fluid and the second fluid through the at least one conduit to and through the needle;
    wherein the at least one electronic controller is selectively removable from the handpiece assembly; and
    wherein simultaneous delivery of the first and the second fluids is performed by combining the first and second fluids at a location proximal to the needle.

2. The method of claim 1, wherein the at least one electronic controller comprises a button.

3. The method of claim 1, wherein the at least one electronic controller comprises at least one of a rollerball and a rollerwheel.

4. The method of claim 1, wherein the at least one electronic controller is configured to communicate with the fluid delivery module using a wireless connection.

5. The method of claim 4, wherein the wireless connection comprises Bluetooth.

6. The method of claim 1, further comprising monitoring a position of the needle using an imaging device to accurately locate a target joint of the patient.

7. The method of claim 6, wherein the imaging device comprises an ultrasound device that is operatively coupled to the injection system.

8. The method of claim 1, wherein a predetermined volume of the first fluid and the second fluid are configured to delivered through the handpiece assembly to the patient.

9. The method of claim 1, wherein the first fluid comprises an anesthetic and wherein the second fluid comprises a steroid.

10. The method of claim 1, wherein the first and second medicaments are delivered simultaneously to a joint of the patient.

11. The method of claim 1, wherein the first and second medicaments are delivered sequentially to a joint of the patient.

12. A method of injecting two or more fluids into an anatomy using a handpiece assembly, comprising:
- moving a needle of a handpiece assembly within an anatomy of a patient, wherein said handpiece assembly comprises a main body and the needle positioned at a distal end of said main body, wherein the handpiece assembly is configured to be selectively grasped and manipulated by a user;
- wherein the handpiece assembly comprises at least one fluid conduit, said at least one fluid conduit being positioned, at least partially, within an interior of said main body;
- wherein the handpiece assembly is configured to be in data and fluid communication with a fluid delivery module;
- wherein at least one of a first fluid and a second fluid is configured to flow from the fluid delivery module to the at least one fluid conduit;
- wherein the at least one fluid conduit is configured to convey at least one of the first fluid and the second fluid to the needle of the handpiece assembly;
- wherein the fluid delivery module comprises at least one movable member configured to slide within an interior of at least one fluid reservoir to selectively transfer at least one of the first fluid and the second fluid from the fluid delivery module to the needle;
- wherein the handpiece assembly is configured such that a flow of fluid proximally through the handpiece assembly, toward the fluid delivery module, is prevented;
- wherein the main body comprises an electronic control portion, said electronic control portion comprising at least one button configured to control at least one parameter of the delivery of at least one the first fluid and the second fluid through the at least one fluid conduit;
- wherein the electronic control portion is selectively removable from and attachable to the main body of the handpiece assembly;
- manipulating the handpiece assembly in order to position the needle into a target anatomical location of the patient;
- delivering a volume of at least one of the first fluid and the second fluid through the at least one fluid conduit to the needle of the handpiece assembly; and
- removing the needle from the target anatomical location of the patient once a desired volume of the first and second fluids has been delivered to said target anatomical location.

13. The method of claim 12, wherein the electronic control portion is configured to communicate with the fluid delivery module using a wireless connection.

14. The method of claim 13, wherein the wireless connection comprises Bluetooth.

15. The method of claim 12, wherein the target anatomical location of the patient comprises a joint.

16. The method of claim 12, wherein manipulating the handpiece assembly comprises using an imaging device to accurately locate the target anatomical location.

17. The method of claim 16, wherein the imaging device comprises an ultrasound device that is operatively coupled to at least one of the handpiece assembly and the fluid delivery module.

18. The method of claim 12, wherein a predetermined volume of the first fluid and the second fluid are configured to delivered through the handpiece assembly to the target anatomical location of the patient during an injection procedure.

* * * * *